United States Patent
Yu

(10) Patent No.: US 9,394,293 B2
(45) Date of Patent: Jul. 19, 2016

(54) TRPV1 ANTAGONISTS INCLUDING DIHYDROXY SUBSTITUENT AND USES THEREOF

(75) Inventor: Jianming Yu, Plainsboro, NJ (US)

(73) Assignee: Purdue Pharma L.P., Stamford, CT (US)

(*) Notice: Subject to any disclaimer, the term of this patent is extended or adjusted under 35 U.S.C. 154(b) by 21 days.

(21) Appl. No.: 14/237,848

(22) PCT Filed: Aug. 9, 2012

(86) PCT No.: PCT/IB2012/001575
§ 371 (c)(1),
(2), (4) Date: Feb. 7, 2014

(87) PCT Pub. No.: WO2013/021276
PCT Pub. Date: Feb. 14, 2013

(65) Prior Publication Data
US 2014/0350056 A1   Nov. 27, 2014

Related U.S. Application Data

(60) Provisional application No. 61/522,085, filed on Aug. 10, 2011.

(51) Int. Cl.
| | |
|---|---|
| A61K 31/44 | (2006.01) |
| C07D 417/00 | (2006.01) |
| C07D 417/12 | (2006.01) |
| C07D 401/14 | (2006.01) |
| C07D 401/04 | (2006.01) |
| C07D 401/12 | (2006.01) |
| C07D 239/26 | (2006.01) |
| C07D 241/12 | (2006.01) |
| C07D 213/56 | (2006.01) |
| A61K 31/4164 | (2006.01) |
| A61K 31/422 | (2006.01) |
| A61K 31/428 | (2006.01) |
| A61K 31/4427 | (2006.01) |
| A61K 31/444 | (2006.01) |
| C07D 405/06 | (2006.01) |

(52) U.S. Cl.
CPC .......... *C07D 417/12* (2013.01); *A61K 31/4164* (2013.01); *A61K 31/422* (2013.01); *A61K 31/428* (2013.01); *A61K 31/44* (2013.01); *A61K 31/444* (2013.01); *A61K 31/4427* (2013.01); *C07D 213/56* (2013.01); *C07D 239/26* (2013.01); *C07D 241/12* (2013.01); *C07D 401/04* (2013.01); *C07D 401/12* (2013.01); *C07D 401/14* (2013.01); *C07D 405/06* (2013.01)

(58) Field of Classification Search
None
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,797,419 A | 1/1989 | Moos et al. | |
| 5,059,595 A | 10/1991 | Le Grazie | |
| 5,073,543 A | 12/1991 | Marshall et al. | |
| 5,120,548 A | 6/1992 | McClelland et al. | |
| 5,354,556 A | 10/1994 | Sparks et al. | |
| 5,529,998 A | 6/1996 | Habich et al. | |
| 5,591,767 A | 1/1997 | Mohr et al. | |
| 5,639,476 A | 6/1997 | Oshlack et al. | |
| 5,674,533 A | 10/1997 | Santus et al. | |
| 5,698,155 A | 12/1997 | Grosswald et al. | |

(Continued)

FOREIGN PATENT DOCUMENTS

| | | |
|---|---|---|
| DE | 199 34 799 | 2/2001 |
| JP | 11-199573 | 7/1999 |

(Continued)

OTHER PUBLICATIONS

Sirotnak, FM. et al. Stereochemical Characteristics of the Folate-Antifolate Transport Mechanism in L1210 Leukemia Cells. Cancer Research. 1974, vol. 34, p. 372.*
Carey, FA. Organic Chemistry 6th Ed. McGraw Hill. 2006, chapter 1, p. 9.*
Amadji et al., "Chirons in the 1,3-dioxane series: Stereospecific cross-coupling reactions and chirality transfer," *Tetrahedron: Assymetry* 9:1657-1660 (1998).
Bartho et al., "Involvement of capsaicin-sensitive neurons in hyperalgesia and enhanced opioid antinociception in inflammation," *Naunyn-Schmiedeberg's Archives of Pharmacol.* 342:666-670 (1990).

(Continued)

*Primary Examiner* — Rita Desai
*Assistant Examiner* — Ben S Michelson
(74) *Attorney, Agent, or Firm* — Dechert LLP

(57) ABSTRACT

The disclosure relates to Compounds of Formula (I):

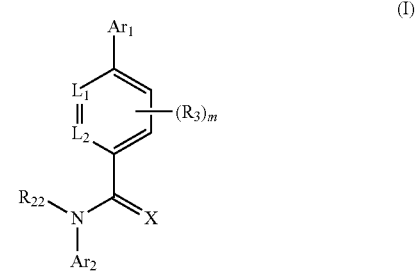

and pharmaceutically acceptable derivatives thereof wherein $Ar_1$, $Ar_2$, $L_1$, $L_2$, X, $R_3$, $R_{22}$, and m are as defined herein, compositions comprising an effective amount of a Compound of Formula (I), and methods for treating or preventing a condition such as pain, UI, an ulcer, IBD and IBS, comprising administering to an animal in need thereof an effective amount of a Compound of Formula (I).

32 Claims, No Drawings

(56) References Cited

U.S. PATENT DOCUMENTS

| | | | |
|---|---|---|---|
| 5,733,566 A | 3/1998 | Lewis | |
| 5,891,889 A | 4/1999 | Anthony et al. | |
| 6,136,839 A | 10/2000 | Isakson et al. | |
| 6,150,129 A | 11/2000 | Cook et al. | |
| 6,239,267 B1 | 5/2001 | Duckworth et al. | |
| 6,248,756 B1 | 6/2001 | Anthony et al. | |
| 6,335,180 B1 | 1/2002 | Julius et al. | |
| 6,406,908 B1 | 6/2002 | McIntyre et al. | |
| 6,562,319 B2 | 5/2003 | Mishani et al. | |
| 7,338,950 B2 | 3/2008 | Kelly et al. | |
| 7,355,045 B2 | 4/2008 | Dey et al. | |
| 7,572,812 B2 | 8/2009 | Sun et al. | |
| 7,582,635 B2 | 9/2009 | Sun et al. | |
| 7,696,208 B2 | 4/2010 | Kyle et al. | |
| 7,772,254 B2 | 8/2010 | Sun | |
| 7,776,861 B2 | 8/2010 | Sun et al. | |
| 7,799,807 B2 | 9/2010 | Sun | |
| 8,030,310 B2 | 10/2011 | Kyle et al. | |
| 8,178,560 B2 | 5/2012 | Sun et al. | |
| 8,389,549 B2 | 3/2013 | Tafesse | |
| 8,476,271 B2 | 7/2013 | Tsuno et al. | |
| 8,476,277 B2 | 7/2013 | Tafesse | |
| 8,546,388 B2 | 10/2013 | Kyle et al. | |
| 8,575,199 B2 | 11/2013 | Tafesse | |
| 8,637,548 B2 | 1/2014 | Sun et al. | |
| 8,703,962 B2 | 4/2014 | Kyle et al. | |
| 8,759,362 B2 | 6/2014 | Tafesse | |
| 8,889,690 B2 | 11/2014 | Tafesse | |
| 8,921,373 B2 | 12/2014 | Kurose | |
| 9,145,408 B2 | 9/2015 | Tsuno et al. | |
| 9,156,830 B2 | 10/2015 | Kurose et al. | |
| 2005/0165015 A1 | 7/2005 | Ncube et al. | |
| 2006/0100245 A1 | 5/2006 | Bakthavatchalam et al. | |
| 2006/0235022 A1 | 10/2006 | Sun | |
| 2006/0241117 A1 | 10/2006 | Sun | |
| 2007/0191363 A1 | 8/2007 | Hodgetts et al. | |
| 2007/0232661 A1 | 10/2007 | Beachy et al. | |
| 2008/0312235 A1 | 12/2008 | Lane et al. | |
| 2009/0170867 A1 | 7/2009 | Kurose | |
| 2009/0176796 A1 | 7/2009 | Tafesse | |
| 2010/0120862 A1* | 5/2010 | Tafesse | 514/334 |
| 2011/0104301 A1 | 5/2011 | Ahern et al. | |
| 2014/0249159 A1 | 9/2014 | Kurose et al. | |

FOREIGN PATENT DOCUMENTS

| | | |
|---|---|---|
| WO | WO 97/28140 | 8/1997 |
| WO | WO 97/38665 | 10/1997 |
| WO | WO 98/31669 | 7/1998 |
| WO | WO 98/31677 | 7/1998 |
| WO | WO 99/37304 | 7/1999 |
| WO | WO 00/59510 | 10/2000 |
| WO | WO 01/27107 | 4/2001 |
| WO | WO 01/57008 | 8/2001 |
| WO | WO 02/08221 | 1/2002 |
| WO | WO 2004-056774 A2 | 7/2004 |
| WO | WO 2004/058754 A1 | 7/2004 |
| WO | WO 2005/009987 A1 | 2/2005 |
| WO | WO 2005/009988 A1 | 2/2005 |
| WO | WO 2005/030766 | 4/2005 |
| WO | WO 2005/030766 A1 * | 4/2005 |
| WO | WO 2005-032493 A2 | 4/2005 |
| WO | WO 2011-162409 A1 | 12/2011 |

OTHER PUBLICATIONS

Berkow et al., eds., "Crohn's Disease," *Merck Manual of Medical Information*, pp. 528-530 (1997).

Berkow et al., eds., "Irritable Bowel Syndrome," *Merck Manual of Medical Information*, pp. 525-526 (1997).

Billotte, "Synthesis of C-Substituted Cyclic Amines Using Azacycloalkyl Organozinc Reagents," *Synlett*. pp. 379-380 (Apr. 1998).

Bingham et al.," Over one hundred solvates of sulfathiazole," *Chem. Comm.*, pp. 603-604 (2001).

Buchwald et al., "Long-term, Continuous Intravenous Heparin Administration by an Implantable Infusion Pump in Ambulatory Patients with Recurrent Venous Thrombosis," *Surgery* 88:507-516 (1980).

Bundgaard, ed., *Design of Prodrugs*, Elsevier (1985).

Bundgaard et al.,"Glycolamide Esters as Biolabile Prodrugs of Carboxylic Acid Agents: Synthesis, Stability, Bioconversion, and Physicochemical Properties," *J. Pharmaceut. Sci.* 77(4):285-298 (1988).

Bundgaard, "Design and Application of Prodrugs," Chapter 5, pp. 113-191 in *A Textbook of Drug Design and Development*, Krogsgaard-Larsen and Bundgaard Eds., Harwood Academic Publishers (1991).

Bundgaard et al.,"(C) Means to Enhance Penetration (1) Prodrugs as a means to improve the delivery of peptide drugs," *Adv. Drug Delivery Revs*. 8:1-38 (1992).

Caira et al, "Preparation and Crystal Characterization of a Polymorph, a Monohydrate, and an Ethyl Acetate Solvate of the Antifungal Fluconazole," *J. Pharmaceut. Sci.*, 93(3):601-611 (2004).

Chu-Moyer et al., "Orally-Effective, Long-Acting Sorbitol Dehydrogenase Inhibitors: Synthesis, Structure-Activity Relationships, and in Vivo Evaluations of Novel Heterocycle-Substituted Piperazino-Pyrimidines," *J. Med. Chem.* 45:511-528 (2002).

D'Amour et al., "A Method for Determining Loss of Pain Sensation," *J. Pharmacol. Exp. Ther.* 72:74-79 (1941).

Di Marzo et al., "Endovanilloid signaling in pain," *Current Opinion Neurobiol.* 12:372-379 (2002).

During et al., "Controlled Release of Dopamine from a Polymeric Brain Implant: In Vivo Characterization," *Ann. Neurol.* 25:351-356 (1989).

Filer, "The Preparation and Characterization of Tritiated Neurochemicals," Chapter 6, pp. 155-192 in *Isotopes in the Physical and Biomedical Sciences*, vol. 1, *Labeled Compounds (Part A)* (1987).

Fillon et aL, "Electrosynthesis of functionalized organodizinc compounds from aromatic dihalides via a cobalt catalysis in acetonitrile/pyridine as solvent," *Tet. Lett.* 42:3843-3846 (2001).

Foley, "Pain," in *Cecil Textbook of Medicine*, pp. 100-107 (Bennett and Plum eds., 20th ed. 1996).

Gavva et al., "AMG 9810 [(E)-3-(4-t-Butylphenyl)-N-(2,3-dihydrobenzo[b][1,4]dioxin-6-yl)acrylamide], a Novel Vanilloid Receptor 1 (TRPV1) Antagonist with Antihyperalgesic Properties", *J. Pharmacol. Exp. Ther.* 313:474-484 (2005).

Goodson, "Dental Applications," pp. 115-138 in *Medical Applications of Controlled Release*, vol. 2, *Applications and Evaluation*, Langer and Wise, eds., CRC Press (1984).

Greene et al., *Protective Groups in Organic Synthesis*, 3rd Ed., pp. 494-653, Wiley-Interscience, New York (1999).

Greene, *Protective Groups in Organic Synthesis*, pp. 10-86, Wiley-Interscience, New York (1981).

Grupp et al., "Protection against Hypoxia-reoxygenation in the Absence of Poly (ADP-ribose) Synthetase in Isolated Working Hearts," *J. Mol. Cell Cardiol.* 31:297-303 (1999).

*Handbook of Pharmaceutical Excipients*, (Amer. Pharmaceutical Ass'n, Washington, DC, 1986).

Hanson, "Analgesic, Antipyretic and Anti-Inflammatory Drugs," pp. 1196-1221 in *Remington: The Science and Practice of Pharmacy* vol. 2 (Gennaro, ed., 19th ed., Mack Publishing, Easton, PA, 1995).

Hargreaves et al., "A New and Sensitive Method for Measuring Thermal Nociception in Cutaneous Hyperalgesia," *Pain* 32(1):77-88 (1988).

Howard et al., "Intracerebral drug delivery in rats with lesion-induced memory deficits," *J. Neurosurg.* 71:105 (1989).

Insel, "Analgesic-Antipyretic and Anti-inflammatory Agents and Drugs Employed in the Treatment of Gout," pp. 617-657 in *Goodman & Gilman's The Pharmacological Basis of Therapeutics* (Goodman et al., Eds., 9th Ed., McGraw-Hill, New York 1996).

IUPAC Compendium of Chemical Terminology, 2nd Ed. (the "Gold Book"), McNaught et al., eds., Blackwell Scientific Publications, Oxford (1997).

Kakeya et al., "Studies on Prodrugs of Cephalosporins. I. Synthesis and Biological Properties of Glycyloxygenzoyloxymethyl and Glycylaminobenzoyloxymethyl Esters of 7β-[2-(2-Aminothiazol-4-

(56) References Cited

OTHER PUBLICATIONS yl)-(Z)-2-methoxyiminoacetamido]3-methyl-3-cephem-4-carboxylic Acid," *Chem. Pharm. Bull.* 32:692-698 (1984).

Khadse et al., "Synthesis and study of 2-($N^4$-substituted-$N^1$-piperazinyl)-pyrido-(3,2-d)-thiazoles, 5-nitro-2-($N^4$-substituted-$N^1$-piperazinyl)-benzthiazoles and allied compounds as possible anthelmintic agents," *Bull. Haff. Instt.* 1(3):27-32 (1975).

Kim, "An Experimental Model for Peripheral Neuropathy Produced by Segmental Spinal Nerve Ligation in the Rat," *Pain* 50(3):355-363 (1992).

King, "Tablets, Capsules, and Pills," pp. 1553-1593 in *Remington's Pharmaceutical Sciences* (Osol, ed., 16th ed., Mack Publishing, Easton, PA, 1980).

Langer et al., "Chemical and Physical Structure of Polymers as Carriers for Controlled Release of Bioactive Agents: A Review," *J. Macromol. Sci. Rev. Macromol. Chem.* C23(1):61-126 (1983).

Langer, "New Methods of Drug Delivery," *Science* 249:1527-1533 (1990).

Levy et al., "Inhibition of Calcification of Bioprosthetic Heart Valves by Local Controlled-Release Diphosphonate," *Science* 228:190-192 (1985).

Lopez-Berestein, "Treatment of Systemic Fungal Infections with Liposomal-Amphotericin B," *Liposomes in the Therapy of Infectious Disease and Cancer*, pp. 317-327 (1989).

March, *Advanced Organic Chemistry: Reactions, Mechanisms, and Structure*, 4th Ed., pp. 891-892, Wiley-Interscience, New York (1992).

*Pharmaceutical Dosage Forms: Disperse Systems* (Lieberman et al., eds., 2nd ed., Marcel Dekker, Inc., 1996 & 1998).

*Pharmaceutical Dosage Forms: Tablets* (Lieberman et al., eds., 2nd ed., Marcel Dekker, Inc., 1989 & 1990).

Radebough et al., "Preformulation," pp. 1447-1676 in *Remington's Pharmaceutical Sciences* vol. 2 (Gennaro, ed., 19th ed., Mack Publishing, Easton, PA, 1995).

Reubish et al., "Functional assessment of temperature-gated ion-channel activity using a real-time PCR machine," www.BioTechniques.com 47(3):iii-ix (2009).

Ross et al., *Pharmacodynamics: Mechanisms of Drug Action and the Relationship Between Drug Concentration and Effect*, Chapter 2 in *Goodman & Gilman's The Pharmacological Basis of Therapeutics* 31-32 (Hardman et al., eds., 10th ed 2001).

Saudek et al, "A Preliminary Trial of the Programmable Implantable Medication System for Insulin Delivery," *New Engl. J. Med.* 321:574-579 (1989).

Sefton, "Implantable Pumps," in *CRC Crit. Rev. Biomed. Eng.* 14(3):201-240 (1987).

Seltzer et al., "A Novel Behavioral Model of Neuropathic Pain Disorders Produced in Rats by Partial Sciatic Nerve Injury," *Pain* 43:205-218 (1990).

Sharpless et al., "From Styrenes to Enantiopure R-Arylglycines in Two Steps," *J. Am. Chem. Soc.* 120:1207-1217 (1998).

Sharpless et al., "The osmium-catalyzed asymmetric dihydroxylation: a new ligand class and a process improvement," *J. Org. Chem.* 57:2768-2771 (1992).

Smith et al., *March's Advanced Organic Chemistry: Reaction Mechanisms and Structure*, 5th Ed., pp. 804-807, Wiley-Interscience, New York (2001).

Smolen et al., "Drug Product Design and Performance," *Controlled Drug Bioavailability* vol. 1, John Wiley & Sons, New York (1984).

Stein, "Unilateral Inflammation of the Hindpaw in Rats as a Model of Prolonged Noxious Stimulation: Alterations in Behavior and Nociceptive Thresholds," *Pharmacol. Biochem. and Behavior* 31:451-455 (1988).

Treat et al., "Liposome encapsulated doxorubicin—preliminary results of phase I and phase II trials" Liposomes in the Therapy of Infectious Disease and Cancer, pp. 353-365 (1989).

Van Tonder et al., "Preparation and Physicochemical Characterization of 5 Niclosamide Solvates and 1 Hemisolvate," *AAPS Pharm. Sci. Tech.*, 5(1):Article 12 (2004).

Widder et al., "Drug and Enzyme Targeting, Part A," eds., vol. 112 in *Methods in Enzymology*, Academic Press (1985).

International Application No. PCT/IB2012/001575: International Search Report dated Nov. 21, 2012.

Fletcher et al., "The search for novel TRPV1-antagonists: From carboxamides to benzimidazoles and indazolones," *Bioorg Med. Chem. Lett.* 16(11):2872-2876 (2006).

Westaway et al., "N-Tetrahydroquinolinyl, N-quinolinyl and N-isoquinolinyl biaryl carboxamides as antagonists of TRPV1," *Bioorg Med. Chem. Lett.* 16(17):4533-4536 (2006).

Zheng et al., "From arylureas to biarylamides to aminoquinazolines: Discovery of a novel, potent TRPV1 antagonist," *Bioorg Med. Chem. Lett.* 16(19):5217-5221 (2006).

\* cited by examiner

TRPV1 ANTAGONISTS INCLUDING DIHYDROXY SUBSTITUENT AND USES THEREOF

CROSS REFERENCE TO RELATED APPLICATIONS

This application is a national stage of International Application No. PCT/IB2012/001575, filed Aug. 9, 2012, which claims the benefit under 35 U.S.C. §119(e) of U.S. provisional application No. 61/522,085, filed Aug. 10, 2011, the contents of all of which are incorporated herein by reference.

1. FIELD

The disclosure relates to Compounds of Formula (I), and pharmaceutically acceptable derivatives thereof, compositions comprising an effective amount of a Compound of Formula (I) and methods for treating or preventing a condition such as pain, UI, an ulcer, IBD, and IBS, comprising administering to an animal in need thereof an effective amount of a Compound of Formula (I).

2. BACKGROUND

Pain is the most common symptom for which patients seek medical advice and treatment. Pain can be acute or chronic. While acute pain is usually self-limited, chronic pain persists for three months or longer and can lead to significant changes in a patient's personality, lifestyle, functional ability and overall quality of life (Foley, "Pain," in *Cecil Textbook of Medicine*, pp. 100-107 (Bennett and Plum eds., 20th ed. 1996)).

Moreover, chronic pain can be classified as either nociceptive or neuropathic. Nociceptive pain includes tissue injury-induced pain and inflammatory pain such as that associated with arthritis. Neuropathic pain is caused by damage to the peripheral or central nervous system and is maintained by aberrant somatosensory processing. There is a large body of evidence relating activity at vanilloid receptors (Di Marzo et al., "Endovanilloid signaling in pain," *Current Opinion in Neurobiology* 12:372-379 (2002)) to pain processing.

Nociceptive pain has been traditionally managed by administering non-opioid analgesics, such as acetylsalicylic acid, choline magnesium trisalicylate, acetaminophen, ibuprofen, fenoprofen, diflusinal, and naproxen; or opioid analgesics, including morphine, hydromorphone, methadone, levorphanol, fentanyl, oxycodone, and oxymorphone. Id. In addition to the above-listed treatments, neuropathic pain, which can be difficult to treat, has also been treated with anti-epileptics (e.g., gabapentin, carbamazepine, valproic acid, topiramate, phenytoin), NMDA antagonists (e.g., ketamine, dextromethorphan), topical lidocaine (for post-herpetic neuralgia), and tricyclic antidepressants (e.g., fluoxetine, sertraline and amitriptyline).

UI is uncontrollable urination, generally caused by bladder-detrusor-muscle instability. UI affects people of all ages and levels of physical health, both in health care settings and in the community at large. Physiologic bladder contraction results in large part from acetylcholine-induced stimulation of post-ganglionic muscarinic-receptor sites on bladder smooth muscle. Treatments for UI include the administration of drugs having bladder-relaxant properties, which help to control bladder-detrusor-muscle overactivity.

None of the existing commercial drug treatments for UI has achieved complete success in all classes of UI patients, nor has treatment occurred without significant adverse side effects.

Treatment of ulcers often involves reducing or inhibiting the aggressive factors. For example, antacids such as aluminum hydroxide, magnesium hydroxide, sodium bicarbonate, and calcium bicarbonate can be used to neutralize stomach acids. Antacids, however, can cause alkalosis, leading to nausea, headache, and weakness. Antacids can also interfere with the absorption of other drugs into the blood stream and cause diarrhea.

$H_2$ antagonists, such as cimetidine, ranitidine, famotidine, and nizatidine, are also used to treat ulcers. $H_2$ antagonists promote ulcer healing by reducing gastric acid and digestive-enzyme secretion elicited by histamine and other $H_2$ agonists in the stomach and duodenum. $H_2$ antagonists, however, can cause breast enlargement and impotence in men, mental changes (especially in the elderly), headache, dizziness, nausea, myalgia, diarrhea, rash, and fever.

$H^+$, $K^+$-ATPase inhibitors such as omeprazole and lansoprazole are also used to treat ulcers. $H^+$, $K^+$-ATPase inhibitors inhibit the production of enzymes used by the stomach to secrete acid. Side effects associated with $H^+$, $K^+$-ATPase inhibitors include nausea, diarrhea, abdominal colic, headache, dizziness, somnolence, skin rashes, and transient elevations of plasma activities of aminotransferases.

Inflammatory-bowel disease ("IBD") is a chronic disorder in which the bowel becomes inflamed, often causing recurring abdominal cramps and diarrhea. The two types of IBD are Crohn's disease and ulcerative colitis.

Crohn's disease, which can include regional enteritis, granulomatous ileitis, and ileocolitis, is a chronic inflammation of the intestinal wall. Crohn's disease occurs equally in both sexes and is more common in Jews of eastern-European ancestry. Most cases of Crohn's disease begin before age 30 and the majority start between the ages of 14 and 24. The disease often affects the full thickness of the intestinal wall. Generally the disease affects the lowest portion of the small intestine (ileum) and the large intestine, but can occur in any part of the digestive tract.

Cramps and diarrhea, side effects associated with Crohn's disease, can be relieved by anticholinergic drugs, diphenoxylate, loperamide, deodorized opium tincture, or codeine.

When Crohn's disease causes the intestine to be obstructed or when abscesses or fistulas do not heal, surgery can be necessary to remove diseased sections of the intestine. Surgery, however, does not cure the disease, and inflammation tends to recur where the intestine is rejoined. In almost half of the cases a second operation is needed. Berkow et al., eds., "Crohn's Disease," *Merck Manual of Medical Information*, pp. 528-530 (1997).

Ulcerative colitis is a chronic disease in which the large intestine becomes inflamed and ulcerated, leading to episodes of bloody diarrhea, abdominal cramps, and fever. Ulcerative colitis usually begins between ages 15 and 30; however, a small group of people have their first attack between ages 50 and 70. Unlike Crohn's disease, ulcerative colitis never affects the small intestine and does not affect the full thickness of the intestine. The disease usually begins in the rectum and the sigmoid colon and eventually spreads partially or completely throughout the large intestine. The cause of ulcerative colitis is unknown.

Treatment of ulcerative colitis is directed to controlling inflammation, reducing symptoms, and replacing lost fluids and nutrients. Anticholinergic drugs and low doses of diphenoxylate or loperamide are administered for treating mild diarrhea. For more intense diarrhea higher doses of diphenoxylate or loperamide, or deodorized opium tincture or codeine are administered.

Irritable-bowel syndrome ("IBS") is a disorder of motility of the entire gastrointestinal tract, causing abdominal pain, constipation, and/or diarrhea. IBS affects three-times more women than men. In IBS, stimuli such as stress, diet, drugs, hormones, or irritants can cause the gastrointestinal tract to contract abnormally. During an episode of IBS, contractions of the gastrointestinal tract become stronger and more frequent, resulting in the rapid transit of food and feces through the small intestine, often leading to diarrhea. Cramps result from the strong contractions of the large intestine and increased sensitivity of pain receptors in the large intestine.

Treatment of IBS often involves modification of an IBS-patient's diet. Often it is recommended that an IBS patient avoid beans, cabbage, sorbitol, and fructose. A low-fat, high-fiber diet can also help some IBS patients. Regular physical activity can also help keep the gastrointestinal tract functioning properly. Drugs such as propantheline that slow the function of the gastrointestinal tract are generally not effective for treating IBS. Antidiarrheal drugs, such as diphenoxylate and loperamide, help with diarrhea. Berkow et al., eds., "Irritable Bowel Syndrome," *Merck Manual of Medical Information*, pp. 525-526 (1997).

U.S. Pat. No. 7,772,254 B2 to Sun and U.S. Pat. No. 7,799,807 B2 to Sun each describes a class of compounds that are useful for treating pain.

U.S. Patent Application Publication Nos. 2009/0170867 A1, 2009/0170868 A1, 2009/0176796 A1, 2010/0120862 A1, 2010/0130499 A1, 2010/0130552 A1, and 2010/0137306 A1 each describe a class of compounds that are useful for treating pain.

International publication no. WO 98/31677 describes a class of aromatic amines derived from cyclic amines that are useful as antidepressant drugs.

International publication no. WO 01/027107 describes a class of heterocyclic compounds that are sodium/proton exchange inhibitors.

International publication no. WO 99/37304 describes substituted oxoazaheterocycly compounds useful for inhibiting factor Xa.

U.S. Pat. No. 6,248,756 to Anthony et al. and international publication no. WO 97/38665 describe a class of piperidine-containing compounds that inhibit farnesyl-protein transferase (Ftase).

International publication no. WO 98/31669 describes a class of aromatic amines derived from cyclic amines useful as antidepressant drugs.

International publication no. WO 97/28140 describes a class of piperidines derived from 1-(piperazin-1-yl)aryl(oxy/amino)carbonyl-4-aryl-piperidine that are useful as 5-HT$_{1Db}$ receptor antagonists.

International publication no. WO 97/38665 describes a class of piperidine containing compounds that are useful as inhibitors of farnesyl-protein transferase.

U.S. Pat. No. 4,797,419 to Moos et al. describes a class of urea compounds for stimulating the release of acetylcholine and useful for treating symptoms of senile cognitive decline.

U.S. Pat. No. 5,891,889 describes a class of substituted piperidine compounds that are useful as inhibitors of farnesyl-protein transferase, and the farnesylation of the oncogene protein Ras.

U.S. Pat. No. 6,150,129 to Cook et al. describes a class of dinitrogen heterocycles useful as antibiotics.

U.S. Pat. No. 5,529,998 to Habich et al. describes a class of benzooxazolyl- and benzothiazolyloxazolidones useful as antibacterials.

International publication no. WO 01/57008 describes a class of 2-benzothiazolyl urea derivatives useful as inhibitors of serine/threonine and tyrosine kinases.

International publication no. WO 02/08221 describes aryl piperazine compounds useful for treating chronic and acute pain conditions, itch, and urinary incontinence.

International publication no. WO 00/59510 describes aminopyrimidines useful as sorbitol dehydrogenase inhibitors.

Japanese patent application no. 11-199573 to Kiyoshi et al. describes benzothiazole derivatives that are neuronal 5HT3 receptor agonists in the intestinal canal nervous system and useful for treating digestive disorders and pancreatic insufficiency.

German patent application no 199 34 799 to Rainer et al. describes a chiral-smectic liquid crystal mixture containing compounds with 2 linked (hetero)aromatic rings or compounds with 3 linked (hetero)aromatic rings.

Chu-Moyer et al., "Orally-Effective, Long-Acting Sorbitol Dehydrogenase Inhibitors: Synthesis, Structure-Activity Relationships, and in Vivo Evaluations of Novel Heterocycle-Substituted Piperazino-Pyrimidines," *J. Med. Chem.* 45:511-528 (2002) describes heterocycle-substituted piperazino-pyrimidines useful as sorbitol dehydrogenase inhibitors.

B. G. Khadse et al., "Synthesis and study of 2-($N^4$-substituted-$N^1$-piperazinyl)-pyrido-(3,2-d)-thiazoles, 5-nitro-2-($N^4$-substituted-$N^1$-piperazinyl)-benzthiazoles and allied compounds as possible anthelmintic agents," *Bull. Haff. Instt.* 1(3):27-32 (1975) describes 2-($N^4$-substituted-$N^1$-piperazinyl)pyrido(3,2-d)thiazoles and 5-nitro-2-($N^4$-substituted-$N^1$-piperazinyl)benzthiazoles useful as anthelmintic agents.

U.S. Patent Application Publication No. US 2004/0186111 A1 and International publication no. WO 2004/058754 A1 describe a class of compounds that are useful for treating pain.

U.S. Patent Application Publication No. US 2006/0199824 A1 and International publication no. WO 2005/009987 A1 describe a class of compounds that are useful for treating pain.

U.S. Patent Application Publication No. US 2006/0128717 A1 and International publication no. WO 2005/009988 A1 describe a class of compounds that are useful for treating pain.

There remains, however, a clear need in the art for new drugs useful for treating or preventing pain, UI, an ulcer, IBD, and IBS. Citation of any reference in Section 2 of this application is not to be construed as an admission that such reference is prior art to the present application.

3. SUMMARY

In a first aspect of the disclosure, new compounds that exhibit affinity for the TRPV1 receptor are described.

In some embodiments, such new compounds exhibit antagonist activity at the TRPV1 receptor. In other embodiments, such new compounds exhibit partial antagonist activity at the TRPV1 receptor.

Certain new compounds of the disclosure can be used to treat an animal suffering from pain, e.g., chronic or acute pain.

In another aspect of the disclosure, methods of treating chronic or acute pain in an animal by administering one or more Compounds of Formula (I) to an animal in need of such treatment are described. In certain embodiments, such new Compounds of Formula (I) effectively treat chronic or acute pain in the animal, while producing fewer or reduced side effects compared to previously available compounds.

Compounds of Formula (I) are herein disclosed:

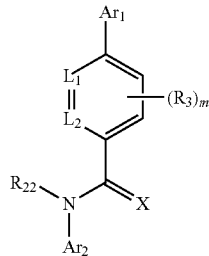
(I)

or a pharmaceutically acceptable derivative thereof, wherein:

X is O, S, or N—OR$_{10}$;

L$_1$ and L$_2$ are each independently N or C(R$_3$) provided that L$_1$ and L$_2$ are not both N;

Ar$_1$ is:

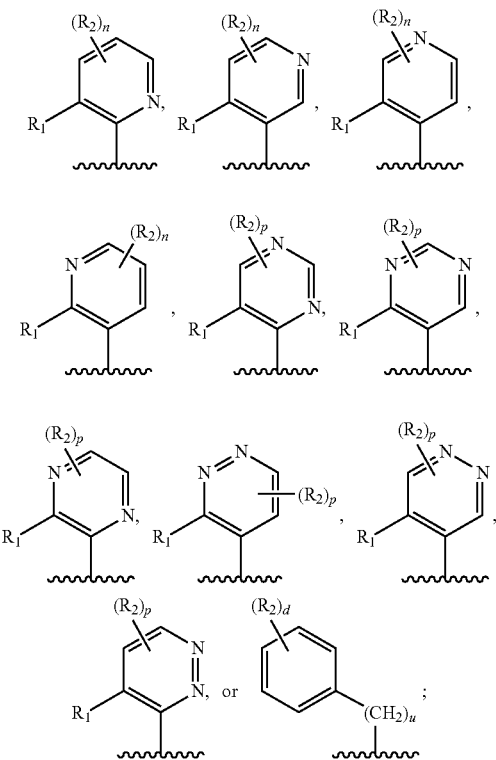

Ar$_2$ is:

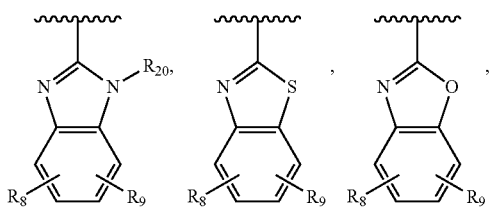

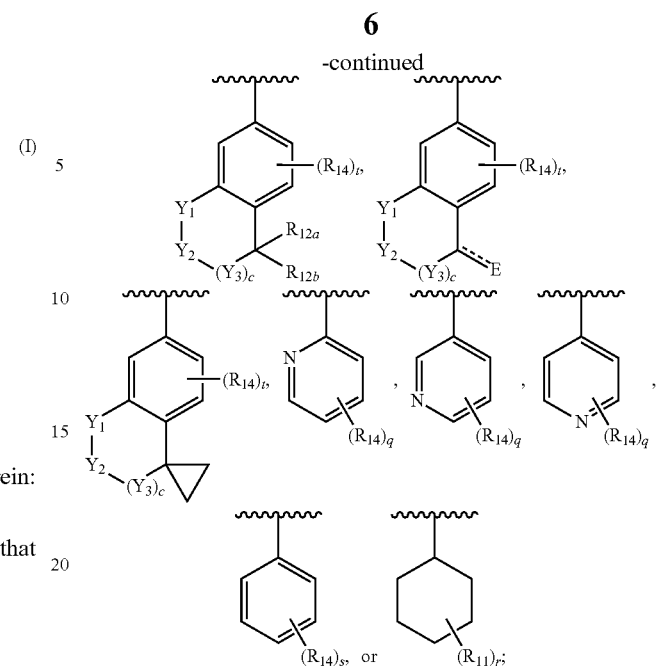

c is the integer 0, 1, or 2;

Y$_1$, Y$_2$, and Y$_3$ are each independently C, N, or O, wherein no more than one of Y$_1$, Y$_2$, or Y$_3$ can be O, and for each Y$_1$, Y$_2$, or Y$_3$ that is N, the N is bonded to one R$_{21}$ group, and for each Y$_1$, Y$_2$, or Y$_3$ that is C, the C is bonded to two R$_{20}$ groups, provided that there are no more than a total of two (C$_1$-C$_6$) alkyl groups substituted on all of Y$_1$, Y$_2$, and Y$_3$;

R$_{12a}$ and R$_{12b}$ are each independently —H or —(C$_1$-C$_6$) alkyl;

E is =O, =S, =CH(C$_1$-C$_6$)alkyl, =CH(C$_2$-C$_6$)alkenyl, —NH(C$_1$-C$_6$)alkyl, or =N—OR$_{20}$;

R$_1$ is -halo, —(C$_1$-C$_4$)alkyl, —NO$_2$, —CN, —S(O)$_2$N(R$_{20}$)$_2$, —OH, —OCH$_3$, —NH$_2$, —C(halo)$_3$, —CH(halo)$_2$, —CH$_2$(halo), —OC(halo)$_3$, —OCH(halo)$_2$, or —OCH$_2$(halo);

each R$_2$ is independently:
(a) -halo, —OH, —O(C$_1$-C$_4$)alkyl, —CN, —NO$_2$, —NH$_2$, —(C$_1$-C$_{10}$)alkyl, —(C$_2$-C$_6$)alkenyl, —(C$_2$-C$_6$)alkynyl, —S(O)$_2$(C$_1$-C$_6$)alkyl, —N(R$_{20}$)S(O)$_2$(C$_1$-C$_6$)alkyl, or -phenyl; or
(b) a group of formula Q, wherein Q is:

$$\begin{array}{c} Z_1 \; Z_2 \\ Z_3 \diagdown \diagup Z_3 \\ Z_3 \diagup \diagdown Z_3 \; J \end{array}$$

Z$_1$ is independently —H, —OR$_{20}$, —N(R$_{20}$)$_2$, —CH$_2$OR$_{20}$, or —CH$_2$N(R$_{20}$)$_2$;

Z$_2$ is independently —H, —(C$_1$-C$_6$)alkyl, or —CH$_2$OR$_{20}$;

each Z$_3$ is independently —H, —(C$_1$-C$_6$)alkyl, or —(C$_3$-C$_8$)cycloalkyl;

J is —OR$_{20}$ or —N(R$_{20}$)$_2$;

provided that at least one R$_2$ group is a group of formula Q;

each R$_3$ is independently —H, —OCF$_3$, -halo, —(C$_1$-C$_6$)alkyl, —(C$_1$-C$_6$)haloalkyl, —(C$_1$-C$_6$)alkoxy, —N(R$_{20}$)S(O)$_2$(C$_1$-C$_6$)alkyl, -(3- to 7-membered)heterocycle, —OR$_{23}$, —SR$_{23}$, —N(R$_{20}$)(R$_{23}$), —C(O)OR$_{23}$, —C(O)R$_{23}$, —OC(O)R$_{23}$, —OC(O)NHR$_{20}$, —NHC(O)R$_{13}$, —C(O)N(R$_{13}$)$_2$, —S(O)$_2$R$_{20}$, —N(R$_{20}$)S(O)$_2$R$_{13}$, or —CH$_2$OR$_7$;

each $R_7$ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, —($C_1$-$C_6$)haloalkyl, —($C_1$-$C_6$)hydroxyalkyl, —($C_1$-$C_6$)alkoxy($C_2$-$C_6$)alkyl, —($C_1$-$C_6$)alkyl-N($R_{20}$)$_2$, or —C(O)N($R_{20}$)$_2$;

each $R_8$ and $R_9$ is independently:
(a) —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, or -phenyl, each of which is optionally substituted with 1 or 2 —OH groups; or
(b) —H, —CH$_2$C(halo)$_3$, —C(halo)$_3$, —CH(halo)$_2$, —CH$_2$(halo), —OC(halo)$_3$, —OCH(halo)$_2$, —OCH$_2$(halo), —SC(halo)$_3$, —SCH(halo)$_2$, —SCH$_2$(halo), —CN, —O—CN, —OH, -halo, —N$_3$, —NO$_2$, —CH=NR$_7$, —N(R$_7$)$_2$, —NR$_7$OH, —OR$_7$, —C(O)R$_7$, —C(O)OR$_7$, —OC(O)R$_7$, —OC(O)OR$_7$, —SR$_7$, —S(O)R$_7$, or —S(O)$_2$R$_7$;

$R_{10}$ is —H, —($C_1$-$C_4$)alkyl, or —($C_3$-$C_7$)cycloalkyl;

each $R_{11}$ is independently —CN, —OH, —($C_1$-$C_6$)alkyl, —($C_2$-$C_6$)alkenyl, -halo, —C(halo)$_3$, —CH(halo)$_2$, —CH$_2$(halo), —OC(halo)$_3$, —N$_3$, —NO$_2$, —N(R$_7$)$_2$, —CH=NR$_7$, —NR$_7$OH, —OR$_7$, —C(O)R$_7$, —C(O)OR$_7$, —OC(O)R$_7$, or —OC(O)OR$_7$;

each $R_{13}$ is independently —H, —($C_1$-$C_4$)alkyl, —($C_2$-$C_4$)alkenyl, —($C_2$-$C_4$)alkynyl, -(3- to 7-membered)heterocycle, or -phenyl;

each $R_{14}$ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, —($C_1$-$C_6$)alkoxy, —($C_1$-$C_6$)alkoxy-($C_1$-$C_6$)alkyl, -phenyl, —C(halo)$_3$, —CH(halo)$_2$, —CH$_2$(halo), -(3- to 7-membered)heterocycle, —($C_1$-$C_6$)haloalkyl, —($C_1$-$C_6$)alkoxy($C_2$-$C_6$)alkyl, —($C_1$-$C_6$)alkoxy($C_3$-$C_8$)cycloalkyl, —CN, —OH, -halo, —OC(halo)$_3$, —N$_3$, —NO$_2$, —CH=NR$_7$, —N(R$_7$)$_2$, —NR$_7$OH, —OR$_7$, —SR$_7$, —O(CH$_2$)$_b$OR$_7$, —O(CH$_2$)$_b$SR$_7$, —O(CH$_2$)$_b$N(R$_7$)$_2$, —N(R$_7$)(CH$_2$)$_b$OR$_7$, —N(R$_7$)(CH$_2$)$_b$SR$_7$, —N(R$_7$)(CH$_2$)$_b$N(R$_7$)$_2$, —N(R$_7$)C(O)R$_7$, —C(O)R$_7$, —C(O)OR$_7$, —OC(O)R$_7$, —OC(O)OR$_7$, —S(O)R$_7$, —S(O)$_2$R$_7$, —S(O)$_2$N(R$_7$)$_2$, —S(O)$_2$C(halo)$_3$, —S(O)$_2$(3- to 7-membered)heterocycle, —C(O)N(R$_7$)$_2$, —($C_1$-$C_6$)alkyl-C=NOR$_7$, —($C_1$-$C_6$)alkyl-C(O)—N(R$_7$)$_2$, —($C_1$-$C_6$)alkyl-NHS(O)$_2$N(R$_7$)$_2$, or —($C_1$-$C_6$)alkyl-C(=NH)—N(R$_7$)$_2$;

each $R_{20}$ is independently —H, —($C_1$-$C_6$)alkyl, or —($C_3$-$C_8$)cycloalkyl;

each $R_{21}$ is independently —H, —($C_1$-$C_6$)alkyl,

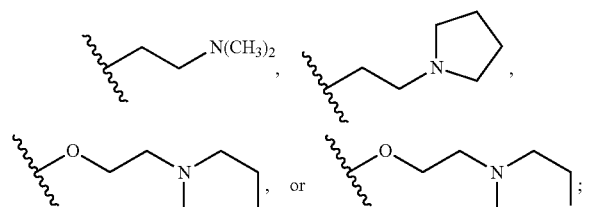

$R_{22}$ is —H, —($C_1$-$C_6$)alkyl, or —($C_3$-$C_8$)cycloalkyl;

each $R_{23}$ is independently —($C_1$-$C_6$)alkyl or —($C_3$-$C_8$)cycloalkyl;

each -halo is independently —F, —Cl, —Br, or —I;
each b is independently the integer 1 or 2;
d is the integer 1, 2, 3, 4, or 5;
m is the integer 0, 1, or 2;
n is the integer 1, 2, or 3;
p is the integer 1 or 2;
q is the integer 0, 1, 2, 3, or 4;
r is the integer 0, 1, 2, 3, 4, 5, or 6;
s is the integer 0, 1, 2, 3, 4, or 5;
t is the integer 0, 1, 2, or 3; and
u is the integer 0, 1, 2, 3, or 4.

A Compound of Formula (I), or a pharmaceutically acceptable derivative thereof, is useful for treating or preventing pain, UI, an ulcer, IBD, or IBS (each being a "Condition") in an animal.

The disclosure also relates to compositions comprising an effective amount of a Compound of Formula (I), or a pharmaceutically acceptable derivative thereof, and a pharmaceutically acceptable carrier or excipient. The compositions are useful for treating or preventing a Condition in an animal.

The disclosure further relates to methods for treating a Condition comprising administering to an animal in need thereof an effective amount of a Compound of Formula (I), or a pharmaceutically acceptable derivative thereof.

The disclosure further relates to a Compound of Formula (I), a pharmaceutically acceptable derivative thereof, a composition containing a Compound of Formula (I), and/or a composition containing a pharmaceutically acceptable derivative of a Compound of Formula (I) for use in the treatment of pain, UI, an ulcer, IBD, or IBS in an animal.

The disclosure further relates to use of a Compound of Formula (I), or a pharmaceutically acceptable derivative thereof, in the manufacture of a medicament for treating and/or preventing a Condition, such as pain. The disclosure further relates to a Compound of Formula (I), or a pharmaceutically acceptable derivative thereof, for use in the treatment and/or prevention of a Condition, such as pain.

The disclosure further relates to methods for preventing a Condition comprising administering to an animal in need thereof an effective amount of a Compound of Formula (I), or a pharmaceutically acceptable derivative thereof.

The disclosure still further relates to methods for inhibiting Transient Receptor Potential Vanilloid 1 ("TRPV1," formerly known as Vanilloid Receptor 1 or VR1) function in a cell, comprising contacting a cell capable of expressing TRPV1 with an effective amount of a Compound of Formula (I), or a pharmaceutically acceptable derivative thereof.

The disclosure still further relates to a method for preparing a composition comprising the step of admixing a Compound of Formula (I), or a pharmaceutically acceptable derivative thereof, and a pharmaceutically acceptable carrier or excipient.

The disclosure still further relates to a kit comprising a container containing an effective amount of a Compound of Formula (I), or a pharmaceutically acceptable derivative thereof.

Preferred Compounds of Formula (I) are Compounds of Formula (II):

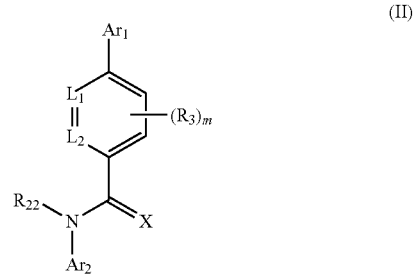

or a pharmaceutically acceptable derivative thereof, where
X is O or S;
$Ar_1$ is:

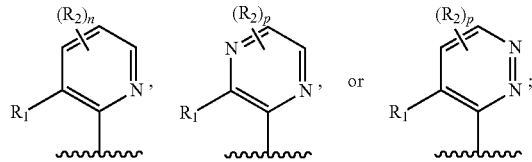

$Ar_2$ is:

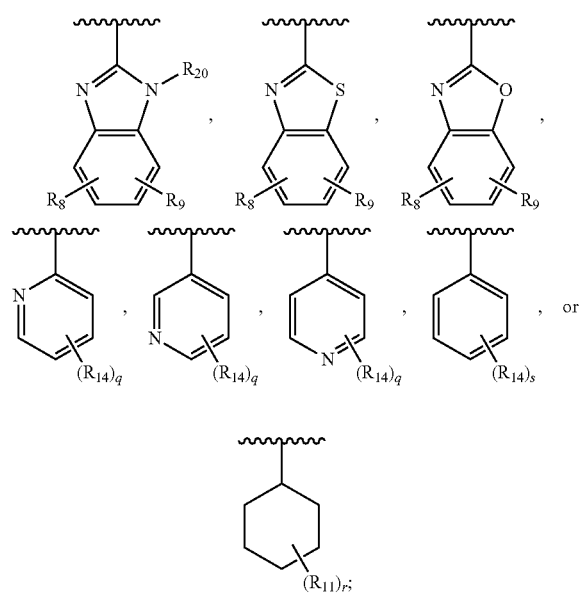

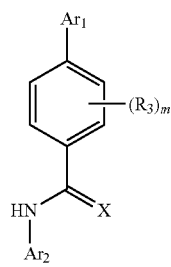

each $R_3$ is independently —H, —$OCF_3$, -halo, —($C_1$-$C_6$)alkyl, —($C_1$-$C_6$)haloalkyl, —($C_1$-$C_6$)alkoxy, —$N(R_{20})S(O)_2$($C_1$-$C_6$)alkyl, —$OR_{23}$, —$SR_{23}$, —$N(R_{20})(R_{23})$, —$NHC(O)R_{13}$, —$C(O)N(R_{13})_2$, —$S(O)_2R_{20}$, —$N(R_{20})S(O)_2R_{13}$, or —$CH_2OR_7$; and $R_{22}$ is —H or —($C_1$-$C_3$)alkyl;

where $L_1$, $L_2$, $R_{22}$, $R_1$, $R_2$, $R_8$, $R_9$, $R_{11}$, $R_{13}$, $R_{14}$, $R_{20}$, $R_{23}$, m, n, p, q, r, s, and halo are as defined above for Compounds of Formula (I).

Preferred Compounds of Formula (II) are Compounds of Formula (III):

(III)

or a pharmaceutically acceptable derivative thereof, wherein
$Ar_1$ is:

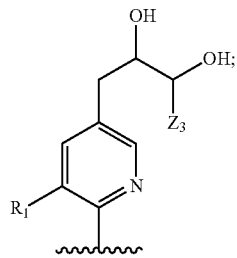

$Ar_2$ is:

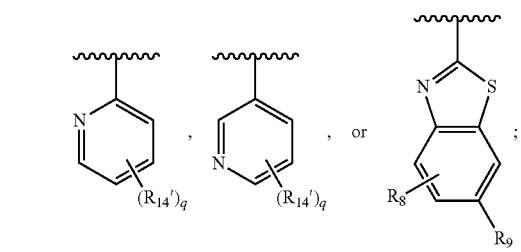

$Z_3$ is —H or —($C_1$-$C_3$)alkyl;

$R_1$ is -halo, —($C_1$-$C_4$)alkyl, —$OCH_3$, —$C(halo)_3$, —$CH(halo)_2$, —$CH_2(halo)$, —$OC(halo)_3$, —$OCH(halo)_2$, or —$OCH_2(halo)$;

each $R_3$ is independently —H, —$OCF_3$, -halo, —($C_1$-$C_3$)alkyl, —($C_1$-$C_3$)haloalkyl, —($C_1$-$C_6$)alkoxy, —$N(R_{20})S(O)_2$($C_1$-$C_3$)alkyl, —$OR_{23}$, —$N(R_{20})(R_{23})$, —$NHC(O)R_{13}$, —$C(O)N(R_{13})_2$, —$S(O)_2R_{20}$, —$N(R_{20})S(O)_2R_{13}$, or —$CH_2OR_7$;

each $R_7$ is independently —H, —($C_1$-$C_3$)alkyl, —($C_2$-$C_4$)alkenyl, —($C_2$-$C_4$)alkynyl, —($C_3$-$C_8$)cycloalkyl, —($C_5$-$C_8$)cycloalkenyl, -phenyl, —($C_1$-$C_3$)haloalkyl, —($C_1$-$C_6$)hydroxyalkyl, —($C_1$-$C_6$)alkoxy($C_2$-$C_6$)alkyl, —($C_1$-$C_3$)alkyl-$N(R_{20})_2$, or —$C(O)N(R_{20})_2$;

each $R_8$ and $R_9$ is independently —H, —Cl, —Br, —F, —$CH_3$, —$OCH_3$, —$OCH_2CH_3$, —$CF_3$, —$OCF_3$, -iso-propyl, -tert-butyl, —$S(O)_2CF_3$, —$S(O)_2CH_3$, or —$S(O)_2CH_2CH_3$;

each $R_{13}$ is independently —H, —($C_1$-$C_4$)alkyl, —($C_2$-$C_4$)alkenyl, —($C_2$-$C_4$)alkynyl, -(3- to 7-membered)heterocycle, or -phenyl;

each $R_{14}'$ is independently —H, —Cl, —F, —Br, —$CF_3$, —$OCF_3$, —($C_1$-$C_6$)alkyl, —$S(O)_2CF_3$, —$S(O)_2$($C_1$-$C_6$)alkyl, —$OCH_3$, —$OCH_2CH_3$, or —$OCH(CH_3)_2$;

each $R_{20}$ is independently —H, —($C_1$-$C_6$)alkyl, or —($C_3$-$C_8$)cycloalkyl;

each $R_{23}$ is independently —($C_1$-$C_6$)alkyl or —($C_3$-$C_8$)cycloalkyl;

each -halo is independently —F, —Cl, —Br, or —I;

m is the integer 0, 1, or 2; and q is the integer 0, 1, or 2.

The disclosure can be understood more fully by reference to the following detailed description and illustrative examples, which are intended to exemplify non-limiting embodiments of the disclosure.

4. DETAILED DESCRIPTION

The invention includes the following:

(1) A compound of formula (I):

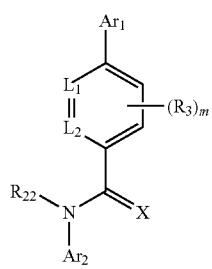
(I)

or a pharmaceutically acceptable salt thereof, wherein:

X is O, S, or N—OR$_{10}$;

L$_1$ and L$_2$ are each independently N or C(R$_3$) provided that L$_1$ and L$_2$ are not both N;

Ar$_1$ is:

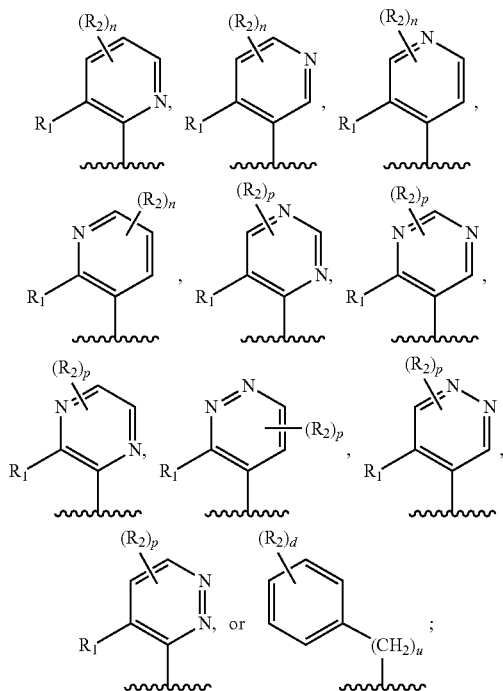

Ar$_2$ is:

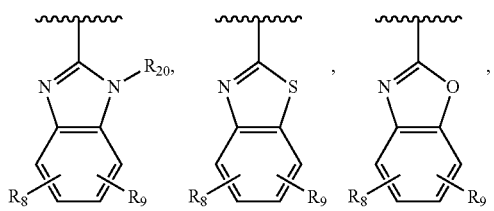

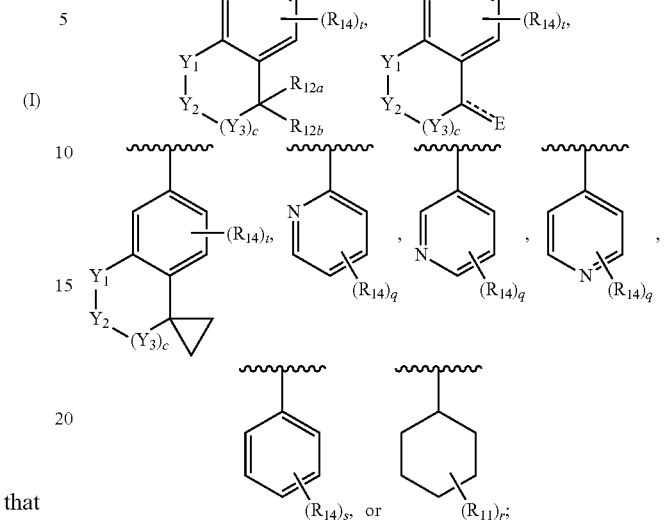

c is the integer 0, 1, or 2;

Y$_1$, Y$_2$, and Y$_3$ are each independently C, N, or O, wherein no more than one of Y$_1$, Y$_2$, or Y$_3$ can be O, and for each Y$_1$, Y$_2$, or Y$_3$ that is N, the N is bonded to one R$_{21}$ group, and for each Y$_1$, Y$_2$, or Y$_3$ that is C, the C is bonded to two R$_{20}$ groups, provided that there are no more than a total of two (C$_1$-C$_6$) alkyl groups substituted on all of Y$_1$, Y$_2$, and Y$_3$;

R$_{12a}$ and R$_{12b}$ are each independently —H or —(C$_1$-C$_6$) alkyl;

E is =O, =S, =CH(C$_1$-C$_6$)alkyl, =CH(C$_2$-C$_6$)alkenyl, —NH(C$_1$-C$_6$)alkyl, or =N—OR$_{20}$;

R$_1$ is -halo, —(C$_1$-C$_4$)alkyl, —NO$_2$, —CN, —S(O)$_2$N(R$_{20}$)$_2$, —OH, —OCH$_3$, —NH$_2$, —C(halo)$_3$, —CH(halo)$_2$, —CH$_2$(halo), —OC(halo)$_3$, —OCH(halo)$_2$, or —OCH$_2$(halo);

each R$_2$ is independently:

(a) -halo, —OH, —O(C$_1$-C$_4$)alkyl, —CN, —NO$_2$, —NH$_2$, —(C$_1$-C$_{10}$)alkyl, —(C$_2$-C$_6$)alkenyl, —(C$_2$-C$_6$)alkynyl, —S(O)$_2$(C$_1$-C$_6$)alkyl, —N(R$_{20}$)S(O)$_2$(C$_1$-C$_6$)alkyl, or -phenyl; or (b) a group of formula Q, wherein Q is:

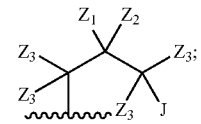

Z$_1$ is independently —H, —OR$_{20}$, —N(R$_{20}$)$_2$, —CH$_2$OR$_{20}$, or —CH$_2$N(R$_{20}$)$_2$;

Z$_2$ is independently —H, —(C$_1$-C$_6$)alkyl, or —CH$_2$OR$_{20}$;

each Z$_3$ is independently —H, —(C$_1$-C$_6$)alkyl, or —(C$_3$-C$_8$)cycloalkyl;

J is —OR$_{20}$ or —N(R$_{20}$)$_2$;

provided that at least one R$_2$ group is a group of formula Q;

each R$_3$ is independently —H, —OCF$_3$, -halo, —(C$_1$-C$_6$) alkyl, —(C$_1$-C$_6$)haloalkyl, —(C$_1$-C$_6$)alkoxy, —N(R$_{20}$)S(O)$_2$(C$_1$-C$_6$)alkyl, -(3- to 7-membered)heterocycle, —OR$_{23}$, —SR$_{23}$, —N(R$_{20}$)(R$_{23}$), —C(O)OR$_{23}$, —C(O)R$_{23}$, —OC(O)R$_{23}$, —OC(O)NHR$_{20}$, —NHC(O)R$_{13}$, —C(O)N(R$_{13}$)$_2$, —S(O)$_2$R$_{20}$, —N(R$_{20}$)S(O)$_2$R$_{13}$, or —CH$_2$OR$_7$;

each $R_7$ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, —($C_1$-$C_6$)haloalkyl, —($C_1$-$C_6$)hydroxyalkyl, —($C_1$-$C_6$)alkoxy($C_2$-$C_6$)alkyl, —($C_1$-$C_6$)alkyl-N($R_{20}$)$_2$, or —C(O)N($R_{20}$)$_2$;

each $R_8$ and $R_9$ is independently:
(a) —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, or -phenyl, each of which is optionally substituted with 1 or 2 —OH groups; or
(b) —H, —CH$_2$C(halo)$_3$, —C(halo)$_3$, —CH(halo)$_2$, —CH$_2$(halo), —OC(halo)$_3$, —OCH(halo)$_2$, —OCH$_2$(halo), —SC(halo)$_3$, —SCH(halo)$_2$, —SCH$_2$(halo), —CN, —O—CN, —OH, -halo, —N$_3$, —NO$_2$, —CH=NR$_7$, —N(R$_7$)$_2$, —NR$_7$OH, —OR$_7$, —C(O)R$_7$, —C(O)OR$_7$, —OC(O)R$_7$, —OC(O)OR$_7$, —SR$_7$, —S(O)R$_7$, or —S(O)$_2$R$_7$;

$R_{10}$ is —H, —($C_1$-$C_4$)alkyl, or —($C_3$-$C_7$)cycloalkyl;

each $R_{11}$ is independently —CN, —OH, —($C_1$-$C_6$)alkyl, —($C_2$-$C_6$)alkenyl, -halo, —C(halo)$_3$, —CH(halo)$_2$, —CH$_2$(halo), —OC(halo)$_3$, —N$_3$, —NO$_2$, —N(R$_7$)$_2$, —CH=NR$_7$, —NR$_7$OOH, —OR$_7$, —C(O)R$_7$, —C(O)OR$_7$, —OC(O)R$_7$, or —OC(O)OR$_7$;

each $R_{13}$ is independently —H, —($C_1$-$C_4$)alkyl, —($C_2$-$C_4$)alkenyl, —($C_2$-$C_4$)alkynyl, -(3- to 7-membered)heterocycle, or -phenyl;

each $R_{14}$ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, —($C_1$-$C_6$)alkoxy, —($C_1$-$C_6$)alkoxy-($C_1$-$C_6$)alkyl, -phenyl, —C(halo)$_3$, —CH(halo)$_2$, —CH$_2$(halo), -(3- to 7-membered)heterocycle, —($C_1$-$C_6$)haloalkyl, —($C_1$-$C_6$)alkoxy($C_2$-$C_6$)alkyl, —($C_1$-$C_6$)alkoxy($C_3$-$C_8$)cycloalkyl, —CN, —OH, -halo, —OC(halo)$_3$, —N$_3$, —NO$_2$, —CH=NR$_7$, —N(R$_7$)$_2$, —NR$_7$OOH, —OR$_7$, —SR$_7$, —O(CH$_2$)$_b$OR$_7$, —O(CH$_2$)$_b$SR$_7$, —O(CH$_2$)$_b$N(R$_7$)$_2$, —N(R$_7$)(CH$_2$)$_b$OR$_7$, —N(R$_7$)(CH$_2$)$_b$SR$_7$, —N(R$_7$)(CH$_2$)$_b$N(R$_7$)$_2$, —N(R$_7$)C(O)R$_7$, —C(O)R$_7$, —C(O)OR$_7$, —OC(O)R$_7$, —OC(O)OR$_7$, —S(O)R$_7$, —S(O)$_2$R$_7$, —S(O)$_2$N(R$_7$)$_2$, —S(O)$_2$C(halo)$_3$, —S(O)$_2$(3- to 7-membered)heterocycle, —C(O)N(R$_7$)$_2$, —($C_1$-$C_6$)alkyl-C=NOR$_7$, —($C_1$-$C_6$)alkyl-C(O)—N(R$_7$)$_2$, —($C_1$-$C_6$)alkyl-NHS(O)$_2$N(R$_7$)$_2$, or —($C_1$-$C_6$)alkyl-C(=NH)—N(R$_7$)$_2$;

each $R_{20}$ is independently —H, —($C_1$-$C_6$)alkyl, or —($C_3$-$C_8$)cycloalkyl;

each $R_{21}$ is independently —H, —($C_1$-$C_6$)alkyl,

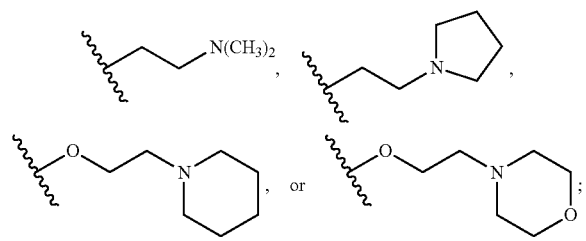

$R_{22}$ is —H, —($C_1$-$C_6$)alkyl, or —($C_3$-$C_8$)cycloalkyl;
each $R_{23}$ is independently —($C_1$-$C_6$)alkyl or —($C_3$-$C_8$)cycloalkyl;
each -halo is independently —F, —Cl, —Br, or —I;
each b is independently the integer 1 or 2;
d is the integer 1, 2, 3, 4, or 5;
m is the integer 0, 1, or 2;
n is the integer 1, 2, or 3;
p is the integer 1 or 2;
q is the integer 0, 1, 2, 3, or 4;
r is the integer 0, 1, 2, 3, 4, 5, or 6;
s is the integer 0, 1, 2, 3, 4, or 5;
t is the integer 0, 1, 2, or 3; and
u is the integer 0, 1, 2, 3, or 4.

(2) The compound of the above (1), wherein X is O or S and $R_{22}$ is —H.

(3) The compound of the above (1) or (2), wherein $R_1$ is -halo, —($C_1$-$C_4$)alkyl, or —C(halo)$_3$.

(4) The compound of any one of the above (1) to (3), wherein $R_1$ is —Cl, —F, —CF$_3$, or —CH$_3$.

(5) The compound of any one of the above (1) to (4), wherein Ar$_2$ is:

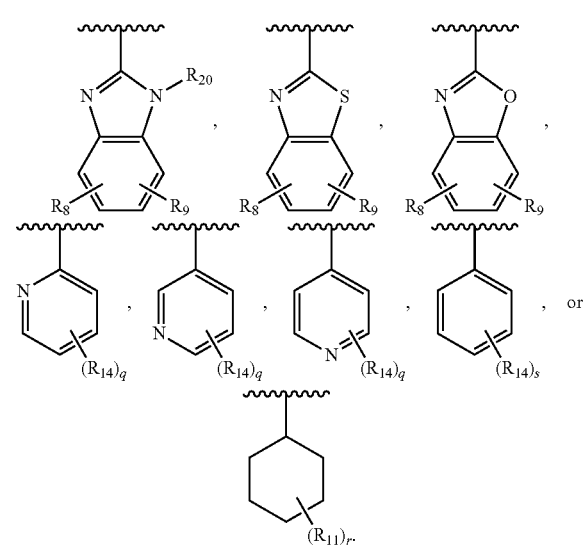

(6) The compound of any one of the above (1) to (5), wherein m is 0.

(7) The compound of any one of the above (1) to (5), wherein each $R_3$ is independently —H, —OCF$_3$, -halo, —($C_1$-$C_6$)alkyl, —($C_1$-$C_6$)haloalkyl, —OR$_{23}$, —SR$_{23}$, or —N(R$_{20}$)(R$_{23}$).

(8) The compound of any one of the above (1) to (5) or (7), wherein m is 1.

(9) The compound of any one of the above (1) to (5), (7), or (8), wherein $R_3$ is —H, —($C_1$-$C_3$)alkyl, —C(halo)$_3$, —CH(halo)$_2$, or —CH$_2$(halo).

(10) The compound of any one of the above (1) to (5) or (7) to (9), wherein $R_3$ is —H, —CH$_3$, or —CF$_3$.

(11) The compound of any one of the above (1) to (10), wherein d, n, or p is 1.

(12) The compound of any one of the above (1) to (11), wherein Ar$_1$ is:

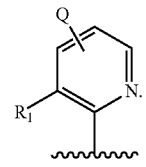

(13) The compound of any one of the above (1) to (12), wherein Ar$_1$ is:

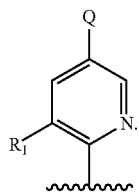

(14) The compound of any one of the above (1) to (13), wherein X is O.

(15) The compound of any one of the above (1) to (14), wherein L₁ and L₂ are each C(R₃).

(16) The compound of any one of the above (1) to (15), wherein the R₃ of each L₁ and L₂C(R₃) group is independently H, CH₃, or CF₃.

(17) The compound of any one of the above (1) to (16), wherein the R₃ of each L₁ and L₂C(R₃) group is H.

(18) The compound of the above (17), wherein m is 0.

(19) The compound of any one of the above (1) to (18), wherein Q is:

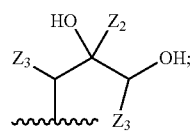

Z₂ is —H or —(C₁-C₃)alkyl; and
each Z₃ is independently —H or —(C₁-C₃)alkyl.

(20) The compound of any one of the above (1) to (19), wherein Q is:

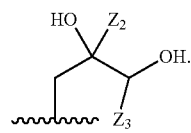

(21) The compound of any one of the above (1) to (20), wherein Z₂ is —H and Z₃ is —H.

(22) The compound of any one of the above (1) to (20), wherein Z₂ is —H and Z₃ is —CH₃.

(23) The compound of any one of the above (1) to (22), wherein Ar₂ is:

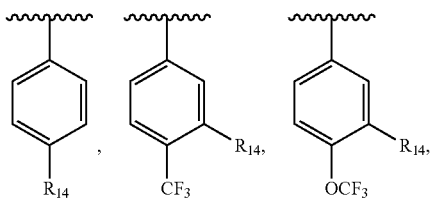

-continued

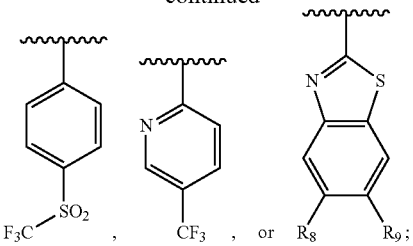

R₁₄ is —H, —Cl, —F, —Br, —OCF₃, —(C₁-C₆)alkyl, —C(halo)₃, —S(O)₂CF₃, —S(O)₂(C₁-C₆)alkyl, —OCH₃, —OCH₂CH₃, or —OCH(CH₃)₂; and each R₈ and R₉ is independently —H, —Cl, —Br, —F, —CH₃, —OCH₃, —OCH₂CH₃, —CF₃, —OCF₃, -iso-propyl, -tert-butyl, —S(O)₂CF₃, —S(O)₂CH₃, or —S(O)₂CH₂CH₃.

(24) The compound of any one of the above (1) to (23), wherein R₁₄ is —CF₃, —OCF₃, —Cl, or —F.

(25) The compound of any one of the above (1) to (22), wherein Ar₂ is:

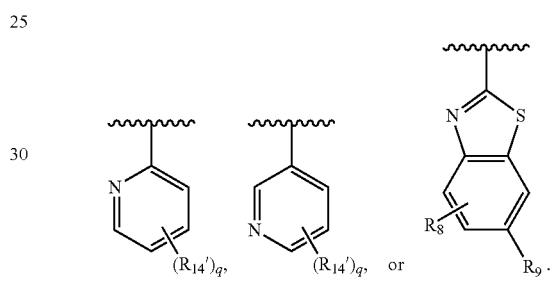

(26) The compound of any one of the above (1) to (25), wherein Ar₂ is:

(27) The compound of any one of the above (1), (2), (11), (13), (14), (17), or (25) which is a compound of formula (III):

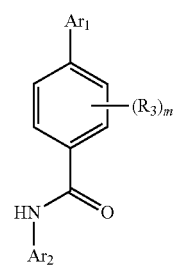

(III)

or a pharmaceutically acceptable salt thereof, wherein Ar$_1$ is:

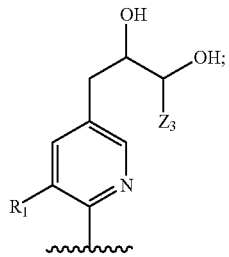

Ar$_2$ is:

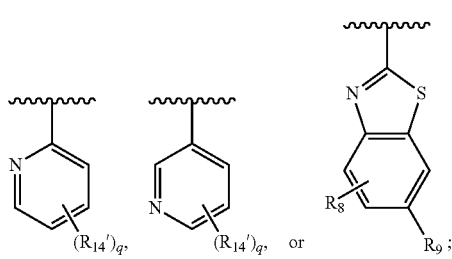

Z$_3$ is —H or —(C$_1$-C$_3$)alkyl;

R$_1$ is -halo, —(C$_1$-C$_4$)alkyl, —OCH$_3$, —C(halo)$_3$, —CH(halo)$_2$, —CH$_2$(halo), —OC(halo)$_3$, —OCH(halo)$_2$, or —OCH$_2$(halo);

each R$_3$ is independently —H, —OCF$_3$, -halo, —(C$_1$-C$_3$)alkyl, —(C$_1$-C$_3$)haloalkyl, —(C$_1$-C$_6$)alkoxy, —N(R$_{20}$)S(O)$_2$(C$_1$-C$_3$)alkyl, —OR$_{23}$, —N(R$_{20}$)(R$_{23}$), —NHC(O)R$_{13}$, —C(O)N(R$_{13}$)$_2$, —S(O)$_2$R$_{20}$, —N(R$_{20}$)S(O)$_2$R$_{13}$, or —CH$_2$OR$_7$;

each R$_7$ is independently —H, —(C$_1$-C$_3$)alkyl, —(C$_2$-C$_4$)alkenyl, —(C$_2$-C$_4$)alkynyl, —(C$_3$-C$_8$)cycloalkyl, —(C$_5$-C$_8$)cycloalkenyl, -phenyl, —(C$_1$-C$_3$)haloalkyl, —(C$_1$-C$_6$)hydroxyalkyl, —(C$_1$-C$_6$)alkoxy(C$_2$-C$_6$)alkyl, —(C$_1$-C$_3$)alkyl-N(R$_{20}$)$_2$, or —C(O)N(R$_{20}$)$_2$;

each R$_8$ and R$_9$ is independently —H, —Cl, —Br, —F, —CH$_3$, —OCH$_3$, —OCH$_2$CH$_3$, —CF$_3$, —OCF$_3$, -iso-propyl, -tert-butyl, —S(O)$_2$CF$_3$, —S(O)$_2$CH$_3$, or —S(O)$_2$CH$_2$CH$_3$;

each R$_{13}$ is independently —H, —(C$_1$-C$_4$)alkyl, —(C$_2$-C$_4$)alkenyl, —(C$_2$-C$_4$)alkynyl, -(3- to 7-membered)heterocycle, or -phenyl;

each R$_{14}$' is independently —H, —Cl, —F, —Br, —CF$_3$, —OCF$_3$, —(C$_1$-C$_6$)alkyl, —S(O)$_2$CF$_3$, —S(O)$_2$(C$_1$-C$_6$)alkyl, —OCH$_3$, —OCH$_2$CH$_3$, or —OCH(CH$_3$)$_2$;

each R$_{20}$ is independently —H, —(C$_1$-C$_6$)alkyl, or —(C$_3$-C$_8$)cycloalkyl;

each R$_{23}$ is independently —(C$_1$-C$_6$)alkyl or —(C$_3$-C$_8$)cycloalkyl;

each -halo is independently —F, —Cl, —Br, or —I;

m is the integer 0, 1, or 2; and q is the integer 0, 1, or 2.

(28) The compound of any one of the above (1), (2), (6), (11), (13), (14), (17), (25), or (27), wherein m is 0.

(29) The compound of any one of the above (1), (2), (8), (11), (13), (14), (17), (25), or (27), wherein m is 1 and R$_3$ is —H, —OCF$_3$, -halo, —(C$_1$-C$_3$)alkyl, or —(C$_1$-C$_3$)haloalkyl.

(30) The compound of any one of the above (1), (2), (10), (11), (13), (14), (17), (25), (27), or (29), wherein R$_3$ is —H, —CH$_3$, or —CF$_3$.

(31) The compound of any one of the above (1), (2), (11), (13), (14), (17), or (25) to (30), wherein Ar$_2$ is:

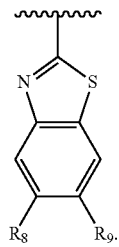

(32) The compound of any one of the above (1), (2), (11), (13), (14), (17), (21), or (25) to (31), wherein Z$_3$ is —H.

(33) The compound of any one of the above (1), (2), (11), (13), (14), (17), (22), or (25) to (31), wherein Z$_3$ is —CH$_3$.

(34) The compound of any one of the above (1) to (33), which is a free base.

(35) A pharmaceutically acceptable salt of the compound of any one of the above (1) to (33), wherein the pharmaceutically acceptable salt is a hydrochloride-salt, a sodium-salt, a potassium-salt, or a para-toluenesulfonic acid-salt.

(36) The compound or a pharmaceutically acceptable salt thereof of any one of the above (1) to (35), which comprises the Q group

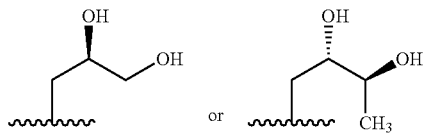

and has an enantiomeric excess of at least about 60%.

(37) The compound or a pharmaceutically acceptable salt thereof of any one of the above (1) to (36), which is radiolabeled.

(38) A composition comprising a compound of any one of the above (1) to (37) or a pharmaceutically acceptable salt thereof and a pharmaceutically acceptable carrier or excipient.

(39) A method for preparing a composition comprising admixing a compound of any one of the above (1) to (37) or a pharmaceutically acceptable salt thereof with a pharmaceutically acceptable carrier or excipient.

(40) A method for treating pain, UI, an ulcer, IBD, or IBS in an animal, comprising administering to an animal in need thereof, an effective amount of the compound of any one of the above (1) to (37) or a pharmaceutically acceptable salt thereof.

(41) A method of inhibiting TRPV1 function in a cell comprising contacting a cell capable of expressing TRPV1 with an effective amount of a compound of any one of the above (1) to (37) or a pharmaceutically acceptable salt thereof.

(42) A compound or composition of any one of the above (1) to (38) for use in the treatment of pain, UI, an ulcer, IBD, or IBS in an animal.

4.1 Compounds of Formula (I)

As stated above, the disclosure encompasses Compounds of Formula (I):

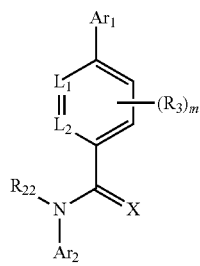
(I)

or a pharmaceutically acceptable derivative thereof, where $Ar_1$, $Ar_2$, $L_1$, $L_2$, X, $R_3$, $R_{22}$, and m are as defined above for Compounds of Formula (I).

Compounds of Formula (I) are potent at TRPV1 receptors.

Certain embodiments of formula (I) are presented below.

In one embodiment, a Compound of Formula (I) is a free base.

In another embodiment, a Compound of Formula (I) is a pharmaceutically acceptable derivative of a Compound of Formula (I). In another embodiment, the pharmaceutically acceptable derivative of a Compound of Formula (I) is a pharmaceutically acceptable salt.

In another embodiment, $L_1$ is N and $L_2$ is $C(R_3)$.
In another embodiment, $L_1$ is N and $L_2$ is C(H).
In another embodiment, $L_1$ is $C(R_3)$ and $L_2$ is N.
In another embodiment, $L_1$ is C(H) and $L_2$ is N.
In another embodiment, $L_1$ is $C(R_3)$ and $L_2$ is $C(R_3)$.
In another embodiment, $L_1$ is C(H) and $L_2$ is $C(R_3)$.
In another embodiment, $L_1$ is $C(R_3)$ and $L_2$ is C(H).
In another embodiment, $L_1$ is C(H) and $L_2$ is C(H).
In another embodiment, d, n, or p is 1.
In another embodiment, d, n, or p is 2.
In another embodiment, d or n is 3.
In another embodiment, u is 0, 1, or 2.
In another embodiment, u is 1 or 2.
In another embodiment, u is 2.
In another embodiment, u is 1.
In another embodiment, u is 0.
In another embodiment, $Ar_1$ is:

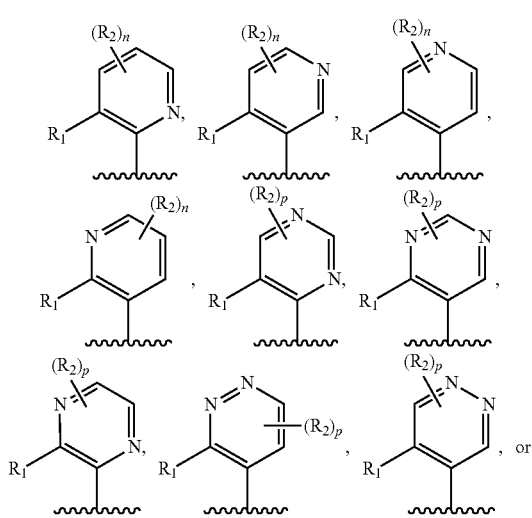

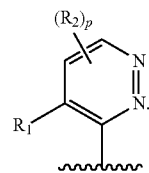

In another embodiment, $Ar_1$ is a pyridyl group.
In another embodiment, $Ar_1$ is:

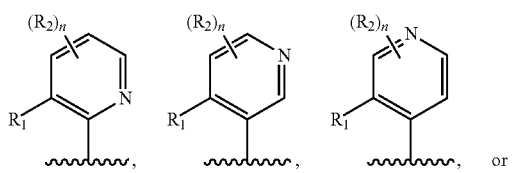

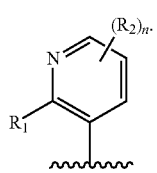

In another embodiment, $Ar_1$ is:

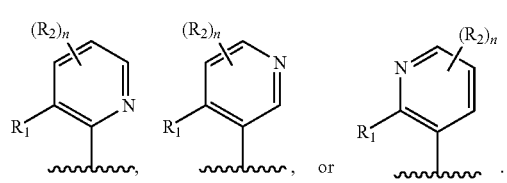

In another embodiment, $Ar_1$ is a pyrimidinyl group.
In another embodiment, $Ar_1$ is:

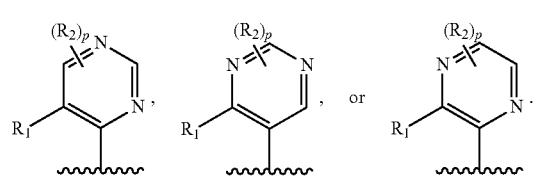

In another embodiment, $Ar_1$ is:

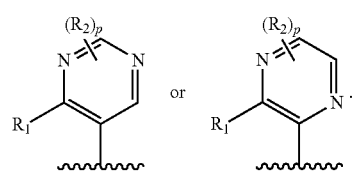

In another embodiment, $Ar_1$ is pyridazinyl group.

In another embodiment, $Ar_1$ is:

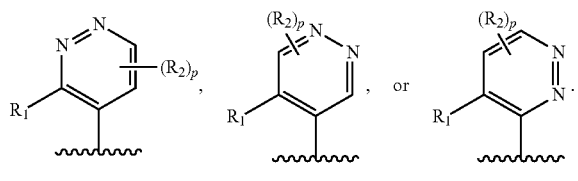

In another embodiment, $Ar_1$ is:

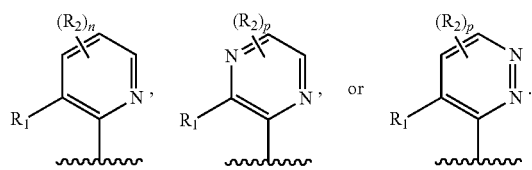

In another embodiment, $Ar_1$ is:

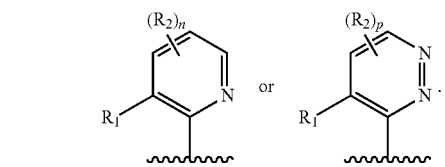

In another embodiment, $Ar_1$ is:

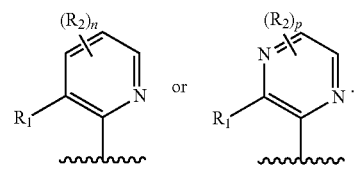

In another embodiment, $Ar_1$ is:

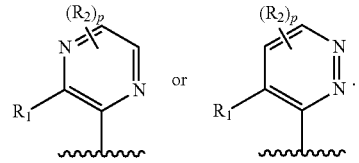

In another embodiment, $Ar_1$ is:

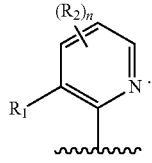

In another embodiment, $Ar_1$ is a pyrazinyl group.

In another embodiment, $Ar_1$ is:

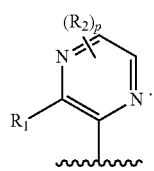

In another embodiment, $Ar_1$ is:

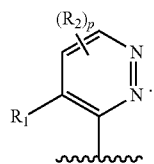

In another embodiment, $Ar_1$ is a pyridyl group and n is 1.
In another embodiment, the $Ar_1$ pyridyl group is

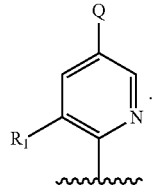

In another embodiment, $Ar_1$ is a pyrazinyl group and p is 1.
In another embodiment, the $Ar_1$ pyrazinyl group is

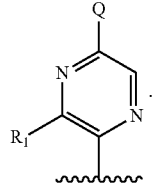

In another embodiment, $Ar_1$ is a pyrimidinyl group and p is 1.

In another embodiment, the $Ar_1$ pyrimidinyl group is

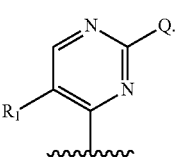

In another embodiment, $Ar_1$ is a pyridazinyl group and p is 1.

In another embodiment, the $Ar_1$ pyridazinyl group is

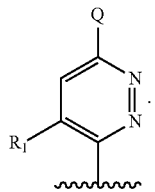

In another embodiment, $R_1$ is -halo, —$(C_1$-$C_4)$alkyl, —$OCH_3$, —$C(halo)_3$, —$CH(halo)_2$, —$CH_2(halo)$, or —$OC(halo)_3$.
In another embodiment, $R_1$ is -halo, —$(C_1$-$C_4)$alkyl, —$OCH_3$, —$C(halo)_3$, —$CH(halo)_2$, or —$CH_2(halo)$.
In another embodiment, $R_1$ is -halo, —$(C_1$-$C_4)$alkyl, —$C(halo)_3$, —$CH(halo)_2$, or —$CH_2(halo)$.
In another embodiment, $R_1$ is -halo, —$(C_1$-$C_4)$alkyl, —$C(halo)_3$, or —$CH(halo)_2$.
In another embodiment, $R_1$ is -halo, —$(C_1$-$C_4)$alkyl, or —$C(halo)_3$.
In another embodiment, $R_1$ is -halo.
In another embodiment, $R_1$ is —$(C_1$-$C_4)$alkyl.
In another embodiment, $R_1$ is —$OCH_3$.
In another embodiment, $R_1$ is —$C(halo)_3$.
In another embodiment, $R_1$ is —$CH(halo)_2$.
In another embodiment, $R_1$ is —$CH_2(halo)$.
In another embodiment, $R_1$ is —$OC(halo)_3$.
In another embodiment, $R_1$ is —$OCH(halo)_2$.
In another embodiment, $R_1$ is —$OCH_2(halo)$.
In another embodiment, $R_1$ is —Cl, —F, —$(C_1$-$C_4)$alkyl, or —$C(halo)_3$.
In another embodiment, $R_1$ is —Cl, —F, —$(C_1$-$C_4)$alkyl, —$OCF_3$, or —$CF_3$.
In another embodiment, $R_1$ is —Cl, —F, —$CH_3$, —$OCF_3$, or —$CF_3$.
In another embodiment, $R_1$ is —Cl, —F, —$CH_3$, or —$CF_3$.
In another embodiment, $R_1$ is —Cl, —F, or —$CF_3$.
In another embodiment, $R_1$ is —Cl or —F.
In another embodiment, $R_1$ is —Cl.
In another embodiment, $R_1$ is —F.
In another embodiment, $R_1$ is —$CH_3$.
In another embodiment, $R_1$ is —$OCF_3$.
In another embodiment, $R_1$ is —$CF_3$.
In another embodiment, $R_1$ is —$NO_2$, —CN, —OH, or —$NH_2$.
In another embodiment, $R_1$ is —$NO_2$.
In another embodiment, $R_1$ is —CN.
In another embodiment, $R_1$ is —OH.
In another embodiment, $R_1$ is —$NH_2$.
In another embodiment, X is O, S, or N—$OR_{10}$.
In another embodiment, X is O or S.
In another embodiment, X is O or N—$OR_{10}$.
In another embodiment, X is S or N—$OR_{10}$.
In another embodiment, $R_{10}$ is —$(C_1$-$C_4)$alkyl or —$(C_3$-$C_7)$cycloalkyl.
In another embodiment, $R_{10}$ is —H or —$(C_3$-$C_7)$cycloalkyl.
In another embodiment, $R_{10}$ is —H or —$(C_1$-$C_4)$alkyl.
In another embodiment, $R_{10}$ is —H, —$CH_3$, —$CH_2CH_3$, or -cyclohexyl.
In another embodiment, $R_{10}$ is —H, —$CH_3$, or —$CH_2CH_3$.
In another embodiment, $R_{10}$ is —H or —$CH_3$.
In another embodiment, $R_{10}$ is —H.

In another embodiment, X is O, S, N—OH, N—$OCH_3$, or N—$OCH_2CH_3$.
In another embodiment, X is O, S, N—OH, or N—$OCH_3$.
In another embodiment, X is O, S, or N—OH.
In another embodiment, X is O, S, or N—$OCH_3$.
In another embodiment, X is O, S, or N—$OCH_2CH_3$.
In another embodiment, X is O, S, N—OH, N—$OCH_3$, or N—$OCH_2CH_3$.
In another embodiment, X is O, S, N—OH, or N—$OCH_3$.
In another embodiment, X is O, S, or N—OH.
In another embodiment, X is O, S, or N—$OCH_3$.
In another embodiment, X is O, S, or N—$OCH_2CH_3$.
In another embodiment, X is O or S.
In another embodiment, X is O or N—$OR_{10}$.
In another embodiment, X is O or N—OH.
In another embodiment, X is O or N—$OCH_3$.
In another embodiment, X is O or N—$OCH_2CH_3$.
In another embodiment, X is S or N—$OR_{10}$.
In another embodiment, X is S or N—OH.
In another embodiment, X is S or N—$OCH_3$.
In another embodiment, X is S or N—$OCH_2CH_3$.
In another embodiment, X is O.
In another embodiment, X is S.
In another embodiment, X is N—$OR_{10}$.
In another embodiment, X is N—OH.
In another embodiment, X is N—$OCH_3$.
In another embodiment, X is N—$OCH_2CH_3$.
In another embodiment, $R_{22}$ is —H or —$(C_1$-$C_6)$alkyl.
In another embodiment, $R_{22}$ is —H or —$(C_1$-$C_3)$alkyl.
In another embodiment, $R_{22}$ is —H or —$CH_3$.
In another embodiment, $R_{22}$ is —$CH_3$.
In another embodiment, $R_{22}$ is —H.
In another embodiment, each $R_{20}$ is independently —H or —$(C_1$-$C_6)$alkyl.
In another embodiment, each $R_{20}$ is independently —H or —$(C_3$-$C_8)$cycloalkyl.
In another embodiment, each $R_{20}$ is independently —$(C_1$-$C_6)$alkyl or —$(C_3$-$C_8)$cycloalkyl.
In another embodiment, each $R_{20}$ is —$(C_3$-$C_8)$cycloalkyl.
In another embodiment, each $R_{20}$ is -cyclohexyl.
In another embodiment, each $R_{20}$ is —H.
In another embodiment, each $R_{20}$ is —$(C_1$-$C_6)$alkyl.
In another embodiment, each $R_{20}$ is independently —H or —$CH_3$.
In another embodiment, each $R_{21}$ is —$(C_1$-$C_6)$alkyl.
In another embodiment, each $R_{21}$ is —H.
In another embodiment, each $R_{21}$ is independently —H or —$CH_3$.
In another embodiment, each $R_{21}$ is —$CH_3$.
In another embodiment, each $R_{13}$ is independently —H, —$(C_1$-$C_4)$alkyl, -(3- to 7-membered)heterocycle, or -phenyl.
In another embodiment, each $R_{13}$ is independently —H, —$(C_1$-$C_4)$alkyl, or -(3- to 7-membered)heterocycle.
In another embodiment, each $R_{13}$ is independently —H, —$(C_1$-$C_4)$alkyl, or -phenyl.
In another embodiment, each $R_{13}$ is independently —H or —$(C_1$-$C_4)$alkyl.
In another embodiment, each $R_{13}$ is independently —H or —$(C_1$-$C_3)$alkyl.
In another embodiment, each $R_{13}$ is independently —H or —$CH_3$.
In another embodiment, each $R_{13}$ is —H.
In another embodiment, each $R_{13}$ is —$CH_3$.
In another embodiment, r, s, q, or t is 0.
In another embodiment, r, s, q, or t is 1.
In another embodiment, r, s, q, or t is 2.

In another embodiment, $R_{12a}$ and $R_{12b}$ are each independently —H or —($C_1$-$C_3$)alkyl.

In another embodiment, $R_{12a}$ and $R_{12b}$ are each independently —H, —$CH_3$, or —$CH_2CH_3$.

In another embodiment, $R_{12a}$ and $R_{12b}$ are each independently —H or —$CH_3$.

In another embodiment, $R_{12a}$ and $R_{12b}$ are each —H.

In another embodiment, $R_{12a}$ and $R_{12b}$ are each —$CH_3$.

In another embodiment, c is 0 or 1.

In another embodiment, c is 0.

In another embodiment, c is 1.

In another embodiment, c is 1, $Y_1$ is O and $Y_2$ and $Y_3$ are $CH_2$.

In another embodiment, c is 1, $Y_2$ is O and $Y_1$ and $Y_3$ are $CH_2$.

In another embodiment, c is 1, $Y_1$ is N($R_{21}$) and $Y_2$ and $Y_3$ are $CH_2$.

In another embodiment, c is 1, $Y_2$ is N($R_{21}$) and $Y_1$ and $Y_3$ are $CH_2$.

In another embodiment, $Ar_2$ is

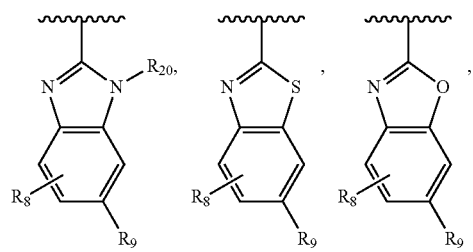

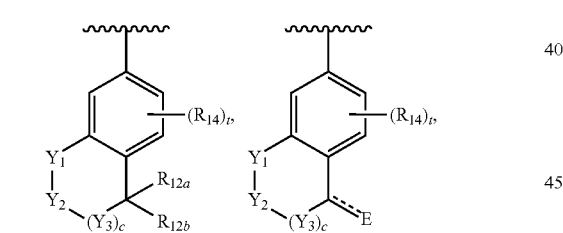

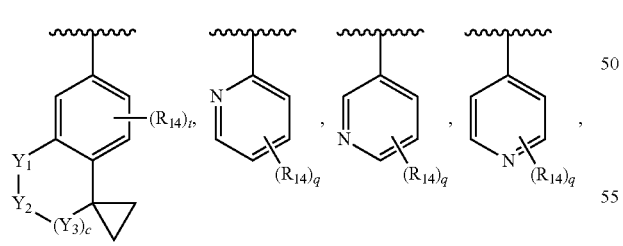

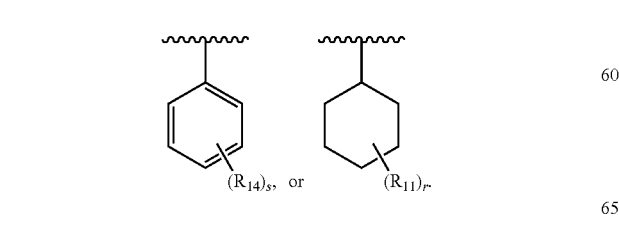

In another embodiment, $Ar_2$ is a benzoimidazolyl group.

In another embodiment, $Ar_2$ is:

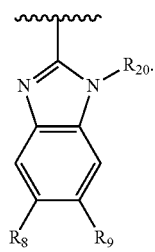

In another embodiment, $Ar_2$ is:

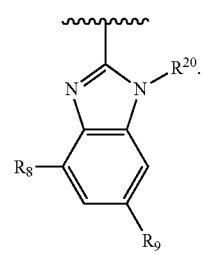

In another embodiment, $Ar_2$ is:

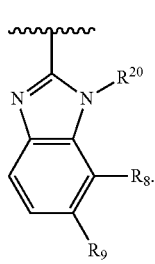

In another embodiment, $Ar_2$ is:

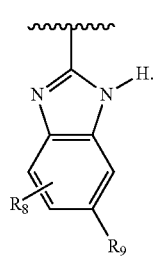

In another embodiment, $Ar_2$ is:

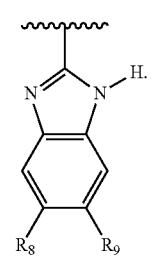

In another embodiment, Ar$_2$ is:

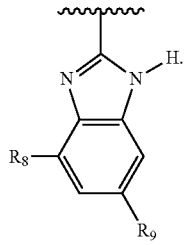

In another embodiment, Ar$_2$ is:

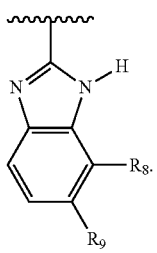

In another embodiment, Ar$_2$ is:

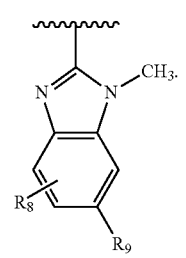

In another embodiment, Ar$_2$ is:

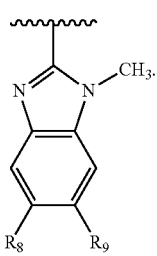

In another embodiment, Ar$_2$ is:

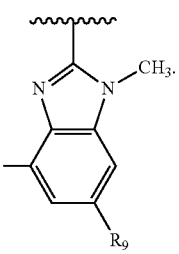

In another embodiment, Ar$_2$ is:

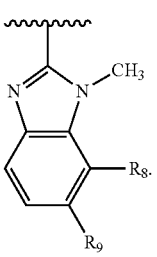

In another embodiment, Ar$_2$ is a benzothiazolyl group.
In another embodiment, Ar$_2$ is:

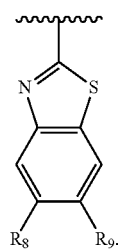

In another embodiment, Ar$_2$ is:

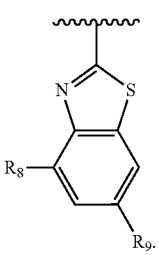

In another embodiment, Ar$_2$ is:

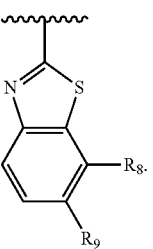

In another embodiment, Ar$_2$ is a benzooxazolyl group.

In another embodiment, Ar₂ is:

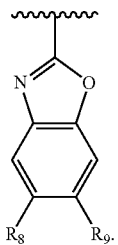

In another embodiment, Ar₂ is:

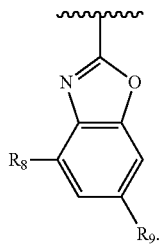

In another embodiment, Ar₂ is:

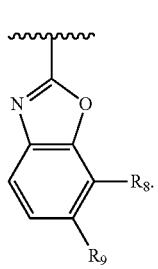

In another embodiment, R₈ and R₉ are independently —H, —(C₁-C₆)alkyl, —(C₃-C₈)cycloalkyl, -phenyl, —CH₂C(halo)₃, —C(halo)₃, —CH(halo)₂, —CH₂(halo), —OC(halo)₃, —OCH(halo)₂, —OCH₂(halo), -halo, —N(R₇)₂, —NR₇OH, —OR₇, —C(O)OR₇, or —S(O)₂R₇.

In another embodiment, R₈ and R₉ are independently —H, —(C₁-C₆)alkyl, —C(halo)₃, —CH(halo)₂, —CH₂(halo), —OC(halo)₃, —OCH(halo)₂, —OCH₂(halo), -halo, —N(R₇)₂, —OR₇, —C(O)OR₇, or —S(O)₂R₇.

In another embodiment, R₈ and R₉ are independently —H, —Cl, —Br, —F, —CH₃, —OCH₃, —OCH₂CH₃, —CF₃, —OCF₃, -iso-propyl, or -tert-butyl.

In another embodiment, R₈ and R₉ are independently —H, —Cl, —F, —CH₃, —OCH₃, —OCH₂CH₃, —CF₃, —OCF₃, or -tert-butyl.

In another embodiment, Ar₂ is:

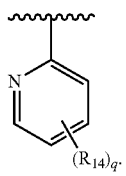

In another embodiment, Ar₂ is:

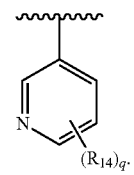

In another embodiment, Ar₂ is:

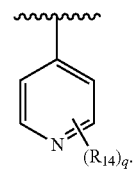

In another embodiment, Ar₂ is:

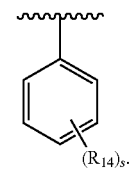

In another embodiment, each R₁₄ is independently —(C₁-C₆)alkyl, —(C₂-C₆)alkenyl, —(C₃-C₈)cycloalkyl, —(C₁-C₆)alkoxy, -phenyl, —C(halo)₃, —CH(halo)₂, —CH₂(halo), -(3- to 7-membered)heterocycle, —(C₁-C₆)haloalkyl, -halo, —OC(halo)₃, —N(R₇)₂, —NR₇OH, —OR₇, —SR₇, —N(R₇)C(O)R₇, —C(O)OR₇, —S(O)R₇, —S(O)₂R₇, —S(O)₂N(R₇)₂, —S(O)₂C(halo)₃, —C(O)N(R₇)₂, or —(C₁-C₆)alkyl-NHS(O)₂N(R₇)₂.

In another embodiment, each R₁₄ is independently —(C₁-C₆)alkyl, —(C₃-C₈)cycloalkyl, —(C₁-C₆)alkoxy, -phenyl, —C(halo)₃, —CH(halo)₂, —CH₂(halo), -(3- to 7-membered)heterocycle, —(C₁-C₆)haloalkyl, -halo, —OC(halo)₃, —N(R₇)₂, —OR₇, —N(R₇)C(O)R₇, —C(O)OR₇, —S(O)R₇, —S(O)₂R₇, —S(O)₂N(R₇)₂, —S(O)₂C(halo)₃, or —C(O)N(R₇)₂.

In another embodiment, each R₁₄ is independently —Cl, —F, —Br, —(C₁-C₆)alkyl, —S(O)₂CF₃, —S(O)₂(C₁-C₆)alkyl, —OCH₃, —OCH₂CH₃, —OCH(CH₃)₂, —CF₃, or —OCF₃.

In another embodiment, each R₁₄ is independently —Cl, —F, —CH₃, —S(O)₂CF₃, —S(O)₂CH₃, —OCH₃, —OCH₂CH₃, —OCH(CH₃)₂, —CF₃, or —OCF₃.

In another embodiment, each R₁₄ is independently —Cl, —F, —CH₃, —CH₂CH₃, —OCH₃, —OCH(CH₃)₂, —OCH₂CH₃, —CF₃ or —OCF₃.

In another embodiment, each R₁₄ is independently —Cl, —F, —CF₃, or —OCF₃.

In another embodiment, Ar₂ is:

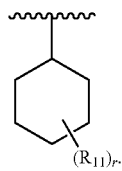

In another embodiment, each $R_{11}$ is independently —CN, —OH, —($C_1$-$C_6$)alkyl, —($C_2$-$C_6$)alkenyl, -halo, —C(halo)₃, —CH(halo)₂, —CH₂(halo), —OC(halo)₃, —NO₂, —N($R_7$)₂, —NR₇OH, —OR₇, or —C(O)OR₇.

In another embodiment, each $R_{11}$ is independently —($C_1$-$C_6$)alkyl, -halo, —C(halo)₃, —CH(halo)₂, —CH₂(halo), —OC(halo)₃, —N($R_7$)₂, —NR₇OH, —OR₇, or —C(O)OR₇.

In another embodiment, each $R_{11}$ is independently —($C_1$-$C_6$)alkyl, -halo, —C(halo)₃, —OC(halo)₃, —N($R_7$)₂, or —OR₇.

In another embodiment, each $R_{11}$ is —Cl, —F, —CH₃, —CH₂CH₃, —CF₃, —OCH₃, —OCH(CH₃)₂, or —OCH₂CH₃.

In another embodiment, each $R_{11}$ is —CF₃, —OCF₃, —Cl, or —F.

In another embodiment, Ar₂ is:

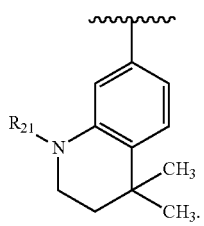

In another embodiment, Ar₂ is:

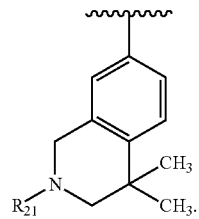

In another embodiment, Ar₂ is:

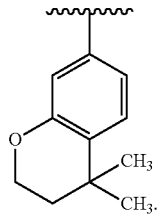 [SMILES: *c1ccc2c(c1)OCCC2(C)C]

In another embodiment, Ar₂ is:

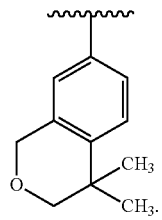

In another embodiment, each $R_3$ is independently —H, —OCF₃, -halo, —($C_1$-$C_6$)alkyl, —($C_1$-$C_6$)haloalkyl, —OR₂₃, —SR₂₃, or —N($R_{20}$)($R_{23}$).

In another embodiment, $R_{10}$ is —($C_1$-$C_4$)alkyl or —($C_3$-$C_7$)cycloalkyl.

In another embodiment, $R_{10}$ is —H or —($C_3$-$C_7$)cycloalkyl.

In another embodiment, $R_{10}$ is —H or —($C_1$-$C_4$)alkyl.

In another embodiment, $R_{10}$ is —H, —CH₃, or —CH₂CH₃.

In another embodiment, $R_{10}$ is —H or —CH₃.

In another embodiment, $R_{10}$ is —H.

In another embodiment, each $R_3$ is independently —H, —CH₃, —OCH₃, —NH(CH₃), —CF₃, or —OCF₃.

In another embodiment, each $R_3$ is independently —H, —($C_1$-$C_6$)alkyl, or —($C_1$-$C_6$)haloalkyl.

In another embodiment, each $R_3$ is independently —H, —CH₃, or —CF₃

In another embodiment, m is 2.

In another embodiment, m is 1.

In another embodiment, each $R_3$ is independently —H or —($C_1$-$C_6$)alkyl.

In another embodiment, m is 1 and each $R_3$ is independently —H, —CH₃, or —CH₂CH₃.

In another embodiment, m is 1 and each $R_3$ is independently —H or —CH₃.

In another embodiment, m is 1 and each $R_3$ is independently —H or —CF₃.

In another embodiment, each $R_3$ is —H.

In another embodiment, one $R_3$ is —CH₃.

In another embodiment, one $R_3$ is —CH₃ and another $R_3$ is —H.

In another embodiment, m is 0.

In another embodiment, each $R_7$ is independently —H, —($C_1$-$C_6$)alkyl, —($C_3$-$C_8$)cycloalkyl, or -phenyl.

In another embodiment, each $R_7$ is independently —H, —($C_1$-$C_4$)alkyl, -cyclohexyl, or -phenyl.

In another embodiment, each $R_7$ is independently —H, -cyclohexyl, or -phenyl.

In another embodiment, each $R_7$ is independently —H or —($C_1$-$C_3$)alkyl.

In another embodiment, each $R_7$ is independently —H, —CH₃, or —CH₂CH₃.

In another embodiment, each $R_7$ is independently —H or —CH₃.

In another embodiment, when d, n or p are 1, then $R_2$ must be Q.

In another embodiment, a Q group is substituted on Ar₁ at the Ar₁ position para to the point of attachment of Ar₁ to the ring comprising $L_1$ and $L_2$.

In another embodiment, J is —OR₂₀.

In another embodiment, J is —OH.

In another embodiment, $Z_1$ is —H.

In another embodiment, $Z_1$ is —OR₂₀ or —CH₂OR₂₀.

In another embodiment, $Z_1$ is —CH₂OR₂₀.

In another embodiment, $Z_1$ is —CH₂OH.

In another embodiment, $Z_1$ is —OR₂₀.

In another embodiment, $Z_1$ is —OH.
In another embodiment, $Z_1$ is —OCH$_3$.
In another embodiment, $Z_2$ is —CH$_2$OR$_{20}$.
In another embodiment, $Z_2$ is —CH$_2$OH.
In another embodiment, $Z_2$ is —H.
In another embodiment, $Z_2$ is —CH$_3$.
In another embodiment, one $Z_3$ group is —H.
In another embodiment, one $Z_3$ group is —(C$_1$-C$_6$)alkyl.
In another embodiment, one $Z_3$ group is —(C$_1$-C$_3$)alkyl.
In another embodiment, one $Z_3$ group is —CH$_3$.
In another embodiment, one $Z_3$ group is —H and one $Z_3$ group is —(C$_1$-C$_6$)alkyl.
In another embodiment, one $Z_3$ group is —H and one $Z_3$ group is —(C$_1$-C$_3$)alkyl.
In another embodiment, one $Z_3$ group is —H and one $Z_3$ group is —CH$_3$.
In another embodiment, one $Z_3$ group is —CH$_3$ and the other three $Z_3$ groups are —H.
In another embodiment, each $Z_3$ group is —H.
In another embodiment, one $Z_3$ group is —CH$_3$, the other three $Z_3$ groups are —H, and $Z_2$ is —H.
In another embodiment, one $Z_3$ group is —CH$_3$, the other three $Z_3$ groups are —H, $Z_2$ is —H, and $Z_1$ is —OR$_{20}$.
In another embodiment, one $Z_3$ group is —CH$_3$, the other three $Z_3$ groups are —H, $Z_2$ is —H, and $Z_1$ is —OH.
In another embodiment, one $Z_3$ group is —CH$_3$, the other three $Z_3$ groups are —H, $Z_2$ is —H, $Z_1$ is OR$_{20}$, and J is —OR$_{20}$.
In another embodiment, one $Z_3$ group is —CH$_3$, the other three $Z_3$ groups are —H, $Z_2$ is —H, $Z_1$ is —OH, and J is —OR$_{20}$.
In another embodiment, one $Z_3$ group is —CH$_3$, the other three $Z_3$ groups are —H, $Z_2$ is —H, $Z_1$ is —OH, and J is —OH.
In another embodiment, each $Z_3$ group is —H and $Z_2$ is —H.
In another embodiment, each $Z_3$ group is —H, $Z_2$ is —H, and $Z_1$ is —OR$_{20}$.
In another embodiment, each $Z_3$ group is —H, $Z_2$ is —H, and $Z_1$ is —OH.
In another embodiment, each $Z_3$ group is —H, $Z_2$ is —H, $Z_1$ is —OR$_{20}$, and J is —OR$_{20}$.
In another embodiment, each $Z_3$ group is —H, $Z_2$ is —H, $Z_1$ is —OH, and J is —OR$_{20}$.
In another embodiment, each $Z_3$ group is —H, $Z_2$ is —H, $Z_1$ is —OH, and J is —OH.

4.2 Compounds of Formula (II)

Preferred Compounds of Formula (I) are Compounds of Formula (II):

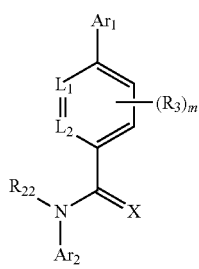

(II)

or a pharmaceutically acceptable derivative thereof, where $Ar_1$, $Ar_2$, $L_1$, $L_2$, X, $R_3$, $R_{22}$, and m are as defined above for Compounds of Formula (II).

Compounds of Formula (II) are potent at TRPV1 receptors.
Certain embodiments of formula (II) are presented below.
In one embodiment, a Compound of Formula (II) is a free base.
In another embodiment, a Compound of Formula (II) is a pharmaceutically acceptable derivative of a Compound of Formula (II). In another embodiment, the pharmaceutically acceptable derivative of a Compound of Formula (II) is a pharmaceutically acceptable salt.
In another embodiment, $L_1$ is N and $L_2$ is C($R_3$).
In another embodiment, $L_1$ is N and $L_2$ is C(H).
In another embodiment, $L_1$ is C($R_3$) and $L_2$ is N.
In another embodiment, $L_1$ is C(H) and $L_2$ is N.
In another embodiment, $L_1$ is C($R_3$) and $L_2$ is C($R_3$).
In another embodiment, $L_1$ is C(H) and $L_2$ is C($R_3$).
In another embodiment, $L_1$ is C($R_3$) and $L_2$ is C(H).
In another embodiment, $L_1$ is C(H) and $L_2$ is C(H).
In another embodiment, n or p is 1.
In another embodiment, n or p is 2.
In another embodiment, n is 3.
In another embodiment $Ar_1$ is:

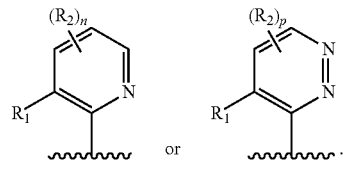

In another embodiment, $Ar_1$ is:

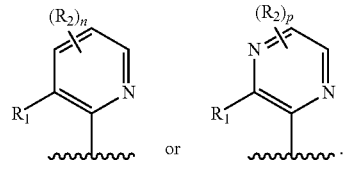

In another embodiment, $Ar_1$ is:

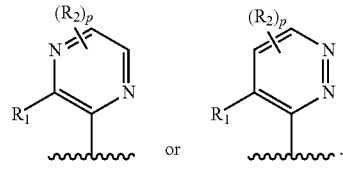

In another embodiment, $Ar_1$ is:

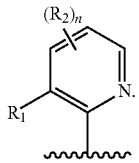

In another embodiment, Ar₁ is:

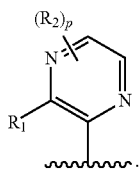

In another embodiment, Ar₁ is:

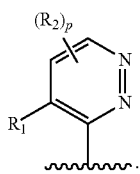

In another embodiment, n or p is 1.
In another embodiment, Ar₁ is:

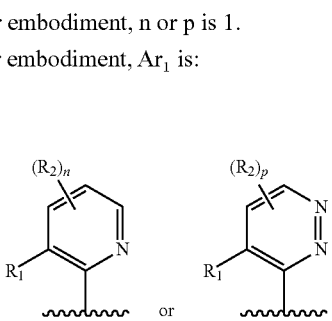

and n or p is 1.
In another embodiment, Ar₁ is:

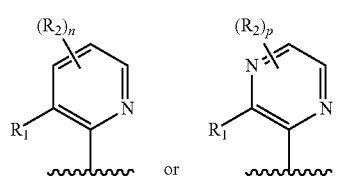

and n or p is 1.
In another embodiment, Ar₁ is:

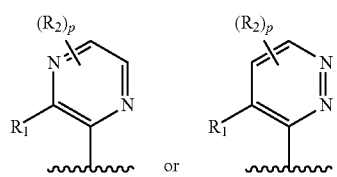

and p is 1.

In another embodiment, Ar₁ is:

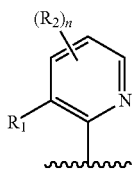

and n is 1.
In another embodiment, Ar₁ is:

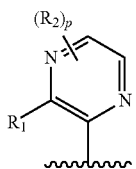

and p is 1.
In another embodiment, Ar₁ is:

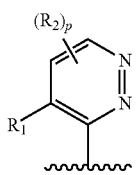

and p is 1.
In another embodiment, Ar₁ is:

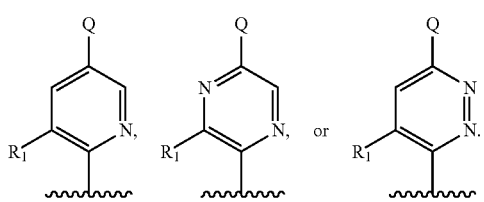

In another embodiment, Ar₁ is:

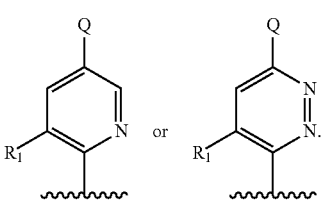

In another embodiment, $Ar_1$ is:

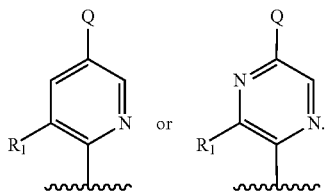

In another embodiment, $Ar_1$ is:

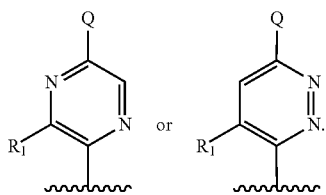

In another embodiment, $Ar_1$ is:

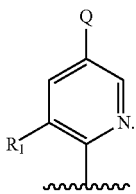

In another embodiment, $Ar_1$ is:

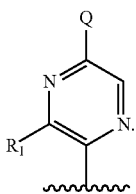

In another embodiment, $Ar_1$ is:

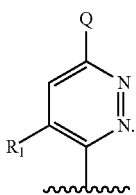

In another embodiment, $R_1$ is -halo, —$(C_1$-$C_4)$alkyl, —$OCH_3$, —$C(halo)_3$, —$CH(halo)_2$, or —$CH_2(halo)$.
In another embodiment, $R_1$ is -halo, —$(C_1$-$C_4)$alkyl, —$C(halo)_3$, —$CH(halo)_2$, or —$CH_2(halo)$.
In another embodiment, $R_1$ is -halo, —$(C_1$-$C_4)$alkyl, —$C(halo)_3$, or —$CH(halo)_2$.
In another embodiment, $R_1$ is -halo, —$(C_1$-$C_4)$alkyl, or —$C(halo)_3$, —$CH(halo)_2$ or $CH_2(halo)$.
In another embodiment, $R_1$ is -halo.
In another embodiment, $R_1$ is —$(C_1$-$C_4)$alkyl.
In another embodiment, $R_1$ is —$OCH_3$.
In another embodiment, $R_1$ is —$C(halo)_3$.
In another embodiment, $R_1$ is —$CH(halo)_2$.
In another embodiment, $R_1$ is —$CH_2(halo)$.
In another embodiment, $R_1$ is —$OC(halo)_3$.
In another embodiment, $R_1$ is —$OCH(halo)_2$.
In another embodiment, $R_1$ is —$OCH(halo)$.
In another embodiment, $R_1$ is —Cl, —F, —$(C_1$-$C_4)$alkyl, or —$C(halo)_3$.
In another embodiment, $R_1$ is —Cl, —F, —$(C_1$-$C_4)$alkyl, —$OCF_3$, or —$CF_3$.
In another embodiment, $R_1$ is —Cl, —F, —$CH_3$, —$OCF_3$ or —$CF_3$.
In another embodiment, $R_1$ is —Cl, —F, —$CH_3$, or —$CF_3$.
In another embodiment, $R_1$ is —Cl, —F, or —$CF_3$.
In another embodiment, $R_1$ is —Cl or —F.
In another embodiment, $R_1$ is —Cl.
In another embodiment, $R_1$ is —F.
In another embodiment, $R_1$ is —$CH_3$.
In another embodiment, $R_1$ is —$OCF_3$.
In another embodiment, $R_1$ is —$CF_3$.
In another embodiment, $R_1$ is —$NO_2$, —CN, —OH, or —$NH_2$.
In another embodiment, $R_1$ is —$NO_2$.
In another embodiment, $R_1$ is —CN.
In another embodiment, $R_1$ is —OH.
In another embodiment, $R_1$ is —$NH_2$.
In another embodiment, X is O.
In another embodiment, X is S.
In another embodiment, $R_{22}$ is —H or —$(C_1$-$C_6)$alkyl.
In another embodiment, $R_{22}$ is —H or —$(C_1$-$C_3)$alkyl.
In another embodiment, $R_{22}$ is —H or —$CH_3$.
In another embodiment, $R_{22}$ is —$CH_3$.
In another embodiment, $R_{22}$ is —H.
In another embodiment, each $R_{20}$ is independently —H or —$(C_1$-$C_6)$alkyl.
In another embodiment, each $R_{20}$ is independently —H or —$(C_3$-$C_8)$cycloalkyl.
In another embodiment, each $R_{20}$ is independently —$(C_1$-$C_6)$alkyl or —$(C_3$-$C_8)$cycloalkyl.
In another embodiment, each $R_{20}$ is —$(C_3$-$C_8)$cycloalkyl.
In another embodiment, each $R_{20}$ is -cyclohexyl.
In another embodiment, each $R_{20}$ is —H.
In another embodiment, each $R_{20}$ is —$(C_1$-$C_6)$alkyl.
In another embodiment, each $R_{20}$ is independently —H or —$CH_3$.
In another embodiment, each $R_{13}$ is independently —H, —$(C_1$-$C_4)$alkyl, -(3- to 7-membered)heterocycle, or -phenyl.
In another embodiment, each $R_{13}$ is independently —H, —$(C_1$-$C_4)$alkyl, or -(3- to 7-membered)heterocycle.
In another embodiment, each $R_{13}$ is independently —H, —$(C_1$-$C_4)$alkyl, or -phenyl.
In another embodiment, each $R_{13}$ is independently —H or —$(C_1$-$C_4)$alkyl.
In another embodiment, each $R_{13}$ is independently —H or —$(C_1$-$C_3)$alkyl.
In another embodiment, each $R_{13}$ is independently —H or —$CH_3$.
In another embodiment, each $R_{13}$ is —H.
In another embodiment, each $R_{13}$ is —$CH_3$.

In another embodiment. Ar$_2$ is
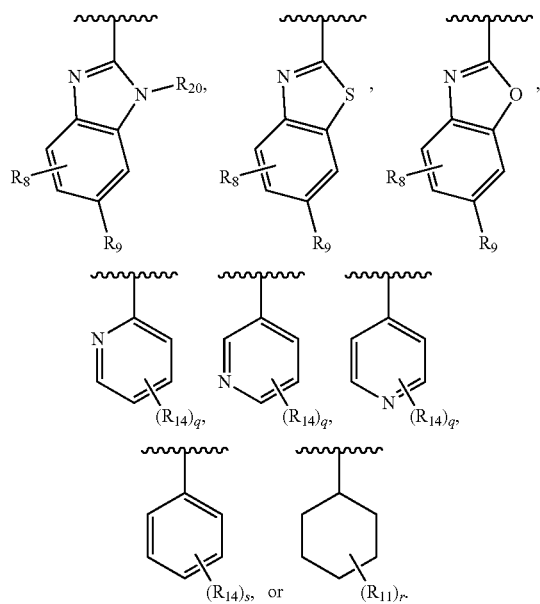
In another embodiment, Ar$_2$ is a benzoimidazolyl group.
In another embodiment, Ar$_2$ is:
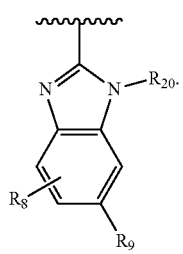
In another embodiment, Ar$_2$ is:
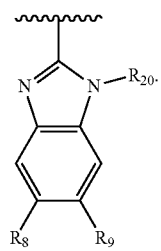
In another embodiment, Ar$_2$ is:
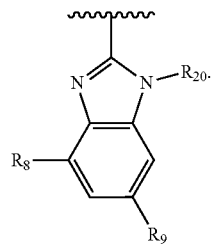
In another embodiment, Ar$_2$ is:
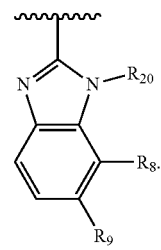
In another embodiment, Ar$_2$ is:
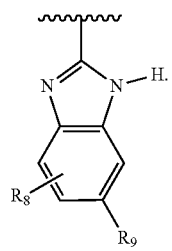
In another embodiment, Ar$_2$ is:
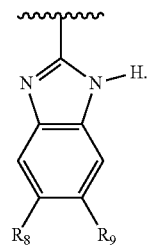
In another embodiment, Ar$_2$ is:
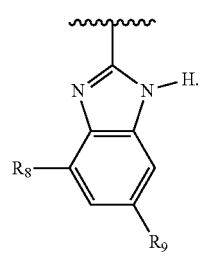
In another embodiment, Ar$_2$ is:
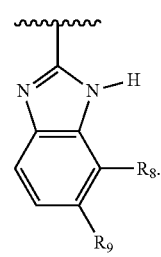

In another embodiment, Ar$_2$ is:

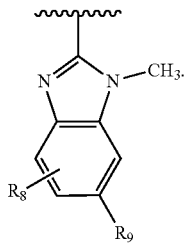

In another embodiment, Ar$_2$ is:

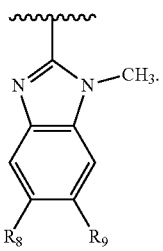

In another embodiment, Ar$_2$ is:

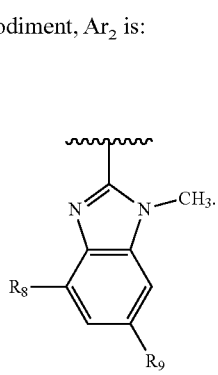

In another embodiment, Ar$_2$ is:

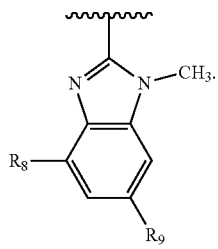

In another embodiment, Ar$_2$ is:

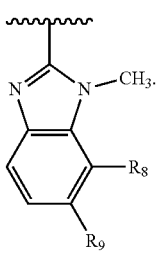

In another embodiment, Ar$_2$ is a benzothiazolyl group.

In another embodiment, Ar$_2$ is:

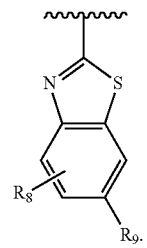

In another embodiment, Ar$_2$ is:

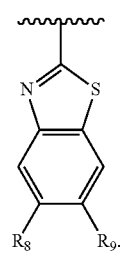

In another embodiment, Ar$_2$ is:

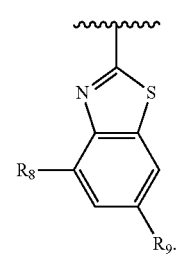

In another embodiment, Ar$_2$ is:

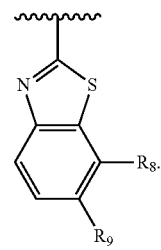

In another embodiment, Ar$_2$ is a benzooxazolyl group.
In another embodiment, Ar$_2$ is:

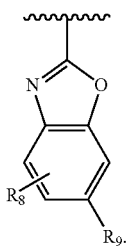

In another embodiment, Ar$_2$ is:

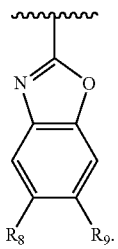

In another embodiment, Ar$_2$ is:

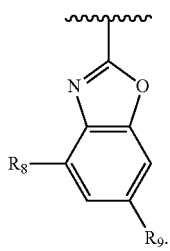

In another embodiment, Ar$_2$ is:

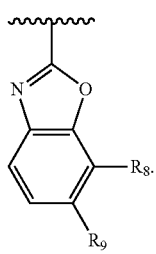

In another embodiment, R$_8$ and R$_9$ are independently —H, —(C$_1$-C$_6$)alkyl, —(C$_3$-C$_8$)cycloalkyl, -phenyl, —CH$_2$C(halo)$_3$, —C(halo)$_3$, —CH(halo)$_2$, —CH$_2$(halo), —OC(halo)$_3$, —OCH(halo)$_2$, —OCH$_2$(halo), -halo, —N(R$_7$)$_2$, —NR$_7$OH, —OR$_7$, —C(O)OR$_7$, or —S(O)$_2$R$_7$.

In another embodiment, R$_8$ and R$_9$ are independently —H, —(C$_1$-C$_6$)alkyl, —C(halo)$_3$, —CH(halo)$_2$, —CH$_2$(halo), —OC(halo)$_3$, —OCH(halo)$_2$, —OCH$_2$(halo), -halo, —N(R$_7$)$_2$, —OR$_7$, —C(O)OR$_7$, or —S(O)$_2$R$_7$.

In another embodiment, R$_8$ and R$_9$ are independently —H, —Cl, —Br, —F, —CH$_3$, —OCH$_3$, —OCH$_2$CH$_3$, —CF$_3$, —OCF$_3$, -iso-propyl, or -tert-butyl.

In another embodiment, R$_8$ and R$_9$ are independently —H, —Cl, —F, —CH$_3$, —OCH$_3$, —OCH$_2$CH$_3$, —CF$_3$, —OCF$_3$, or -tert-butyl.

In another embodiment, Ar$_2$ is a benzothiazolyl, benzoimidazolyl, or benzooxazolyl group; and at least one of R$_8$ and R$_9$ is —H.

In another embodiment, Ar$_2$ is a benzothiazolyl, benzoimidazolyl, or benzooxazolyl group; and at least one of R$_8$ and R$_9$ is not —H.

In another embodiment, Ar$_2$ is a benzothiazolyl, benzoimidazolyl, or benzooxazolyl group; and at least one of R$_8$ and R$_9$ is -halo.

In another embodiment, Ar$_2$ is:

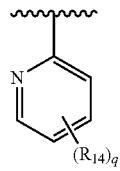

and q is 0, 1, or 2.

In another embodiment, Ar$_2$ is:

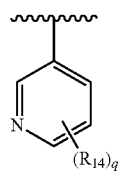

and q is 0, 1, or 2.

In another embodiment, Ar$_2$ is:

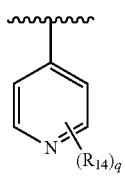

and q is 0, 1, or 2.

In another embodiment, Ar$_2$ is:

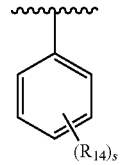

and s is 0, 1, or 2.

In another embodiment Ar$_2$ is:

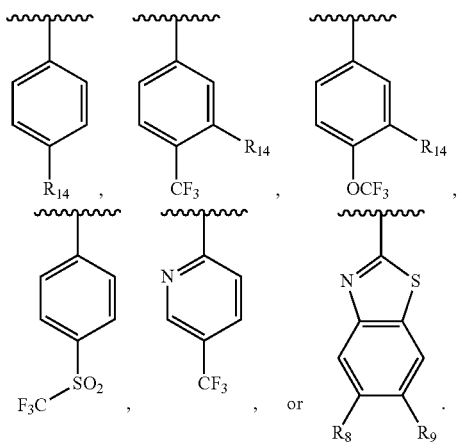

In another embodiment, each R$_{14}$ is independently —(C$_1$-C$_6$)alkyl, —(C$_2$-C$_6$)alkenyl, —(C$_3$-C$_8$)cycloalkyl, —(C$_1$-C$_6$)

alkoxy, -phenyl, —C(halo)$_3$, —CH(halo)$_2$, —CH$_2$(halo), -(3- to 7-membered)heterocycle, —(C$_1$-C$_6$)haloalkyl, -halo, —OC(halo)$_3$, —N(R$_7$)$_2$, —NR$_7$OH, —OR$_7$, —SR$_7$, —N(R$_7$)C(O)R$_7$, —C(O)OR$_7$, —S(O)R$_7$, —S(O)$_2$R$_7$, —S(O)$_2$N(R$_7$)$_2$, —S(O)$_2$C(halo)$_3$, —C(O)N(R$_7$)$_2$, or —(C$_1$-C$_6$)alkyl-NHS(O)$_2$N(R$_7$)$_2$.

In another embodiment, each R$_{14}$ is independently —(C$_1$-C$_6$)alkyl, —(C$_3$-C$_8$)cycloalkyl, —(C$_1$-C$_6$)alkoxy, -phenyl, —C(halo)$_3$, —CH(halo)$_2$, —CH$_2$(halo), -(3- to 7-membered)heterocycle, —(C$_1$-C$_6$)haloalkyl, -halo, —OC(halo)$_3$, —N(R$_7$)$_2$, —OR$_7$, —N(R$_7$)C(O)R$_7$, —C(O)OR$_7$, —S(O)R$_7$, —S(O)$_2$R$_7$, —S(O)$_2$N(R$_7$)$_2$, —S(O)$_2$C(halo)$_3$, or —C(O)N(R$_7$)$_2$.

In another embodiment, each R$_{14}$ is independently —Cl, —F, —Br, —(C$_1$-C$_6$)alkyl, —S(O)$_2$CF$_3$, —S(O)$_2$(C$_1$-C$_6$)alkyl, —OCH$_3$, —OCH$_2$CH$_3$, —OCH(CH$_3$)$_2$, —CF$_3$, or —OCF$_3$.

In another embodiment, each R$_{14}$ is independently —Cl, —F, —CH$_3$, —S(O)$_2$CF$_3$, —S(O)$_2$CH$_3$, —OCH$_3$, —OCH$_2$CH$_3$, —OCH(CH$_3$)$_2$, —CF$_3$, or —OCF$_3$.

In another embodiment, each R$_{14}$ is independently —Cl, —F, —CH$_3$, —CH$_2$CH$_3$, —OCH$_3$, —OCH(CH$_3$)$_2$, —OCH$_2$CH$_3$, —CF$_3$ or —OCF$_3$.

In another embodiment, each R$_{14}$ is independently —Cl, —F, —CF$_3$, or —OCF$_3$.

In another embodiment, Ar$_2$ is:

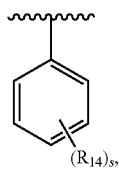

s is 1 and R$_{14}$ is —(C$_1$-C$_6$)alkyl, -halo, —C(halo)$_3$, —OC(halo)$_3$, —OR$_7$, —N(R$_7$)$_2$, —S(O)$_2$R$_7$, or —S(O)$_2$C(halo)$_3$.

In another embodiment, Ar$_2$ is:

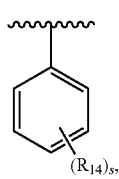

s is 2, and each R$_{14}$ is independently —(C$_1$-C$_6$)alkyl, -halo, —C(halo)$_3$, —OC(halo)$_3$, —OR$_7$, —N(R$_7$)$_2$, —S(O)$_2$R$_7$, or —S(O)$_2$C(halo)$_3$.

In another embodiment, Ar$_2$ is:

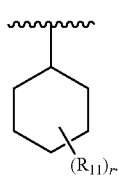

In another embodiment, each R$_{11}$ is independently —CN, —OH, —(C$_1$-C$_6$)alkyl, —(C$_2$-C$_6$)alkenyl, -halo, —C(halo)$_3$, —CH(halo)$_2$, —CH$_2$(halo), —OC(halo)$_3$, —NO$_2$, —N(R$_7$)$_2$, —NR$_7$OH, —OR$_7$, or —C(O)OR$_7$.

In another embodiment, each R$_{11}$ is independently —(C$_1$-C$_6$)alkyl, -halo, —C(halo)$_3$, —CH(halo)$_2$, —CH$_2$(halo), —OC(halo)$_3$, —N(R$_7$)$_2$, —NR$_7$OH, —OR$_7$, or —C(O)OR$_7$.

In another embodiment, each R$_{11}$ is independently —(C$_1$-C$_6$)alkyl, -halo, —C(halo)$_3$, —OC(halo)$_3$, —N(R$_7$)$_2$, or —OR$_7$.

In another embodiment, each R$_{11}$ is —Cl, —F, —CH$_3$, —CH$_2$CH$_3$, —CF$_3$, —OCH$_3$, —OCH(CH$_3$)$_2$, or —OCH$_2$CH$_3$.

In another embodiment, each R$_{11}$ is —CF$_3$, —OCF$_3$, —Cl, or —F.

In another embodiment, each R$_3$ is independently —H, —OCF$_3$, -halo, —(C$_1$-C$_6$)alkyl, —(C$_1$-C$_6$)haloalkyl, —OR$_{23}$, —SR$_{23}$, or —N(R$_{20}$)(R$_{23}$).

In another embodiment, R$_{10}$ is —(C$_1$-C$_4$)alkyl or —(C$_3$-C$_7$)cycloalkyl.

In another embodiment, R$_{10}$ is —H or —(C$_3$-C$_7$)cycloalkyl.

In another embodiment, R$_{10}$ is —H or —(C$_1$-C$_4$)alkyl.

In another embodiment, R$_{10}$ is —H, —CH$_3$, —CH$_2$CH$_3$, or -cyclohexyl.

In another embodiment, R$_{10}$ is —H, —CH$_3$, or —CH$_2$CH$_3$.

In another embodiment, R$_{10}$ is —H or —CH$_3$.

In another embodiment, R$_{10}$ is —H.

In another embodiment, each R$_3$ is independently —H, —CH$_3$, —OCH$_3$, —NH(CH$_3$), —CF$_3$, or —OCF$_3$.

In another embodiment, each R$_3$ is independently —H, —(C$_1$-C$_6$)alkyl, or —(C$_1$-C$_6$)haloalkyl.

In another embodiment, each R$_3$ is independently —H, —CH$_3$, or —CF$_3$

In another embodiment, m is 2.

In another embodiment, m is 1.

In another embodiment, each R$_3$ is independently —H or —(C$_1$-C$_6$)alkyl.

In another embodiment, m is 1 and each R$_3$ is independently —H, —CH$_3$, or —CH$_2$CH$_3$.

In another embodiment, m is 1 and each R$_3$ is independently —H or —CH$_3$.

In another embodiment, m is 1 and each R$_3$ is independently —H or —CF$_3$.

In another embodiment, each R$_3$ is —H.

In another embodiment, one R$_3$ is —CH$_3$.

In another embodiment, one R$_3$ is —CH$_3$ and another R$_3$ is —H.

In another embodiment, m is 0.

In another embodiment, r, s, or q is 0.

In another embodiment, r, s, or q is 1.

In another embodiment, r, s, or q is 2.

In another embodiment, each R$_{20}$ is independently —H or —(C$_1$-C$_6$)alkyl.

In another embodiment, each R$_{20}$ is independently —H or —(C$_3$-C$_8$)cycloalkyl.

In another embodiment, each R$_{20}$ is independently —(C$_1$-C$_6$)alkyl or —(C$_3$-C$_8$)cycloalkyl.

In another embodiment, each R$_{20}$ is —H.

In another embodiment, each R$_{20}$ is —(C$_1$-C$_6$)alkyl.

In another embodiment, each R$_{20}$ is —(C$_3$-C$_8$)cycloalkyl.

In another embodiment, each R$_7$ is independently —H, —(C$_1$-C$_6$)alkyl, —(C$_3$-C$_8$)cycloalkyl, or -phenyl.

In another embodiment, each R$_7$ is independently —H, —(C$_1$-C$_4$)alkyl, -cyclohexyl, or -phenyl.

In another embodiment, each R$_7$ is independently —H, -cyclohexyl, or -phenyl.

In another embodiment, each R$_7$ is independently —H or —(C$_1$-C$_3$)alkyl.

In another embodiment, each R$_7$ is independently —H, —CH$_3$, or —CH$_2$CH$_3$.

In another embodiment, each $R_7$ is independently —H or —$CH_3$.

In another embodiment, when n or p are 1, then $R_2$ must be Q.

In another embodiment, a Q group is substituted on $Ar_1$ at the $Ar_1$ position para to the point of attachment of $Ar_1$ to the ring comprising $L_1$ and $L_2$.

In another embodiment, J is —$OR_{20}$.
In another embodiment, J is —OH.
In another embodiment, $Z_1$ is —H.
In another embodiment, $Z_1$ is —$OR_{20}$ or —$CH_2OR_{20}$.
In another embodiment, $Z_1$ is —$CH_2OR_{20}$.
In another embodiment, $Z_1$ is —$CH_2OH$.
In another embodiment, $Z_1$ is —$OR_{20}$.
In another embodiment, $Z_1$ is —OH.
In another embodiment, $Z_1$ is —$OCH_3$.
In another embodiment, $Z_2$ is —$CH_2OR_{20}$.
In another embodiment, $Z_2$ is —$CH_2OH$.
In another embodiment, $Z_2$ is —H.
In another embodiment, $Z_2$ is —$CH_3$.
In another embodiment, one $Z_3$ group is —H.
In another embodiment, one $Z_3$ group is —$(C_1-C_6)$alkyl.
In another embodiment, one $Z_3$ group is —$(C_1-C_3)$alkyl.
In another embodiment, one $Z_3$ group is —$CH_3$.
In another embodiment, one $Z_3$ group is —H and one $Z_3$ group is —$(C_1-C_6)$alkyl.
In another embodiment, one $Z_3$ group is —H and one $Z_3$ group is —$(C_1-C_3)$alkyl.
In another embodiment, one $Z_3$ group is —H and one $Z_3$ group is —$CH_3$.
In another embodiment, one $Z_3$ group is —$CH_3$ and the other three $Z_3$ groups are —H.
In another embodiment, each $Z_3$ group is —H.
In another embodiment, one $Z_3$ group is —$CH_3$, the other three $Z_3$ groups are —H, and $Z_2$ is —H.
In another embodiment, one $Z_3$ group is —$CH_3$, the other three $Z_3$ groups are —H, $Z_2$ is —H, and $Z_1$ is —$OR_{20}$.
In another embodiment, one $Z_3$ group is —$CH_3$, the other three $Z_3$ groups are —H, $Z_2$ is —H, and $Z_1$ is —OH.
In another embodiment, one $Z_3$ group is —$CH_3$, the other three $Z_3$ groups are —H, $Z_2$ is —H, $Z_1$ is —$OR_{20}$, and J is —$OR_{20}$.
In another embodiment, one $Z_3$ group is —$CH_3$, the other three $Z_3$ groups are —H, $Z_2$ is —H, $Z_1$ is —OH, and J is —$OR_{20}$.
In another embodiment, one $Z_3$ group is —$CH_3$, the other three $Z_3$ groups are —H, $Z_2$ is —H, $Z_1$ is —OH, and J is —OH.
In another embodiment, each $Z_3$ group is —H and $Z_2$ is —H.
In another embodiment, each $Z_3$ group is —H, $Z_2$ is —H, and $Z_1$ is —$OR_{20}$.
In another embodiment, each $Z_3$ group is —H, $Z_2$ is —H, and $Z_1$ is —OH.
In another embodiment, each $Z_3$ group is —H, $Z_2$ is —H, $Z_1$ is —$OR_{20}$, and J is —$OR_{20}$.
In another embodiment, each $Z_3$ group is —H, $Z_2$ is —H, $Z_1$ is —OH, and J is —$OR_{20}$.
In another embodiment, each $Z_3$ group is —H, $Z_2$ is —H, $Z_1$ is —OH, and J is —OH.

In another embodiment, Q is:

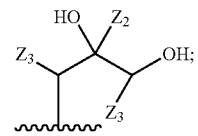

$Z_2$ is —H or —$(C_1-C_3)$alkyl; and each $Z_3$ group is independently —H or —$(C_1-C_3)$alkyl.

In another embodiment, Q is:

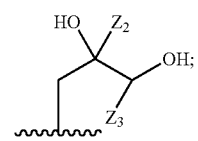

$Z_2$ is —H or —$(C_1-C_3)$alkyl; and $Z_3$ is —H or —$(C_1-C_3)$alkyl.

In another embodiment, Q is:

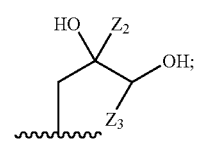

$Z_2$ is —H; and $Z_3$ is —H or —$(C_1-C_3)$alkyl.

In another embodiment, Q is:

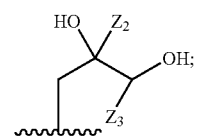

$Z_2$ is —H; and $Z_3$ is —H.

In another embodiment, Q is:

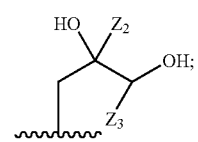

$Z_2$ is —H; and $Z_3$ is —$CH_3$.

In another embodiment, n or p is 1, $R_2$ is Q, wherein Q is:

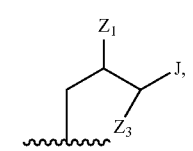

J is —$OR_{20}$, and $Z_1$ is —$OR_{20}$.

In another embodiment, n or p is 1, $R_2$ is Q, wherein Q is:

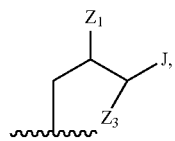

J is —$OR_{20}$, and $Z_1$ is —$CH_2OR_{20}$.

In another embodiment, n or p is 1, $R_2$ is Q, wherein Q is:

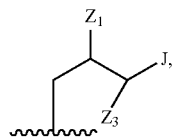

J is —OH, and $Z_1$ is —OH.

In another embodiment, n or p is 1, $R_2$ is Q, wherein Q is:

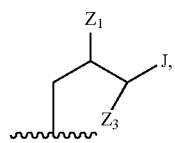

J is —OH, and $Z_1$ is —$CH_2OH$.

In another embodiment, n or p is 1, $R_2$ is Q, wherein Q is:

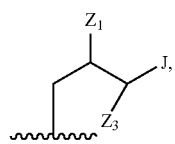

J is —OH, and $Z_1$ is —OH.

In another embodiment, n or p is 1, $R_2$ is Q, wherein Q is:

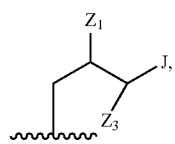

J is —OH, and $Z_1$ is —$CH_2OH$.

In another embodiment, $R_1$ is -halo, n or p is 1, $R_2$ is Q, wherein Q is:

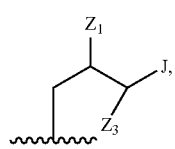

J is —$OR_{20}$, and $Z_1$ is —$OR_{20}$.

In another embodiment, $R_1$ is -halo, n or p is 1, $R_2$ is Q, wherein Q is:

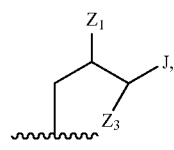

J is —$OR_{20}$, and $Z_1$ is —$CH_2OR_{20}$.

In another embodiment, $R_1$ is —Cl, n or p is 1, $R_2$ is Q, wherein Q is:

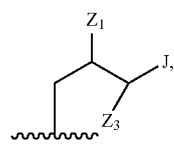

J is —$OR_{20}$, and $Z_1$ is —$OR_{20}$.

In another embodiment, $R_1$ is —Cl, n or p is 1, $R_2$ is Q, wherein Q is:

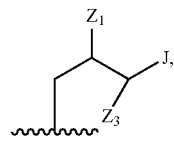

J is —$OR_{20}$, and $Z_1$ is —$CH_2OR_{20}$.

In another embodiment, $R_1$ is —Cl, n or p is 1, $R_2$ is Q, wherein Q is:

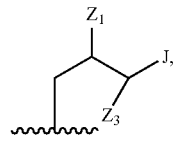

J is —OH, and $Z_1$ is —OH.

In another embodiment, $R_1$ is —Cl, n or p is 1, $R_2$ is Q, wherein Q is:

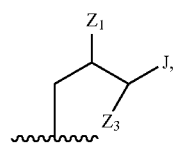

J is —OH, and $Z_1$ is —$CH_2OH$.

In another embodiment, $Ar_1$ is a pyridyl group, wherein n is 1, and $R_2$ is Q.

In another embodiment, $Ar_1$ is a pyridyl group, wherein n is 1, $R_2$ is Q, and Q is:

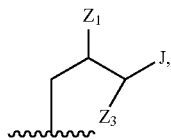

J is —OR$_{20}$, and Z$_1$ is —OR$_{20}$.

In another embodiment, Ar$_1$ is a pyridyl group, wherein n is 1, R$_2$ is Q, and Q is:

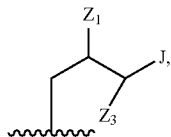

J is —OH, and Z$_1$ is —OH.

In another embodiment, Ar$_1$ is a pyridyl group, wherein n is 1, R$_2$ is Q, and Q is:

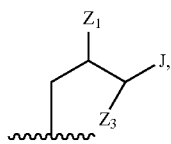

J is —OR$_{20}$, and Z$_1$ is —CH$_2$OR$_{20}$.

In another embodiment, Ar$_1$ is a pyridyl group, wherein n is 1, R$_2$ is Q, and Q is:

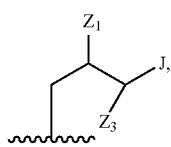

J is —OH, and Z$_1$ is —CH$_2$OH.

In another embodiment, R$_1$ is -halo, and Ar$_1$ is a pyridyl group, wherein n is 1, R$_2$ is Q, and Q is:

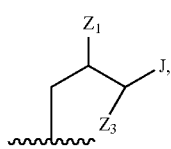

J is —OR$_{20}$, and Z$_1$ is —OR$_{20}$.

In another embodiment, R$_1$ is -halo, and Ar$_1$ is a pyridyl group, wherein n is 1, R$_2$ is Q, and Q is:

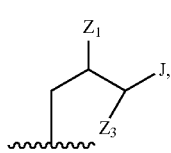

J is —OH, and Z$_1$ is —OH.

In another embodiment, R$_1$ is -halo, and Ar$_1$ is a pyridyl group, wherein n is 1, R$_2$ is Q, and Q is:

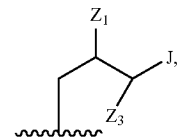

J is —OR$_{20}$, and Z$_1$ is —CH$_2$OR$_{20}$.

In another embodiment, R$_1$ is -halo, and Ar$_1$ is a pyridyl group, wherein n is 1, R$_2$ is Q, and Q is:

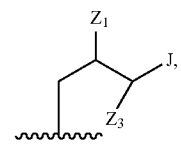

J is —OH, and Z$_1$ is —CH$_2$OH.

In another embodiment, R$_1$ is -halo, and Ar$_1$ is a pyridyl group, wherein n is 1, R$_2$ is Q, and Q is:

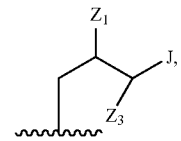

J is —OH, Z$_1$ is —OH, and Ar$_2$ is benzothiazolyl, wherein at least one of R$_8$ or R$_9$ is not —H.

In another embodiment, R$_1$ is -halo, and Ar$_1$ is a pyridyl group, wherein n is 1, R$_2$ is Q, and Q is:

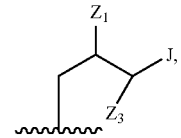

J is —OH, Z$_1$ is —CH$_2$OH, and Ar$_2$ is benzothiazolyl, wherein at least one of R$_8$ or R$_9$ is not —H.

In another embodiment, R$_1$ is -halo, and Ar$_1$ is a pyridyl group, wherein n is 1, R$_2$ is Q, and Q is:

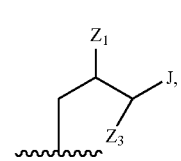

J is —OH, Z$_1$ is —OH, and Ar$_2$ is benzooxazolyl, wherein at least one of R$_8$ or R$_9$ is not —H.

In another embodiment, R$_1$ is -halo, and Ar$_1$ is a pyridyl group, wherein n is 1, R$_2$ is Q, and Q is:

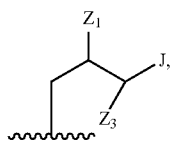

J is —OH, $Z_1$ is —CH$_2$OH, and Ar$_2$ is benzooxazolyl, wherein at least one of $R_8$ or $R_9$ is not —H.

In another embodiment, $R_1$ is -halo, and Ar$_1$ is a pyridyl group, wherein n is 1, $R_2$ is Q, and Q is:

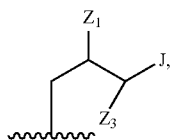

J is —OH, $Z_1$ is —OH, and Ar$_2$ is benzoimidazolyl, wherein at least one of $R_8$ or $R_9$ is not —H.

In another embodiment, $R_1$ is -halo, and Ar$_1$ is a pyridyl group, wherein n is 1, $R_2$ is Q, and Q is:

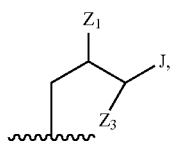

J is —OH, $Z_1$ is —CH$_2$OH, and Ar$_2$ is benzoimidazolyl, wherein at least one of $R_8$ or $R_9$ is not —H.

In another embodiment, $R_1$ is -halo, and Ar$_1$ is a pyridyl group, wherein n is 1, $R_2$ is Q, and Q is:

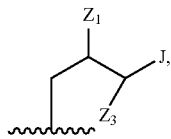

J is —OH, $Z_1$ is —OH, and Ar$_2$ is phenyl, wherein s is 0 or 1.

In another embodiment, $R_1$ is -halo, and Ar$_1$ is a pyridyl group, wherein n is 1, $R_2$ is Q, and Q is:

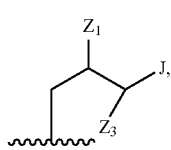

J is —OH, $Z_1$ is —CH$_2$OH, and Ar$_2$ is phenyl, wherein s is 0 or 1.

In another embodiment, $R_1$ is -halo, and Ar$_1$ is a pyridyl group, wherein n is 1, $R_2$ is Q, and Q is:

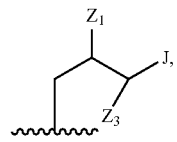

J is —OH, $Z_1$ is —OH, and Ar$_2$ is phenyl, wherein s is 2.

In another embodiment, $R_1$ is -halo, and Ar$_1$ is a pyridyl group, wherein n is 1, $R_2$ is Q, and Q is:

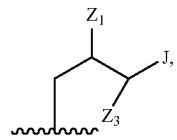

J is —OH, $Z_1$ is —CH$_2$OH, and Ar$_2$ is phenyl, wherein s is 2.

In another embodiment, n or p is 1, $R_2$ is Q, wherein Q is:

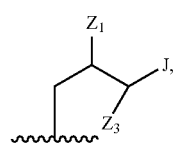

J is —OR$_{20}$, and $Z_1$ is —OR$_{20}$.

In another embodiment, n or p is 1, $R_2$ is Q, wherein Q is:

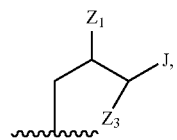

J is —OR$_{20}$, and $Z_1$ is —CH$_2$OR$_{20}$.

In another embodiment, n or p is 1, $R_2$ is Q, wherein Q is:

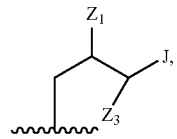

J is —OH, and $Z_1$ is —OH.

In another embodiment, n or p is 1, $R_2$ is Q, wherein Q is:

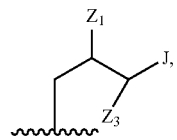

J is —OH, and $Z_1$ is —CH$_2$OH.

In another embodiment, $R_1$ is -halo, n or p is 1, $R_2$ is Q, wherein Q is:

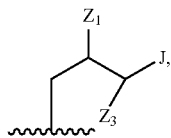

J is —OH, and $Z_1$ is —OH.

In another embodiment, $R_1$ is -halo, n or p is 1, $R_2$ is Q, wherein Q is:

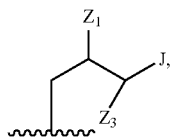

J is —OH, and $Z_1$ is —CH$_2$OH.

In another embodiment, $R_1$ is -halo, and $Ar_1$ is a pyridyl group, wherein n is 1, $R_2$ is Q, and Q is:

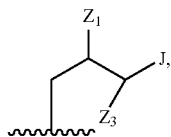

J is —OH, and $Z_1$ is —OH.

In another embodiment, $R_1$ is -halo, and $Ar_1$ is a pyridyl group, wherein n is 1, $R_2$ is Q, and Q is:

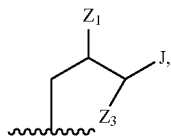

J is —OH, and $Z_1$ is —CH$_2$OH.

In another embodiment, $R_1$ is -halo, and $Ar_1$ is a pyridyl group, wherein n is 1, $R_2$ is Q, and Q is:

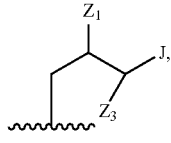

J is —OH, $Z_1$ is —OH, and $Ar_2$ is benzothiazolyl, wherein at least one of $R_8$ or $R_9$ is not —H.

In another embodiment, $R_1$ is -halo, and $Ar_1$ is a pyridyl group, wherein n is 1, $R_2$ is Q, and Q is:

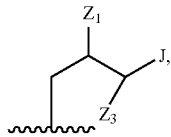

J is —OH, $Z_1$ is —CH$_2$OH, and $Ar_2$ is benzothiazolyl, wherein at least one of $R_8$ or $R_9$ is not —H.

In another embodiment, $R_1$ is -halo, and $Ar_1$ is a pyridyl group, and Q is:

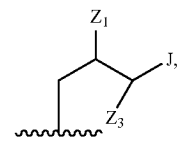

J is —OH, $Z_1$ is —OH, and $Ar_2$ is benzooxazolyl, wherein at least one of $R_8$ or $R_9$ is not —H.

In another embodiment, $R_1$ is -halo, and $Ar_1$ is a pyridyl group, wherein n is 1, and Q is:

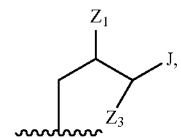

J is —OH, $Z_1$ is —CH$_2$OH, and $Ar_2$ is benzooxazolyl, wherein at least one of $R_8$ or $R_9$ is not —H.

In another embodiment, $R_1$ is -halo, and $Ar_1$ is a pyridyl group, wherein n is 1, is Q, and Q is:

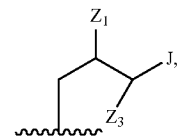

J is —OH, $Z_1$ is —OH, and $Ar_2$ is benzoimidazolyl, wherein at least one of $R_8$ or $R_9$ is not —H.

In another embodiment, $R_1$ is -halo, and $Ar_1$ is a pyridyl group, wherein n is 1, $R_2$ is Q, and Q is:

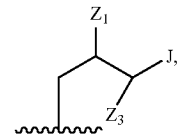

J is —OH, $Z_1$ is —CH$_2$OH, and $Ar_2$ is benzoimidazolyl, wherein at least one of $R_8$ or $R_9$ is not —H.

In another embodiment, $R_1$ is -halo, and $Ar_1$ is a pyridyl group, wherein n is 1, $R_2$ is Q, and Q is:

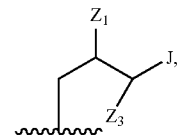

J is —OH, $Z_1$ is —OH, and $Ar_2$ is phenyl, wherein s is 0 or 1 and $R_{14}$ is —(C$_1$-C$_6$)alkyl, -halo, —C(halo)$_3$, —OC(halo)$_3$, —OR$_7$, —N(R$_7$)$_2$, —S(O)$_2$R$_7$, or —S(O)$_2$C(halo)$_3$, and preferably is —F, —Cl, —CF$_3$, or —OCF$_3$.

In another embodiment, $R_1$ is -halo, and $Ar_1$ is a pyridyl group, wherein n is 1, $R_2$ is Q, and Q is:

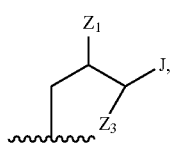

J is —OH, $Z_1$ is —CH$_2$OH, Ar$_2$ is phenyl, wherein s is 0 or 1, and $R_{14}$ is —(C$_1$-C$_6$)alkyl, -halo, —C(halo)$_3$, —OC(halo)$_3$, —OR$_7$, —N(R$_7$)$_2$, —S(O)$_2$R$_7$, or —S(O)$_2$C(halo)$_3$, and preferably is —F, —Cl, —CF$_3$, or —OCF$_3$.

In another embodiment, $R_1$ is -halo and $Ar_1$ is a pyridyl group, wherein n is 1, $R_2$ is Q, and Q is:

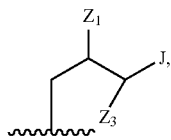

J is —OH, $Z_1$ is —OH, Ar$_2$ is phenyl, wherein s is 2, and each $R_{14}$ is independently —(C$_1$-C$_6$)alkyl, -halo, —C(halo)$_3$, —OC(halo)$_3$, —OR$_7$, —N(R$_7$)$_2$, —S(O)$_2$R$_7$, or —S(O)$_2$C(halo)$_3$, and preferably is —F, —Cl, —CF$_3$, or —OCF$_3$.

In another embodiment, $R_1$ is -halo and $Ar_1$ is a pyridyl group, wherein n is 1, $R_2$ is Q, and Q is:

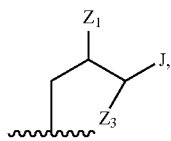

J is —OH, $Z_1$ is —CH$_2$OH, Ar$_2$ is phenyl, wherein s is 2, and each $R_{14}$ is independently —(C$_1$-C$_6$)alkyl, -halo, —C(halo)$_3$, —OC(halo)$_3$, —OR$_7$, —N(R$_7$)$_2$, —S(O)$_2$R$_7$, or —S(O)$_2$C(halo)$_3$, and preferably is —F, —Cl, —CF$_3$, or —OCF$_3$.

In another embodiment Q is:

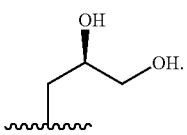 [SMILES: *C[C@@H](O)CO]

In another embodiment Q is:

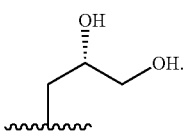 [SMILES: *C[C@H](O)CO]

In another embodiment Q is:

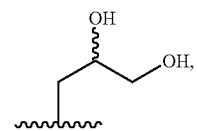 [SMILES: *CC(O)CO]

wherein the Compound of Formula (II) is racemic.

In another embodiment Q is:

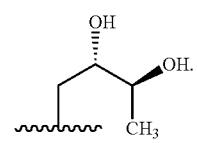

In another embodiment Q is:

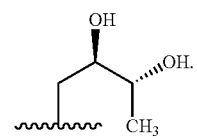

In another embodiment Q is:

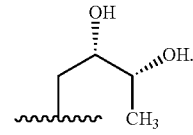

In another embodiment Q is:

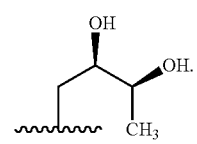

In another embodiment Q is:

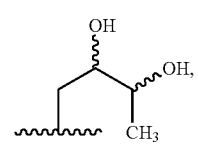

wherein the Compound of Formula (II) is racemic.

Illustrative Compounds of Formula (II) are listed below in Tables 1-6:

TABLE 1
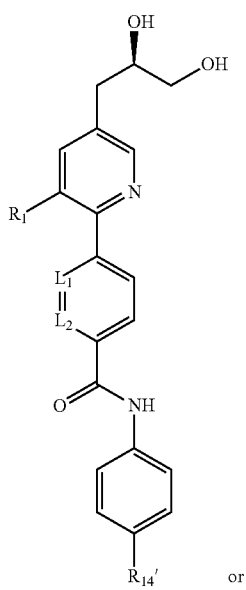
(IIa)
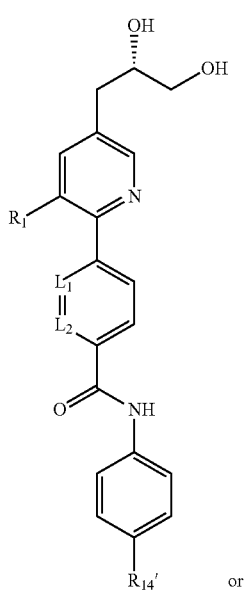
(IIb)
TABLE 1-continued
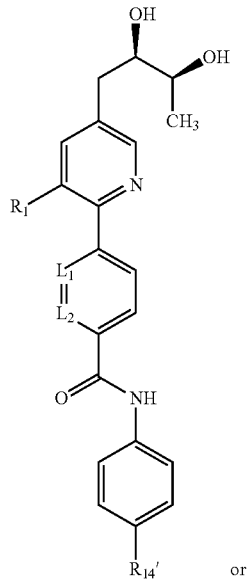
(IIc)
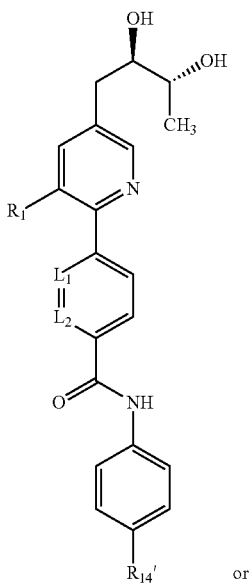
(IId)

TABLE 1-continued

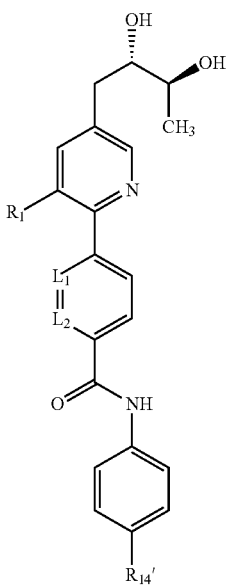

(IIe)

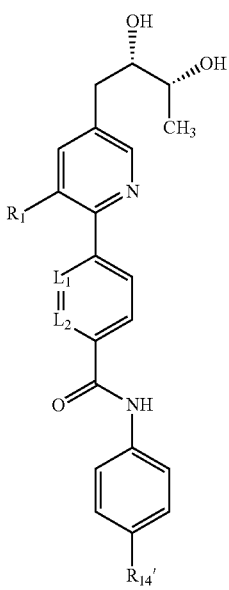

(IIf)

and pharmaceutically acceptable derivatives thereof, where:

| Compound | L₁ | L₂ | R₁ | R₁₄' |
|---|---|---|---|---|
| A1 a, b, c, d, e or f | N | CH | —Cl | —H |
| A2 a, b, c, d, e or f | N | CH | —Cl | —Cl |
| A3 a, b, c, d, e or f | N | CH | —Cl | —F |
| A4 a, b, c, d, e or f | N | CH | —Cl | —Br |
| A5 a, b, c, d, e or f | N | CH | —Cl | —CF₃ |
| A6 a, b, c, d, e or f | N | CH | —Cl | —OCF₃ |
| A7 a, b, c, d, e or f | N | CH | —Cl | —CH₃ |
| A8 a, b, c, d, e or f | N | CH | —Cl | —CH₂CH₃ |
| A9 a, b, c, d, e or f | N | CH | —Cl | -iso-propyl |
| A10 a, b, c, d, e or f | N | CH | —Cl | -tert-butyl |
| A11 a, b, c, d, e or f | N | CH | —Cl | —S(O)₂CF₃ |
| A12 a, b, c, d, e or f | N | CH | —Cl | —S(O)₂CH₃ |
| A13 a, b, c, d, e or f | N | CH | —Cl | —S(O)₂CH₃CH₃ |
| A14 a, b, c, d, e or f | N | CH | —Cl | —OCH₃ |
| A15 a, b, c, d, e or f | N | CH | —Cl | —OCH₂CH₃ |
| A16 a, b, c, d, e or f | N | CH | —Cl | —OCH(CH₃)₂ |
| A17 a, b, c, d, e or f | N | CH | —F | —H |
| A18 a, b, c, d, e or f | N | CH | —F | —Cl |
| A19 a, b, c, d, e or f | N | CH | —F | —F |
| A20 a, b, c, d, e or f | N | CH | —F | —Br |
| A21 a, b, c, d, e or f | N | CH | —F | —CF₃ |
| A22 a, b, c, d, e or f | N | CH | —F | —OCF₃ |
| A23 a, b, c, d, e or f | N | CH | —F | —CH₃ |
| A24 a, b, c, d, e or f | N | CH | —F | —CH₂CH₃ |
| A25 a, b, c, d, e or f | N | CH | —F | -iso-propyl |
| A26 a, b, c, d, e or f | N | CH | —F | -tert-butyl |
| A27 a, b, c, d, e, or f | N | CH | —F | —S(O)₂CF₃ |
| A28 a, b, c, d, e or r | N | CH | —F | —S(O)₂CH₃ |
| A29 a, b, c, d, e or f | N | CH | —F | —S(O)₂CH₃CH₃ |
| A30 a, b, c, d, e or f | N | CH | —F | —OCH₃ |
| A31 a, b, c, d, e or f | N | CH | —F | —OCH₂CH₃ |
| A32 a, b, c, d, e or f | N | CH | —F | —OCH(CH₃)₂ |
| A33 a, b, c, d, e or f | N | CH | —CF₃ | —H |
| A34 a, b, c, d, e or f | N | CH | —CF₃ | —Cl |
| A35 a, b, c, d, e or f | N | CH | —CF₃ | —F |
| A36 a, b, c, d, e or f | N | CH | —CF₃ | —Br |
| A37 a, b, c, d, e or f | N | CH | —CF₃ | —CF₃ |
| A38 a, b, c, d, e or f | N | CH | —CF₃ | —OCF₃ |
| A39 a, b, c, d, e or f | N | CH | —CF₃ | —CH₃ |
| A40 a, b, c, d, e or f | N | CH | —CF₃ | —CH₂CH₃ |
| A41 a, b, c, d, e or f | N | CH | —CF₃ | -iso-propyl |
| A42 a, b, c, d, e or f | N | CH | —CF₃ | -tert-butyl |
| A43 a, b, c, d, e or f | N | CH | —CF₃ | —S(O)₂CF₃ |
| A44 a, b, c, d, e or f | N | CH | —CF₃ | —S(O)₂CH₃ |
| A45 a, b, c, d, e or f | N | CH | —CF₃ | —S(O)₂CH₃CH₃ |
| A46 a, b, c, d, e or f | N | CH | —CF₃ | —S(O)₂CH₃CH₃ |
| A47 a, b, c, d, e or f | N | CH | —CF₃ | —OCH₃ |
| A48 a, b, c, d, e or f | N | CH | —CF₃ | —OCH(CH₃)₂ |
| A49 a, b, c, d, e or f | N | CH | —CH₃ | —H |
| A50 a, b, c, d, e or f | N | CH | —CH₃ | —Cl |
| A51 a, b, c, d, e or f | N | CH | —CH₃ | —F |
| A52 a, b, c, d, e or f | N | CH | —CH₃ | —Br |
| A53 a, b, c, d, e or f | N | CH | —CH₃ | —CF₃ |
| A54 a, b, c, d, e or f | N | CH | —CH₃ | —OCF₃ |
| A55 a, b, c, d, e or f | N | CH | —CH₃ | —CH₃ |
| A56 a, b, c, d, e or f | N | CH | —CH₃ | —CH₂CH₃ |
| A57 a, b, c, d, e or f | N | CH | —CH₃ | -iso-propyl |
| A58 a, b, c, d, e or f | N | CH | —CH₃ | -tert-butyl |
| A59 a, b, c, d, e or f | N | CH | —CH₃ | —S(O)₂CF₃ |
| A60 a, b, c, d, e or f | N | CH | —CH₃ | —S(O)₂CH₃ |
| A61 a, b, c, d, e or f | N | CH | —CH₃ | —S(O)₂CH₃CH₃ |
| A62 a, b, c, d, e or f | N | CH | —CH₃ | —OCH₃ |
| A63 a, b, c, d, e or f | N | CH | —CH₃ | —OCH₂CH₃ |
| A64 a, b, c, d, e or f | N | CH | —CH₃ | —OCH(CH₃)₂ |
| A65 a, b, c, d, e or f | CH | N | —Cl | —H |
| A66 a, b, c, d, e or f | CH | N | —Cl | —Cl |
| A67 a, b, c, d, e or f | CH | N | —Cl | —F |
| A68 a, b, c, d, e or f | CH | N | —Cl | —Br |
| A69 a, b, c, d, e or f | CH | N | —Cl | —CF₃ |
| A70 a, b, c, d, e or f | CH | N | —Cl | —OCF₃ |
| A71 a, b, c, d, e or f | CH | N | —Cl | —CH₃ |
| A72 a, b, c, d, e or f | CH | N | —Cl | —CH₂CH₃ |
| A73 a, b, c, d, e or f | CH | N | —Cl | -iso-propyl |
| A74 a, b, c, d, e or f | CH | N | —Cl | -tert-butyl |
| A75 a, b, c, d, e or f | CH | N | —Cl | —S(O)₂CF₃ |
| A76 a, b, c, d, e or f | CH | N | —Cl | —S(O)₂CH₃ |
| A77 a, b, c, d, e or f | CH | N | —Cl | —S(O)₂CH₃CH₃ |
| A78 a, b, c, d, e or f | CH | N | —Cl | —OCH₃ |
| A79 a, b, c, d, e or f | CH | N | —Cl | —OCH₂CH₃ |
| A80 a, b, c, d, e or f | CH | N | —Cl | —OCH(CH₃)₂ |
| A81 a, b, c, d, e or f | CH | N | —F | —H |
| A82 a, b, c, d, e or f | CH | N | —F | —Cl |
| A83 a, b, c, d, e or f | CH | N | —F | —F |
| A84 a, b, c, d, e or f | CH | N | —F | —Br |
| A85 a, b, c, d, e or f | CH | N | —F | —CF₃ |
| A86 a, b, c, d, e or f | CH | N | —F | —OCF₃ |
| A87 a, b, c, d, e or f | CH | N | —F | —CH₃ |

TABLE 1-continued

| | | | | |
|---|---|---|---|---|
| A88 a, b, c, d, e or f | CH | N | —F | —CH₂CH₃ |
| A89 a, b, c, d, e or f | CH | N | —F | -iso-propyl |
| A90 a, b, c, d, e or f | CH | N | —F | -tert-butyl |
| A91 a, b, c, d, e or f | CH | N | —F | —S(O)₂CF₃ |
| A92 a, b, c, d, e or f | CH | N | —F | —S(O)₂CH₃ |
| A93 a, b, c, d, e or f | CH | N | —F | —S(O)₂CH₃CH₃ |
| A94 a, b, c, d, e or f | CH | N | —F | —OCH₃ |
| A95 a, b, c, d, e or f | CH | N | —F | —OCH₂CH₃ |
| A96 a, b, c, d, e or f | CH | N | —F | —OCH(CH₃)₂ |
| A97 a, b, c, d, e or f | CH | N | —CF₃ | —H |
| A98 a, b, c, d, e or f | CH | N | —CF₃ | —Cl |
| A99 a, b, c, d, e or f | CH | N | —CF₃ | —F |
| A100 a, b, c, d, e or f | CH | N | —CF₃ | —Br |
| A101 a, b, c, d, e or f | CH | N | —CF₃ | —CF₃ |
| A102 a, b, c, d, e or f | CH | N | —CF₃ | —OCF₃ |
| A103 a, b, c, d, e or f | CH | N | —CF₃ | —CH₃ |
| A104 a, b, c, d, e or f | CH | N | —CF₃ | —CH₂CH₃ |
| A105 a, b, c, d, e or f | CH | N | —CF₃ | -iso-propyl |
| A106 a, b, c, d, e or f | CH | N | —CF₃ | -tert-butyl |
| A107 a, b, c, d, e or f | CH | N | —CF₃ | —S(O)₂CF₃ |
| A108 a, b, c, d, e or f | CH | N | —CF₃ | —S(O)₂CH₃ |
| A109 a, b, c, d, e or f | CH | N | —CF₃ | —S(O)₂CH₃CH₃ |
| A111 a, b, c, d, e or f | CH | N | —CF₃ | —OCH₂CH₃ |
| A112 a, b, c, d, e or f | CH | N | —CF₃ | —OCH(CH₃)₂ |
| A113 a, b, c, d, e or f | CH | N | —CH₃ | —H |
| A114 a, b, c, d, e or f | CH | N | —CH₃ | —Cl |
| A115 a, b, c, d, e or f | CH | N | —CH₃ | —F |
| A116 a, b, c, d, e or f | CH | N | —CH₃ | —Br |
| A117 a, b, c, d, e or f | CH | N | —CH₃ | —CF₃ |
| A118 a, b, c, d, e or f | CH | N | —CH₃ | —OCF₃ |
| A119 a, b, c, d, e or f | CH | N | —CH₃ | —CH₃ |
| A120 a, b, c, d, e or f | CH | N | —CH₃ | —CH₂CH₃ |
| A121 a, b, c, d, e or f | CH | N | —CH₃ | -iso-propyl |
| A122 a, b, c, d, e or f | CH | N | —CH₃ | -ter-butyl |
| A123 a, b, c, d, e or f | CH | N | —CH₃ | —S(O)₂CF₃ |
| A124 a, b, c, d, e or f | CH | N | —CH₃ | —S(O)₂CH₃ |
| A125 a, b, c, d, e or f | CH | N | —CH₃ | —S(O)₂CH₃CH₃ |
| A126 a, b, c, d, e or f | CH | N | —CH₃ | —OCH₃ |
| A127 a, b, c, d, e or f | CH | N | —CH₃ | —OCH₂CH₃ |
| A128 a, b, c, d, e or f | CH | N | —CH₃ | —OCH(CH₃)₂ |
| A129 a, b, c, d, e or f | CH | CH | —Cl | —H |
| A130 a, b, c, d, e or f | CH | CH | —Cl | —Cl |
| A131 a, b, c, d, e or f | CH | CH | —Cl | —F |
| A132 a, b, c, d, e or f | CH | CH | —Cl | —Br |
| A133 a, b, c, d, e or f | CH | CH | —Cl | —CF₃ |
| A134 a, b, c, d, e or f | CH | CH | —Cl | —OCF₃ |
| A135 a, b, c, d, e or f | CH | CH | —Cl | —CH₃ |
| A136 a, b, c, d, e or f | CH | CH | —Cl | —CH₂CH₃ |
| A137 a, b, c, d, e or f | CH | CH | —Cl | -iso-propyl |
| A138 a, b, c, d, e or f | CH | CH | —Cl | -tert-butyl |
| A139 a, b, c, d, e or f | CH | CH | —Cl | —S(O)₂CF₃ |
| A140 a, b, c, d, e or f | CH | CH | —Cl | —S(O)₂CH₃ |
| A141 a, b, c, d, e or f | CH | CH | —Cl | —S(O)₂CH₃CH₃ |
| A142 a, b, c, d, e or f | CH | CH | —Cl | —OCH₃ |
| A143 a, b, c, d, e or f | CH | CH | —Cl | —OCH₂CH₃ |
| A144 a, b, c, d, e or f | CH | CH | —Cl | —OCH(CH₃)₂ |
| A145 a, b, c, d, e or f | CH | CH | —F | —H |
| A146 a, b, c, d, e or f | CH | CH | —F | —Cl |
| A147 a, b, c, d, e or f | CH | CH | —F | —F |
| A148 a, b, c, d, e or f | CH | CH | —F | —Br |
| A149 a, b, c, d, e or f | CH | CH | —F | —CF₃ |
| A150 a, b, c, d, e or f | CH | CH | —F | —OCF₃ |
| A151 a, b, c, d, e or f | CH | CH | —F | —CH₃ |
| A152 a, b, c, d, e or f | CH | CH | —F | —CH₂CH₃ |
| A153 a, b, c, d, e or f | CH | CH | —F | -iso-propyl |
| A154 a, b, c, d, e or f | CH | CH | —F | -tert-butyl |
| A155 a, b, c, d, e or f | CH | CH | —F | —S(O)₂CF₃ |
| A156 a, b, c, d, e or f | CH | CH | —F | —S(O)₂CH₃ |
| A157 a, b, c, d, e or f | CH | CH | —F | —S(O)₂CH₃CH₃ |
| A158 a, b, c, d, e or f | CH | CH | —F | —OCH₃ |
| A159 a, b, c, d, e or f | CH | CH | —F | —OCH₂CH₃ |
| A160 a, b, c, d, e or f | CH | CH | —F | —OCH(CH₃)₂ |
| A161 a, b, c, d, e or f | CH | CH | —CF₃ | —H |
| A162 a, b, c, d, e or f | CH | CH | —CF₃ | —Cl |
| A163 a, b, c, d, e or f | CH | CH | —CF₃ | —F |
| A164 a, b, c, d, e or f | CH | CH | —CF₃ | —Br |
| A165 a, b, c, d, e or f | CH | CH | —CF₃ | —CF₃ |
| A166 a, b, c, d, e or f | CH | CH | —CF₃ | —OCF₃ |
| A167 a, b, c, d, e or f | CH | CH | —CF₃ | —CH₃ |
| A168 a, b, c, d, e or f | CH | CH | —CF₃ | —CH₂CH₃ |
| A169 a, b, c, d, e or f | CH | CH | —CF₃ | -iso-propyl |
| A170 a, b, c, d, e or f | CH | CH | —CF₃ | -tert-butyl |
| A171 a, b, c, d, e or f | CH | CH | —CF₃ | —S(O)₂CF₃ |
| A172 a, b, c, d, e or f | CH | CH | —CF₃ | —S(O)₂CH₃ |
| A173 a, b, c, d, e or f | CH | CH | —CF₃ | —S(O)₂CH₃CH₃ |
| A174 a, b, c, d, e or f | CH | CH | —CF₃ | —OCH₃ |
| A175 a, b, c, d, e or f | CH | CH | —CF₃ | —OCH₂CH₃ |
| A176 a, b, c, d, e or f | CH | CH | —CF₃ | —OCH(CH₃)₂ |
| A177 a, b, c, d, e or f | CH | CH | —CH₃ | —H |
| A178 a, b, c, d, e or f | CH | CH | —CH₃ | —Cl |
| A179 a, b, c, d, e or f | CH | CH | —CH₃ | —F |
| A180 a, b, c, d, e or f | CH | CH | —CH₃ | —Br |
| A181 a, b, c, d, e or f | CH | CH | —CH₃ | —CF₃ |
| A182 a, b, c, d, e or f | CH | CH | —CH₃ | —OCF₃ |
| A183 a, b, c, d, e or f | CH | CH | —CH₃ | —CH₃ |
| A184 a, b, c, d, e or f | CH | CH | —CH₃ | —CH₂CH₃ |
| A185 a, b, c, d, e or f | CH | CH | —CH₃ | -iso-propyl |
| A186 a, b, c, d, e or f | CH | CH | —CH₃ | -tert-butyl |
| A187 a, b, c, d, e or f | CH | CH | —CH₃ | —S(O)₂CF₃ |
| A188 a, b, c, d, e or f | CH | CH | —CH₃ | —S(O)₂CH₃ |
| A189 a, b, c, d, e or f | CH | CH | —CH₃ | —S(O)₂CH₃CH₃ |
| A190 a, b, c, d, e or f | CH | CH | —CH₃ | —OCH₃ |
| A191 a, b, c, d, e or f | CH | CH | —CH₃ | —OCH₂CH₃ |
| A192 a, b, c, d, e or f | CH | CH | —CH₃ | —OCH(CH₃)₂ |

TABLE 2

(IIg)

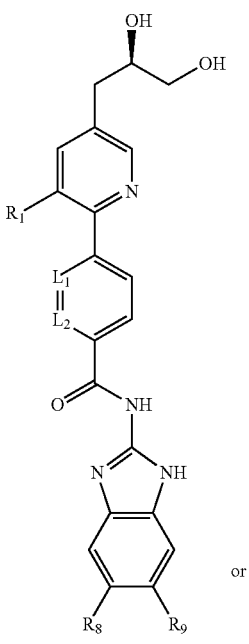

or

TABLE 2-continued
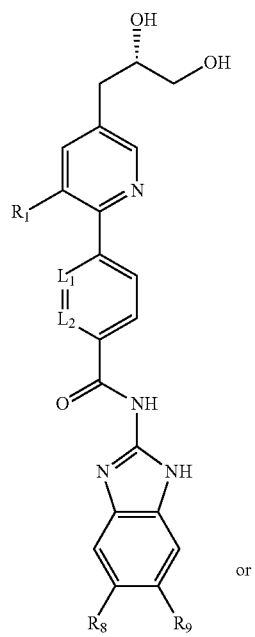 (IIh)
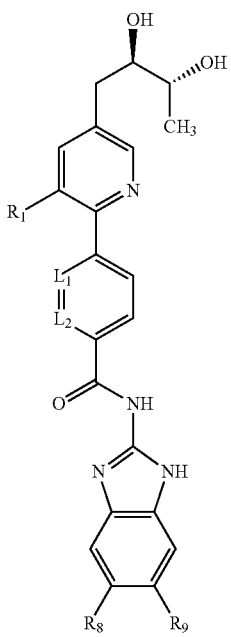 (IIj)
or
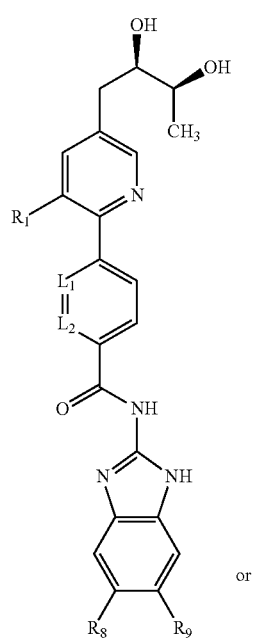 (IIi)
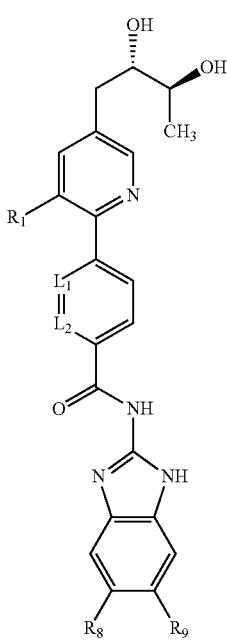 (IIk)
or TABLE 2-continued

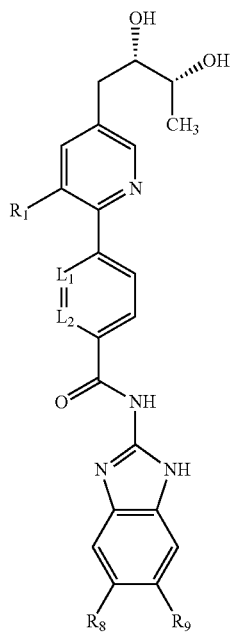

(IIm)

and pharmaceutically acceptable derivatives thereof, where:

| Compound | L₁ | L₂ | R₁ | R₈ | R₉ |
|---|---|---|---|---|---|
| B B1 g, h, i, j, k or m | N | CH | —Cl | —H | —H |
| B2 g, h, i, j, k or m | N | CH | —Cl | —H | —Cl |
| B3 g, h, i, j, k or m | N | CH | —Cl | —H | —F |
| B4 g, h, i, j, k or m | N | CH | —Cl | —H | —CH₃ |
| B5 g, h, i, j, k or m | N | CH | —Cl | —H | —OCH₃ |
| B6 g, h, i, j, k or m | N | CH | —Cl | —H | —OCH₂CH₃ |
| B7 g, h, i, j, k or m | N | CH | —Cl | —H | —CF₃ |
| B8 g, h, i, j, k or m | N | CH | —Cl | —H | —OCF₃ |
| B9 g, h, i, j, k or m | N | CH | —Cl | —H | iso-propyl |
| B10 g, h, i, j, k or m | N | CH | —Cl | —H | tert-butyl |
| B11 g, h, i, j, k or m | N | CH | —Cl | —Cl | —H |
| B12 g, h, i, j, k or m | N | CH | —Cl | —Cl | —Cl |
| B13 g, h, i, j, k or m | N | CH | —Cl | —Cl | —F |
| B14 g, h, i, j, k or m | N | CH | —Cl | —Cl | —CH₃ |
| B15 g, h, i, j, k or m | N | CH | —Cl | —Cl | —OCH₃ |
| B16 g, h, i, j, k or m | N | CH | —Cl | —Cl | —OCH₂CH₃ |
| B17 g, h, i, j, k or m | N | CH | —Cl | —Cl | —CF₃ |
| B18 g, h, i, j, k or m | N | CH | —Cl | —Cl | —OCF₃ |
| B19 g, h, i, j, k or m | N | CH | —Cl | —Cl | iso-propyl |
| B20 g, h, i, j, k or m | N | CH | —Cl | —Cl | tert-butyl |
| B21 g, h, i, j, k or m | N | CH | —Cl | —F | —H |
| B22 g, h, i, j, k or m | N | CH | —Cl | —F | —Cl |
| B23 g, h, i, j, k or m | N | CH | —Cl | —F | —F |
| B24 g, h, i, j, k or m | N | CH | —Cl | —F | —CH₃ |
| B25 g, h, i, j, k or m | N | CH | —Cl | —F | —OCH₃ |
| B26 g, h, i, j, k or m | N | CH | —Cl | —F | —OCH₂CH₃ |
| B27 g, h, i, j, k or m | N | CH | —Cl | —F | —CF₃ |
| B28 g, h, i, j, k or m | N | CH | —Cl | —F | —OCF₃ |
| B29 g, h, i, j, k or m | N | CH | —Cl | —F | iso-propyl |
| B30 g, h, i, j, k or m | N | CH | —Cl | —F | tert-butyl |
| B31 g, h, i, j, k or m | N | CH | —Cl | —CH₃ | —H |
| B32 g, h, i, j, k or m | N | CH | —Cl | —CH₃ | —Cl |
| B33 g, h, i, j, k or m | N | CH | —Cl | —CH₃ | —F |
| B34 g, h, i, j, k or m | N | CH | —Cl | —CH₃ | —CH₃ |
| B35 g, h, i, j, k or m | N | CH | —Cl | —CH₃ | —OCH₃ |
| B36 g, h, i, j, k or m | N | CH | —Cl | —CH₃ | —OCH₂CH₃ |
| B37 g, h, i, j, k or m | N | CH | —Cl | —CH₃ | —CF₃ |
| B38 g, h, i, j, k or m | N | CH | —Cl | —CH₃ | —OCF₃ |
| B39 g, h, i, j, k or m | N | CH | —Cl | —CH₃ | iso-propyl |
| B40 g, h, i, j, k or m | N | CH | —Cl | —CH₃ | tert-butyl |
| B41 g, h, i, j, k or m | N | CH | —Cl | —OCH₃ | —H |
| B42 g, h, i, j, k or m | N | CH | —Cl | —OCH₃ | —Cl |
| B43 g, h, i, j, k or m | N | CH | —Cl | —OCH₃ | —F |
| B44 g, h, i, j, k or m | N | CH | —Cl | —OCH₃ | —CH₃ |
| B45 g, h, i, j, k or m | N | CH | —Cl | —OCH₃ | —OCH₃ |
| B46 g, h, i, j, k or m | N | CH | —Cl | —OCH₃ | —OCH₂CH₃ |
| B47 g, h, i, j, k or m | N | CH | —Cl | —OCH₃ | —CF₃ |
| B48 g, h, i, j, k or m | N | CH | —Cl | —OCH₃ | —OCF₃ |
| B49 g, h, i, j, k or m | N | CH | —Cl | —OCH₃ | iso-propyl |
| B50 g, h, i, j, k or m | N | CH | —Cl | —OCH₃ | tert-butyl |
| B51 g, h, i, j, k or m | N | CH | —Cl | —OCH₂CH₃ | —H |
| B52 g, h, i, j, k or m | N | CH | —Cl | —OCH₂CH₃ | —Cl |
| B53 g, h, i, j, k or m | N | CH | —Cl | —OCH₂CH₃ | —F |
| B54 g, h, i, j, k or m | N | CH | —Cl | —OCH₂CH₃ | —CH₃ |
| B55 g, h, i, j, k or m | N | CH | —Cl | —OCH₂CH₃ | —OCH₃ |
| B56 g, h, i, j, k or m | N | CH | —Cl | —OCH₂CH₃ | —OCH₂CH₃ |
| B57 g, h, i, j, k or m | N | CH | —Cl | —OCH₂CH₃ | —CF₃ |
| B58 g, h, i, j, k or m | N | CH | —Cl | —OCH₂CH₃ | —OCF₃ |
| B59 g, h, i, j, k or m | N | CH | —Cl | —OCH₂CH₃ | iso-propyl |
| B60 g, h, i, j, k or m | N | CH | —Cl | —OCH₂CH₃ | tert-butyl |
| B61 g, h, i, j, k or m | N | CH | —Cl | —CF₃ | —H |
| B62 g, h, i, j, k or m | N | CH | —Cl | —CF₃ | —Cl |
| B63 g, h, i, j, k or m | N | CH | —Cl | —CF₃ | —F |
| B64 g, h, i, j, k or m | N | CH | —Cl | —CF₃ | —CH₃ |
| B65 g, h, i, j, k or m | N | CH | —Cl | —CF₃ | —OCH₃ |
| B66 g, h, i, j, k or m | N | CH | —Cl | —CF₃ | —OCH₂CH₃ |
| B67 g, h, i, j, k or m | N | CH | —Cl | —CF₃ | —CF₃ |
| B68 g, h, i, j, k or m | N | CH | —Cl | —CF₃ | —OCF₃ |
| B69 g, h, i, j, k or m | N | CH | —Cl | —CF₃ | iso-propyl |
| B70 g, h, i, j, k or m | N | CH | —Cl | —CF₃ | tert-butyl |
| B71 g, h, i, j, k or m | N | CH | —Cl | —OCF₃ | —H |
| B72 g, h, i, j, k or m | N | CH | —Cl | —OCF₃ | —Cl |
| B73 g, h, i, j, k or m | N | CH | —Cl | —OCF₃ | —F |
| B74 g, h, i, j, k or m | N | CH | —Cl | —OCF₃ | —CH₃ |
| B75 g, h, i, j, k or m | N | CH | —Cl | —OCF₃ | —OCH₃ |
| B76 g, h, i, j, k or m | N | CH | —Cl | —OCF₃ | —OCH₂CH₃ |
| B77 g, h, i, j, k or m | N | CH | —Cl | —OCF₃ | —CF₃ |
| B78 g, h, i, j, k or m | N | CH | —Cl | —OCF₃ | —OCF₃ |
| B79 g, h, i, j, k or m | N | CH | —Cl | —OCF₃ | iso-propyl |
| B80 g, h, i, j, k or m | N | CH | —Cl | —OCF₃ | tert-butyl |
| B81 g, h, i, j, k or m | N | CH | —Cl | iso-propyl | —H |
| B82 g, h, i, j, k or m | N | CH | —Cl | iso-propyl | —Cl |
| B83 g, h, i, j, k or m | N | CH | —Cl | iso-propyl | —F |
| B84 g, h, i, j, k or m | N | CH | —Cl | iso-propyl | —CH₃ |
| B85 g, h, i, j, k or m | N | CH | —Cl | iso-propyl | —OCH₃ |
| B86 g, h, i, j, k or m | N | CH | —Cl | iso-propyl | —OCH₂CH₃ |
| B87 g, h, i, j, k or m | N | CH | —Cl | iso-propyl | —CF₃ |
| B88 g, h, i, j, k or m | N | CH | —Cl | iso-propyl | —OCF₃ |
| B89 g, h, i, j, k or m | N | CH | —Cl | iso-propyl | iso-propyl |
| B90 g, h, i, j, k or m | N | CH | —Cl | iso-propyl | tert-butyl |
| B91 g, h, i, j, k or m | N | CH | —Cl | tert-butyl | —H |
| B92 g, h, i, j, k or m | N | CH | —Cl | tert-butyl | —Cl |
| B93 g, h, i, j, k or m | N | CH | —Cl | tert-butyl | —F |
| B94 g, h, i, j, k or m | N | CH | —Cl | tert-butyl | —CH₃ |
| B95 g, h, i, j, k or m | N | CH | —Cl | tert-butyl | —OCH₃ |
| B96 g, h, i, j, k or m | N | CH | —Cl | tert-butyl | —OCH₂CH₃ |
| B97 g, h, i, j, k or m | N | CH | —Cl | tert-butyl | —CF₃ |
| B98 g, h, i, j, k or m | N | CH | —Cl | tert-butyl | —OCF₃ |
| B99 g, h, i, j, k or m | N | CH | —Cl | tert-butyl | iso-propyl |
| B100 g, h, i, j, k or m | N | CH | —Cl | tert-butyl | tert-butyl |
| B101 g, h, i, j, k or m | N | CH | —F | —H | —H |
| B102 g, h, i, j, k or m | N | CH | —F | —H | —Cl |
| B103 g, h, i, j, k or m | N | CH | —F | —H | —F |
| B104 g, h, i, j, k or m | N | CH | —F | —H | —CH₃ |
| B105 g, h, i, j, k or m | N | CH | —F | —H | —OCH₃ |
| B106 g, h, i, j, k or m | N | CH | —F | —H | —OCH₂CH₃ |
| B107 g, h, i, j, k or m | N | CH | —F | —H | —CF₃ |
| B108 g, h, i, j, k or m | N | CH | —F | —H | —OCF₃ |
| B109 g, h, i, j, k or m | N | CH | —F | —H | iso-propyl |
| B110 g, h, i, j, k or m | N | CH | —F | —H | tert-butyl |
| B111 g, h, i, j, k or m | N | CH | —F | —Cl | —H |
| B112 g, h, i, j, k or m | N | CH | —F | —Cl | —Cl |
| B113 g, h, i, j, k or m | N | CH | —F | —Cl | —F |
| B114 g, h, i, j, k or m | N | CH | —F | —Cl | —CH₃ |
| B115 g, h, i, j, k or m | N | CH | —F | —Cl | —OCH₃ |
| B116 g, h, i, j, k or m | N | CH | —F | —Cl | —OCH₂CH₃ |
| B117 g, h, i, j, k or m | N | CH | —F | —Cl | —CF₃ |
| B118 g, h, i, j, k or m | N | CH | —F | —Cl | —OCF₃ |
| B119 g, h, i, j, k or m | N | CH | —F | —Cl | iso-propyl |
| B120 g, h, i, j, k or m | N | CH | —F | —Cl | tert-butyl |
| B121 g, h, i, j, k or m | N | CH | —F | —F | —H |
| B122 g, h, i, j, k or m | N | CH | —F | —F | —Cl |
| B123 g, h, i, j, k or m | N | CH | —F | —F | —F |
| B124 g, h, i, j, k or m | N | CH | —F | —F | —CH₃ |

TABLE 2-continued

| | | | | | |
|---|---|---|---|---|---|
| B125 g, h, i, j, k or m | N | CH | —F | —F | —OCH₃ |
| B126 g, h, i, j, k or m | N | CH | —F | —F | —OCH₂CH₃ |
| B127 g, h, i, j, k or m | N | CH | —F | —F | —CF₃ |
| B128 g, h, i, j, k or m | N | CH | —F | —F | —OCF₃ |
| B129 g, h, i, j, k or m | N | CH | —F | —F | iso-propyl |
| B130 g, h, i, j, k or m | N | CH | —F | —F | tert-butyl |
| B131 g, h, i, j, k or m | N | CH | —F | —CH₃ | —H |
| B132 g, h, i, j, k or m | N | CH | —F | —CH₃ | —Cl |
| B133 g, h, i, j, k or m | N | CH | —F | —CH₃ | —F |
| B134 g, h, i, j, k or m | N | CH | —F | —CH₃ | —CH₃ |
| B135 g, h, i, j, k or m | N | CH | —F | —CH₃ | —OCH₃ |
| B136 g, h, i, j, k or m | N | CH | —F | —CH₃ | —OCH₂CH₃ |
| B137 g, h, i, j, k or m | N | CH | —F | —CH₃ | —CF₃ |
| B138 g, h, i, j, k or m | N | CH | —F | —CH₃ | —OCF₃ |
| B139 g, h, i, j, k or m | N | CH | —F | —CH₃ | iso-propyl |
| B140 g, h, i, j, k or m | N | CH | —F | —CH₃ | tert-butyl |
| B141 g, h, i, j, k or m | N | CH | —F | —OCH₃ | —H |
| B142 g, h, i, j, k or m | N | CH | —F | —OCH₃ | —Cl |
| B143 g, h, i, j, k or m | N | CH | —F | —OCH₃ | —F |
| B144 g, h, i, j, k or m | N | CH | —F | —OCH₃ | —CH₃ |
| B145 g, h, i, j, k or m | N | CH | —F | —OCH₃ | —OCH₃ |
| B146 g, h, i, j, k or m | N | CH | —F | —OCH₃ | —OCH₂CH₃ |
| B147 g, h, i, j, k or m | N | CH | —F | —OCH₃ | —CF₃ |
| B148 g, h, i, j, k or m | N | CH | —F | —OCH₃ | —OCF₃ |
| B149 g, h, i, j, k or m | N | CH | —F | —OCH₃ | iso-propyl |
| B150 g, h, i, j, k or m | N | CH | —F | —OCH₃ | tert-butyl |
| B151 g, h, i, j, k or m | N | CH | —F | —OCH₂CH₃ | —H |
| B152 g, h, i, j, k or m | N | CH | —F | —OCH₂CH₃ | —Cl |
| B153 g, h, i, j, k or m | N | CH | —F | —OCH₂CH₃ | —F |
| B154 g, h, i, j, k or m | N | CH | —F | —OCH₂CH₃ | —CH₃ |
| B155 g, h, i, j, k or m | N | CH | —F | —OCH₂CH₃ | —OCH₃ |
| B156 g, h, i, j, k or m | N | CH | —F | —OCH₂CH₃ | —OCH₂CH₃ |
| B157 g, h, i, j, k or m | N | CH | —F | —OCH₂CH₃ | —CF₃ |
| B158 g, h, i, j, k or m | N | CH | —F | —OCH₂CH₃ | —OCF₃ |
| B159 g, h, i, j, k or m | N | CH | —F | —OCH₂CH₃ | iso-propyl |
| B160 g, h, i, j, k or m | N | CH | —F | —OCH₂CH₃ | tert-butyl |
| B161 g, h, i, j, k or m | N | CH | —F | —CF₃ | —H |
| B162 g, h, i, j, k or m | N | CH | —F | —CF₃ | —Cl |
| B163 g, h, i, j, k or m | N | CH | —F | —CF₃ | —F |
| B164 g, h, i, j, k or m | N | CH | —F | —CF₃ | —CH₃ |
| B165 g, h, i, j, k or m | N | CH | —F | —CF₃ | —OCH₃ |
| B166 g, h, i, j, k or m | N | CH | —F | —CF₃ | —OCH₂CH₃ |
| B167 g, h, i, j, k or m | N | CH | —F | —CF₃ | —CF₃ |
| B168 g, h, i, j, k or m | N | CH | —F | —CF₃ | —OCF₃ |
| B169 g, h, i, j, k or m | N | CH | —F | —CF₃ | iso-propyl |
| B170 g, h, i, j, k or m | N | CH | —F | —CF₃ | tert-butyl |
| B171 g, h, i, j, k or m | N | CH | —F | —OCF₃ | —H |
| B172 g, h, i, j, k or m | N | CH | —F | —OCF₃ | —Cl |
| B173 g, h, i, j, k or m | N | CH | —F | —OCF₃ | —F |
| B174 g, h, i, j, k or m | N | CH | —F | —OCF₃ | —CH₃ |
| B175 g, h, i, j, k or m | N | CH | —F | —OCF₃ | —OCH₃ |
| B176 g, h, i, j, k or m | N | CH | —F | —OCF₃ | —OCH₂CH₃ |
| B177 g, h, i, j, k or m | N | CH | —F | —OCF₃ | —CF₃ |
| B178 g, h, i, j, k or m | N | CH | —F | —OCF₃ | —OCF₃ |
| B179 g, h, i, j, k or m | N | CH | —F | —OCF₃ | iso-propyl |
| B180 g, h, i, j, k or m | N | CH | —F | —OCF₃ | tert-butyl |
| B181 g, h, i, j, k or m | N | CH | —F | iso-propyl | —H |
| B182 g, h, i, j, k or m | N | CH | —F | iso-propyl | —Cl |
| B183 g, h, i, j, k or m | N | CH | —F | iso-propyl | —F |
| B184 g, h, i, j, k or m | N | CH | —F | iso-propyl | —CH₃ |
| B185 g, h, i, j, k or m | N | CH | —F | iso-propyl | —OCH₃ |
| B186 g, h, i, j, k or m | N | CH | —F | iso-propyl | —OCH₂CH₃ |
| B187 g, h, i, j, k or m | N | CH | —F | iso-propyl | —CF₃ |
| B188 g, h, i, j, k or m | N | CH | —F | iso-propyl | —OCF₃ |
| B189 g, h, i, j, k or m | N | CH | —F | iso-propyl | iso-propyl |
| B190 g, h, i, j, k or m | N | CH | —F | iso-propyl | tert-butyl |
| B191 g, h, i, j, k or m | N | CH | —F | tert-butyl | —H |
| B192 g, h, i, j, k or m | N | CH | —F | tert-butyl | —Cl |
| B193 g, h, i, j, k or m | N | CH | —F | tert-butyl | —F |
| B194 g, h, i, j, k or m | N | CH | —F | tert-butyl | —CH₃ |
| B195 g, h, i, j, k or m | N | CH | —F | tert-butyl | —OCH₃ |
| B196 g, h, i, j, k or m | N | CH | —F | tert-butyl | —OCH₂CH₃ |
| B197 g, h, i, j, k or m | N | CH | —F | tert-butyl | —CF₃ |
| B198 g, h, i, j, k or m | N | CH | —F | tert-butyl | —OCF₃ |
| B199 g, h, i, j, k or m | N | CH | —F | tert-butyl | iso-propyl |
| B200 g, h, i, j, k or m | N | CH | —F | tert-butyl | tert-butyl |
| B201 g, h, i, j, k or m | N | CH | —CF₃ | —H | —H |
| B202 g, h, i, j, k or m | N | CH | —CF₃ | —H | —Cl |
| B203 g, h, i, j, k or m | N | CH | —CF₃ | —H | —F |
| B204 g, h, i, j, k or m | N | CH | —CF₃ | —H | —CH₃ |
| B205 g, h, i, j, k or m | N | CH | —CF₃ | —H | —OCH₃ |
| B206 g, h, i, j, k or m | N | CH | —CF₃ | —H | —OCH₂CH₃ |
| B207 g, h, i, j, k or m | N | CH | —CF₃ | —H | —CF₃ |
| B208 g, h, i, j, k or m | N | CH | —CF₃ | —H | —OCF₃ |
| B209 g, h, i, j, k or m | N | CH | —CF₃ | —H | iso-propyl |
| B210 g, h, i, j, k or m | N | CH | —CF₃ | —H | tert-butyl |
| B211 g, h, i, j, k or m | N | CH | —CF₃ | —Cl | —H |
| B212 g, h, i, j, k or m | N | CH | —CF₃ | —Cl | —Cl |
| B213 g, h, i, j, k or m | N | CH | —CF₃ | —Cl | —F |
| B214 g, h, i, j, k or m | N | CH | —CF₃ | —Cl | —CH₃ |
| B215 g, h, i, j, k or m | N | CH | —CF₃ | —Cl | —OCH₃ |
| B216 g, h, i, j, k or m | N | CH | —CF₃ | —Cl | —OCH₂CH₃ |
| B217 g, h, i, j, k or m | N | CH | —CF₃ | —Cl | —CF₃ |
| B218 g, h, i, j, k or m | N | CH | —CF₃ | —Cl | —OCF₃ |
| B219 g, h, i, j, k or m | N | CH | —CF₃ | —Cl | iso-propyl |
| B220 g, h, i, j, k or m | N | CH | —CF₃ | —Cl | tert-butyl |
| B221 g, h, i, j, k or m | N | CH | —CF₃ | —F | —H |
| B222 g, h, i, j, k or m | N | CH | —CF₃ | —F | —Cl |
| B223 g, h, i, j, k or m | N | CH | —CF₃ | —F | —F |
| B224 g, h, i, j, k or m | N | CH | —CF₃ | —F | —CH₃ |
| B225 g, h, i, j, k or m | N | CH | —CF₃ | —F | —OCH₃ |
| B226 g, h, i, j, k or m | N | CH | —CF₃ | —F | —OCH₂CH₃ |
| B227 g, h, i, j, k or m | N | CH | —CF₃ | —F | —CF₃ |
| B228 g, h, i, j, k or m | N | CH | —CF₃ | —F | —OCF₃ |
| B229 g, h, i, j, k or m | N | CH | —CF₃ | —F | iso-butyl |
| B230 g, h, i, j, k or m | N | CH | —CF₃ | —F | tert-butyl |
| B231 g, h, i, j, k or m | N | CH | —CF₃ | —CH₃ | —H |
| B232 g, h, i, j, k or m | N | CH | —CF₃ | —CH₃ | —Cl |
| B233 g, h, i, j, k or m | N | CH | —CF₃ | —CH₃ | —F |
| B234 g, h, i, j, k or m | N | CH | —CF₃ | —CH₃ | —CH₃ |
| B235 g, h, i, j, k or m | N | CH | —CF₃ | —CH₃ | —OCH₃ |
| B236 g, h, i, j, k or m | N | CH | —CF₃ | —CH₃ | —OCH₂CH₃ |
| B237 g, h, i, j, k or m | N | CH | —CF₃ | —CH₃ | —CF₃ |
| B238 g, h, i, j, k or m | N | CH | —CF₃ | —CH₃ | —OCF₃ |
| B239 g, h, i, j, k or m | N | CH | —CF₃ | —CH₃ | iso-propyl |
| B240 g, h, i, j, k or m | N | CH | —CF₃ | —CH₃ | tert-butyl |
| B241 g, h, i, j, k or m | N | CH | —CF₃ | —OCH₃ | —H |
| B242 g, h, i, j, k or m | N | CH | —CF₃ | —OCH₃ | —Cl |
| B243 g, h, i, j, k or m | N | CH | —CF₃ | —OCH₃ | —F |
| B244 g, h, i, j, k or m | N | CH | —CF₃ | —OCH₃ | —CH₃ |
| B245 g, h, i, j, k or m | N | CH | —CF₃ | —OCH₃ | —OCH₃ |
| B246 g, h, i, j, k or m | N | CH | —CF₃ | —OCH₃ | —OCH₂CH₃ |
| B247 g, h, i, j, k or m | N | CH | —CF₃ | —OCH₃ | —CF₃ |
| B248 g, h, i, j, k or m | N | CH | —CF₃ | —OCH₃ | —OCF₃ |
| B249 g, h, i, j, k or m | N | CH | —CF₃ | —OCH₃ | iso-propyl |
| B250 g, h, i, j, k or m | N | CH | —CF₃ | —OCH₃ | tert-butyl |
| B251 g, h, i, j, k or m | N | CH | —CF₃ | —OCH₂CH₃ | —H |
| B252 g, h, i, j, k or m | N | CH | —CF₃ | —OCH₂CH₃ | —Cl |
| B253 g, h, i, j, k or m | N | CH | —CF₃ | —OCH₂CH₃ | —F |
| B254 g, h, i, j, k or m | N | CH | —CF₃ | —OCH₂CH₃ | —CH₃ |
| B255 g, h, i, j, k or m | N | CH | —CF₃ | —OCH₂CH₃ | —OCH₃ |
| B256 g, h, i, j, k or m | N | CH | —CF₃ | —OCH₂CH₃ | —OCH₂CH₃ |
| B257 g, h, i, j, k or m | N | CH | —CF₃ | —OCH₂CH₃ | —CF₃ |
| B258 g, h, i, j, k or m | N | CH | —CF₃ | —OCH₂CH₃ | —OCF₃ |
| B259 g, h, i, j, k or m | N | CH | —CF₃ | —OCH₂CH₃ | iso-propyl |
| B260 g, h, i, j, k or m | N | CH | —CF₃ | —OCH₂CH₃ | tert-butyl |
| B261 g, h, i, j, k or m | N | CH | —CF₃ | —CF₃ | —H |
| B262 g, h, i, j, k or m | N | CH | —CF₃ | —CF₃ | —Cl |
| B263 g, h, i, j, k or m | N | CH | —CF₃ | —CF₃ | —F |
| B264 g, h, i, j, k or m | N | CH | —CF₃ | —CF₃ | —CH₃ |
| B265 g, h, i, j, k or m | N | CH | —CF₃ | —CF₃ | —OCH₃ |
| B266 g, h, i, j, k or m | N | CH | —CF₃ | —CF₃ | —OCH₂CH₃ |
| B267 g, h, i, j, k or m | N | CH | —CF₃ | —CF₃ | —CF₃ |
| B268 g, h, i, j, k or m | N | CH | —CF₃ | —CF₃ | —OCF₃ |
| B269 g, h, i, j, k or m | N | CH | —CF₃ | —CF₃ | iso-propyl |
| B270 g, h, i, j, k or m | N | CH | —CF₃ | —CF₃ | tert-butyl |
| B271 g, h, i, j, k or m | N | CH | —CF₃ | —OCF₃ | —H |
| B272 g, h, i, j, k or m | N | CH | —CF₃ | —OCF₃ | —Cl |
| B273 g, h, i, j, k or m | N | CH | —CF₃ | —OCF₃ | —F |
| B274 g, h, i, j, k or m | N | CH | —CF₃ | —OCF₃ | —CH₃ |
| B275 g, h, i, j, k or m | N | CH | —CF₃ | —OCF₃ | —OCH₃ |
| B276 g, h, i, j, k or m | N | CH | —CF₃ | —OCF₃ | —OCH₂CH₃ |
| B277 g, h, i, j, k or m | N | CH | —CF₃ | —OCF₃ | —CF₃ |
| B278 g, h, i, j, k or m | N | CH | —CF₃ | —OCF₃ | —OCF₃ |
| B279 g, h, i, j, k or m | N | CH | —CF₃ | —OCF₃ | iso-propyl |
| B280 g, h, i, j, k or m | N | CH | —CF₃ | —OCF₃ | tert-butyl |
| B281 g, h, i, j, k or m | N | CH | —CF₃ | iso-propyl | —H |
| B282 g, h, i, j, k or m | N | CH | —CF₃ | iso-propyl | —Cl |
| B283 g, h, i, j, k or m | N | CH | —CF₃ | iso-propyl | —F |
| B284 g, h, i, j, k or m | N | CH | —CF₃ | iso-propyl | —CH₃ |

TABLE 2-continued

| | | | | | |
|---|---|---|---|---|---|
| B285 | g, h, i, j, k or m | N  CH | —CF₃ | iso-propyl | —OCH₃ |
| B286 | g, h, i, j, k or m | N  CH | —CF₃ | iso-propyl | —OCH₂CH₃ |
| B287 | g, h, i, j, k or m | N  CH | —CF₃ | iso-propyl | —CF₃ |
| B288 | g, h, i, j, k or m | N  CH | —CF₃ | iso-propyl | —OCF₃ |
| B289 | g, h, i, j, k or m | N  CH | —CF₃ | iso-propyl | iso-propyl |
| B290 | g, h, i, j, k or m | N  CH | —CF₃ | iso-propyl | tert-butyl |
| B291 | g, h, i, j, k or m | N  CH | —CF₃ | tert-butyl | —H |
| B292 | g, h, i, j, k or m | N  CH | —CF₃ | tert-butyl | —Cl |
| B293 | g, h, i, j, k or m | N  CH | —CF₃ | tert-butyl | —F |
| B294 | g, h, i, j, k or m | N  CH | —CF₃ | tert-butyl | —CH₃ |
| B295 | g, h, i, j, k or m | N  CH | —CF₃ | tert-butyl | —OCH₃ |
| B296 | g, h, i, j, k or m | N  CH | —CF₃ | tert-butyl | —OCH₂CH₃ |
| B297 | g, h, i, j, k or m | N  CH | —CF₃ | tert-butyl | —CF₃ |
| B298 | g, h, i, j, k or m | N  CH | —CF₃ | tert-butyl | —OCF₃ |
| B299 | g, h, i, j, k or m | N  CH | —CF₃ | tert-butyl | iso-propyl |
| B300 | g, h, i, j, k or m | N  CH | —CF₃ | tert-butyl | tert-butyl |
| B301 | g, h, i, j, k or m | CH  N | —Cl | —H | —H |
| B302 | g, h, i, j, k or m | CH  N | —Cl | —H | —Cl |
| B303 | g, h, i, j, k or m | CH  N | —Cl | —H | —F |
| B304 | g, h, i, j, k or m | CH  N | —Cl | —H | —CH₃ |
| B305 | g, h, i, j, k or m | CH  N | —Cl | —H | —OCH₃ |
| B306 | g, h, i, j, k or m | CH  N | —Cl | —H | —OCH₂CH₃ |
| B307 | g, h, i, j, k or m | CH  N | —Cl | —H | —CF₃ |
| B308 | g, h, i, j, k or m | CH  N | —Cl | —H | —OCF₃ |
| B309 | g, h, i, j, k or m | CH  N | —Cl | —H | iso-propyl |
| B310 | g, h, i, j, k or m | CH  N | —Cl | —H | tert-butyl |
| B311 | g, h, i, j, k or m | CH  N | —Cl | —Cl | —H |
| B312 | g, h, i, j, k or m | CH  N | —Cl | —Cl | —Cl |
| B313 | g, h, i, j, k or m | CH  N | —Cl | —Cl | —F |
| B314 | g, h, i, j, k or m | CH  N | —Cl | —Cl | —CH₃ |
| B315 | g, h, i, j, k or m | CH  N | —Cl | —Cl | —OCH₃ |
| B316 | g, h, i, j, k or m | CH  N | —Cl | —Cl | —OCH₂CH₃ |
| B317 | g, h, i, j, k or m | CH  N | —Cl | —Cl | —CF₃ |
| B318 | g, h, i, j, k or m | CH  N | —Cl | —Cl | —OCF₃ |
| B319 | g, h, i, j, k or m | CH  N | —Cl | —Cl | iso-propyl |
| B320 | g, h, i, j, k or m | CH  N | —Cl | —Cl | tert-butyl |
| B321 | g, h, i, j, k or m | CH  N | —Cl | —F | —H |
| B322 | g, h, i, j, k or m | CH  N | —Cl | —F | —Cl |
| B323 | g, h, i, j, k or m | CH  N | —Cl | —F | —F |
| B324 | g, h, i, j, k or m | CH  N | —Cl | —F | —CH₃ |
| B325 | g, h, i, j, k or m | CH  N | —Cl | —F | —OCH₃ |
| B326 | g, h, i, j, k or m | CH  N | —Cl | —F | —OCH₂CH₃ |
| B327 | g, h, i, j, k or m | CH  N | —Cl | —F | —CF₃ |
| B328 | g, h, i, j, k or m | CH  N | —Cl | —F | —OCF₃ |
| B329 | g, h, i, j, k or m | CH  N | —Cl | —F | iso-propyl |
| B330 | g, h, i, j, k or m | CH  N | —Cl | —F | tert-butyl |
| B331 | g, h, i, j, k or m | CH  N | —Cl | —CH₃ | —H |
| B332 | g, h, i, j, k or m | CH  N | —Cl | —CH₃ | —Cl |
| B333 | g, h, i, j, k or m | CH  N | —Cl | —CH₃ | —F |
| B334 | g, h, i, j, k or m | CH  N | —Cl | —CH₃ | —CH₃ |
| B335 | g, h, i, j, k or m | CH  N | —Cl | —CH₃ | —OCH₃ |
| B336 | g, h, i, j, k or m | CH  N | —Cl | —CH₃ | —OCH₂CH₃ |
| B337 | g, h, i, j, k or m | CH  N | —Cl | —CH₃ | —CF₃ |
| B338 | g, h, i, j, k or m | CH  N | —Cl | —CH₃ | —OCF₃ |
| B339 | g, h, i, j, k or m | CH  N | —Cl | —CH₃ | iso-propyl |
| B340 | g, h, i, j, k or m | CH  N | —Cl | —CH₃ | tert-butyl |
| B341 | g, h, i, j, k or m | CH  N | —Cl | —OCH₃ | —H |
| B342 | g, h, i, j, k or m | CH  N | —Cl | —OCH₃ | —Cl |
| B343 | g, h, i, j, k or m | CH  N | —Cl | —OCH₃ | —F |
| B344 | g, h, i, j, k or m | CH  N | —Cl | —OCH₃ | —CH₃ |
| B345 | g, h, i, j, k or m | CH  N | —Cl | —OCH₃ | —OCH₃ |
| B346 | g, h, i, j, k or m | CH  N | —Cl | —OCH₃ | —OCH₂CH₃ |
| B347 | g, h, i, j, k or m | CH  N | —Cl | —OCH₃ | —CF₃ |
| B348 | g, h, i, j, k or m | CH  N | —Cl | —OCH₃ | —OCF₃ |
| B349 | g, h, i, j, k or m | CH  N | —Cl | —OCH₃ | iso-propyl |
| B350 | g, h, i, j, k or m | CH  N | —Cl | —OCH₃ | tert-butyl |
| B351 | g, h, i, j, k or m | CH  N | —Cl | —OCH₂CH₃ | —H |
| B352 | g, h, i, j, k or m | CH  N | —Cl | —OCH₂CH₃ | —Cl |
| B353 | g, h, i, j, k or m | CH  N | —Cl | —OCH₂CH₃ | —F |
| B354 | g, h, i, j, k or m | CH  N | —Cl | —OCH₂CH₃ | —CH₃ |
| B355 | g, h, i, j, k or m | CH  N | —Cl | —OCH₂CH₃ | —OCH₃ |
| B356 | g, h, i, j, k or m | CH  N | —Cl | —OCH₂CH₃ | —OCH₂CH₃ |
| B357 | g, h, i, j, k or m | CH  N | —Cl | —OCH₂CH₃ | —CF₃ |
| B358 | g, h, i, j, k or m | CH  N | —Cl | —OCH₂CH₃ | —OCF₃ |
| B359 | g, h, i, j, k or m | CH  N | —Cl | —OCH₂CH₃ | iso-propyl |
| B360 | g, h, i, j, k or m | CH  N | —Cl | —OCH₂CH₃ | tert-butyl |
| B361 | g, h, i, j, k or m | CH  N | —Cl | —CF₃ | —H |
| B362 | g, h, i, j, k or m | CH  N | —Cl | —CF₃ | —Cl |
| B363 | g, h, i, j, k or m | CH  N | —Cl | —CF₃ | —F |
| B364 | g, h, i, j, k or m | CH  N | —Cl | —CF₃ | —CH₃ |
| B365 | g, h, i, j, k or m | CH  N | —Cl | —CF₃ | —OCH₃ |
| B366 | g, h, i, j, k or m | CH  N | —Cl | —CF₃ | —OCH₂CH₃ |
| B367 | g, h, i, j, k or m | CH  N | —Cl | —CF₃ | —CF₃ |
| B368 | g, h, i, j, k or m | CH  N | —Cl | —CF₃ | —OCF₃ |
| B369 | g, h, i, j, k or m | CH  N | —Cl | —CF₃ | iso-propyl |
| B370 | g, h, i, j, k or m | CH  N | —Cl | —CF₃ | tert-butyl |
| B371 | g, h, i, j, k or m | CH  N | —Cl | —OCF₃ | —H |
| B372 | g, h, i, j, k or m | CH  N | —Cl | —OCF₃ | —Cl |
| B373 | g, h, i, j, k or m | CH  N | —Cl | —OCF₃ | —F |
| B374 | g, h, i, j, k or m | CH  N | —Cl | —OCF₃ | —CH₃ |
| B375 | g, h, i, j, k or m | CH  N | —Cl | —OCF₃ | —OCH₃ |
| B376 | g, h, i, j, k or m | CH  N | —Cl | —OCF₃ | —OCH₂CH₃ |
| B377 | g, h, i, j, k or m | CH  N | —Cl | —OCF₃ | —CF₃ |
| B378 | g, h, i, j, k or m | CH  N | —Cl | —OCF₃ | —OCF₃ |
| B379 | g, h, i, j, k or m | CH  N | —Cl | —OCF₃ | iso-propyl |
| B380 | g, h, i, j, k or m | CH  N | —Cl | —OCF₃ | tert-butyl |
| B381 | g, h, i, j, k or m | CH  N | —Cl | iso-propyl | —H |
| B382 | g, h, i, j, k or m | CH  N | —Cl | iso-propyl | —Cl |
| B383 | g, h, i, j, k or m | CH  N | —Cl | iso-propyl | —F |
| B384 | g, h, i, j, k or m | CH  N | —Cl | iso-propyl | —CH₃ |
| B385 | g, h, i, j, k or m | CH  N | —Cl | iso-propyl | —OCH₃ |
| B386 | g, h, i, j, k or m | CH  N | —Cl | iso-propyl | —OCH₂CH₃ |
| B387 | g, h, i, j, k or m | CH  N | —Cl | iso-propyl | —CF₃ |
| B388 | g, h, i, j, k or m | CH  N | —Cl | iso-propyl | —OCF₃ |
| B389 | g, h, i, j, k or m | CH  N | —Cl | iso-propyl | iso-propyl |
| B390 | g, h, i, j, k or m | CH  N | —Cl | iso-propyl | tert-butyl |
| B391 | g, h, i, j, k or m | CH  N | —Cl | tert-butyl | —H |
| B392 | g, h, i, j, k or m | CH  N | —Cl | tert-butyl | —Cl |
| B393 | g, h, i, j, k or m | CH  N | —Cl | tert-butyl | —F |
| B394 | g, h, i, j, k or m | CH  N | —Cl | tert-butyl | —CH₃ |
| B395 | g, h, i, j, k or m | CH  N | —Cl | tert-butyl | —OCH₃ |
| B396 | g, h, i, j, k or m | CH  N | —Cl | tert-butyl | —OCH₂CH₃ |
| B397 | g, h, i, j, k or m | CH  N | —Cl | tert-butyl | —CF₃ |
| B398 | g, h, i, j, k or m | CH  N | —Cl | tert-butyl | —OCF₃ |
| B399 | g, h, i, j, k or m | CH  N | —Cl | tert-butyl | iso-propyl |
| B400 | g, h, i, j, k or m | CH  N | —Cl | tert-butyl | tert-butyl |
| B401 | g, h, i, j, k or m | CH  N | —F | —H | —H |
| B402 | g, h, i, j, k or m | CH  N | —F | —H | —Cl |
| B403 | g, h, i, j, k or m | CH  N | —F | —H | —F |
| B404 | g, h, i, j, k or m | CH  N | —F | —H | —CH₃ |
| B405 | g, h, i, j, k or m | CH  N | —F | —H | —OCH₃ |
| B406 | g, h, i, j, k or m | CH  N | —F | —H | —OCH₂CH₃ |
| B407 | g, h, i, j, k or m | CH  N | —F | —H | —CF₃ |
| B408 | g, h, i, j, k or m | CH  N | —F | —H | —OCF₃ |
| B409 | g, h, i, j, k or m | CH  N | —F | —H | iso-propyl |
| B410 | g, h, i, j, k or m | CH  N | —F | —H | tert-butyl |
| B411 | g, h, i, j, k or m | CH  N | —F | —Cl | —H |
| B412 | g, h, i, j, k or m | CH  N | —F | —Cl | —Cl |
| B413 | g, h, i, j, k or m | CH  N | —F | —Cl | —F |
| B414 | g, h, i, j, k or m | CH  N | —F | —Cl | —CH₃ |
| B415 | g, h, i, j, k or m | CH  N | —F | —Cl | —OCH₃ |
| B416 | g, h, i, j, k or m | CH  N | —F | —Cl | —OCH₂CH₃ |
| B417 | g, h, i, j, k or m | CH  N | —F | —Cl | —CF₃ |
| B418 | g, h, i, j, k or m | CH  N | —F | —Cl | —OCF₃ |
| B419 | g, h, i, j, k or m | CH  N | —F | —Cl | iso-propyl |
| B420 | g, h, i, j, k or m | CH  N | —F | —Cl | tert-butyl |
| B421 | g, h, i, j, k or m | CH  N | —F | —F | —H |
| B422 | g, h, i, j, k or m | CH  N | —F | —F | —Cl |
| B423 | g, h, i, j, k or m | CH  N | —F | —F | —F |
| B424 | g, h, i, j, k or m | CH  N | —F | —F | —CH₃ |
| B425 | g, h, i, j, k or m | CH  N | —F | —F | —OCH₃ |
| B426 | g, h, i, j, k or m | CH  N | —F | —F | —OCH₂CH₃ |
| B427 | g, h, i, j, k or m | CH  N | —F | —F | —CF₃ |
| B428 | g, h, i, j, k or m | CH  N | —F | —F | —OCF₃ |
| B429 | g, h, i, j, k or m | CH  N | —F | —F | iso-propyl |
| B430 | g, h, i, j, k or m | CH  N | —F | —F | tert-butyl |
| B431 | g, h, i, j, k or m | CH  N | —F | —CH₃ | —H |
| B432 | g, h, i, j, k or m | CH  N | —F | —CH₃ | —Cl |
| B433 | g, h, i, j, k or m | CH  N | —F | —CH₃ | —F |
| B434 | g, h, i, j, k or m | CH  N | —F | —CH₃ | —CH₃ |
| B435 | g, h, i, j, k or m | CH  N | —F | —CH₃ | —OCH₃ |
| B436 | g, h, i, j, k or m | CH  N | —F | —CH₃ | —OCH₂CH₃ |
| B437 | g, h, i, j, k or m | CH  N | —F | —CH₃ | —CF₃ |
| B438 | g, h, i, j, k or m | CH  N | —F | —CH₃ | —OCF₃ |
| B439 | g, h, i, j, k or m | CH  N | —F | —CH₃ | iso-propyl |
| B440 | g, h, i, j, k or m | CH  N | —F | —CH₃ | tert-butyl |
| B441 | g, h, i, j, k or m | CH  N | —F | —OCH₃ | —H |
| B442 | g, h, i, j, k or m | CH  N | —F | —OCH₃ | —Cl |
| B443 | g, h, i, j, k or m | CH  N | —F | —OCH₃ | —F |
| B444 | g, h, i, j, k or m | CH  N | —F | —OCH₃ | —CH₃ |

TABLE 2-continued

| | | | | | |
|---|---|---|---|---|---|
| B445 g, h, i, j, k or m | CH | N | —F | —OCH$_3$ | —OCH$_3$ |
| B446 g, h, i, j, k or m | CH | N | —F | —OCH$_3$ | —OCH$_2$CH$_3$ |
| B447 g, h, i, j, k or m | CH | N | —F | —OCH$_3$ | —CF$_3$ |
| B448 g, h, i, j, k or m | CH | N | —F | —OCH$_3$ | —OCF$_3$ |
| B449 g, h, i, j, k or m | CH | N | —F | —OCH$_3$ | iso-propyl |
| B450 g, h, i, j, k or m | CH | N | —F | —OCH$_3$ | tert-butyl |
| B451 g, h, i, j, k or m | CH | N | —F | —OCH$_2$CH$_3$ | —H |
| B452 g, h, i, j, k or m | CH | N | —F | —OCH$_2$CH$_3$ | —Cl |
| B453 g, h, i, j, k or m | CH | N | —F | —OCH$_2$CH$_3$ | —F |
| B454 g, h, i, j, k or m | CH | N | —F | —OCH$_2$CH$_3$ | —CH$_3$ |
| B455 g, h, i, j, k or m | CH | N | —F | —OCH$_2$CH$_3$ | —OCH$_3$ |
| B456 g, h, i, j, k or m | CH | N | —F | —OCH$_2$CH$_3$ | —OCH$_2$CH$_3$ |
| B457 g, h, i, j, k or m | CH | N | —F | —OCH$_2$CH$_3$ | —CF$_3$ |
| B458 g, h, i, j, k or m | CH | N | —F | —OCH$_2$CH$_3$ | —OCF$_3$ |
| B459 g, h, i, j, k or m | CH | N | —F | —OCH$_2$CH$_3$ | iso-propyl |
| B460 g, h, i, j, k or m | CH | N | —F | —OCH$_2$CH$_3$ | tert-butyl |
| B461 g, h, i, j, k or m | CH | N | —F | —CF$_3$ | —H |
| B462 g, h, i, j, k or m | CH | N | —F | —CF$_3$ | —Cl |
| B463 g, h, i, j, k or m | CH | N | —F | —CF$_3$ | —F |
| B464 g, h, i, j, k or m | CH | N | —F | —CF$_3$ | —CH$_3$ |
| B465 g, h, i, j, k or m | CH | N | —F | —CF$_3$ | —OCH$_3$ |
| B466 g, h, i, j, k or m | CH | N | —F | —CF$_3$ | —OCH$_2$CH$_3$ |
| B467 g, h, i, j, k or m | CH | N | —F | —CF$_3$ | —CF$_3$ |
| B468 g, h, i, j, k or m | CH | N | —F | —CF$_3$ | —OCF$_3$ |
| B469 g, h, i, j, k or m | CH | N | —F | —CF$_3$ | iso-propyl |
| B470 g, h, i, j, k or m | CH | N | —F | —CF$_3$ | tert-butyl |
| B471 g, h, i, j, k or m | CH | N | —F | —OCF$_3$ | —H |
| B472 g, h, i, j, k or m | CH | N | —F | —OCF$_3$ | —Cl |
| B473 g, h, i, j, k or m | CH | N | —F | —OCF$_3$ | —F |
| B474 g, h, i, j, k or m | CH | N | —F | —OCF$_3$ | —CH$_3$ |
| B475 g, h, i, j, k or m | CH | N | —F | —OCF$_3$ | —OCH$_3$ |
| B476 g, h, i, j, k or m | CH | N | —F | —OCF$_3$ | —OCH$_2$CH$_3$ |
| B477 g, h, i, j, k or m | CH | N | —F | —OCF$_3$ | —CF$_3$ |
| B478 g, h, i, j, k or m | CH | N | —F | —OCF$_3$ | —OCF$_3$ |
| B479 g, h, i, j, k or m | CH | N | —F | —OCF$_3$ | iso-propyl |
| B480 g, h, i, j, k or m | CH | N | —F | —OCF$_3$ | tert-butyl |
| B481 g, h, i, j, k or m | CH | N | —F | iso-propyl | —H |
| B482 g, h, i, j, k or m | CH | N | —F | iso-propyl | —Cl |
| B483 g, h, i, j, k or m | CH | N | —F | iso-propyl | —F |
| B484 g, h, i, j, k or m | CH | N | —F | iso-propyl | —CH$_3$ |
| B485 g, h, i, j, k or m | CH | N | —F | iso-propyl | —OCH$_3$ |
| B486 g, h, i, j, k or m | CH | N | —F | iso-propyl | —OCH$_2$CH$_3$ |
| B487 g, h, i, j, k or m | CH | N | —F | iso-propyl | —CF$_3$ |
| B488 g, h, i, j, k or m | CH | N | —F | iso-propyl | —OCF$_3$ |
| B489 g, h, i, j, k or m | CH | N | —F | iso-propyl | iso-propyl |
| B490 g, h, i, j, k or m | CH | N | —F | iso-propyl | tert-butyl |
| B491 g, h, i, j, k or m | CH | N | —F | tert-butyl | —H |
| B492 g, h, i, j, k or m | CH | N | —F | tert-butyl | —Cl |
| B493 g, h, i, j, k or m | CH | N | —F | tert-butyl | —F |
| B494 g, h, i, j, k or m | CH | N | —F | tert-butyl | —CH$_3$ |
| B495 g, h, i, j, k or m | CH | N | —F | tert-butyl | —OCH$_3$ |
| B496 g, h, i, j, k or m | CH | N | —F | tert-butyl | —OCH$_2$CH$_3$ |
| B497 g, h, i, j, k or m | CH | N | —F | tert-butyl | —CF$_3$ |
| B498 g, h, i, j, k or m | CH | N | —F | tert-butyl | —OCF$_3$ |
| B499 g, h, i, j, k or m | CH | N | —F | tert-butyl | iso-propyl |
| B500 g, h, i, j, k or m | CH | N | —F | tert-butyl | tert-butyl |
| B501 g, h, i, j, k or m | CH | N | —CF$_3$ | —H | —H |
| B502 g, h, i, j, k or m | CH | N | —CF$_3$ | —H | —Cl |
| B503 g, h, i, j, k or m | CH | N | —CF$_3$ | —H | —F |
| B504 g, h, i, j, k or m | CH | N | —CF$_3$ | —H | —CH$_3$ |
| B505 g, h, i, j, k or m | CH | N | —CF$_3$ | —H | —OCH$_3$ |
| B506 g, h, i, j, k or m | CH | N | —CF$_3$ | —H | —OCH$_2$CH$_3$ |
| B507 g, h, i, j, k or m | CH | N | —CF$_3$ | —H | —CF$_3$ |
| B508 g, h, i, j, k or m | CH | N | —CF$_3$ | —H | —OCF$_3$ |
| B509 g, h, i, j, k or m | CH | N | —CF$_3$ | —H | iso-propyl |
| B510 g, h, i, j, k or m | CH | N | —CF$_3$ | —H | tert-butyl |
| B511 g, h, i, j, k or m | CH | N | —CF$_3$ | —Cl | —H |
| B512 g, h, i, j, k or m | CH | N | —CF$_3$ | —Cl | —Cl |
| B513 g, h, i, j, k or m | CH | N | —CF$_3$ | —Cl | —F |
| B514 g, h, i, j, k or m | CH | N | —CF$_3$ | —Cl | —CH$_3$ |
| B515 g, h, i, j, k or m | CH | N | —CF$_3$ | —Cl | —OCH$_3$ |
| B516 g, h, i, j, k or m | CH | N | —CF$_3$ | —Cl | —OCH$_2$CH$_3$ |
| B517 g, h, i, j, k or m | CH | N | —CF$_3$ | —Cl | —CF$_3$ |
| B518 g, h, i, j, k or m | CH | N | —CF$_3$ | —Cl | —OCF$_3$ |
| B519 g, h, i, j, k or m | CH | N | —CF$_3$ | —Cl | iso-propyl |
| B520 g, h, i, j, k or m | CH | N | —CF$_3$ | —Cl | tert-butyl |
| B521 g, h, i, j, k or m | CH | N | —CF$_3$ | —F | —H |
| B522 g, h, i, j, k or m | CH | N | —CF$_3$ | —F | —Cl |
| B523 g, h, i, j, k or m | CH | N | —CF$_3$ | —F | —F |
| B524 g, h, i, j, k or m | CH | N | —CF$_3$ | —F | —CH$_3$ |
| B525 g, h, i, j, k or m | CH | N | —CF$_3$ | —F | —OCH$_3$ |
| B526 g, h, i, j, k or m | CH | N | —CF$_3$ | —F | —OCH$_2$CH$_3$ |
| B527 g, h, i, j, k or m | CH | N | —CF$_3$ | —F | —CF$_3$ |
| B528 g, h, i, j, k or m | CH | N | —CF$_3$ | —F | —OCF$_3$ |
| B529 g, h, i, j, k or m | CH | N | —CF$_3$ | —F | iso-propyl |
| B530 g, h, i, j, k or m | CH | N | —CF$_3$ | —F | tert-butyl |
| B531 g, h, i, j, k or m | CH | N | —CF$_3$ | —CH$_3$ | —H |
| B532 g, h, i, j, k or m | CH | N | —CF$_3$ | —CH$_3$ | —Cl |
| B533 g, h, i, j, k or m | CH | N | —CF$_3$ | —CH$_3$ | —F |
| B534 g, h, i, j, k or m | CH | N | —CF$_3$ | —CH$_3$ | —CH$_3$ |
| B535 g, h, i, j, k or m | CH | N | —CF$_3$ | —CH$_3$ | —OCH$_3$ |
| B536 g, h, i, j, k or m | CH | N | —CF$_3$ | —CH$_3$ | —OCH$_2$CH$_3$ |
| B537 g, h, i, j, k or m | CH | N | —CF$_3$ | —CH$_3$ | —CF$_3$ |
| B538 g, h, i, j, k or m | CH | N | —CF$_3$ | —CH$_3$ | —OCF$_3$ |
| B539 g, h, i, j, k or m | CH | N | —CF$_3$ | —CH$_3$ | iso-propyl |
| B540 g, h, i, j, k or m | CH | N | —CF$_3$ | —CH$_3$ | tert-butyl |
| B541 g, h, i, j, k or m | CH | N | —CF$_3$ | —OCH$_3$ | —H |
| B542 g, h, i, j, k or m | CH | N | —CF$_3$ | —OCH$_3$ | —Cl |
| B543 g, h, i, j, k or m | CH | N | —CF$_3$ | —OCH$_3$ | —F |
| B544 g, h, i, j, k or m | CH | N | —CF$_3$ | —OCH$_3$ | —CH$_3$ |
| B545 g, h, i, j, k or m | CH | N | —CF$_3$ | —OCH$_3$ | —OCH$_3$ |
| B546 g, h, i, j, k or m | CH | N | —CF$_3$ | —OCH$_3$ | —OCH$_2$CH$_3$ |
| B547 g, h, i, j, k or m | CH | N | —CF$_3$ | —OCH$_3$ | —CF$_3$ |
| B548 g, h, i, j, k or m | CH | N | —CF$_3$ | —OCH$_3$ | —OCF$_3$ |
| B549 g, h, i, j, k or m | CH | N | —CF$_3$ | —OCH$_3$ | iso-propyl |
| B550 g, h, i, j, k or m | CH | N | —CF$_3$ | —OCH$_3$ | tert-butyl |
| B551 g, h, i, j, k or m | CH | N | —CF$_3$ | —OCH$_2$CH$_3$ | —H |
| B552 g, h, i, j, k or m | CH | N | —CF$_3$ | —OCH$_2$CH$_3$ | —Cl |
| B553 g, h, i, j, k or m | CH | N | —CF$_3$ | —OCH$_2$CH$_3$ | —F |
| B554 g, h, i, j, k or m | CH | N | —CF$_3$ | —OCH$_2$CH$_3$ | —CH$_3$ |
| B555 g, h, i, j, k or m | CH | N | —CF$_3$ | —OCH$_2$CH$_3$ | —OCH$_3$ |
| B556 g, h, i, j, k or m | CH | N | —CF$_3$ | —OCH$_2$CH$_3$ | —OCH$_2$CH$_3$ |
| B557 g, h, i, j, k or m | CH | N | —CF$_3$ | —OCH$_2$CH$_3$ | —CF$_3$ |
| B558 g, h, i, j, k or m | CH | N | —CF$_3$ | —OCH$_2$CH$_3$ | —OCF$_3$ |
| B559 g, h, i, j, k or m | CH | N | —CF$_3$ | —OCH$_2$CH$_3$ | iso-propyl |
| B560 g, h, i, j, k or m | CH | N | —CF$_3$ | —OCH$_2$CH$_3$ | tert-butyl |
| B561 g, h, i, j, k or m | CH | N | —CF$_3$ | —CF$_3$ | —H |
| B562 g, h, i, j, k or m | CH | N | —CF$_3$ | —CF$_3$ | —Cl |
| B563 g, h, i, j, k or m | CH | N | —CF$_3$ | —CF$_3$ | —F |
| B564 g, h, i, j, k or m | CH | N | —CF$_3$ | —CF$_3$ | —CH$_3$ |
| B565 g, h, i, j, k or m | CH | N | —CF$_3$ | —CF$_3$ | —OCH$_3$ |
| B566 g, h, i, j, k or m | CH | N | —CF$_3$ | —CF$_3$ | —OCH$_2$CH$_3$ |
| B567 g, h, i, j, k or m | CH | N | —CF$_3$ | —CF$_3$ | —CF$_3$ |
| B568 g, h, i, j, k or m | CH | N | —CF$_3$ | —CF$_3$ | —OCF$_3$ |
| B569 g, h, i, j, k or m | CH | N | —CF$_3$ | —CF$_3$ | iso-propyl |
| B570 g, h, i, j, k or m | CH | N | —CF$_3$ | —CF$_3$ | tert-butyl |
| B571 g, h, i, j, k or m | CH | N | —CF$_3$ | —OCF$_3$ | —H |
| B572 g, h, i, j, k or m | CH | N | —CF$_3$ | —OCF$_3$ | —Cl |
| B573 g, h, i, j, k or m | CH | N | —CF$_3$ | —OCF$_3$ | —F |
| B574 g, h, i, j, k or m | CH | N | —CF$_3$ | —OCF$_3$ | —CH$_3$ |
| B575 g, h, i, j, k or m | CH | N | —CF$_3$ | —OCF$_3$ | —OCH$_3$ |
| B576 g, h, i, j, k or m | CH | N | —CF$_3$ | —OCF$_3$ | —OCH$_2$CH$_3$ |
| B577 g, h, i, j, k or m | CH | N | —CF$_3$ | —OCF$_3$ | —CF$_3$ |
| B578 g, h, i, j, k or m | CH | N | —CF$_3$ | —OCF$_3$ | —OCF$_3$ |
| B579 g, h, i, j, k or m | CH | N | —CF$_3$ | —OCF$_3$ | iso-propyl |
| B580 g, h, i, j, k or m | CH | N | —CF$_3$ | —OCF$_3$ | tert-butyl |
| B581 g, h, i, j, k or m | CH | N | —CF$_3$ | iso-propyl | —H |
| B582 g, h, i, j, k or m | CH | N | —CF$_3$ | iso-propyl | —Cl |
| B583 g, h, i, j, k or m | CH | N | —CF$_3$ | iso-propyl | —F |
| B584 g, h, i, j, k or m | CH | N | —CF$_3$ | iso-propyl | —CH$_3$ |
| B585 g, h, i, j, k or m | CH | N | —CF$_3$ | iso-propyl | —OCH$_3$ |
| B586 g, h, i, j, k or m | CH | N | —CF$_3$ | iso-propyl | —OCH$_2$CH$_3$ |
| B587 g, h, i, j, k or m | CH | N | —CF$_3$ | iso-propyl | —CF$_3$ |
| B588 g, h, i, j, k or m | CH | N | —CF$_3$ | iso-propyl | —OCF$_3$ |
| B589 g, h, i, j, k or m | CH | N | —CF$_3$ | iso-propyl | iso-propyl |
| B590 g, h, i, j, k or m | CH | N | —CF$_3$ | iso-propyl | tert-butyl |
| B591 g, h, i, j, k or m | CH | N | —CF$_3$ | tert-butyl | —H |
| B592 g, h, i, j, k or m | CH | N | —CF$_3$ | tert-butyl | —Cl |
| B593 g, h, i, j, k or m | CH | N | —CF$_3$ | tert-butyl | —F |
| B594 g, h, i, j, k or m | CH | N | —CF$_3$ | tert-butyl | —CH$_3$ |
| B595 g, h, i, j, k or m | CH | N | —CF$_3$ | tert-butyl | —OCH$_3$ |
| B596 g, h, i, j, k or m | CH | N | —CF$_3$ | tert-butyl | —OCH$_2$CH$_3$ |
| B597 g, h, i, j, k or m | CH | N | —CF$_3$ | tert-butyl | —CF$_3$ |
| B598 g, h, i, j, k or m | CH | N | —CF$_3$ | tert-butyl | —OCF$_3$ |
| B599 g, h, i, j, k or m | CH | N | —CF$_3$ | tert-butyl | iso-propyl |
| B600 g, h, i, j, k or m | CH | N | —CF$_3$ | tert-butyl | tert-butyl |
| B601 g, h, i, j, k or m | CH | CH | —Cl | —H | —H |
| B602 g, h, i, j, k or m | CH | CH | —Cl | —H | —Cl |
| B603 g, h, i, j, k or m | CH | CH | —Cl | —H | —F |
| B604 g, h, i, j, k or m | CH | CH | —Cl | —H | —CH$_3$ |

TABLE 2-continued

| | | | | | |
|---|---|---|---|---|---|
| B605 g, h, i, j, k or m | CH | CH | —Cl | —H | —OCH$_3$ |
| B606 g, h, i, j, k or m | CH | CH | —Cl | —H | —OCH$_2$CH$_3$ |
| B607 g, h, i, j, k or m | CH | CH | —Cl | —H | —CF$_3$ |
| B608 g, h, i, j, k or m | CH | CH | —Cl | —H | —OCF$_3$ |
| B609 g, h, i, j, k or m | CH | CH | —Cl | —H | iso-propyl |
| B610 g, h, i, j, k or m | CH | CH | —Cl | —H | tert-butyl |
| B611 g, h, i, j, k or m | CH | CH | —Cl | —Cl | —H |
| B612 g, h, i, j, k or m | CH | CH | —Cl | —Cl | —Cl |
| B613 g, h, i, j, k or m | CH | CH | —Cl | —Cl | —F |
| B614 g, h, i, j, k or m | CH | CH | —Cl | —Cl | —CH$_3$ |
| B615 g, h, i, j, k or m | CH | CH | —Cl | —Cl | —OCH$_3$ |
| B616 g, h, i, j, k or m | CH | CH | —Cl | —Cl | —OCH$_2$CH$_3$ |
| B617 g, h, i, j, k or m | CH | CH | —Cl | —Cl | —CF$_3$ |
| B618 g, h, i, j, k or m | CH | CH | —Cl | —Cl | —OCF$_3$ |
| B619 g, h, i, j, k or m | CH | CH | —Cl | —Cl | iso-propyl |
| B620 g, h, i, j, k or m | CH | CH | —Cl | —Cl | tert-butyl |
| B621 g, h, i, j, k or m | CH | CH | —Cl | —F | —H |
| B622 g, h, i, j, k or m | CH | CH | —Cl | —F | —Cl |
| B623 g, h, i, j, k or m | CH | CH | —Cl | —F | —F |
| B624 g, h, i, j, k or m | CH | CH | —Cl | —F | —CH$_3$ |
| B625 g, h, i, j, k or m | CH | CH | —Cl | —F | —OCH$_3$ |
| B626 g, h, i, j, k or m | CH | CH | —Cl | —F | —OCH$_2$CH$_3$ |
| B627 g, h, i, j, k or m | CH | CH | —Cl | —F | —CF$_3$ |
| B628 g, h, i, j, k or m | CH | CH | —Cl | —F | —OCF$_3$ |
| B629 g, h, i, j, k or m | CH | CH | —Cl | —F | iso-propyl |
| B630 g, h, i, j, k or m | CH | CH | —Cl | —F | tert-butyl |
| B631 g, h, i, j, k or m | CH | CH | —Cl | —CH$_3$ | —H |
| B632 g, h, i, j, k or m | CH | CH | —Cl | —CH$_3$ | —Cl |
| B633 g, h, i, j, k or m | CH | CH | —Cl | —CH$_3$ | —F |
| B634 g, h, i, j, k or m | CH | CH | —Cl | —CH$_3$ | —CH$_3$ |
| B635 g, h, i, j, k or m | CH | CH | —Cl | —CH$_3$ | —OCH$_3$ |
| B636 g, h, i, j, k or m | CH | CH | —Cl | —CH$_3$ | —OCH$_2$CH$_3$ |
| B637 g, h, i, j, k or m | CH | CH | —Cl | —CH$_3$ | —CF$_3$ |
| B638 g, h, i, j, k or m | CH | CH | —Cl | —CH$_3$ | —OCF$_3$ |
| B639 g, h, i, j, k or m | CH | CH | —Cl | —CH$_3$ | iso-propyl |
| B640 g, h, i, j, k or m | CH | CH | —Cl | —CH$_3$ | tert-butyl |
| B641 g, h, i, j, k or m | CH | CH | —Cl | —OCH$_3$ | —H |
| B642 g, h, i, j, k or m | CH | CH | —Cl | —OCH$_3$ | —Cl |
| B643 g, h, i, j, k or m | CH | CH | —Cl | —OCH$_3$ | —F |
| B644 g, h, i, j, k or m | CH | CH | —Cl | —OCH$_3$ | —CH$_3$ |
| B645 g, h, i, j, k or m | CH | CH | —Cl | —OCH$_3$ | —OCH$_3$ |
| B646 g, h, i, j, k or m | CH | CH | —Cl | —OCH$_3$ | —OCH$_2$CH$_3$ |
| B647 g, h, i, j, k or m | CH | CH | —Cl | —OCH$_3$ | —CF$_3$ |
| B648 g, h, i, j, k or m | CH | CH | —Cl | —OCH$_3$ | —OCF$_3$ |
| B649 g, h, i, j, k or m | CH | CH | —Cl | —OCH$_3$ | iso-propyl |
| B650 g, h, i, j, k or m | CH | CH | —Cl | —OCH$_3$ | tert-butyl |
| B651 g, h, i, j, k or m | CH | CH | —Cl | —OCH$_2$CH$_3$ | —H |
| B652 g, h, i, j, k or m | CH | CH | —Cl | —OCH$_2$CH$_3$ | —Cl |
| B653 g, h, i, j, k or m | CH | CH | —Cl | —OCH$_2$CH$_3$ | —F |
| B654 g, h, i, j, k or m | CH | CH | —Cl | —OCH$_2$CH$_3$ | —CH$_3$ |
| B655 g, h, i, j, k or m | CH | CH | —Cl | —OCH$_2$CH$_3$ | —OCH$_3$ |
| B656 g, h, i, j, k or m | CH | CH | —Cl | —OCH$_2$CH$_3$ | —OCH$_2$CH$_3$ |
| B657 g, h, i, j, k or m | CH | CH | —Cl | —OCH$_2$CH$_3$ | —CF$_3$ |
| B658 g, h, i, j, k or m | CH | CH | —Cl | —OCH$_2$CH$_3$ | —OCF$_3$ |
| B659 g, h, i, j, k or m | CH | CH | —Cl | —OCH$_2$CH$_3$ | iso-propyl |
| B660 g, h, i, j, k or m | CH | CH | —Cl | —OCH$_2$CH$_3$ | tert-butyl |
| B661 g, h, i, j, k or m | CH | CH | —Cl | —CF$_3$ | —H |
| B662 g, h, i, j, k or m | CH | CH | —Cl | —CF$_3$ | —Cl |
| B663 g, h, i, j, k or m | CH | CH | —Cl | —CF$_3$ | —F |
| B664 g, h, i, j, k or m | CH | CH | —Cl | —CF$_3$ | —CH$_3$ |
| B665 g, h, i, j, k or m | CH | CH | —Cl | —CF$_3$ | —OCH$_3$ |
| B666 g, h, i, j, k or m | CH | CH | —Cl | —CF$_3$ | —OCH$_2$CH$_3$ |
| B667 g, h, i, j, k or m | CH | CH | —Cl | —CF$_3$ | —CF$_3$ |
| B668 g, h, i, j, k or m | CH | CH | —Cl | —CF$_3$ | —OCF$_3$ |
| B669 g, h, i, j, k or m | CH | CH | —Cl | —CF$_3$ | iso-propyl |
| B670 g, h, i, j, k or m | CH | CH | —Cl | —CF$_3$ | tert-butyl |
| B671 g, h, i, j, k or m | CH | CH | —Cl | —OCF$_3$ | —H |
| B672 g, h, i, j, k or m | CH | CH | —Cl | —OCF$_3$ | —Cl |
| B673 g, h, i, j, k or m | CH | CH | —Cl | —OCF$_3$ | —F |
| B674 g, h, i, j, k or m | CH | CH | —Cl | —OCF$_3$ | —CH$_3$ |
| B675 g, h, i, j, k or m | CH | CH | —Cl | —OCF$_3$ | —OCH$_3$ |
| B676 g, h, i, j, k or m | CH | CH | —Cl | —OCF$_3$ | —OCH$_2$CH$_3$ |
| B677 g, h, i, j, k or m | CH | CH | —Cl | —OCF$_3$ | —CF$_3$ |
| B678 g, h, i, j, k or m | CH | CH | —Cl | —OCF$_3$ | —OCF$_3$ |
| B679 g, h, i, j, k or m | CH | CH | —Cl | —OCF$_3$ | iso-propyl |
| B680 g, h, i, j, k or m | CH | CH | —Cl | —OCF$_3$ | tert-butyl |
| B681 g, h, i, j, k or m | CH | CH | —Cl | iso-propyl | —H |
| B682 g, h, i, j, k or m | CH | CH | —Cl | iso-propyl | —Cl |
| B683 g, h, i, j, k or m | CH | CH | —Cl | iso-propyl | —F |
| B684 g, h, i, j, k or m | CH | CH | —Cl | iso-propyl | —CH$_3$ |
| B685 g, h, i, j, k or m | CH | CH | —Cl | iso-propyl | —OCH$_3$ |
| B686 g, h, i, j, k or m | CH | CH | —Cl | iso-propyl | —OCH$_2$CH$_3$ |
| B687 g, h, i, j, k or m | CH | CH | —Cl | iso-propyl | —CF$_3$ |
| B688 g, h, i, j, k or m | CH | CH | —Cl | iso-propyl | —OCF$_3$ |
| B689 g, h, i, j, k or m | CH | CH | —Cl | iso-propyl | iso-propyl |
| B690 g, h, i, j, k or m | CH | CH | —Cl | iso-propyl | tert-butyl |
| B691 g, h, i, j, k or m | CH | CH | —Cl | tert-butyl | —H |
| B692 g, h, i, j, k or m | CH | CH | —Cl | tert-butyl | —Cl |
| B693 g, h, i, j, k or m | CH | CH | —Cl | tert-butyl | —F |
| B694 g, h, i, j, k or m | CH | CH | —Cl | tert-butyl | —CH$_3$ |
| B695 g, h, i, j, k or m | CH | CH | —Cl | tert-butyl | —OCH$_3$ |
| B696 g, h, i, j, k or m | CH | CH | —Cl | tert-butyl | —OCH$_2$CH$_3$ |
| B697 g, h, i, j, k or m | CH | CH | —Cl | tert-butyl | —CF$_3$ |
| B698 g, h, i, j, k or m | CH | CH | —Cl | tert-butyl | —OCF$_3$ |
| B699 g, h, i, j, k or m | CH | CH | —Cl | tert-butyl | iso-propyl |
| B700 g, h, i, j, k or m | CH | CH | —Cl | tert-butyl | tert-butyl |
| B701 g, h, i, j, k or m | CH | CH | —F | —H | —H |
| B702 g, h, i, j, k or m | CH | CH | —F | —H | —Cl |
| B703 g, h, i, j, k or m | CH | CH | —F | —H | —F |
| B704 g, h, i, j, k or m | CH | CH | —F | —H | —CH$_3$ |
| B705 g, h, i, j, k or m | CH | CH | —F | —H | —OCH$_3$ |
| B706 g, h, i, j, k or m | CH | CH | —F | —H | —OCH$_2$CH$_3$ |
| B707 g, h, i, j, k or m | CH | CH | —F | —H | —CF$_3$ |
| B708 g, h, i, j, k or m | CH | CH | —F | —H | —OCF$_3$ |
| B709 g, h, i, j, k or m | CH | CH | —F | —H | iso-propyl |
| B710 g, h, i, j, k or m | CH | CH | —F | —H | tert-butyl |
| B711 g, h, i, j, k or m | CH | CH | —F | —Cl | —H |
| B712 g, h, i, j, k or m | CH | CH | —F | —Cl | —Cl |
| B713 g, h, i, j, k or m | CH | CH | —F | —Cl | —F |
| B714 g, h, i, j, k or m | CH | CH | —F | —Cl | —CH$_3$ |
| B715 g, h, i, j, k or m | CH | CH | —F | —Cl | —OCH$_3$ |
| B716 g, h, i, j, k or m | CH | CH | —F | —Cl | —OCH$_2$CH$_3$ |
| B717 g, h, i, j, k or m | CH | CH | —F | —Cl | —CF$_3$ |
| B718 g, h, i, j, k or m | CH | CH | —F | —Cl | —OCF$_3$ |
| B719 g, h, i, j, k or m | CH | CH | —F | —Cl | iso-propyl |
| B720 g, h, i, j, k or m | CH | CH | —F | —Cl | tert-butyl |
| B721 g, h, i, j, k or m | CH | CH | —F | —F | —H |
| B722 g, h, i, j, k or m | CH | CH | —F | —F | —Cl |
| B723 g, h, i, j, k or m | CH | CH | —F | —F | —F |
| B724 g, h, i, j, k or m | CH | CH | —F | —F | —CH$_3$ |
| B725 g, h, i, j, k or m | CH | CH | —F | —F | —OCH$_3$ |
| B726 g, h, i, j, k or m | CH | CH | —F | —F | —OCH$_2$CH$_3$ |
| B727 g, h, i, j, k or m | CH | CH | —F | —F | —CF$_3$ |
| B728 g, h, i, j, k or m | CH | CH | —F | —F | —OCF$_3$ |
| B729 g, h, i, j, k or m | CH | CH | —F | —F | iso-propyl |
| B730 g, h, i, j, k or m | CH | CH | —F | —F | tert-butyl |
| B731 g, h, i, j, k or m | CH | CH | —F | —CH$_3$ | —H |
| B732 g, h, i, j, k or m | CH | CH | —F | —CH$_3$ | —Cl |
| B733 g, h, i, j, k or m | CH | CH | —F | —CH$_3$ | —F |
| B734 g, h, i, j, k or m | CH | CH | —F | —CH$_3$ | —CH$_3$ |
| B735 g, h, i, j, k or m | CH | CH | —F | —CH$_3$ | —OCH$_3$ |
| B736 g, h, i, j, k or m | CH | CH | —F | —CH$_3$ | —OCH$_2$CH$_3$ |
| B737 g, h, i, j, k or m | CH | CH | —F | —CH$_3$ | —CF$_3$ |
| B738 g, h, i, j, k or m | CH | CH | —F | —CH$_3$ | —OCF$_3$ |
| B739 g, h, i, j, k or m | CH | CH | —F | —CH$_3$ | iso-propyl |
| B740 g, h, i, j, k or m | CH | CH | —F | —CH$_3$ | tert-butyl |
| B741 g, h, i, j, k or m | CH | CH | —F | —OCH$_3$ | —H |
| B742 g, h, i, j, k or m | CH | CH | —F | —OCH$_3$ | —Cl |
| B743 g, h, i, j, k or m | CH | CH | —F | —OCH$_3$ | —F |
| B744 g, h, i, j, k or m | CH | CH | —F | —OCH$_3$ | —CH$_3$ |
| B745 g, h, i, j, k or m | CH | CH | —F | —OCH$_3$ | —OCH$_3$ |
| B746 g, h, i, j, k or m | CH | CH | —F | —OCH$_3$ | —OCH$_2$CH$_3$ |
| B747 g, h, i, j, k or m | CH | CH | —F | —OCH$_3$ | —CF$_3$ |
| B748 g, h, i, j, k or m | CH | CH | —F | —OCH$_3$ | —OCF$_3$ |
| B749 g, h, i, j, k or m | CH | CH | —F | —OCH$_3$ | iso-propyl |
| B750 g, h, i, j, k or m | CH | CH | —F | —OCH$_3$ | tert-butyl |
| B751 g, h, i, j, k or m | CH | CH | —F | —OCH$_2$CH$_3$ | —H |
| B752 g, h, i, j, k or m | CH | CH | —F | —OCH$_2$CH$_3$ | —Cl |
| B753 g, h, i, j, k or m | CH | CH | —F | —OCH$_2$CH$_3$ | —F |
| B754 g, h, i, j, k or m | CH | CH | —F | —OCH$_2$CH$_3$ | —CH$_3$ |
| B755 g, h, i, j, k or m | CH | CH | —F | —OCH$_2$CH$_3$ | —OCH$_3$ |
| B756 g, h, i, j, k or m | CH | CH | —F | —OCH$_2$CH$_3$ | —OCH$_2$CH$_3$ |
| B757 g, h, i, j, k or m | CH | CH | —F | —OCH$_2$CH$_3$ | —CF$_3$ |
| B758 g, h, i, j, k or m | CH | CH | —F | —OCH$_2$CH$_3$ | —OCF$_3$ |
| B759 g, h, i, j, k or m | CH | CH | —F | —OCH$_2$CH$_3$ | iso-propyl |
| B760 g, h, i, j, k or m | CH | CH | —F | —OCH$_2$CH$_3$ | tert-butyl |
| B761 g, h, i, j, k or m | CH | CH | —F | —CF$_3$ | —H |
| B762 g, h, i, j, k or m | CH | CH | —F | —CF$_3$ | —Cl |
| B763 g, h, i, j, k or m | CH | CH | —F | —CF$_3$ | —F |
| B764 g, h, i, j, k or m | CH | CH | —F | —CF$_3$ | —CH$_3$ |

TABLE 2-continued

| | | | | | |
|---|---|---|---|---|---|
| B765 g, h, i, j, k or m | CH | CH | —F | —CF₃ | —OCH₃ |
| B766 g, h, i, j, k or m | CH | CH | —F | —CF₃ | —OCH₂CH₃ |
| B767 g, h, i, j, k or m | CH | CH | —F | —CF₃ | —CF₃ |
| B768 g, h, i, j, k or m | CH | CH | —F | —CF₃ | —OCF₃ |
| B769 g, h, i, j, k or m | CH | CH | —F | —CF₃ | iso-propyl |
| B770 g, h, i, j, k or m | CH | CH | —F | —CF₃ | tert-butyl |
| B771 g, h, i, j, k or m | CH | CH | —F | —OCF₃ | —H |
| B772 g, h, i, j, k or m | CH | CH | —F | —OCF₃ | —Cl |
| B773 g, h, i, j, k or m | CH | CH | —F | —OCF₃ | —F |
| B774 g, h, i, j, k or m | CH | CH | —F | —OCF₃ | —CH₃ |
| B775 g, h, i, j, k or m | CH | CH | —F | —OCF₃ | —OCH₃ |
| B776 g, h, i, j, k or m | CH | CH | —F | —OCF₃ | —OCH₂CH₃ |
| B777 g, h, i, j, k or m | CH | CH | —F | —OCF₃ | —CF₃ |
| B778 g, h, i, j, k or m | CH | CH | —F | —OCF₃ | —OCF₃ |
| B779 g, h, i, j, k or m | CH | CH | —F | —OCF₃ | iso-propyl |
| B780 g, h, i, j, k or m | CH | CH | —F | —OCF₃ | tert-butyl |
| B781 g, h, i, j, k or m | CH | CH | —F | iso-propyl | —H |
| B782 g, h, i, j, k or m | CH | CH | —F | iso-propyl | —Cl |
| B783 g, h, i, j, k or m | CH | CH | —F | iso-propyl | —F |
| B784 g, h, i, j, k or m | CH | CH | —F | iso-propyl | —CH₃ |
| B785 g, h, i, j, k or m | CH | CH | —F | iso-propyl | —OCH₃ |
| B786 g, h, i, j, k or m | CH | CH | —F | iso-propyl | —OCH₂CH₃ |
| B787 g, h, i, j, k or m | CH | CH | —F | iso-propyl | —CF₃ |
| B788 g, h, i, j, k or m | CH | CH | —F | iso-propyl | —OCF₃ |
| B789 g, h, i, j, k or m | CH | CH | —F | iso-propyl | iso-propyl |
| B790 g, h, i, j, k or m | CH | CH | —F | iso-propyl | tert-butyl |
| B791 g, h, i, j, k or m | CH | CH | —F | tert-butyl | —H |
| B792 g, h, i, j, k or m | CH | CH | —F | tert-butyl | —Cl |
| B793 g, h, i, j, k or m | CH | CH | —F | tert-butyl | —F |
| B794 g, h, i, j, k or m | CH | CH | —F | tert-butyl | —CH₃ |
| B795 g, h, i, j, k or m | CH | CH | —F | tert-butyl | —OCH₃ |
| B796 g, h, i, j, k or m | CH | CH | —F | tert-butyl | —OCH₂CH₃ |
| B797 g, h, i, j, k or m | CH | CH | —F | tert-butyl | —CF₃ |
| B798 g, h, i, j, k or m | CH | CH | —F | tert-butyl | —OCF₃ |
| B799 g, h, i, j, k or m | CH | CH | —F | tert-butyl | iso-propyl |
| B800 g, h, i, j, k or m | CH | CH | —F | tert-butyl | tert-butyl |
| B801 g, h, i, j, k or m | CH | CH | —CF₃ | —H | —H |
| B802 g, h, i, j, k or m | CH | CH | —CF₃ | —H | —Cl |
| B803 g, h, i, j, k or m | CH | CH | —CF₃ | —H | —F |
| B804 g, h, i, j, k or m | CH | CH | —CF₃ | —H | —CH₃ |
| B805 g, h, i, j, k or m | CH | CH | —CF₃ | —H | —OCH₃ |
| B806 g, h, i, j, k or m | CH | CH | —CF₃ | —H | —OCH₂CH₃ |
| B807 g, h, i, j, k or m | CH | CH | —CF₃ | —H | —CF₃ |
| B808 g, h, i, j, k or m | CH | CH | —CF₃ | —H | —OCF₃ |
| B809 g, h, i, j, k or m | CH | CH | —CF₃ | —H | iso-propyl |
| B810 g, h, i, j, k or m | CH | CH | —CF₃ | —H | tert-butyl |
| B811 g, h, i, j, k or m | CH | CH | —CF₃ | —Cl | —H |
| B812 g, h, i, j, k or m | CH | CH | —CF₃ | —Cl | —Cl |
| B813 g, h, i, j, k or m | CH | CH | —CF₃ | —Cl | —F |
| B814 g, h, i, j, k or m | CH | CH | —CF₃ | —Cl | —CH₃ |
| B815 g, h, i, j, k or m | CH | CH | —CF₃ | —Cl | —OCH₃ |
| B816 g, h, i, j, k or m | CH | CH | —CF₃ | —Cl | —OCH₂CH₃ |
| B817 g, h, i, j, k or m | CH | CH | —CF₃ | —Cl | —CF₃ |
| B818 g, h, i, j, k or m | CH | CH | —CF₃ | —Cl | —OCF₃ |
| B819 g, h, i, j, k or m | CH | CH | —CF₃ | —Cl | iso-propyl |
| B820 g, h, i, j, k or m | CH | CH | —CF₃ | —Cl | tert-butyl |
| B821 g, h, i, j, k or m | CH | CH | —CF₃ | —F | —H |
| B822 g, h, i, j, k or m | CH | CH | —CF₃ | —F | —Cl |
| B823 g, h, i, j, k or m | CH | CH | —CF₃ | —F | —F |
| B824 g, h, i, j, k or m | CH | CH | —CF₃ | —F | —CH₃ |
| B825 g, h, i, j, k or m | CH | CH | —CF₃ | —F | —OCH₃ |
| B826 g, h, i, j, k or m | CH | CH | —CF₃ | —F | —OCH₂CH₃ |
| B827 g, h, i, j, k or m | CH | CH | —CF₃ | —F | —CF₃ |
| B828 g, h, i, j, k or m | CH | CH | —CF₃ | —F | —OCF₃ |
| B829 g, h, i, j, k or m | CH | CH | —CF₃ | —F | iso-propyl |
| B830 g, h, i, j, k or m | CH | CH | —CF₃ | —F | tert-butyl |
| B831 g, h, i, j, k or m | CH | CH | —CF₃ | —CH₃ | —H |
| B832 g, h, i, j, k or m | CH | CH | —CF₃ | —CH₃ | —Cl |
| B833 g, h, i, j, k or m | CH | CH | —CF₃ | —CH₃ | —F |
| B834 g, h, i, j, k or m | CH | CH | —CF₃ | —CH₃ | —CH₃ |
| B835 g, h, i, j, k or m | CH | CH | —CF₃ | —CH₃ | —OCH₃ |
| B836 g, h, i, j, k or m | CH | CH | —CF₃ | —CH₃ | —OCH₂CH₃ |
| B837 g, h, i, j, k or m | CH | CH | —CF₃ | —CH₃ | —CF₃ |
| B838 g, h, i, j, k or m | CH | CH | —CF₃ | —CH₃ | —OCF₃ |
| B839 g, h, i, j, k or m | CH | CH | —CF₃ | —CH₃ | iso-propyl |
| B840 g, h, i, j, k or m | CH | CH | —CF₃ | —CH₃ | tert-butyl |
| B841 g, h, i, j, k or m | CH | CH | —CF₃ | —OCH₃ | —H |
| B842 g, h, i, j, k or m | CH | CH | —CF₃ | —OCH₃ | —Cl |
| B843 g, h, i, j, k or m | CH | CH | —CF₃ | —OCH₃ | —F |
| B844 g, h, i, j, k or m | CH | CH | —CF₃ | —OCH₃ | —CH₃ |
| B845 g, h, i, j, k or m | CH | CH | —CF₃ | —OCH₃ | —OCH₃ |
| B846 g, h, i, j, k or m | CH | CH | —CF₃ | —OCH₃ | —OCH₂CH₃ |
| B847 g, h, i, j, k or m | CH | CH | —CF₃ | —OCH₃ | —CF₃ |
| B848 g, h, i, j, k or m | CH | CH | —CF₃ | —OCH₃ | —OCF₃ |
| B849 g, h, i, j, k or m | CH | CH | —CF₃ | —OCH₃ | iso-propyl |
| B850 g, h, i, j, k or m | CH | CH | —CF₃ | —OCH₃ | tert-butyl |
| B851 g, h, i, j, k or m | CH | CH | —CF₃ | —OCH₂CH₃ | —H |
| B852 g, h, i, j, k or m | CH | CH | —CF₃ | —OCH₂CH₃ | —Cl |
| B853 g, h, i, j, k or m | CH | CH | —CF₃ | —OCH₂CH₃ | —F |
| B854 g, h, i, j, k or m | CH | CH | —CF₃ | —OCH₂CH₃ | —CH₃ |
| B855 g, h, i, j, k or m | CH | CH | —CF₃ | —OCH₂CH₃ | —OCH₃ |
| B856 g, h, i, j, k or m | CH | CH | —CF₃ | —OCH₂CH₃ | —OCH₂CH₃ |
| B857 g, h, i, j, k or m | CH | CH | —CF₃ | —OCH₂CH₃ | —CF₃ |
| B858 g, h, i, j, k or m | CH | CH | —CF₃ | —OCH₂CH₃ | —OCF₃ |
| B859 g, h, i, j, k or m | CH | CH | —CF₃ | —OCH₂CH₃ | iso-propyl |
| B860 g, h, i, j, k or m | CH | CH | —CF₃ | —OCH₂CH₃ | tert-butyl |
| B861 g, h, i, j, k or m | CH | CH | —CF₃ | —CF₃ | —H |
| B862 g, h, i, j, k or m | CH | CH | —CF₃ | —CF₃ | —Cl |
| B863 g, h, i, j, k or m | CH | CH | —CF₃ | —CF₃ | —F |
| B864 g, h, i, j, k or m | CH | CH | —CF₃ | —CF₃ | —CH₃ |
| B865 g, h, i, j, k or m | CH | CH | —CF₃ | —CF₃ | —OCHF₃ |
| B866 g, h, i, j, k or m | CH | CH | —CF₃ | —CF₃ | —OCH₂CH₃ |
| B867 g, h, i, j, k or m | CH | CH | —CF₃ | —CF₃ | —CF₃ |
| B868 g, h, i, j, k or m | CH | CH | —CF₃ | —CF₃ | —OCF₃ |
| B869 g, h, i, j, k or m | CH | CH | —CF₃ | —CF₃ | iso-propyl |
| B870 g, h, i, j, k or m | CH | CH | —CF₃ | —CF₃ | tert-butyl |
| B871 g, h, i, j, k or m | CH | CH | —CF₃ | —OCF₃ | —H |
| B872 g, h, i, j, k or m | CH | CH | —CF₃ | —OCF₃ | —Cl |
| B873 g, h, i, j, k or m | CH | CH | —CF₃ | —OCF₃ | —F |
| B874 g, h, i, j, k or m | CH | CH | —CF₃ | —OCF₃ | —CH₃ |
| B875 g, h, i, j, k or m | CH | CH | —CF₃ | —OCF₃ | —OCH₃ |
| B876 g, h, i, j, k or m | CH | CH | —CF₃ | —OCF₃ | —OCH₂CH₃ |
| B877 g, h, i, j, k or m | CH | CH | —CF₃ | —OCF₃ | —CF₃ |
| B878 g, h, i, j, k or m | CH | CH | —CF₃ | —OCF₃ | —OCF₃ |
| B879 g, h, i, j, k or m | CH | CH | —CF₃ | —OCF₃ | iso-propyl |
| B880 g, h, i, j, k or m | CH | CH | —CF₃ | —OCF₃ | tert-butyl |
| B881 g, h, i, j, k or m | CH | CH | —CF₃ | iso-propyl | —H |
| B882 g, h, i, j, k or m | CH | CH | —CF₃ | iso-propyl | —Cl |
| B883 g, h, i, j, k or m | CH | CH | —CF₃ | iso-propyl | —F |
| B884 g, h, i, j, k or m | CH | CH | —CF₃ | iso-propyl | —CH₃ |
| B885 g, h, i, j, k or m | CH | CH | —CF₃ | iso-propyl | —OCH₃ |
| B886 g, h, i, j, k or m | CH | CH | —CF₃ | iso-propyl | —OCH₂CH₃ |
| B887 g, h, i, j, k or m | CH | CH | —CF₃ | iso-propyl | —CF₃ |
| B888 g, h, i, j, k or m | CH | CH | —CF₃ | iso-propyl | —OCF₃ |
| B889 g, h, i, j, k or m | CH | CH | —CF₃ | iso-propyl | iso-propyl |
| B890 g, h, i, j, k or m | CH | CH | —CF₃ | iso-propyl | tert-butyl |
| B891 g, h, i, j, k or m | CH | CH | —CF₃ | tert-butyl | —H |
| B892 g, h, i, j, k or m | CH | CH | —CF₃ | tert-butyl | —Cl |
| B893 g, h, i, j, k or m | CH | CH | —CF₃ | tert-butyl | —F |
| B894 g, h, i, j, k or m | CH | CH | —CF₃ | tert-butyl | —CH₃ |
| B895 g, h, i, j, k or m | CH | CH | —CF₃ | tert-butyl | —OCH₃ |
| B896 g, h, i, j, k or m | CH | CH | —CF₃ | tert-butyl | —OCH₂CH₃ |
| B897 g, h, i, j, k or m | CH | CH | —CF₃ | tert-butyl | —CF₃ |
| B898 g, h, i, j, k or m | CH | CH | —CF₃ | tert-butyl | —OCF₃ |
| B899 g, h, i, j, k or m | CH | CH | —CF₃ | tert-butyl | iso-propyl |
| B900 g, h, i, j, k or m | CH | CH | —CF₃ | tert-butyl | tert-butyl |

TABLE 3
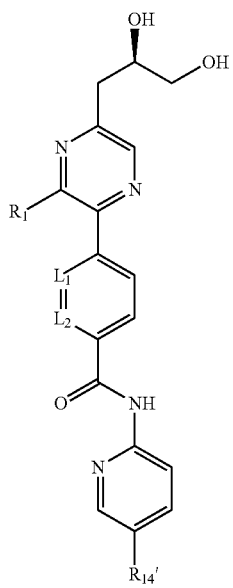
(IIn)
or
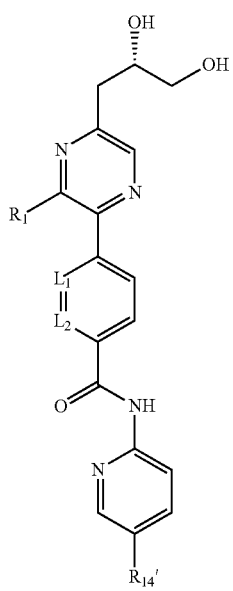
(IIo)
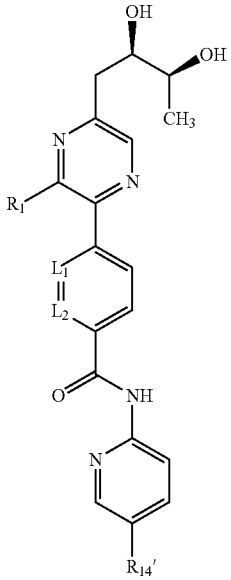
(IIp)
or
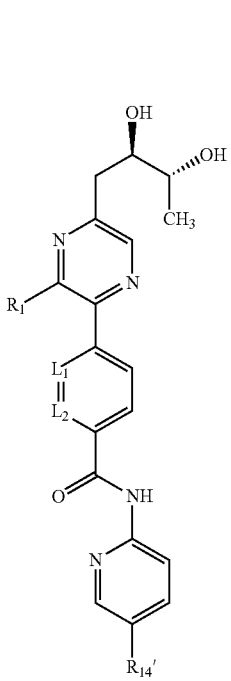
(IIq)

TABLE 3-continued

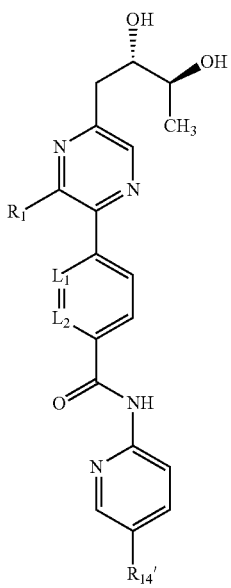

(IIr)

or

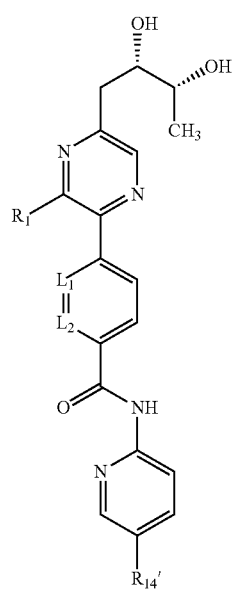

(IIs)

and pharmaceutically acceptable derivatives thereof, where:

| | Compound | L$_1$ | L$_2$ | R$_1$ | R$_{14}'$ |
|---|---|---|---|---|---|
| C | C1 n, o, p, q, r or s | N | CH | —Cl | —H |
| | C2 n, o, p, q, r or s | N | CH | —Cl | —Cl |
| | C3 n, o, p, q, r or s | N | CH | —Cl | —F |
| | C4 n, o, p, q, r or s | N | CH | —Cl | —Br |
| | C5 n, o, p, q, r or s | N | CH | —Cl | —CF$_3$ |
| | C6 n, o, p, q, r or s | N | CH | —Cl | —OCF$_3$ |
| | C7 n, o, p, q, r or s | N | CH | —Cl | —CH$_3$ |
| | C8 n, o, p, q, r or s | N | CH | —Cl | —CH$_2$CH$_3$ |
| | C9 n, o, p, q, r or s | N | CH | —Cl | -iso-propyl |
| | C10 n, o, p, q, r or s | N | CH | —Cl | -tert-butyl |
| | C11 n, o, p, q, r or s | N | CH | —Cl | —S(O)$_2$CF$_3$ |
| | C12 n, o, p, q, r or s | N | CH | —Cl | —S(O)$_2$CH$_3$ |
| | C13 n, o, p, q, r or s | N | CH | —Cl | —S(O)$_2$CH$_3$CH$_3$ |
| | C14 n, o, p, q, r or s | N | CH | —Cl | —OCH$_3$ |
| | C15 n, o, p, q, r or s | N | CH | —Cl | —OCH$_2$CH$_3$ |
| | C16 n, o, p, q, r or s | N | CH | —Cl | —OCH(CH$_3$)$_2$ |
| | C17 n, o, p, q, r or s | N | CH | —F | —H |
| | C18 n, o, p, q, r or s | N | CH | —F | —Cl |
| | C19 n, o, p, q, r or s | N | CH | —F | —F |
| | C20 n, o, p, q, r or s | N | CH | —F | —Br |
| | C21 n, o, p, q, r or s | N | CH | —F | —CF$_3$ |
| | C22 n, o, p, q, r or s | N | CH | —F | —OCF$_3$ |
| | C23 n, o, p, q, r or s | N | CH | —F | —CH$_3$ |
| | C24 n, o, p, q, r or s | N | CH | —F | —CH$_2$CH$_3$ |
| | C25 n, o, p, q, r or s | N | CH | —F | -iso-propyl |
| | C26 n, o, p, q, r or s | N | CH | —F | -tert-butyl |
| | C27 n, o, p, q, r or s | N | CH | —F | —S(O)$_2$CF$_3$ |
| | C28 n, o, p, q, r or s | N | CH | —F | —S(O)$_2$CH$_3$ |
| | C29 n, o, p, q, r or s | N | CH | —F | —S(O)$_2$CH$_3$CH$_3$ |
| | C30 n, o, p, q, r or s | N | CH | —F | —OCH$_3$ |
| | C31 n, o, p, q, r or s | N | CH | —F | —OCH$_2$CH$_3$ |
| | C32 n, o, p, q, r or s | N | CH | —F | —OCH(CH$_3$)$_2$ |
| | C33 n, o, p, q, r or s | N | CH | —CF$_3$ | —H |
| | C34 n, o, p, q, r or s | N | CH | —CF$_3$ | —Cl |
| | C35 n, o, p, q, r or s | N | CH | —CF$_3$ | —F |
| | C36 n, o, p, q, r or s | N | CH | —CF$_3$ | —Br |
| | C37 n, o, p, q, r or s | N | CH | —CF$_3$ | —CF$_3$ |
| | C38 n, o, p, q, r or s | N | CH | —CF$_3$ | —OCF$_3$ |
| | C39 n, o, p, q, r or s | N | CH | —CF$_3$ | —CH$_3$ |
| | C40 n, o, p, q, r or s | N | CH | —CF$_3$ | —CH$_2$CH$_3$ |
| | C41 n, o, p, q, r or s | N | CH | —CF$_3$ | -iso-propyl |
| | C42 n, o, p, q, r or s | N | CH | —CF$_3$ | -tert-butyl |
| | C43 n, o, p, q, r or s | N | CH | —CF$_3$ | —S(O)$_2$CF$_3$ |
| | C44 n, o, p, q, r or s | N | CH | —CF$_3$ | —S(O)$_2$CH$_3$ |
| | C45 n, o, p, q, r or s | N | CH | —CF$_3$ | —S(O)$_2$CH$_3$CH$_3$ |
| | C46 n, o, p, q, r or s | N | CH | —CF$_3$ | —OCH$_3$ |
| | C47 n, o, p, q, r or s | N | CH | —CF$_3$ | —OCH$_2$CH$_3$ |
| | C48 n, o, p, q, r or s | N | CH | —CF$_3$ | —OCH(CH$_3$)$_2$ |
| | C49 n, o, p, q, r or s | N | CH | —CH$_3$ | —H |
| | C50 n, o, p, q, r or s | N | CH | —CH$_3$ | —Cl |
| | C51 n, o, p, q, r or s | N | CH | —CH$_3$ | —F |
| | C52 n, o, p, q, r or s | N | CH | —CH$_3$ | —Br |
| | C53 n, o, p, q, r or s | N | CH | —CH$_3$ | —CF$_3$ |
| | C54 n, o, p, q, r or s | N | CH | —CH$_3$ | —OCF$_3$ |
| | C55 n, o, p, q, r or s | N | CH | —CH$_3$ | —CH$_3$ |
| | C56 n, o, p, q, r or s | N | CH | —CH$_3$ | —CH$_2$CH$_3$ |
| | C57 n, o, p, q, r or s | N | CH | —CH$_3$ | -iso-propyl |
| | C58 n, o, p, q, r or s | N | CH | —CH$_3$ | -tert-butyl |
| | C59 n, o, p, q, r or s | N | CH | —CH$_3$ | —S(O)$_2$CF$_3$ |
| | C60 n, o, p, q, r or s | N | CH | —CH$_3$ | —S(O)$_2$CH$_3$ |
| | C61 n, o, p, q, r or s | N | CH | —CH$_3$ | —S(O)$_2$CH$_3$CH$_3$ |
| | C62 n, o, p, q, r or s | N | CH | —CH$_3$ | —OCH$_3$ |
| | C63 n, o, p, q, r or s | N | CH | —CH$_3$ | —OCH$_2$CH$_3$ |
| | C64 n, o, p, q, r or s | N | CH | —CH$_3$ | —OCH(CH$_3$)$_2$ |
| | C65 n, o, p, q, r or s | CH | N | —Cl | —H |
| | C66 n, o, p, q, r or s | CH | N | —Cl | —Cl |
| | C67 n, o, p, q, r or s | CH | N | —Cl | —F |
| | C68 n, o, p, q, r or s | CH | N | —Cl | —Br |
| | C69 n, o, p, q, r or s | CH | N | —Cl | —CF$_3$ |
| | C70 n, o, p, q, r or s | CH | N | —Cl | —OCF$_3$ |
| | C71 n, o, p, q, r or s | CH | N | —Cl | —CH$_3$ |
| | C72 n, o, p, q, r or s | CH | N | —Cl | —CH$_2$CH$_3$ |
| | C73 n, o, p, q, r or s | CH | N | —Cl | -iso-propyl |
| | C74 n, o, p, q, r or s | CH | N | —Cl | -tert-butyl |
| | C75 n, o, p, q, r or s | CH | N | —Cl | —S(O)$_2$CF$_3$ |
| | C76 n, o, p, q, r or s | CH | N | —Cl | —S(O)$_2$CH$_3$ |
| | C77 n, o, p, q, r or s | CH | N | —Cl | —S(O)$_2$CH$_3$CH$_3$ |
| | C78 n, o, p, q, r or s | CH | N | —Cl | —OCH$_3$ |
| | C79 n, o, p, q, r or s | CH | N | —Cl | —OCH$_2$CH$_3$ |
| | C80 n, o, p, q, r or s | CH | N | —Cl | —OCH(CH$_3$)$_2$ |
| | C81 n, o, p, q, r or s | CH | N | —F | —H |
| | C82 n, o, p, q, r or s | CH | N | —F | —Cl |
| | C83 n, o, p, q, r or s | CH | N | —F | —F |
| | C84 n, o, p, q, r or s | CH | N | —F | —Br |
| | C85 n, o, p, q, r or s | CH | N | —F | —CF$_3$ |
| | C86 n, o, p, q, r or s | CH | N | —F | —OCF$_3$ |
| | C87 n, o, p, q, r or s | CH | N | —F | —CH$_3$ |
| | C88 n, o, p, q, r or s | CH | N | —F | —CH$_2$CH$_3$ |
| | C89 n, o, p, q, r or s | CH | N | —F | -iso-propyl |
| | C90 n, o, p, q, r or s | CH | N | —F | -tert-butyl |
| | C91 n, o, p, q, r or s | CH | N | —F | —S(O)$_2$CF$_3$ |
| | C92 n, o, p, q, r or s | CH | N | —F | —S(O)$_2$CH$_3$ |
| | C93 n, o, p, q, r or s | CH | N | —F | —S(O)$_2$CH$_3$CH$_3$ |
| | C94 n, o, p, q, r or s | CH | N | —F | —OCH$_3$ |
| | C95 n, o, p, q, r or s | CH | N | —F | —OCH$_2$CH$_3$ |
| | C96 n, o, p, q, r or s | CH | N | —F | —OCH(CH$_3$)$_2$ |
| | C97 n, o, p, q, r or s | CH | N | —CF$_3$ | —H |

TABLE 3-continued

| | | | | |
|---|---|---|---|---|
| C98 n, o, p, q, r or s | CH | N | —CF$_3$ | —Cl |
| C99 n, o, p, q, r or s | CH | N | —CF$_3$ | —F |
| C100 n, o, p, q, r or s | CH | N | —CF$_3$ | —Br |
| C101 n, o, p, q, r or s | CH | N | —CF$_3$ | —CF$_3$ |
| C102 n, o, p, q, r or s | CH | N | —CF$_3$ | —OCF$_3$ |
| C103 n, o, p, q, r or s | CH | N | —CF$_3$ | —CH$_3$ |
| C104 n, o, p, q, r or s | CH | N | —CF$_3$ | —CH$_2$CH$_3$ |
| C105 n, o, p, q, r or s | CH | N | —CF$_3$ | -iso-propyl |
| C106 n, o, p, q, r or s | CH | N | —CF$_3$ | -tert-butyl |
| C107 n, o, p, q, r or s | CH | N | —CF$_3$ | —S(O)$_2$CF$_3$ |
| C108 n, o, p, q, r or s | CH | N | —CF$_3$ | —S(O)$_2$CH$_3$ |
| C109 n, o, p, q, r or s | CH | N | —CF$_3$ | —S(O)$_2$CH$_3$CH$_3$ |
| C110 n, o, p, q, r or s | CH | N | —CF$_3$ | —OCH$_3$ |
| C111 n, o, p, q, r or s | CH | N | —CF$_3$ | —OCH$_2$CH$_3$ |
| C112 n, o, p, q, r or s | CH | N | —CF$_3$ | —OCH(CH$_3$)$_2$ |
| C113 n, o, p, q, r or s | CH | N | —CH$_3$ | —H |
| C114 n, o, p, q, r or s | CH | N | —CH$_3$ | —Cl |
| C115 n, o, p, q, r or s | CH | N | —CH$_3$ | —F |
| C116 n, o, p, q, r or s | CH | N | —CH$_3$ | —Br |
| C117 n, o, p, q, r or s | CH | N | —CH$_3$ | —CF$_3$ |
| C118 n, o, p, q, r or s | CH | N | —CH$_3$ | —OCF$_3$ |
| C119 n, o, p, q, r or s | CH | N | —CH$_3$ | —CH$_3$ |
| C120 n, o, p, q, r or s | CH | N | —CH$_3$ | —CH$_2$CH$_3$ |
| C121 n, o, p, q, r or s | CH | N | —CH$_3$ | -iso-propyl |
| C122 n, o, p, q, r or s | CH | N | —CH$_3$ | -tert-butyl |
| C123 n, o, p, q, r or s | CH | N | —CH$_3$ | —S(O)$_2$CF$_3$ |
| C124 n, o, p, q, r or s | CH | N | —CH$_3$ | —S(O)$_2$CH$_3$ |
| C125 n, o, p, q, r or s | CH | N | —CH$_3$ | —S(O)$_2$CH$_3$CH$_3$ |
| C126 n, o, p, q, r or s | CH | N | —CH$_3$ | —OCH$_3$ |
| C127 n, o, p, q, r or s | CH | N | —CH$_3$ | —OCH$_2$CH$_3$ |
| C128 n, o, p, q, r or s | CH | N | —CH$_3$ | —OCH(CH$_3$)$_2$ |
| C129 n, o, p, q, r or s | CH | CH | —Cl | —H |
| C130 n, o, p, q, r or s | CH | CH | —Cl | —Cl |
| C131 n, o, p, q, r or s | CH | CH | —Cl | —F |
| C132 n, o, p, q, r or s | CH | CH | —Cl | —Br |
| C133 n, o, p, q, r or s | CH | CH | —Cl | —CF$_3$ |
| C134 n, o, p, q, r or s | CH | CH | —Cl | —OCF$_3$ |
| C135 n, o, p, q, r or s | CH | CH | —Cl | —CH$_3$ |
| C136 n, o, p, q, r or s | CH | CH | —Cl | —CH$_2$CH$_3$ |
| C137 n, o, p, q, r or s | CH | CH | —Cl | -iso-propyl |
| C138 n, o, p, q, r or s | CH | CH | —Cl | -tert-butyl |
| C139 n, o, p, q, r or s | CH | CH | —Cl | —S(O)$_2$CF$_3$ |
| C140 n, o, p, q, r or s | CH | CH | —Cl | —S(O)$_2$CH$_3$ |
| C141 n, o, p, q, r or s | CH | CH | —Cl | —S(O)$_2$CH$_3$CH$_3$ |
| C142 n, o, p, q, r or s | CH | CH | —Cl | —OCH$_3$ |
| C143 n, o, p, q, r or s | CH | CH | —Cl | —OCH$_2$CH$_3$ |
| C144 n, o, p, q, r or s | CH | CH | —Cl | —OCH(CH$_3$)$_2$ |
| C145 n, o, p, q, r or s | CH | CH | —F | —H |
| C146 n, o, p, q, r or s | CH | CH | —F | —Cl |
| C147 n, o, p, q, r or s | CH | CH | —F | —F |
| C148 n, o, p, q, r or s | CH | CH | —F | —Br |
| C149 n, o, p, q, r or s | CH | CH | —F | —CF$_3$ |
| C150 n, o, p, q, r or s | CH | CH | —F | —OCF$_3$ |
| C151 n, o, p, q, r or s | CH | CH | —F | —CH$_3$ |
| C152 n, o, p, q, r or s | CH | CH | —F | —CH$_2$CH$_3$ |
| C153 n, o, p, q, r or s | CH | CH | —F | -iso-propyl |
| C154 n, o, p, q, r or s | CH | CH | —F | -tert-butyl |
| C155 n, o, p, q, r or s | CH | CH | —F | —S(O)$_2$CF$_3$ |
| C156 n, o, p, q, r or s | CH | CH | —F | —S(O)$_2$CH$_3$ |
| C157 n, o, p, q, r or s | CH | CH | —F | —S(O)$_2$CH$_3$CH$_3$ |
| C158 n, o, p, q, r or s | CH | CH | —F | —OCH$_3$ |
| C159 n, o, p, q, r or s | CH | CH | —F | —OCH$_2$CH$_3$ |
| C160 n, o, p, q, r or s | CH | CH | —F | —OCH(CH$_3$)$_2$ |
| C161 n, o, p, q, r or s | CH | CH | —CF$_3$ | —H |
| C162 n, o, p, q, r or s | CH | CH | —CF$_3$ | —Cl |
| C163 n, o, p, q, r or s | CH | CH | —CF$_3$ | —F |
| C164 n, o, p, q, r or s | CH | CH | —CF$_3$ | —Br |
| C165 n, o, p, q, r or s | CH | CH | —CF$_3$ | —CF$_3$ |
| C166 n, o, p, q, r or s | CH | CH | —CF$_3$ | —OCF$_3$ |
| C167 n, o, p, q, r or s | CH | CH | —CF$_3$ | —CH$_3$ |
| C168 n, o, p, q, r or s | CH | CH | —CF$_3$ | —CH$_2$CH$_3$ |
| C169 n, o, p, q, r or s | CH | CH | —CF$_3$ | -iso-propyl |
| C170 n, o, p, q, r or s | CH | CH | —CF$_3$ | -tert-butyl |
| C171 n, o, p, q, r or s | CH | CH | —CF$_3$ | —S(O)$_2$CF$_3$ |
| C172 n, o, p, q, r or s | CH | CH | —CF$_3$ | —S(O)$_2$CH$_3$ |
| C173 n, o, p, q, r or s | CH | CH | —CF$_3$ | —S(O)$_2$CH$_3$CH$_3$ |
| C174 n, o, p, q, r or s | CH | CH | —CF$_3$ | —OCH$_3$ |
| C175 n, o, p, q, r or s | CH | CH | —CF$_3$ | —OCH$_2$CH$_3$ |
| C176 n, o, p, q, r or s | CH | CH | —CF$_3$ | —OCH(CH$_3$)$_2$ |
| C177 n, o, p, q, r or s | CH | CH | —CH$_3$ | —H |
| C178 n, o, p, q, r or s | CH | CH | —CH$_3$ | —Cl |
| C179 n, o, p, q, r or s | CH | CH | —CH$_3$ | —F |
| C180 n, o, p, q, r or s | CH | CH | —CH$_3$ | —Br |
| C181 n, o, p, q, r or s | CH | CH | —CH$_3$ | —CF$_3$ |
| C182 n, o, p, q, r or s | CH | CH | —CH$_3$ | —OCF$_3$ |
| C183 n, o, p, q, r or s | CH | CH | —CH$_3$ | —CH$_3$ |
| C184 n, o, p, q, r or s | CH | CH | —CH$_3$ | —CH$_2$CH$_3$ |
| C185 n, o, p, q, r or s | CH | CH | —CH$_3$ | -iso-propyl |
| C186 n, o, p, q, r or s | CH | CH | —CH$_3$ | -tert-butyl |
| C187 n, o, p, q, r or s | CH | CH | —CH$_3$ | —S(O)$_2$CF$_3$ |
| C188 n, o, p, q, r or s | CH | CH | —CH$_3$ | —S(O)$_2$CH$_3$ |
| C189 n, o, p, q, r or s | CH | CH | —CH$_3$ | —S(O)$_2$CH$_3$CH$_3$ |
| C190 n, o, p, q, r or s | CH | CH | —CH$_3$ | —OCH$_3$ |
| C191 n, o, p, q, r or s | CH | CH | —CH$_3$ | —OCH$_2$CH$_3$ |
| C192 n, o, p, q, r or s | CH | CH | —CH$_3$ | —OCH(CH$_3$)$_2$ |

TABLE 4

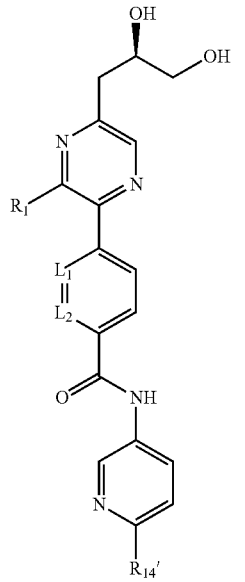

(IIt)

or

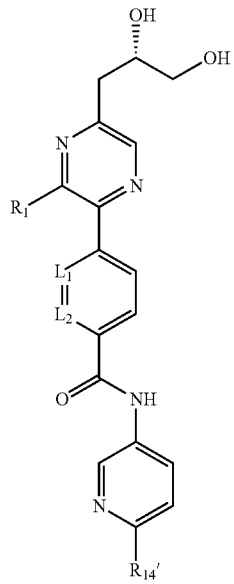

(IIu)

or

TABLE 4-continued

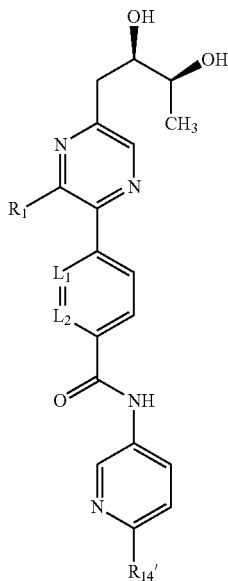

(IIv)

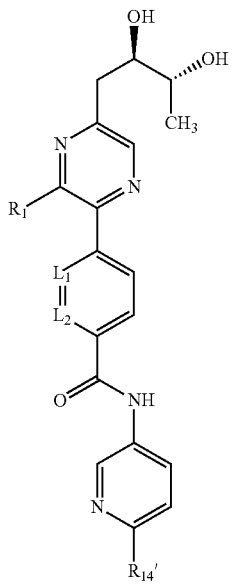

(IIw)

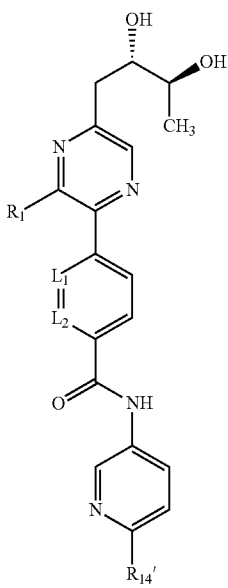

(IIx)

or

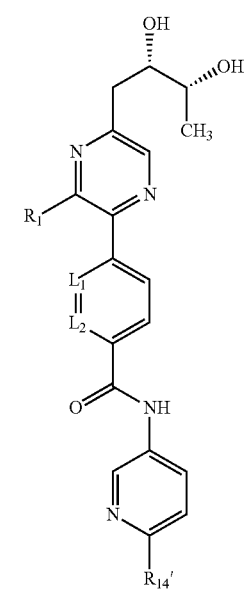

(IIy)

and pharmaceutically acceptable derivatives thereof, where:

| Compound | | L₁ | L₂ | R₁ | R₁₄' |
|---|---|---|---|---|---|
| D | D1 t, u, v, w, x or y | N | CH | —Cl | —H |
| | D2 t, u, v, w, x or y | N | CH | —Cl | —Cl |
| | D3 t, u, v, w, x or y | N | CH | —Cl | —F |
| | D4 t, u, v, w, x or y | N | CH | —Cl | —Br |
| | D5 t, u, v, w, x or y | N | CH | —Cl | —CF₃ |
| | D6 t, u, v, w, x or y | N | CH | —Cl | —OCF₃ |
| | D7 t, u, v, w, x or y | N | CH | —Cl | —CH₃ |
| | D8 t, u, v, w, x or y | N | CH | —Cl | —CH₂CH₃ |
| | D9 t, u, v, w, x or y | N | CH | —Cl | -iso-propyl |
| | D10 t, u, v, w, x or y | N | CH | —Cl | -tert-butyl |
| | D11 t, u, v, w, x or y | N | CH | —Cl | —S(O)₂CF₃ |
| | D12 t, u, v, w, x or y | N | CH | —Cl | —S(O)₂CH₃ |
| | D13 t, u, v, w, x or y | N | CH | —Cl | —S(O)₂CH₃CH₃ |
| | D14 t, u, v, w, x or y | N | CH | —Cl | —OCH₃ |
| | D15 t, u, v, w, x or y | N | CH | —Cl | —OCH₂CH₃ |
| | D16 t, u, v, w, x or y | N | CH | —Cl | —OCH(CH₃)₂ |
| | D17 t, u, v, w, x or y | N | CH | —F | —H |

TABLE 4-continued

| | | | | |
|---|---|---|---|---|
| D18 t, u, v, w, x or y | N | CH | —F | —Cl |
| D19 t, u, v, w, x or y | N | CH | —F | —F |
| D20 t, u, v, w, x or y | N | CH | —F | —Br |
| D21 t, u, v, w, x or y | N | CH | —F | —$CF_3$ |
| D22 t, u, v, w, x or y | N | CH | —F | —$OCF_3$ |
| D23 t, u, v, w, x or y | N | CH | —F | —$CH_3$ |
| D24 t, u, v, w, x or y | N | CH | —F | —$CH_2CH_3$ |
| D25 t, u, v, w, x or y | N | CH | —F | -iso-propyl |
| D26 t, u, v, w, x or y | N | CH | —F | -tert-butyl |
| D27 t, u, v, w, x or y | N | CH | —F | —$S(O)_2CF_3$ |
| D28 t, u, v, w, x or y | N | CH | —F | —$S(O)_2CH_3$ |
| D29 t, u, v, w, x or y | N | CH | —F | —$S(O)_2CH_3CH_3$ |
| D30 t, u, v, w, x or y | N | CH | —F | —$OCH_3$ |
| D31 t, u, v, w, x or y | N | CH | —F | —$OCH_2CH_3$ |
| D32 t, u, v, w, x or y | N | CH | —F | —$OCH(CH_3)_2$ |
| D33 t, u, v, w, x or y | N | CH | —$CF_3$ | —H |
| D34 t, u, v, w, x or y | N | CH | —$CF_3$ | —Cl |
| D35 t, u, v, w, x or y | N | CH | —$CF_3$ | —F |
| D36 t, u, v, w, x or y | N | CH | —$CF_3$ | —Br |
| D37 t, u, v, w, x or y | N | CH | —$CF_3$ | —$CF_3$ |
| D38 t, u, v, w, x or y | N | CH | —$CF_3$ | —$OCF_3$ |
| D39 t, u, v, w, x or y | N | CH | —$CF_3$ | —$CH_3$ |
| D40 t, u, v, w, x or y | N | CH | —$CF_3$ | —$CH_2CH_3$ |
| D41 t, u, v, w, x or y | N | CH | —$CF_3$ | -iso-propyl |
| D42 t, u, v, w, x or y | N | CH | —$CF_3$ | -tert-butyl |
| D43 t, u, v, w, x or y | N | CH | —$CF_3$ | —$S(O)_2CF_3$ |
| D44 t, u, v, w, x or y | N | CH | —$CF_3$ | —$S(O)_2CH_3$ |
| D45 t, u, v, w, x or y | N | CH | —$CF_3$ | —$S(O)_2CH_3CH_3$ |
| D46 t, u, v, w, x or y | N | CH | —$CF_3$ | —$OCH_3$ |
| D47 t, u, v, w, x or y | N | CH | —$CF_3$ | —$OCH_2CH_3$ |
| D48 t, u, v, w, x or y | N | CH | —$CF_3$ | —$OCH(CH_3)_2$ |
| D49 t, u, v, w, x or y | N | CH | —$CH_3$ | —H |
| D50 t, u, v, w, x or y | N | CH | —$CH_3$ | —Cl |
| D51 t, u, v, w, x or y | N | CH | —$CH_3$ | —F |
| D52 t, u, v, w, x or y | N | CH | —$CH_3$ | —Br |
| D53 t, u, v, w, x or y | N | CH | —$CH_3$ | —$CF_3$ |
| D54 t, u, v, w, x or y | N | CH | —$CH_3$ | —$OCF_3$ |
| D55 t, u, v, w, x or y | N | CH | —$CH_3$ | —$CH_3$ |
| D56 t, u, v, w, x or y | N | CH | —$CH_3$ | —$CH_2CH_3$ |
| D57 t, u, v, w, x or y | N | CH | —$CH_3$ | -iso-propyl |
| D58 t, u, v, w, x or y | N | CH | —$CH_3$ | -tert-butyl |
| D59 t, u, v, w, x or y | N | CH | —$CH_3$ | —$S(O)_2CF_3$ |
| D60 t, u, v, w, x or y | N | CH | —$CH_3$ | —$S(O)_2CH_3$ |
| D61 t, u, v, w, x or y | N | CH | —$CH_3$ | —$S(O)_2CH_3CH_3$ |
| D62 t, u, v, w, x or y | N | CH | —$CH_3$ | —$OCH_3$ |
| D63 t, u, v, w, x or y | N | CH | —$CH_3$ | —$OCH_2CH_3$ |
| D64 t, u, v, w, x or y | N | CH | —$CH_3$ | —$OCH(CH_3)_2$ |
| D65 t, u, v, w, x or y | CH | N | —Cl | —H |
| D66 t, u, v, w, x or y | CH | N | —Cl | —Cl |
| D67 t, u, v, w, x or y | CH | N | —Cl | —F |
| D68 t, u, v, w, x or y | CH | N | —Cl | —Br |
| D69 t, u, v, w, x or y | CH | N | —Cl | —$CF_3$ |
| D70 t, u, v, w, x or y | CH | N | —Cl | —$OCF_3$ |
| D71 t, u, v, w, x or y | CH | N | —Cl | —$CH_3$ |
| D72 t, u, v, w, x or y | CH | N | —Cl | —$CH_2CH_3$ |
| D73 t, u, v, w, x or y | CH | N | —Cl | -iso-propyl |
| D74 t, u, v, w, x or y | CH | N | —Cl | -tert-butyl |
| D75 t, u, v, w, x or y | CH | N | —Cl | —$S(O)_2CF_3$ |
| D76 t, u, v, w, x or y | CH | N | —Cl | —$S(O)_2CH_3$ |
| D77 t, u, v, w, x or y | CH | N | —Cl | —$S(O)_2CH_3CH_3$ |
| D78 t, u, v, w, x or y | CH | N | —Cl | —$OCH_3$ |
| D79 t, u, v, w, x or y | CH | N | —Cl | —$OCH_2CH_3$ |
| D80 t, u, v, w, x or y | CH | N | —Cl | —$OCH(CH_3)_2$ |
| D81 t, u, v, w, x or y | CH | N | —F | —H |
| D82 t, u, v, w, x or y | CH | N | —F | —Cl |
| D83 t, u, v, w, x or y | CH | N | —F | —F |
| D84 t, u, v, w, x or y | CH | N | —F | —Br |
| D85 t, u, v, w, x or y | CH | N | —F | —$CF_3$ |
| D86 t, u, v, w, x or y | CH | N | —F | —$OCF_3$ |
| D87 t, u, v, w, x or y | CH | N | —F | —$CH_3$ |
| D88 t, u, v, w, x or y | CH | N | —F | —$CH_2CH_3$ |
| D89 t, u, v, w, x or y | CH | N | —F | -iso-propyl |
| D90 t, u, v, w, x or y | CH | N | —F | -tert-butyl |
| D91 t, u, v, w, x or y | CH | N | —F | —$S(O)_2CF_3$ |
| D92 t, u, v, w, x or y | CH | N | —F | —$S(O)_2CH_3$ |
| D93 t, u, v, w, x or y | CH | N | —F | —$S(O)_2CH_3CH_3$ |
| D94 t, u, v, w, x or y | CH | N | —F | —$OCH_3$ |
| D95 t, u, v, w, x or y | CH | N | —F | —$OCH_2CH_3$ |
| D96 t, u, v, w, x or y | CH | N | —F | —$OCH(CH_3)_2$ |
| D97 t, u, v, w, x or y | CH | N | —$CF_3$ | —H |
| D98 t, u, v, w, x or y | CH | N | —$CF_3$ | —Cl |
| D99 t, u, v, w, x or y | CH | N | —$CF_3$ | —F |
| D100 t, u, v, w, x or y | CH | N | —$CF_3$ | —Br |
| D101 t, u, v, w, x or y | CH | N | —$CF_3$ | —$CF_3$ |
| D102 t, u, v, w, x or y | CH | N | —$CF_3$ | —$OCF_3$ |
| D103 t, u, v, w, x or y | CH | N | —$CF_3$ | —$CH_3$ |
| D104 t, u, v, w, x or y | CH | N | —$CF_3$ | —$CH_2CH_3$ |
| D105 t, u, v, w, x or y | CH | N | —$CF_3$ | -iso-propyl |
| D106 t, u, v, w, x or y | CH | N | —$CF_3$ | -tert-butyl |
| D107 t, u, v, w, x or y | CH | N | —$CF_3$ | —$S(O)_2CF_3$ |
| D108 t, u, v, w, x or y | CH | N | —$CF_3$ | —$S(O)_2CH_3$ |
| D109 t, u, v, w, x or y | CH | N | —$CF_3$ | —$S(O)_2CH_3CH_3$ |
| D110 t, u, v, w, x or y | CH | N | —$CF_3$ | —$OCH_3$ |
| D111 t, u, v, w, x or y | CH | N | —$CF_3$ | —$OCH_2CH_3$ |
| D112 t, u, v, w, x or y | CH | N | —$CF_3$ | —$OCH(CH_3)_2$ |
| D113 t, u, v, w, x or y | CH | N | —$CH_3$ | —H |
| D114 t, u, v, w, x or y | CH | N | —$CH_3$ | —Cl |
| D115 t, u, v, w, x or y | CH | N | —$CH_3$ | —F |
| D116 t, u, v, w, x or y | CH | N | —$CH_3$ | —Br |
| D117 t, u, v, w, x or y | CH | N | —$CH_3$ | —$CF_3$ |
| D118 t, u, v, w, x or y | CH | N | —$CH_3$ | —$OCF_3$ |
| D119 t, u, v, w, x or y | CH | N | —$CH_3$ | —$CH_3$ |
| D120 t, u, v, w, x or y | CH | N | —$CH_3$ | —$CH_2CH_3$ |
| D121 t, u, v, w, x or y | CH | N | —$CH_3$ | -iso-propyl |
| D122 t, u, v, w, x or y | CH | N | —$CH_3$ | -tert-butyl |
| D123 t, u, v, w, x or y | CH | N | —$CH_3$ | —$S(O)_2CF_3$ |
| D124 t, u, v, w, x or y | CH | N | —$CH_3$ | —$S(O)_2CH_3$ |
| D125 t, u, v, w, x or y | CH | N | —$CH_3$ | —$S(O)_2CH_3CH_3$ |
| D126 t, u, v, w, x or y | CH | N | —$CH_3$ | —$OCH_3$ |
| D127 t, u, v, w, x or y | CH | N | —$CH_3$ | —$OCH_2CH_3$ |
| D128 t, u, v, w, x or y | CH | N | —$CH_3$ | —$OCH(CH_3)_2$ |
| D129 t, u, v, w, x or y | CH | CH | —Cl | —H |
| D130 t, u, v, w, x or y | CH | CH | —Cl | —Cl |
| D131 t, u, v, w, x or y | CH | CH | —Cl | —F |
| D132 t, u, v, w, x or y | CH | CH | —Cl | —Br |
| D133 t, u, v, w, x or y | CH | CH | —Cl | —$CF_3$ |
| D134 t, u, v, w, x or y | CH | CH | —Cl | —$OCF_3$ |
| D135 t, u, v, w, x or y | CH | CH | —Cl | —$CH_3$ |
| D136 t, u, v, w, x or y | CH | CH | —Cl | —$CH_2CH_3$ |
| D137 t, u, v, w, x or y | CH | CH | —Cl | -iso-propyl |
| D138 t, u, v, w, x or y | CH | CH | —Cl | -tert-butyl |
| D139 t, u, v, w, x or y | CH | CH | —Cl | —$S(O)_2CF_3$ |
| D140 t, u, v, w, x or y | CH | CH | —Cl | —$S(O)_2CH_3$ |
| D141 t, u, v, w, x or y | CH | CH | —Cl | —$S(O)_2CH_3CH_3$ |
| D142 t, u, v, w, x or y | CH | CH | —Cl | —$OCH_3$ |
| D143 t, u, v, w, x or y | CH | CH | —Cl | —$OCH_2CH_3$ |
| D144 t, u, v, w, x or y | CH | CH | —Cl | —$OCH(CH_3)_2$ |
| D145 t, u, v, w, x or y | CH | CH | —F | —H |
| D146 t, u, v, w, x or y | CH | CH | —F | —Cl |
| D147 t, u, v, w, x or y | CH | CH | —F | —F |
| D148 t, u, v, w, x or y | CH | CH | —F | —Br |
| D149 t, u, v, w, x or y | CH | CH | —F | —$CF_3$ |
| D150 t, u, v, w, x or y | CH | CH | —F | —$OCF_3$ |
| D151 t, u, v, w, x or y | CH | CH | —F | —$CH_3$ |
| D152 t, u, v, w, x or y | CH | CH | —F | —$CH_2CH_3$ |
| D153 t, u, v, w, x or y | CH | CH | —F | -iso-propyl |
| D154 t, u, v, w, x or y | CH | CH | —F | -tert-butyl |
| D155 t, u, v, w, x or y | CH | CH | —F | —$S(O)_2CF_3$ |
| D156 t, u, v, w, x or y | CH | CH | —F | —$S(O)_2CH_3$ |
| D157 t, u, v, w, x or y | CH | CH | —F | —$S(O)_2CH_3CH_3$ |
| D158 t, u, v, w, x or y | CH | CH | —F | —$OCH_3$ |
| D159 t, u, v, w, x or y | CH | CH | —F | —$OCH_2CH_3$ |
| D160 t, u, v, w, x or y | CH | CH | —F | —$OCH(CH_3)_2$ |
| D161 t, u, v, w, x or y | CH | CH | —$CF_3$ | —H |
| D162 t, u, v, w, x or y | CH | CH | —$CF_3$ | —Cl |
| D163 t, u, v, w, x or y | CH | CH | —$CF_3$ | —F |
| D164 t, u, v, w, x or y | CH | CH | —$CF_3$ | —Br |
| D165 t, u, v, w, x or y | CH | CH | —$CF_3$ | —$CF_3$ |
| D166 t, u, v, w, x or y | CH | CH | —$CF_3$ | —$OCF_3$ |
| D167 t, u, v, w, x or y | CH | CH | —$CF_3$ | —$CH_3$ |
| D168 t, u, v, w, x or y | CH | CH | —$CF_3$ | —$CH_2CH_3$ |
| D169 t, u, v, w, x or y | CH | CH | —$CF_3$ | -iso-propyl |
| D170 t, u, v, w, x or y | CH | CH | —$CF_3$ | -tert-butyl |
| D171 t, u, v, w, x or y | CH | CH | —$CF_3$ | —$S(O)_2CF_3$ |
| D172 t, u, v, w, x or y | CH | CH | —$CF_3$ | —$S(O)_2CH_3$ |
| D173 t, u, v, w, x or y | CH | CH | —$CF_3$ | —$S(O)_2CH_3CH_3$ |
| D174 t, u, v, w, x or y | CH | CH | —$CF_3$ | —$OCH_3$ |
| D175 t, u, v, w, x or y | CH | CH | —$CF_3$ | —$OCH_2CH_3$ |
| D176 t, u, v, w, x or y | CH | CH | —$CF_3$ | —$OCH(CH_3)_2$ |
| D177 t, u, v, w, x or y | CH | CH | —$CH_3$ | —H |

TABLE 4-continued

| | | | | |
|---|---|---|---|---|
| D178 t, u, v, w, x or y | CH | CH | —CH$_3$ | —Cl |
| D179 t, u, v, w, x or y | CH | CH | —CH$_3$ | —F |
| D180 t, u, v, w, x or y | CH | CH | —CH$_3$ | —Br |
| D181 t, u, v, w, x or y | CH | CH | —CH$_3$ | —CF$_3$ |
| D182 t, u, v, w, x or y | CH | CH | —CH$_3$ | —OCF$_3$ |
| D183 t, u, v, w, x or y | CH | CH | —CH$_3$ | —CH$_3$ |
| D184 t, u, v, w, x or y | CH | CH | —CH$_3$ | —CH$_2$CH$_3$ |
| D185 t, u, v, w, x or y | CH | CH | —CH$_3$ | -iso-propyl |
| D186 t, u, v, w, x or y | CH | CH | —CH$_3$ | -tert-butyl |
| D187 t, u, v, w, x or y | CH | CH | —CH$_3$ | —S(O)$_2$CF$_3$ |
| D188 t, u, v, w, x or y | CH | CH | —CH$_3$ | —S(O)$_2$CH$_3$ |
| D189 t, u, v, w, x or y | CH | CH | —CH$_3$ | —S(O)$_2$CH$_2$CH$_3$ |
| D190 t, u, v, w, x or y | CH | CH | —CH$_3$ | —OCH$_3$ |
| D191 t, u, v, w, x or y | CH | CH | —CH$_3$ | —OCH$_2$CH$_3$ |
| D192 t, u, v, w, x or y | CH | CH | —CH$_3$ | —OCH(CH$_3$)$_2$ |

TABLE 5

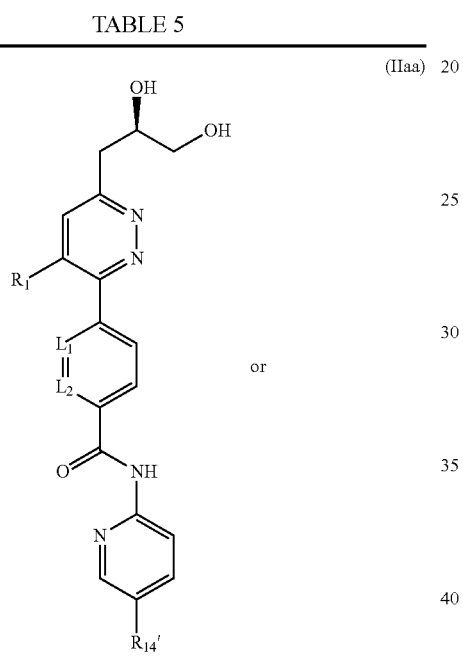

(IIaa)

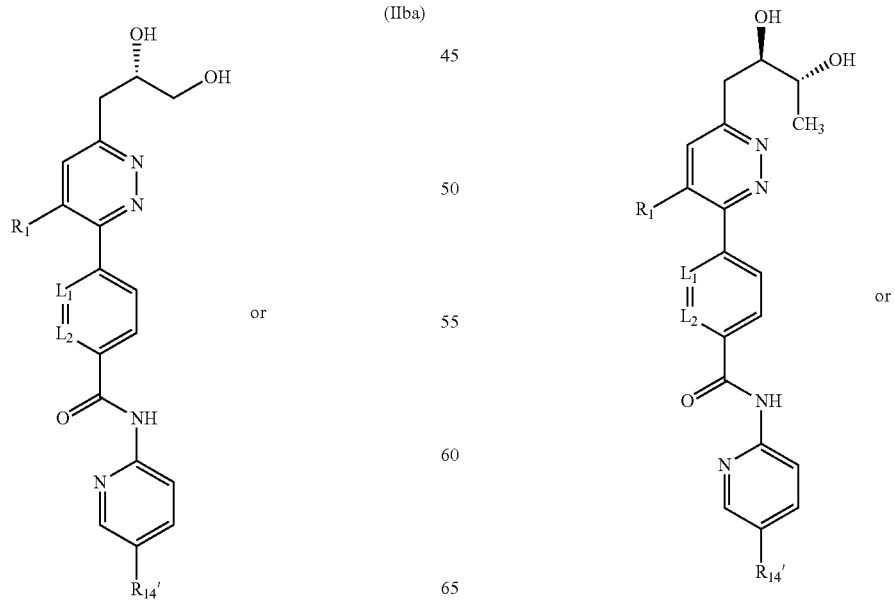

(IIba)

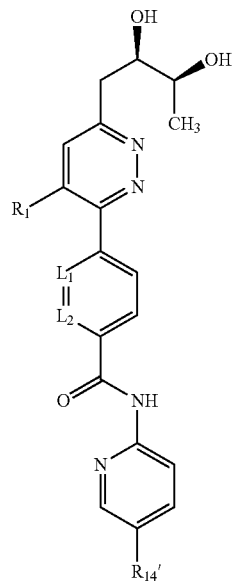

(IIca)

or (IIda)

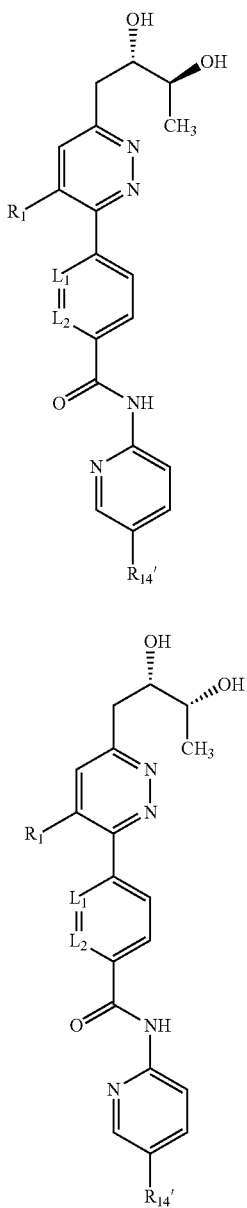

and pharmaceutically acceptable derivatives thereof, where:

| Compound | | $L_1$ | $L_2$ | $R_1$ | $R_{14}'$ |
|---|---|---|---|---|---|
| E | E1 aa, ba, ca, da, ea or fa | N | CH | —Cl | —H |
| | E2 aa, ba, ca, da, ea or fa | N | CH | —Cl | —Cl |
| | E3 aa, ba, ca, da, ea or fa | N | CH | —Cl | —F |
| | E4 aa, ba, ca, da, ea or fa | N | CH | —Cl | —Br |
| | E5 aa, ba, ca, da, ea or fa | N | CH | —Cl | —CF$_3$ |
| | E6 aa, ba, ca, da, ea or fa | N | CH | —Cl | —OCF$_3$ |
| | E7 aa, ba, ca, da, ea or fa | N | CH | —Cl | —CH$_3$ |
| | E8 aa, ba, ca, da, ea or fa | N | CH | —Cl | —CH$_2$CH$_3$ |
| | E9 aa, ba, ca, da, ea or fa | N | CH | —Cl | -iso-propyl |
| | E10 aa, ba, ca, da, ea or fa | N | CH | —Cl | -tert-butyl |
| | E11 aa, ba, ca, da, ea or fa | N | CH | —Cl | —S(O)$_2$CF$_3$ |
| | E12 aa, ba, ca, da, ea or fa | N | CH | —Cl | —S(O)$_2$CH$_3$ |
| | E13 aa, ba, ca, da, ea or fa | N | CH | —Cl | —S(O)$_2$CH$_3$CH$_3$ |
| | E14 aa, ba, ca, da, ea or fa | N | CH | —Cl | —OCH$_3$ |
| | E15 aa, ba, ca, da, ea or fa | N | CH | —Cl | —OCH$_2$CH$_3$ |
| | E16 aa, ba, ca, da, ea or fa | N | CH | —Cl | —OCH(CH$_3$)$_2$ |
| | E17 aa, ba, ca, da, ea or fa | N | CH | —F | —H |
| | E18 aa, ba, ca, da, ea or fa | N | CH | —F | —Cl |
| | E19 aa, ba, ca, da, ea or fa | N | CH | —F | —F |
| | E20 aa, ba, ca, da, ea or fa | N | CH | —F | —Br |
| | E21 aa, ba, ca, da, ea or fa | N | CH | —F | —CF$_3$ |
| | E22 aa, ba, ca, da, ea or fa | N | CH | —F | —OCF$_3$ |
| | E23 aa, ba, ca, da, ea or fa | N | CH | —F | —CH$_3$ |
| | E24 aa, ba, ca, da, ea or fa | N | CH | —F | —CH$_2$CH$_3$ |
| | E25 aa, ba, ca, da, ea or fa | N | CH | —F | -iso-propyl |
| | E26 aa, ba, ca, da, ea or fa | N | CH | —F | -tert-butyl |
| | E27 aa, ba, ca, da, ea or fa | N | CH | —F | —S(O)$_2$CF$_3$ |
| | E28 aa, ba, ca, da, ea or fa | N | CH | —F | —S(O)$_2$CH$_3$ |
| | E29 aa, ba, ca, da, ea or fa | N | CH | —F | —S(O)$_2$CH$_3$CH$_3$ |
| | E30 aa, ba, ca, da, ea or fa | N | CH | —F | —OCH$_3$ |
| | E31 aa, ba, ca, da, ea or fa | N | CH | —F | —OCH$_2$CH$_3$ |
| | E32 aa, ba, ca, da, ea or fa | N | CH | —F | —OCH(CH$_3$)$_2$ |
| | E33 aa, ba, ca, da, ea or fa | N | CH | —CF$_3$ | —H |
| | E34 aa, ba, ca, da, ea or fa | N | CH | —CF$_3$ | —Cl |
| | E35 aa, ba, ca, da, ea or fa | N | CH | —CF$_3$ | —F |
| | E36 aa, ba, ca, da, ea or fa | N | CH | —CF$_3$ | —Br |
| | E37 aa, ba, ca, da, ea or fa | N | CH | —CF$_3$ | —CF$_3$ |
| | E38 aa, ba, ca, da, ea or fa | N | CH | —CF$_3$ | —OCF$_3$ |
| | E39 aa, ba, ca, da, ea or fa | N | CH | —CF$_3$ | —CH$_3$ |
| | E40 aa, ba, ca, da, ea or fa | N | CH | —CF$_3$ | —CH$_2$CH$_3$ |
| | E41 aa, ba, ca, da, ea or fa | N | CH | —CF$_3$ | -iso-propyl |
| | E42 aa, ba, ca, da, ea or fa | N | CH | —CF$_3$ | -tert-butyl |
| | E43 aa, ba, ca, da, ea or fa | N | CH | —CF$_3$ | —S(O)$_2$CF$_3$ |
| | E44 aa, ba, ca, da, ea or fa | N | CH | —CF$_3$ | —S(O)$_2$CH$_3$ |
| | E45 aa, ba, ca, da, ea or fa | N | CH | —CF$_3$ | —S(O)$_2$CH$_3$CH$_3$ |
| | E46 aa, ba, ca, da, ea or fa | N | CH | —CF$_3$ | —OCH$_3$ |
| | E47 aa, ba, ca, da, ea or fa | N | CH | —CF$_3$ | —OCH$_2$CH$_3$ |
| | E48 aa, ba, ca, da, ea or fa | N | CH | —CF$_3$ | —OCH(CH$_3$)$_2$ |
| | E49 aa, ba, ca, da, ea or fa | N | CH | —CH$_3$ | —H |
| | E50 aa, ba, ca, da, ea or fa | N | CH | —CH$_3$ | —Cl |
| | E51 aa, ba, ca, da, ea or fa | N | CH | —CH$_3$ | —F |
| | E52 aa, ba, ca, da, ea or fa | N | CH | —CH$_3$ | —Br |
| | E53 aa, ba, ca, da, ea or fa | N | CH | —CH$_3$ | —CF$_3$ |
| | E54 aa, ba, ca, da, ea or fa | N | CH | —CH$_3$ | —OCF$_3$ |
| | E55 aa, ba, ca, da, ea or fa | N | CH | —CH$_3$ | —CH$_3$ |
| | E56 aa, ba, ca, da, ea or fa | N | CH | —CH$_3$ | —CH$_2$CH$_3$ |
| | E57 aa, ba, ca, da, ea or fa | N | CH | —CH$_3$ | -iso-propyl |
| | E58 aa, ba, ca, da, ea or fa | N | CH | —CH$_3$ | -tert-butyl |
| | E59 aa, ba, ca, da, ea or fa | N | CH | —CH$_3$ | —S(O)$_2$CF$_3$ |
| | E60 aa, ba, ca, da, ea or fa | N | CH | —CH$_3$ | —S(O)$_2$CH$_3$ |
| | E61 aa, ba, ca, da, ea or fa | N | CH | —CH$_3$ | —S(O)$_2$CH$_3$CH$_3$ |
| | E62 aa, ba, ca, da, ea or fa | N | CH | —CH$_3$ | —OCH$_3$ |
| | E63 aa, ba, ca, da, ea or fa | N | CH | —CH$_3$ | —OCH$_2$CH$_3$ |
| | E64 aa, ba, ca, da, ea or fa | N | CH | —CH$_3$ | —OCH(CH$_3$)$_2$ |
| | E65 aa, ba, ca, da, ea or fa | CH | N | —Cl | —H |
| | E66 aa, ba, ca, da, ea or fa | CH | N | —Cl | —Cl |
| | E67 aa, ba, ca, da, ea or fa | CH | N | —Cl | —F |
| | E68 aa, ba, ca, da, ea or fa | CH | N | —Cl | —Br |
| | E69 aa, ba, ca, da, ea or fa | CH | N | —Cl | —CF$_3$ |
| | E70 aa, ba, ca, da, ea or fa | CH | N | —Cl | —OCF$_3$ |
| | E71 aa, ba, ca, da, ea or fa | CH | N | —Cl | —CH$_3$ |
| | E72 aa, ba, ca, da, ea or fa | CH | N | —Cl | —CH$_2$CH$_3$ |
| | E73 aa, ba, ca, da, ea or fa | CH | N | —Cl | -iso-propyl |
| | E74 aa, ba, ca, da, ea or fa | CH | N | —Cl | -tert-butyl |
| | E75 aa, ba, ca, da, ea or fa | CH | N | —Cl | —S(O)$_2$CF$_3$ |
| | E76 aa, ba, ca, da, ea or fa | CH | N | —Cl | —S(O)$_2$CH$_3$ |
| | E77 aa, ba, ca, da, ea or fa | CH | N | —Cl | —S(O)$_2$CH$_3$CH$_3$ |
| | E78 aa, ba, ca, da, ea or fa | CH | N | —Cl | —OCH$_3$ |
| | E79 aa, ba, ca, da, ea or fa | CH | N | —Cl | —OCH$_2$CH$_3$ |
| | E80 aa, ba, ca, da, ea or fa | CH | N | —Cl | —OCH(CH$_3$)$_2$ |
| | E81 aa, ba, ca, da, ea or fa | CH | N | —F | —H |
| | E82 aa, ba, ca, da, ea or fa | CH | N | —F | —Cl |
| | E83 aa, ba, ca, da, ea or fa | CH | N | —F | —F |
| | E84 aa, ba, ca, da, ea or fa | CH | N | —F | —Br |
| | E85 aa, ba, ca, da, ea or fa | CH | N | —F | —CF$_3$ |
| | E86 aa, ba, ca, da, ea or fa | CH | N | —F | —OCF$_3$ |
| | E87 aa, ba, ca, da, ea or fa | CH | N | —F | —CH$_3$ |
| | E88 aa, ba, ca, da, ea or fa | CH | N | —F | —CH$_2$CH$_3$ |
| | E89 aa, ba, ca, da, ea or fa | CH | N | —F | -iso-propyl |
| | E90 aa, ba, ca, da, ea or fa | CH | N | —F | -tert-butyl |
| | E91 aa, ba, ca, da, ea or fa | CH | N | —F | —S(O)$_2$CF$_3$ |
| | E92 aa, ba, ca, da, ea or fa | CH | N | —F | —S(O)$_2$CH$_3$ |
| | E93 aa, ba, ca, da, ea or fa | CH | N | —F | —S(O)$_2$CH$_3$CH$_3$ |
| | E94 aa, ba, ca, da, ea or fa | CH | N | —F | —OCH$_3$ |
| | E95 aa, ba, ca, da, ea or fa | CH | N | —F | —OCH$_2$CH$_3$ |
| | E96 aa, ba, ca, da, ea or fa | CH | N | —F | —OCH(CH$_3$)$_2$ |
| | E97 aa, ba, ca, da, ea or fa | CH | N | —CF$_3$ | —H |

TABLE 5-continued

| | | | |
|---|---|---|---|
| E98 aa, ba, ca, da, ea or fa | CH N | —CF$_3$ | —Cl |
| E99 aa, ba, ca, da, ea or fa | CH N | —CF$_3$ | —F |
| E100 aa, ba, ca, da, ea or fa | CH N | —CF$_3$ | —Br |
| E101 aa, ba, ca, da, ea or fa | CH N | —CF$_3$ | —CF$_3$ |
| E102 aa, ba, ca, da, ea or fa | CH N | —CF$_3$ | —OCF$_3$ |
| E103 aa, ba, ca, da, ea or fa | CH N | —CF$_3$ | —CH$_3$ |
| E104 aa, ba, ca, da, ea or fa | CH N | —CF$_3$ | —CH$_2$CH$_3$ |
| E105 aa, ba, ca, da, ea or fa | CH N | —CF$_3$ | -iso-propyl |
| E106 aa, ba, ca, da, ea or fa | CH N | —CF$_3$ | -tert-butyl |
| E107 aa, ba, ca, da, ea or fa | CH N | —CF$_3$ | —S(O)$_2$CF$_3$ |
| E108 aa, ba, ca, da, ea or fa | CH N | —CF$_3$ | —S(O)$_2$CH$_3$ |
| E109 aa, ba, ca, da, ea or fa | CH N | —CF$_3$ | —S(O)$_2$CH$_3$CH$_3$ |
| E110 aa, ba, ca, da, ea or fa | CH N | —CF$_3$ | —OCH$_3$ |
| E111 aa, ba, ca, da, ea or fa | CH N | —CF$_3$ | —OCH$_2$CH$_3$ |
| E112 aa, ba, ca, da, ea or fa | CH N | —CF$_3$ | —OCH(CH$_3$)$_2$ |
| E113 aa, ba, ca, da, ea or fa | CH N | —CH$_3$ | —H |
| E114 aa, ba, ca, da, ea or fa | CH N | —CH$_3$ | —Cl |
| E115 aa, ba, ca, da, ea or fa | CH N | —CH$_3$ | —F |
| E116 aa, ba, ca, da, ea or fa | CH N | —CH$_3$ | —Br |
| E117 aa, ba, ca, da, ea or fa | CH N | —CH$_3$ | —CF$_3$ |
| E118 aa, ba, ca, da, ea or fa | CH N | —CH$_3$ | —OCF$_3$ |
| E119 aa, ba, ca, da, ea or fa | CH N | —CH$_3$ | —CH$_3$ |
| E120 aa, ba, ca, da, ea or fa | CH N | —CH$_3$ | —CH$_2$CH$_3$ |
| E121 aa, ba, ca, da, ea or fa | CH N | —CH$_3$ | -iso-propyl |
| E122 aa, ba, ca, da, ea or fa | CH N | —CH$_3$ | -tert-butyl |
| E123 aa, ba, ca, da, ea or fa | CH N | —CH$_3$ | —S(O)$_2$CF$_3$ |
| E124 aa, ba, ca, da, ea or fa | CH N | —CH$_3$ | —S(O)$_2$CH$_3$ |
| E125 aa, ba, ca, da, ea or fa | CH N | —CH$_3$ | —S(O)$_2$CH$_3$CH$_3$ |
| E126 aa, ba, ca, da, ea or fa | CH N | —CH$_3$ | —OCH$_3$ |
| E127 aa, ba, ca, da, ea or fa | CH N | —CH$_3$ | —OCH$_2$CH$_3$ |
| E128 aa, ba, ca, da, ea or fa | CH N | —CH$_3$ | —OCH(CH$_3$)$_2$ |
| E129 aa, ba, ca, da, ea or fa | CH CH | —Cl | —H |
| E130 aa, ba, ca, da, ea or fa | CH CH | —Cl | —Cl |
| E131 aa, ba, ca, da, ea or fa | CH CH | —Cl | —F |
| E132 aa, ba, ca, da, ea or fa | CH CH | —Cl | —Br |
| E133 aa, ba, ca, da, ea or fa | CH CH | —Cl | —CF$_3$ |
| E134 aa, ba, ca, da, ea or fa | CH CH | —Cl | —OCF$_3$ |
| E135 aa, ba, ca, da, ea or fa | CH CH | —Cl | —CH$_3$ |
| E136 aa, ba, ca, da, ea or fa | CH CH | —Cl | —CH$_2$CH$_3$ |
| E137 aa, ba, ca, da, ea or fa | CH CH | —Cl | -iso-propyl |
| E138 aa, ba, ca, da, ea or fa | CH CH | —Cl | -tert-butyl |
| E139 aa, ba, ca, da, ea or fa | CH CH | —Cl | —S(O)$_2$CF$_3$ |
| E140 aa, ba, ca, da, ea or fa | CH CH | —Cl | —S(O)$_2$CH$_3$ |
| E141 aa, ba, ca, da, ea or fa | CH CH | —Cl | —S(O)$_2$CH$_3$CH$_3$ |
| E142 aa, ba, ca, da, ea or fa | CH CH | —Cl | —OCH$_3$ |
| E143 aa, ba, ca, da, ea or fa | CH CH | —Cl | —OCH$_2$CH$_3$ |
| E144 aa, ba, ca, da, ea or fa | CH CH | —Cl | —OCH(CH$_3$)$_2$ |
| E145 aa, ba, ca, da, ea or fa | CH CH | —F | —H |
| E146 aa, ba, ca, da, ea or fa | CH CH | —F | —Cl |
| E147 aa, ba, ca, da, ea or fa | CH CH | —F | —F |
| E148 aa, ba, ca, da, ea or fa | CH CH | —F | —Br |
| E149 aa, ba, ca, da, ea or fa | CH CH | —F | —CF$_3$ |
| E150 aa, ba, ca, da, ea or fa | CH CH | —F | —OCF$_3$ |
| E151 aa, ba, ca, da, ea or fa | CH CH | —F | —CH$_3$ |
| E152 aa, ba, ca, da, ea or fa | CH CH | —F | —CH$_2$CH$_3$ |
| E153 aa, ba, ca, da, ea or fa | CH CH | —F | -iso-propyl |
| E154 aa, ba, ca, da, ea or fa | CH CH | —F | -tert-butyl |
| E155 aa, ba, ca, da, ea or fa | CH CH | —F | —S(O)$_2$CF$_3$ |
| E156 aa, ba, ca, da, ea or fa | CH CH | —F | —S(O)$_2$CH$_3$ |
| E157 aa, ba, ca, da, ea or fa | CH CH | —F | —S(O)$_2$CH$_3$CH$_3$ |
| E158 aa, ba, ca, da, ea or fa | CH CH | —F | —OCH$_3$ |
| E159 aa, ba, ca, da, ea or fa | CH CH | —F | —OCH$_2$CH$_3$ |
| E160 aa, ba, ca, da, ea or fa | CH CH | —F | —OCH(CH$_3$)$_2$ |
| E161 aa, ba, ca, da, ea or fa | CH CH | —CF$_3$ | —H |
| E162 aa, ba, ca, da, ea or fa | CH CH | —CF$_3$ | —Cl |
| E163 aa, ba, ca, da, ea or fa | CH CH | —CF$_3$ | —F |
| E164 aa, ba, ca, da, ea or fa | CH CH | —CF$_3$ | —Br |
| E165 aa, ba, ca, da, ea or fa | CH CH | —CF$_3$ | —CF$_3$ |
| E166 aa, ba, ca, da, ea or fa | CH CH | —CF$_3$ | —OCF$_3$ |
| E167 aa, ba, ca, da, ea or fa | CH CH | —CF$_3$ | —CH$_3$ |
| E168 aa, ba, ca, da, ea or fa | CH CH | —CF$_3$ | —CH$_2$CH$_3$ |
| E169 aa, ba, ca, da, ea or fa | CH CH | —CF$_3$ | -iso-propyl |
| E170 aa, ba, ca, da, ea or fa | CH CH | —CF$_3$ | -tert-butyl |
| E171 aa, ba, ca, da, ea or fa | CH CH | —CF$_3$ | —S(O)$_2$CF$_3$ |
| E172 aa, ba, ca, da, ea or fa | CH CH | —CF$_3$ | —S(O)$_2$CH$_3$ |
| E173 aa, ba, ca, da, ea or fa | CH CH | —CF$_3$ | —S(O)$_2$CH$_3$CH$_3$ |
| E174 aa, ba, ca, da, ea or fa | CH CH | —CF$_3$ | —OCH$_3$ |
| E175 aa, ba, ca, da, ea or fa | CH CH | —CF$_3$ | —OCH$_2$CH$_3$ |
| E176 aa, ba, ca, da, ea or fa | CH CH | —CF$_3$ | —OCH(CH$_3$)$_2$ |
| E177 aa, ba, ca, da, ea or fa | CH CH | —CH$_3$ | —H |

TABLE 5-continued

| | | | |
|---|---|---|---|
| E178 aa, ba, ca, da, ea or fa | CH CH | —CH$_3$ | —Cl |
| E179 aa, ba, ca, da, ea or fa | CH CH | —CH$_3$ | —F |
| E180 aa, ba, ca, da, ea or fa | CH CH | —CH$_3$ | —Br |
| E181 aa, ba, ca, da, ea or fa | CH CH | —CH$_3$ | —CF$_3$ |
| E182 aa, ba, ca, da, ea or fa | CH CH | —CH$_3$ | —OCF$_3$ |
| E183 aa, ba, ca, da, ea or fa | CH CH | —CH$_3$ | —CH$_3$ |
| E184 aa, ba, ca, da, ea or fa | CH CH | —CH$_3$ | —CH$_2$CH$_3$ |
| E185 aa, ba, ca, da, ea or fa | CH CH | —CH$_3$ | -iso-propyl |
| E186 aa, ba, ca, da, ea or fa | CH CH | —CH$_3$ | -tert-butyl |
| E187 aa, ba, ca, da, ea or fa | CH CH | —CH$_3$ | —S(O)$_2$CF$_3$ |
| E188 aa, ba, ca, da, ea or fa | CH CH | —CH$_3$ | —S(O)$_2$CH$_3$ |
| E189 aa, ba, ca, da, ea or fa | CH CH | —CH$_3$ | —S(O)$_2$CH$_3$CH$_3$ |
| E190 aa, ba, ca, da, ea or fa | CH CH | —CH$_3$ | —OCH$_3$ |
| E191 aa, ba, ca, da, ea or fa | CH CH | —CH$_3$ | —OCH$_2$CH$_3$ |
| E192 aa, ba, ca, da, ea or fa | CH CH | —CH$_3$ | —OCH(CH$_3$)$_2$ |

TABLE 6

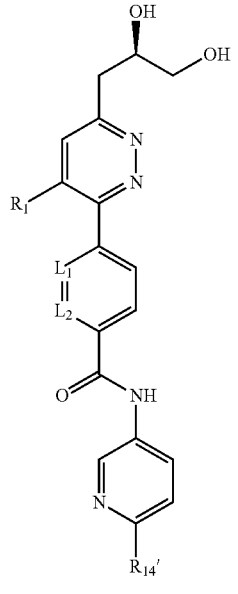

(IIga)

or

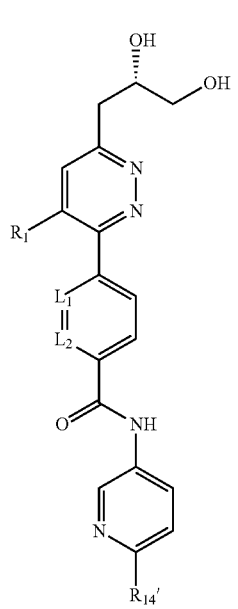

(IIha)

TABLE 6-continued

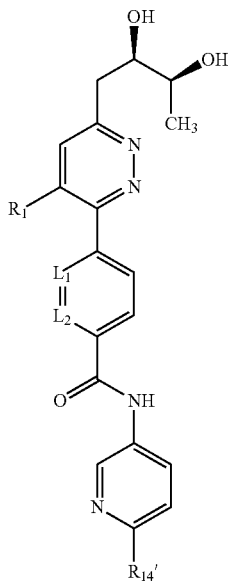

(IIIa)

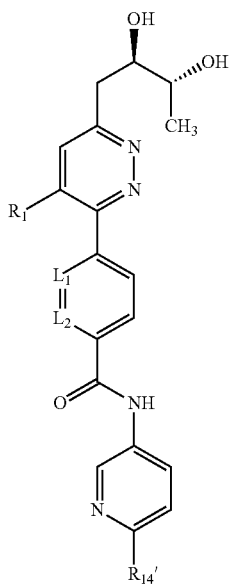

(IIja)

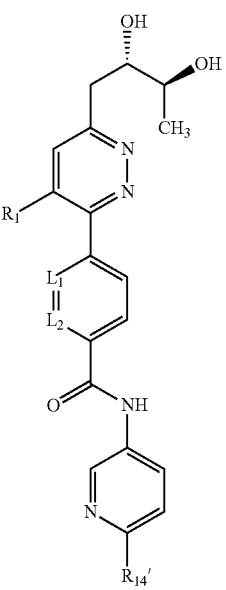

(IIka)

or

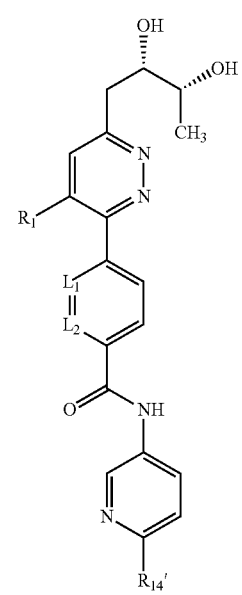

(IIma)

and pharmaceutically acceptable derivatives thereof, where:

| Compound | | $L_1$ | $L_2$ | $R_1$ | $R_{14}'$ |
|---|---|---|---|---|---|
| F | F1 ga, ha, ia, ja, ka or ma | N | CH | —Cl | —H |
|   | F2 ga, ha, ia, ja, ka or ma | N | CH | —Cl | —Cl |
|   | F3 ga, ha, ia, ja, ka or ma | N | CH | —Cl | —F |
|   | F4 ga, ha, ia, ja, ka or ma | N | CH | —Cl | —Br |
|   | F5 ga, ha, ia, ja, ka or ma | N | CH | —Cl | —CF$_3$ |
|   | F6 ga, ha, ia, ja, ka or ma | N | CH | —Cl | —OCF$_3$ |
|   | F7 ga, ha, ia, ja, ka or ma | N | CH | —Cl | —CH$_3$ |
|   | F8 ga, ha, ia, ja, ka or ma | N | CH | —Cl | —CH$_2$CH$_3$ |
|   | F9 ga, ha, ia, ja, ka or ma | N | CH | —Cl | -iso-propyl |
|   | F10 ga, ha, ia, ja, ka or ma | N | CH | —Cl | -tert-butyl |
|   | F11 ga, ha, ia, ja, ka or ma | N | CH | —Cl | —S(O)$_2$CF$_3$ |
|   | F12 ga, ha, ia, ja, ka or ma | N | CH | —Cl | —S(O)$_2$CH$_3$ |
|   | F13 ga, ha, ia, ja, ka or ma | N | CH | —Cl | —S(O)$_2$CH$_3$CH$_3$ |
|   | F14 ga, ha, ia, ja, ka or ma | N | CH | —Cl | —OCH$_3$ |
|   | F15 ga, ha, ia, ja, ka or ma | N | CH | —Cl | —OCH$_2$CH$_3$ |
|   | F16 ga, ha, ia, ja, ka or ma | N | CH | —Cl | —OCH(CH$_3$)$_2$ |
|   | F17 ga, ha, ia, ja, ka or ma | N | CH | —F | —H |

TABLE 6-continued

| | | | | |
|---|---|---|---|---|
| F18 ga, ha, ia, ja, ka or ma | N | CH | —F | —Cl |
| F19 ga, ha, ia, ja, ka or ma | N | CH | —F | —F |
| F20 ga, ha, ia, ja, ka or ma | N | CH | —F | —Br |
| F21 ga, ha, ia, ja, ka or ma | N | CH | —F | —CF$_3$ |
| F22 ga, ha, ia, ja, ka or ma | N | CH | —F | —OCF$_3$ |
| F23 ga, ha, ia, ja, ka or ma | N | CH | —F | —CH$_3$ |
| F24 ga, ha, ia, ja, ka or ma | N | CH | —F | —CH$_2$CH$_3$ |
| F25 ga, ha, ia, ja, ka or ma | N | CH | —F | -iso-propyl |
| F26 ga, ha, ia, ja, ka or ma | N | CH | —F | -tert-butyl |
| F27 ga, ha, ia, ja, ka or ma | N | CH | —F | —S(O)$_2$CF$_3$ |
| F28 ga, ha, ia, ja, ka or ma | N | CH | —F | —S(O)$_2$CH$_3$ |
| F29 ga, ha, ia, ja, ka or ma | N | CH | —F | —S(O)$_2$CH$_3$CH$_3$ |
| F30 ga, ha, ia, ja, ka or ma | N | CH | —F | —OCH$_3$ |
| F31 ga, ha, ia, ja, ka or ma | N | CH | —F | —OCH$_2$CH$_3$ |
| F32 ga, ha, ia, ja, ka or ma | N | CH | —F | —OCH(CH$_3$)$_2$ |
| F33 ga, ha, ia, ja, ka or ma | N | CH | —CF$_3$ | —H |
| F34 ga, ha, ia, ja, ka or ma | N | CH | —CF$_3$ | —Cl |
| F35 ga, ha, ia, ja, ka or ma | N | CH | —CF$_3$ | —F |
| F36 ga, ha, ia, ja, ka or ma | N | CH | —CF$_3$ | —Br |
| F37 ga, ha, ia, ja, ka or ma | N | CH | —CF$_3$ | —CF$_3$ |
| F38 ga, ha, ia, ja, ka or ma | N | CH | —CF$_3$ | —OCF$_3$ |
| F39 ga, ha, ia, ja, ka or ma | N | CH | —CF$_3$ | —CH$_3$ |
| F40 ga, ha, ia, ja, ka or ma | N | CH | —CF$_3$ | —CH$_2$CH$_3$ |
| F41 ga, ha, ia, ja, ka or ma | N | CH | —CF$_3$ | -iso-propyl |
| F42 ga, ha, ia, ja, ka or ma | N | CH | —CF$_3$ | -tert-butyl |
| F43 ga, ha, ia, ja, ka or ma | N | CH | —CF$_3$ | —S(O)$_2$CF$_3$ |
| F44 ga, ha, ia, ja, ka or ma | N | CH | —CF$_3$ | —S(O)$_2$CH$_3$ |
| F45 ga, ha, ia, ja, ka or ma | N | CH | —CF$_3$ | —S(O)$_2$CH$_3$CH$_3$ |
| F46 ga, ha, ia, ja, ka or ma | N | CH | —CF$_3$ | —OCH$_3$ |
| F47 ga, ha, ia, ja, ka or ma | N | CH | —CF$_3$ | —OCH$_2$CH$_3$ |
| F48 ga, ha, ia, ja, ka or ma | N | CH | —CF$_3$ | —OCH(CH$_3$)$_2$ |
| F49 ga, ha, ia, ja, ka or ma | N | CH | —CH$_3$ | —H |
| F50 ga, ha, ia, ja, ka or ma | N | CH | —CH$_3$ | —Cl |
| F51 ga, ha, ia, ja, ka or ma | N | CH | —CH$_3$ | —F |
| F52 ga, ha, ia, ja, ka or ma | N | CH | —CH$_3$ | —Br |
| F53 ga, ha, ia, ja, ka or ma | N | CH | —CH$_3$ | —CF$_3$ |
| F54 ga, ha, ia, ja, ka or ma | N | CH | —CH$_3$ | —OCF$_3$ |
| F55 ga, ha, ia, ja, ka or ma | N | CH | —CH$_3$ | —CH$_3$ |
| F56 ga, ha, ia, ja, ka or ma | N | CH | —CH$_3$ | —CH$_2$CH$_3$ |
| F57 ga, ha, ia, ja, ka or ma | N | CH | —CH$_3$ | -iso-propyl |
| F58 ga, ha, ia, ja, ka or ma | N | CH | —CH$_3$ | -tert-butyl |
| F59 ga, ha, ia, ja, ka or ma | N | CH | —CH$_3$ | —S(O)$_2$CF$_3$ |
| F60 ga, ha, ia, ja, ka or ma | N | CH | —CH$_3$ | —S(O)$_2$CH$_3$ |
| F61 ga, ha, ia, ja, ka or ma | N | CH | —CH$_3$ | —S(O)$_2$CH$_3$CH$_3$ |
| F62 ga, ha, ia, ja, ka or ma | N | CH | —CH$_3$ | —OCH$_3$ |
| F63 ga, ha, ia, ja, ka or ma | N | CH | —CH$_3$ | —OCH$_2$CH$_3$ |
| F64 ga, ha, ia, ja, ka or ma | N | CH | —CH$_3$ | —OCH(CH$_3$)$_2$ |
| F65 ga, ha, ia, ja, ka or ma | CH | N | —Cl | —H |
| F66 ga, ha, ia, ja, ka or ma | CH | N | —Cl | —Cl |
| F67 ga, ha, ia, ja, ka or ma | CH | N | —Cl | —F |
| F68 ga, ha, ia, ja, ka or ma | CH | N | —Cl | —Br |
| F69 ga, ha, ia, ja, ka or ma | CH | N | —Cl | —CF$_3$ |
| F70 ga, ha, ia, ja, ka or ma | CH | N | —Cl | —OCF$_3$ |
| F71 ga, ha, ia, ja, ka or ma | CH | N | —Cl | —CH$_3$ |
| F72 ga, ha, ia, ja, ka or ma | CH | N | —Cl | —CH$_2$CH$_3$ |
| F73 ga, ha, ia, ja, ka or ma | CH | N | —Cl | -iso-propyl |
| F74 ga, ha, ia, ja, ka or ma | CH | N | —Cl | -tert-butyl |
| F75 ga, ha, ia, ja, ka or ma | CH | N | —Cl | —S(O)$_2$CF$_3$ |
| F76 ga, ha, ia, ja, ka or ma | CH | N | —Cl | —S(O)$_2$CH$_3$ |
| F77 ga, ha, ia, ja, ka or ma | CH | N | —Cl | —S(O)$_2$CH$_3$CH$_3$ |
| F78 ga, ha, ia, ja, ka or ma | CH | N | —Cl | —OCH$_3$ |
| F79 ga, ha, ia, ja, ka or ma | CH | N | —Cl | —OCH$_2$CH$_3$ |
| F80 ga, ha, ia, ja, ka or ma | CH | N | —Cl | —OCH(CH$_3$)$_2$ |
| F81 ga, ha, ia, ja, ka or ma | CH | N | —F | —H |
| F82 ga, ha, ia, ja, ka or ma | CH | N | —F | —Cl |
| F83 ga, ha, ia, ja, ka or ma | CH | N | —F | —F |
| F84 ga, ha, ia, ja, ka or ma | CH | N | —F | —Br |
| F85 ga, ha, ia, ja, ka or ma | CH | N | —F | —CF$_3$ |
| F86 ga, ha, ia, ja, ka or ma | CH | N | —F | —OCF$_3$ |
| F87 ga, ha, ia, ja, ka or ma | CH | N | —F | —CH$_3$ |
| F88 ga, ha, ia, ja, ka or ma | CH | N | —F | —CH$_2$CH$_3$ |
| F89 ga, ha, ia, ja, ka or ma | CH | N | —F | -iso-propyl |
| F90 ga, ha, ia, ja, ka or ma | CH | N | —F | -tert-butyl |
| F91 ga, ha, ia, ja, ka or ma | CH | N | —F | —S(O)$_2$CF$_3$ |
| F92 ga, ha, ia, ja, ka or ma | CH | N | —F | —S(O)$_2$CH$_3$ |
| F93 ga, ha, ia, ja, ka or ma | CH | N | —F | —S(O)$_2$CH$_3$CH$_3$ |
| F94 ga, ha, ia, ja, ka or ma | CH | N | —F | —OCH$_3$ |
| F95 ga, ha, ia, ja, ka or ma | CH | N | —F | —OCH$_2$CH$_3$ |
| F96 ga, ha, ia, ja, ka or ma | CH | N | —F | —OCH(CH$_3$)$_2$ |
| F97 ga, ha, ia, ja, ka or ma | CH | N | —CF$_3$ | —H |
| F98 ga, ha, ia, ja, ka or ma | CH | N | —CF$_3$ | —Cl |
| F99 ga, ha, ia, ja, ka or ma | CH | N | —CF$_3$ | —F |
| F100 ga, ha, ia, ja, ka or ma | CH | N | —CF$_3$ | —Br |
| F101 ga, ha, ia, ja, ka or ma | CH | N | —CF$_3$ | —CF$_3$ |
| F102 ga, ha, ia, ja, ka or ma | CH | N | —CF$_3$ | —OCF$_3$ |
| F103 ga, ha, ia, ja, ka or ma | CH | N | —CF$_3$ | —CH$_3$ |
| F104 ga, ha, ia, ja, ka or ma | CH | N | —CF$_3$ | —CH$_2$CH$_3$ |
| F105 ga, ha, ia, ja, ka or ma | CH | N | —CF$_3$ | -iso-propyl |
| F106 ga, ha, ia, ja, ka or ma | CH | N | —CF$_3$ | -tert-butyl |
| F107 ga, ha, ia, ja, ka or ma | CH | N | —CF$_3$ | —S(O)$_2$CF$_3$ |
| F108 ga, ha, ia, ja, ka or ma | CH | N | —CF$_3$ | —S(O)$_2$CH$_3$ |
| F109 ga, ha, ia, ja, ka or ma | CH | N | —CF$_3$ | —S(O)$_2$CH$_3$CH$_3$ |
| F110 ga, ha, ia, ja, ka or ma | CH | N | —CF$_3$ | —OCH$_3$ |
| F111 ga, ha, ia, ja, ka or ma | CH | N | —CF$_3$ | —OCH$_2$CH$_3$ |
| F112 ga, ha, ia, ja, ka or ma | CH | N | —CF$_3$ | —OCH(CH$_3$)$_2$ |
| F113 ga, ha, ia, ja, ka or ma | CH | N | —CH$_3$ | —H |
| F114 ga, ha, ia, ja, ka or ma | CH | N | —CH$_3$ | —Cl |
| F115 ga, ha, ia, ja, ka or ma | CH | N | —CH$_3$ | —F |
| F116 ga, ha, ia, ja, ka or ma | CH | N | —CH$_3$ | —Br |
| F117 ga, ha, ia, ja, ka or ma | CH | N | —CH$_3$ | —CF$_3$ |
| F118 ga, ha, ia, ja, ka or ma | CH | N | —CH$_3$ | —OCF$_3$ |
| F119 ga, ha, ia, ja, ka or ma | CH | N | —CH$_3$ | —CH$_3$ |
| F120 ga, ha, ia, ja, ka or ma | CH | N | —CH$_3$ | —CH$_2$CH$_3$ |
| F121 ga, ha, ia, ja, ka or ma | CH | N | —CH$_3$ | -iso-propyl |
| F122 ga, ha, ia, ja, ka or ma | CH | N | —CH$_3$ | -tert-butyl |
| F123 ga, ha, ia, ja, ka or ma | CH | N | —CH$_3$ | —S(O)$_2$CF$_3$ |
| F124 ga, ha, ia, ja, ka or ma | CH | N | —CH$_3$ | —S(O)$_2$CH$_3$ |
| F125 ga, ha, ia, ja, ka or ma | CH | N | —CH$_3$ | —S(O)$_2$CH$_3$CH$_3$ |
| F126 ga, ha, ia, ja, ka or ma | CH | N | —CH$_3$ | —OCH$_3$ |
| F127 ga, ha, ia, ja, ka or ma | CH | N | —CH$_3$ | —OCH$_2$CH$_3$ |
| F128 ga, ha, ia, ja, ka or ma | CH | N | —CH$_3$ | —OCH(CH$_3$)$_2$ |
| F129 ga, ha, ia, ja, ka or ma | CH | CH | —Cl | —H |
| F130 ga, ha, ia, ja, ka or ma | CH | CH | —Cl | —Cl |
| F131 ga, ha, ia, ja, ka or ma | CH | CH | —Cl | —F |
| F132 ga, ha, ia, ja, ka or ma | CH | CH | —Cl | —Br |
| F133 ga, ha, ia, ja, ka or ma | CH | CH | —Cl | —CF$_3$ |
| F134 ga, ha, ia, ja, ka or ma | CH | CH | —Cl | —OCF$_3$ |
| F135 ga, ha, ia, ja, ka or ma | CH | CH | —Cl | —CH$_3$ |
| F136 ga, ha, ia, ja, ka or ma | CH | CH | —Cl | —CH$_2$CH$_3$ |
| F137 ga, ha, ia, ja, ka or ma | CH | CH | —Cl | -iso-propyl |
| F138 ga, ha, ia, ja, ka or ma | CH | CH | —Cl | -tert-butyl |
| F139 ga, ha, ia, ja, ka or ma | CH | CH | —Cl | —S(O)$_2$CF$_3$ |
| F140 ga, ha, ia, ja, ka or ma | CH | CH | —Cl | —S(O)$_2$CH$_3$ |
| F141 ga, ha, ia, ja, ka or ma | CH | CH | —Cl | —S(O)$_2$CH$_3$CH$_3$ |
| F142 ga, ha, ia, ja, ka or ma | CH | CH | —Cl | —OCH$_3$ |
| F143 ga, ha, ia, ja, ka or ma | CH | CH | —Cl | —OCH$_2$CH$_3$ |
| F144 ga, ha, ia, ja, ka or ma | CH | CH | —Cl | —OCH(CH$_3$)$_2$ |
| F145 ga, ha, ia, ja, ka or ma | CH | CH | —F | —H |
| F146 ga, ha, ia, ja, ka or ma | CH | CH | —F | —Cl |
| F147 ga, ha, ia, ja, ka or ma | CH | CH | —F | —F |
| F148 ga, ha, ia, ja, ka or ma | CH | CH | —F | —Br |
| F149 ga, ha, ia, ja, ka or ma | CH | CH | —F | —CF$_3$ |
| F150 ga, ha, ia, ja, ka or ma | CH | CH | —F | —OCF$_3$ |
| F151 ga, ha, ia, ja, ka or ma | CH | CH | —F | —CH$_3$ |
| F152 ga, ha, ia, ja, ka or ma | CH | CH | —F | —CH$_2$CH$_3$ |
| F153 ga, ha, ia, ja, ka or ma | CH | CH | —F | -iso-propyl |
| F154 ga, ha, ia, ja, ka or ma | CH | CH | —F | -tert-butyl |
| F155 ga, ha, ia, ja, ka or ma | CH | CH | —F | —S(O)$_2$CF$_3$ |
| F156 ga, ha, ia, ja, ka or ma | CH | CH | —F | —S(O)$_2$CH$_3$ |
| F157 ga, ha, ia, ja, ka or ma | CH | CH | —F | —S(O)$_2$CH$_3$CH$_3$ |
| F158 ga, ha, ia, ja, ka or ma | CH | CH | —F | —OCH$_3$ |
| F159 ga, ha, ia, ja, ka or ma | CH | CH | —F | —OCH$_2$CH$_3$ |
| F160 ga, ha, ia, ja, ka or ma | CH | CH | —F | —OCH(CH$_3$)$_2$ |
| F161 ga, ha, ia, ja, ka or ma | CH | CH | —CF$_3$ | —H |
| F162 ga, ha, ia, ja, ka or ma | CH | CH | —CF$_3$ | —Cl |
| F163 ga, ha, ia, ja, ka or ma | CH | CH | —CF$_3$ | —F |
| F164 ga, ha, ia, ja, ka or ma | CH | CH | —CF$_3$ | —Br |
| F165 ga, ha, ia, ja, ka or ma | CH | CH | —CF$_3$ | —CF$_3$ |
| F166 ga, ha, ia, ja, ka or ma | CH | CH | —CF$_3$ | —OCF$_3$ |
| F167 ga, ha, ia, ja, ka or ma | CH | CH | —CF$_3$ | —CH$_3$ |
| F168 ga, ha, ia, ja, ka or ma | CH | CH | —CF$_3$ | —CH$_2$CH$_3$ |
| F169 ga, ha, ia, ja, ka or ma | CH | CH | —CF$_3$ | -iso-propyl |
| F170 ga, ha, ia, ja, ka or ma | CH | CH | —CF$_3$ | -tert-butyl |
| F171 ga, ha, ia, ja, ka or ma | CH | CH | —CF$_3$ | —S(O)$_2$CF$_3$ |
| F172 ga, ha, ia, ja, ka or ma | CH | CH | —CF$_3$ | —S(O)$_2$CH$_3$ |
| F173 ga, ha, ia, ja, ka or ma | CH | CH | —CF$_3$ | —S(O)$_2$CH$_3$CH$_3$ |
| F174 ga, ha, ia, ja, ka or ma | CH | CH | —CF$_3$ | —OCH$_3$ |
| F175 ga, ha, ia, ja, ka or ma | CH | CH | —CF$_3$ | —OCH$_2$CH$_3$ |
| F176 ga, ha, ia, ja, ka or ma | CH | CH | —CF$_3$ | —OCH(CH$_3$)$_2$ |
| F177 ga, ha, ia, ja, ka or ma | CH | CH | —CH$_3$ | —H |

TABLE 6-continued

| | | | | |
|---|---|---|---|---|
| F178 | ga, ha, ia, ja, ka or ma | CH CH | —CH$_3$ | —Cl |
| F179 | ga, ha, ia, ja, ka or ma | CH CH | —CH$_3$ | —F |
| F180 | ga, ha, ia, ja, ka or ma | CH CH | —CH$_3$ | —Br |
| F181 | ga, ha, ia, ja, ka or ma | CH CH | —CH$_3$ | —CF$_3$ |
| F182 | ga, ha, ia, ja, ka or ma | CH CH | —CH$_3$ | —OCF$_3$ |
| F183 | ga, ha, ia, ja, ka or ma | CH CH | —CH$_3$ | —CH$_3$ |
| F184 | ga, ha, ia, ja, ka or ma | CH CH | —CH$_3$ | —CH$_2$CH$_3$ |
| F185 | ga, ha, ia, ja, ka or ma | CH CH | —CH$_3$ | -iso-propyl |
| F186 | ga, ha, ia, ja, ka or ma | CH CH | —CH$_3$ | -tert-butyl |
| F187 | ga, ha, ia, ja, ka or ma | CH CH | —CH$_3$ | —S(O)$_2$CF$_3$ |
| F188 | ga, ha, ia, ja, ka or ma | CH CH | —CH$_3$ | —S(O)$_2$CH$_3$ |
| F189 | ga, ha, ia, ja, ka or ma | CH CH | —CH$_3$ | —S(O)$_2$CH$_2$CH$_3$ |
| F190 | ga, ha, ia, ja, ka or ma | CH CH | —CH$_3$ | —OCH$_3$ |
| F191 | ga, ha, ia, ja, ka or ma | CH CH | —CH$_3$ | —OCH$_2$CH$_3$ |
| F192 | ga, ha, ia, ja, ka or ma | CH CH | —CH$_3$ | —OCH(CH$_3$)$_2$ |

4.3 Compounds of Formula (III)

Preferred Compounds of Formula (II) are Compounds of Formula (III):

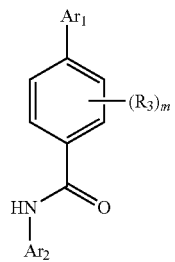

(III)

or a pharmaceutically acceptable derivative thereof, wherein Ar$_1$ is:

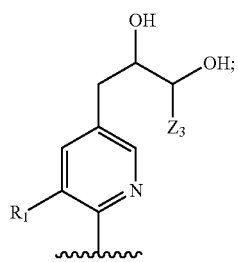

Ar$_2$ is:

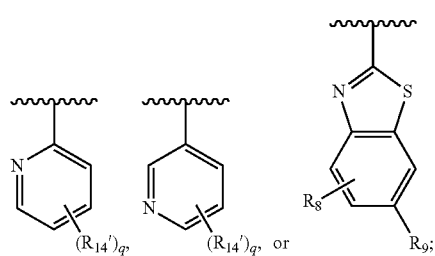

Z$_3$ is —H or —(C$_1$-C$_3$)alkyl;

R$_1$ is -halo, —(C$_1$-C$_4$)alkyl, —OCH$_3$, —C(halo)$_3$, —CH(halo)$_2$, —CH$_2$(halo), —OC(halo)$_3$, —OCH(halo)$_2$, or —OCH$_2$(halo);

each R$_3$ is independently —H, —OCF$_3$, -halo, —(C$_1$-C$_3$) alkyl, —(C$_1$-C$_3$)haloalkyl, —(C$_1$-C$_6$)alkoxy, —N(R$_{20}$)S(O)$_2$ (C$_1$-C$_3$)alkyl, —OR$_{23}$, —N(R$_{20}$)(R$_{23}$), —NHC(O)R$_{13}$, —C(O)N(R$_3$)$_2$, —S(O)$_2$R$_{20}$, —N(R$_{20}$)S(O)$_2$R$_{13}$, or —CH$_2$OR$_7$;

each R$_7$ is independently —H, —(C$_1$-C$_3$)alkyl, —(C$_2$-C$_4$) alkenyl, —(C$_2$-C$_4$)alkynyl, —(C$_3$-C$_8$)cycloalkyl, —(C$_5$-C$_8$) cycloalkenyl, -phenyl, —(C$_1$-C$_3$)haloalkyl, —(C$_1$-C$_6$)hydroxyalkyl, —(C$_1$-C$_6$)alkoxy(C$_2$-C$_6$)alkyl, —(C$_1$-C$_3$)alkyl-N(R$_{20}$)$_2$, or —C(O)N(R$_{20}$)$_2$;

each R$_8$ and R$_9$ is independently —H, —Cl, —Br, —F, —CH$_3$, —OCH$_3$, —OCH$_2$CH$_3$, —CF$_3$, —OCF$_3$, -iso-propyl, -tert-butyl, —S(O)$_2$CF$_3$, —S(O)$_2$CH$_3$, or —S(O)$_2$CH$_2$CH$_3$;

each R$_{13}$ is independently —H, —(C$_1$-C$_4$)alkyl, —(C$_2$-C$_4$) alkenyl, —(C$_2$-C$_4$)alkynyl, -(3- to 7-membered)heterocycle, or -phenyl;

each R$_{14}$' is independently —H, —Cl, —F, —Br, —CF$_3$, —OCF$_3$, —(C$_1$-C$_6$)alkyl, —S(O)$_2$CF$_3$, —S(O)$_2$(C$_1$-C$_6$) alkyl, —OCH$_3$, —OCH$_2$CH$_3$, or —OCH(CH$_3$)$_2$;

each R$_{20}$ is independently —H, —(C$_1$-C$_6$)alkyl, or —(C$_3$-C$_8$)cycloalkyl;

each R$_{23}$ is independently —(C$_1$-C$_6$)alkyl or —(C$_3$-C$_8$) cycloalkyl;

each -halo is independently —F, —Cl, —Br, or —I;

m is the integer 0, 1, or 2; and q is the integer 0, 1, or 2.

Compounds of Formula (III) are potent at TRPV1 receptors.

Certain embodiments of formula (III) are presented below.

In one embodiment, a Compound of Formula (III) is a free base.

In another embodiment, a Compound of Formula (III) is a pharmaceutically acceptable derivative of a Compound of Formula (III). In another embodiment, the pharmaceutically acceptable derivative of a Compound of Formula (III) is a pharmaceutically acceptable salt.

In another embodiment, R$_1$ is -halo, —(C$_1$-C$_4$)alkyl, —OCH$_3$, —C(halo)$_3$, —CH(halo)$_2$, —CH$_2$(halo), or —OC(halo)$_3$.

In another embodiment, R$_1$ is -halo, —(C$_1$-C$_4$)alkyl, —OCH$_3$, —C(halo)$_3$, —CH(halo)$_2$, or —CH$_2$(halo).

In another embodiment, R$_1$ is -halo, —(C$_1$-C$_4$)alkyl, —C(halo)$_3$, —CH(halo)$_2$, or —CH$_2$(halo).

In another embodiment, R$_1$ is -halo, —(C$_1$-C$_4$)alkyl, —C(halo)$_3$, or —CH(halo)$_2$.

In another embodiment, R$_1$ is -halo, —(C$_1$-C$_4$)alkyl, or —C(halo)$_3$.

In another embodiment, R$_1$ is -halo.

In another embodiment, R$_1$ is —(C$_1$-C$_4$)alkyl.

In another embodiment, R$_1$ is —OCH$_3$.

In another embodiment, R$_1$ is —C(halo)$_3$.

In another embodiment, R$_1$ is —CH(halo)$_2$.

In another embodiment, R$_1$ is —CH$_2$(halo).

In another embodiment, R$_1$ is —OC(halo)$_3$.

In another embodiment, R$_1$ is —OCH(halo)$_2$.

In another embodiment, R$_1$ is —OCH$_2$(halo).

In another embodiment, R$_1$ is —Cl, —F, —(C$_1$-C$_4$)alkyl, or —C(halo)$_3$.

In another embodiment, R$_1$ is —Cl, —F, —(C$_1$-C$_4$)alkyl, —OCF$_3$, or —CF$_3$.

In another embodiment, R$_1$ is —Cl, —F, —CH$_3$, —OCF$_3$, or —CF$_3$.

In another embodiment, R$_1$ is —Cl, —F, —CH$_3$, or —CF$_3$.

In another embodiment, R$_1$ is —Cl, —F, or —CF$_3$.

In another embodiment, R$_1$ is —Cl or —F.

In another embodiment, R$_1$ is —Cl.

In another embodiment, $R_1$ is —F.

In another embodiment, $R_1$ is —$CH_3$.

In another embodiment, $R_1$ is —$OCF_3$.

In another embodiment, $R_1$ is —$CF_3$.

In another embodiment, each $R_{20}$ is independently —H or —$(C_1$-$C_6)$alkyl.

In another embodiment, each $R_{20}$ is independently —H or —$(C_3$-$C_8)$cycloalkyl.

In another embodiment, each $R_{20}$ is independently —$(C_1$-$C_6)$alkyl or —$(C_3$-$C_8)$cycloalkyl.

In another embodiment, each $R_{20}$ is —$(C_3$-$C_8)$cycloalkyl.

In another embodiment, each $R_{20}$ is -cyclohexyl.

In another embodiment, each $R_{20}$ is —H.

In another embodiment, each $R_{20}$ is —$(C_1$-$C_6)$alkyl.

In another embodiment, each $R_{20}$ is independently —H or —$CH_3$.

R23

In another embodiment, each $R_{13}$ is independently —H, —$(C_1$-$C_4)$alkyl, -(3- to 7-membered)heterocycle, or -phenyl.

In another embodiment, each $R_{13}$ is independently —H, —$(C_1$-$C_4)$alkyl, or -(3- to 7-membered)heterocycle.

In another embodiment, each $R_{13}$ is independently —H, —$(C_1$-$C_4)$alkyl, or -phenyl.

In another embodiment, each $R_{13}$ is independently —H or —$(C_1$-$C_4)$alkyl.

In another embodiment, each $R_{13}$ is independently —H or —$(C_1$-$C_3)$alkyl.

In another embodiment, each $R_{13}$ is independently —H or —$CH_3$.

In another embodiment, each $R_{13}$ is —H.

In another embodiment, each $R_{13}$ is —$CH_3$.

In another embodiment, $Ar_2$ is:

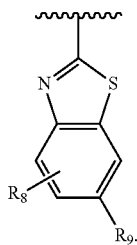

In another embodiment, $Ar_2$ is:

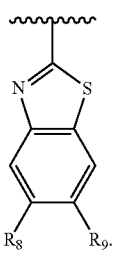

In another embodiment, $Ar_2$ is:

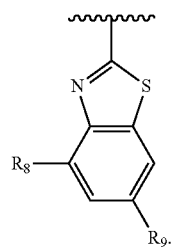

In another embodiment, $Ar_2$ is:

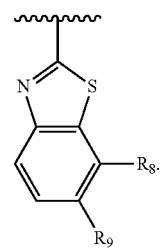

In another embodiment, $Ar_2$ is:

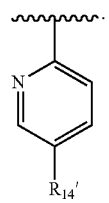

In another embodiment, $Ar_2$ is:

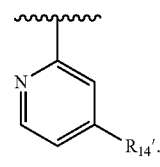

In another embodiment, $Ar_2$ is:

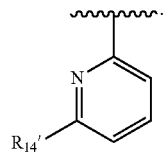

In another embodiment, $Ar_2$ is:

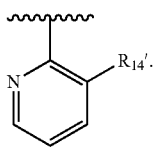

In another embodiment, $Ar_2$ is:

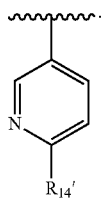

In another embodiment, $Ar_2$ is:

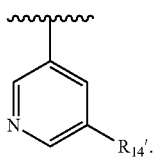

In another embodiment, $Ar_2$ is:

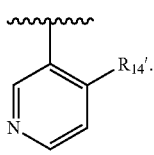

In another embodiment, $Ar_2$ is:

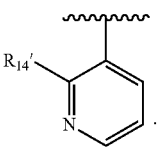

In another embodiment, $Ar_2$ is:

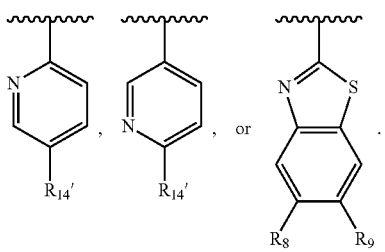

In another embodiment, $R_{14}'$ is —H, —Cl, —F, —$CF_3$, —$OCF_3$, —$CH_3$, —$CH_2CH_3$, —$OCH_3$, —$OCH(CH_3)_2$, or —$OCH_2CH_3$.

In another embodiment, $R_{14}'$ is —H, —Cl, —F, —$CF_3$, or —$OCF_3$:

In another embodiment, $R_8$ and $R_9$ are independently —H, —Cl, —F, —$CH_3$, —$OCH_3$, —$OCH_2CH_3$, —$CF_3$, —$OCF_3$, -iso-propyl, or -tert-butyl.

In another embodiment, each $R_3$ is independently —H, —$OCF_3$, -halo, —$(C_1-C_3)$alkyl, —$(C_1-C_3)$haloalkyl, —$(C_1-C_6)$alkoxy, —$N(R_{20})S(O)_2(C_1-C_3)$alkyl, or —$OR_{23}$.

In another embodiment, each $R_3$ is independently —H, —$N(R_{20})(R_{23})$, —$NHC(O)R_{13}$, —$C(O)N(R_{13})_2$, —$S(O)_2R_{20}$, —$N(R_{20})S(O)_2R_{13}$, or —$CH_2OR_7$.

In another embodiment, each $R_3$ is independently —H, —$OCF_3$, -halo, —$(C_1-C_3)$alkyl, or —$(C_1-C_3)$haloalkyl.

In another embodiment, each $R_3$ is independently —H, —$(C_1-C_6)$alkoxy, —$N(R_{20})S(O)_2(C_1-C_3)$alkyl, —$OR_{23}$, —$N(R_{20})(R_{23})$, or —$NHC(O)R_{13}$.

In another embodiment, each $R_3$ is independently —H, —$C(O)N(R_{13})_2$, —$S(O)_2R_{20}$, —$N(R_{20})S(O)_2R_{13}$, or —$CH_2OR_7$.

In another embodiment, each $R_3$ is independently —H, —$(C_1-C_6)$alkoxy, —$N(R_{20})S(O)_2(C_1-C_3)$alkyl, —$NHC(O)R_{13}$, —$C(O)N(R_{13})_2$, —$S(O)_2R_{20}$, —$N(R_{20})S(O)_2R_{13}$, or —$CH_2OR_7$.

In another embodiment, each $R_3$ is independently —H, —$OCF_3$, -halo, —$(C_1-C_3)$alkyl, —$(C_1-C_3)$haloalkyl, —$OR_{23}$, or —$N(R_{20})(R_{23})$.

In another embodiment, each $R_3$ is independently —H, —$CH_3$, —$OCH_3$, —$NH_2$, —$CF_3$, or —$OCF_3$.

In another embodiment, each $R_3$ is independently —H, —$(C_1-C_3)$alkyl or —$(C_1-C_3)$haloalkyl.

In another embodiment, each $R_3$ is independently —H, —$CH_3$ or —$CF_3$

In another embodiment, m is 2.
In another embodiment, m is 2 and one $R_3$ is —$CH_3$.
In another embodiment, m is 1.
In another embodiment, each $R_3$ is independently —H or —$(C_1-C_3)$alkyl.
In another embodiment, m is 1 and $R_3$ is —H, —$CH_3$, or —$CH_2CH_3$.
In another embodiment, m is 1 and $R_3$ is —H or —$CH_3$.
In another embodiment, m is 1 and $R_3$ is —H or —$OCF_3$.
In another embodiment, m is 0.
In another embodiment, each $R_7$ is independently —H, —$(C_1-C_3)$alkyl, —$(C_3-C_8)$cycloalkyl, or -phenyl.
In another embodiment, each $R_7$ is independently —H, —$(C_1-C_3)$alkyl, -cyclohexyl, or -phenyl.
In another embodiment, each $R_7$ is independently —H, -cyclohexyl, or -phenyl.
In another embodiment, each $R_7$ is independently —H or —$(C_1-C_3)$alkyl.
In another embodiment, each $R_7$ is independently —H, —$CH_3$, or —$CH_2CH_3$.
In another embodiment, each $R_7$ is independently —H or —$CH_3$.
In another embodiment, $Z_3$ is —H, —$CH_3$, or —$CH_2CH_3$.
In another embodiment, $Z_3$ is —H or —$CH_3$.
In another embodiment, $Z_3$ is —H or —$CH_2CH_3$.
In another embodiment, $Z_3$ is —$CH_3$ or —$CH_2CH_3$.
In another embodiment, $Z_3$ is —H.
In another embodiment, $Z_3$ is —$CH_3$.
In another embodiment, $Z_3$ is —$CH_2CH_3$.
In another embodiment, $R_1$ is -halo and $Z_3$ is —H.
In another embodiment, $R_1$ is -halo and $Z_3$ is —$CH_3$.
In another embodiment, $R_1$ is -halo and $Z_3$ is —$CH_2CH_3$.
In another embodiment, $R_1$ is —Cl and $Z_3$ is —H.
In another embodiment, $R_1$ is —Cl and $Z_3$ is —$CH_3$.
In another embodiment, $R_1$ is —Cl and $Z_3$ is —$CH_2CH_3$.

In another embodiment, $R_1$ is —F and $Z_3$ is —H.
In another embodiment, $R_1$ is —F and $Z_3$ is —CH$_3$.
In another embodiment, $R_1$ is —F and $Z_3$ is —CH$_2$CH$_3$.
In another embodiment, $R_1$ is —CF$_3$ and $Z_3$ is —H.
In another embodiment, $R_1$ is —CF$_3$ and $Z_3$ is —CH$_3$.
In another embodiment, $R_1$ is —CF$_3$ and $Z_3$ is —CH$_2$CH$_3$.
In another embodiment, $R_1$ is —CH$_3$ and $Z_3$ is —H.
In another embodiment, $R_1$ is —CH$_3$ and $Z_3$ is —CH$_3$.
In another embodiment, $R_1$ is —CH$_3$ and $Z_3$ is —CH$_2$CH$_3$.
In another embodiment $Ar_1$ is:

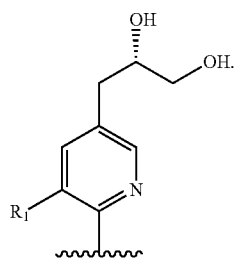

In another embodiment $Ar_1$ is:

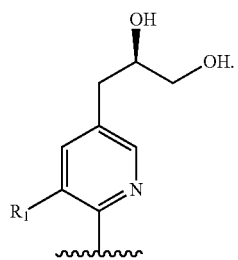

In another embodiment $Ar_1$ is:

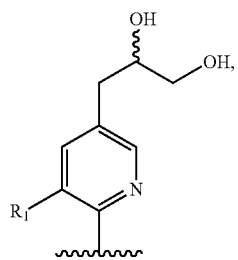

wherein the Compound of Formula (III) is racemic.
In another embodiment $Ar_1$ is:

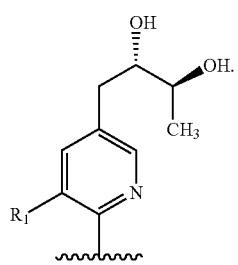

In another embodiment $Ar_1$ is:

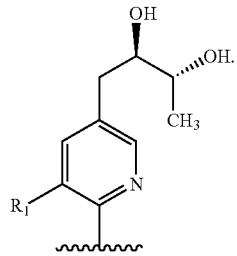

In another embodiment $Ar_1$ is:

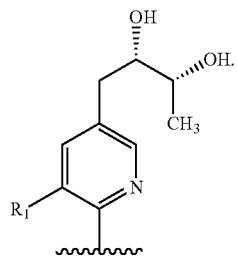

In another embodiment $Ar_1$ is:

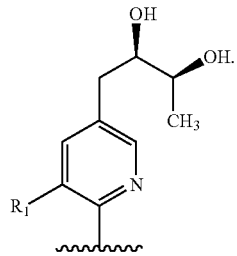

In another embodiment $Ar_1$ is:

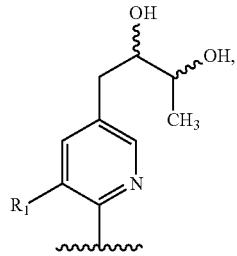

wherein the Compound of Formula (III) is racemic.

Illustrative Compounds of Formula (III) are listed below in Tables 7-9:

TABLE 7
(IIIa)
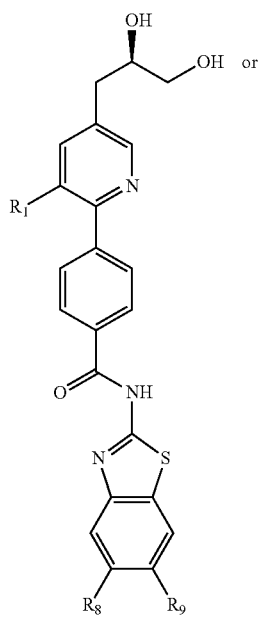
(IIIb)
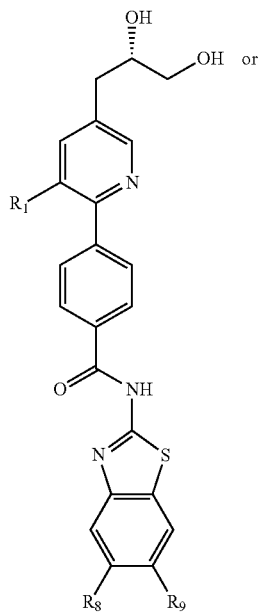
TABLE 7-continued
(IIIc)
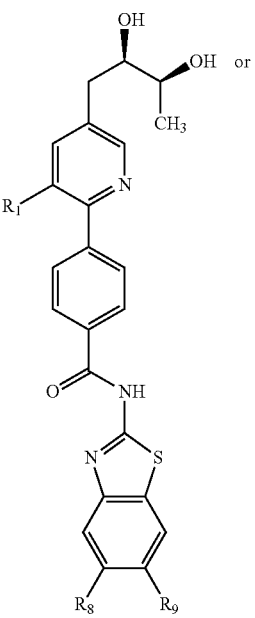
(IIId)
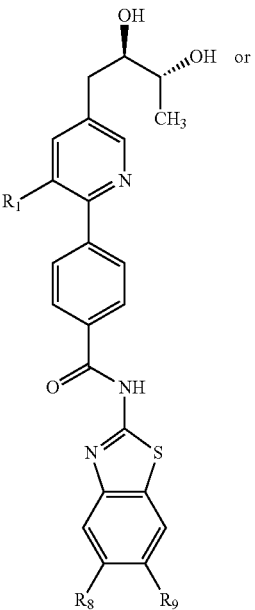

TABLE 7-continued

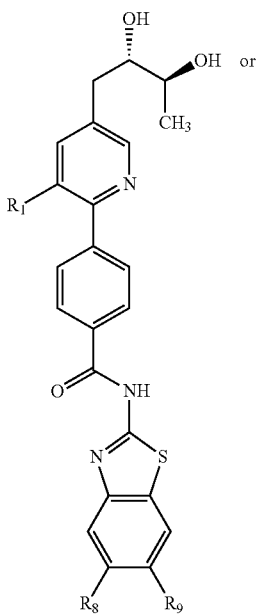

(IIIe)

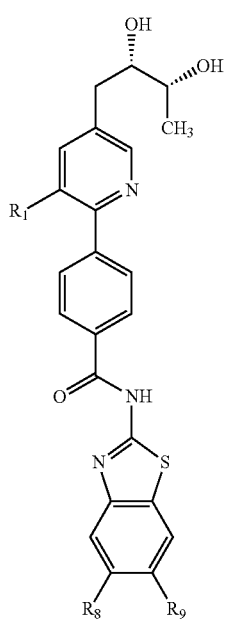

(IIIf)

and pharmaceutically acceptable derivatives thereof, where:

| Compound | $R_1$ | $R_8$ | $R_9$ |
|---|---|---|---|
| G G1 a, b, c, d, e or f | —Cl | —H | —H |
| G2 a, b, c, d, e or f | —Cl | —H | —Cl |
| G3 a, b, c, d, e or f | —Cl | —H | —Br |
| G4 a, b, c, d, e or f | —Cl | —H | —F |
| G5 a, b, c, d, e or f | —Cl | —H | —CH$_3$ |
| G6 a, b, c, d, e or f | —Cl | —H | —OCH$_3$ |
| G7 a, b, c, d, e or f | —Cl | —H | —OCH$_2$CH$_3$ |
| G8 a, b, c, d, e or f | —Cl | —H | —CF$_3$ |
| G9 a, b, c, d, e or f | —Cl | —H | —OCF$_3$ |
| G10 a, b, c, d, e or f | —Cl | —H | iso-propyl |
| G11 a, b, c, d, e or f | —Cl | —H | tert-butyl |
| G12 a, b, c, d, e or f | —Cl | —H | —S(O)$_2$CF$_3$ |
| G13 a, b, c, d, e or f | —Cl | —H | —S(O)$_2$CH$_3$ |
| G14 a, b, c, d, e or f | —Cl | —H | —S(O)$_2$CH$_3$CH$_3$ |
| G15 a, b, c, d, e or f | —Cl | —Cl | —H |
| G16 a, b, c, d, e or f | —Cl | —Cl | —Cl |
| G17 a, b, c, d, e or f | —Cl | —Cl | —Br |
| G18 a, b, c, d, e or f | —Cl | —Cl | —F |
| G19 a, b, c, d, e or f | —Cl | —Cl | —CH$_3$ |
| G20 a, b, c, d, e or f | —Cl | —Cl | —OCH$_3$ |
| G21 a, b, c, d, e or f | —Cl | —Cl | —OCH$_2$CH$_3$ |
| G22 a, b, c, d, e or f | —Cl | —Cl | —CF$_3$ |
| G23 a, b, c, d, e or f | —Cl | —Cl | —OCF$_3$ |
| G24 a, b, c, d, e or f | —Cl | —Cl | iso-propyl |
| G25 a, b, c, d, e or f | —Cl | —Cl | tert-butyl |
| G26 a, b, c, d, e or f | —Cl | —Cl | —S(O)$_2$CF$_3$ |
| G27 a, b, c, d, e or f | —Cl | —Cl | —S(O)$_2$CH$_3$ |
| G28 a, b, c, d, e or f | —Cl | —Cl | —S(O)$_2$CH$_3$CH$_3$ |
| G29 a, b, c, d, e or f | —Cl | —Br | —H |
| G30 a, b, c, d, e or f | —Cl | —Br | —Cl |
| G31 a, b, c, d, e or f | —Cl | —Br | —Br |
| G32 a, b, c, d, e or f | —Cl | —Br | —F |
| G33 a, b, c, d, e or f | —Cl | —Br | —CH$_3$ |
| G34 a, b, c, d, e or f | —Cl | —Br | —OCH$_3$ |
| G35 a, b, c, d, e or f | —Cl | —Br | —OCH$_2$CH$_3$ |
| G36 a, b, c, d, e or f | —Cl | —Br | —CF$_3$ |
| G37 a, b, c, d, e or f | —Cl | —Br | —OCF$_3$ |
| G38 a, b, c, d, e or f | —Cl | —Br | iso-propyl |
| G39 a, b, c, d, e or f | —Cl | —Br | tert-butyl |
| G40 a, b, c, d, e or f | —Cl | —Br | —S(O)$_2$CF$_3$ |
| G41 a, b, c, d, e or f | —Cl | —Br | —S(O)$_2$CH$_3$ |
| G42 a, b, c, d, e or f | —Cl | —Br | —S(O)$_2$CH$_3$CH$_3$ |
| G43 a, b, c, d, e or f | —Cl | —F | —H |
| G44 a, b, c, d, e or f | —Cl | —F | —Cl |
| G45 a, b, c, d, e or f | —Cl | —F | —Br |
| G46 a, b, c, d, e or f | —Cl | —F | —F |
| G47 a, b, c, d, e or f | —Cl | —F | —CH$_3$ |
| G48 a, b, c, d, e or f | —Cl | —F | —OCH$_3$ |
| G49 a, b, c, d, e or f | —Cl | —F | —OCH$_2$CH$_3$ |
| G50 a, b, c, d, e or f | —Cl | —F | —CF$_3$ |
| G51 a, b, c, d, e or f | —Cl | —F | —OCF$_3$ |
| G52 a, b, c, d, e or f | —Cl | —F | iso-propyl |
| G53 a, b, c, d, e or f | —Cl | —F | tert-butyl |
| G54 a, b, c, d, e or f | —Cl | —F | —S(O)$_2$CF$_3$ |
| G55 a, b, c, d, e or f | —Cl | —F | —S(O)$_2$CH$_3$ |
| G56 a, b, c, d, e or f | —Cl | —F | —S(O)$_2$CH$_3$CH$_3$ |
| G57 a, b, c, d, e or f | —Cl | —CH$_3$ | —H |
| G58 a, b, c, d, e or f | —Cl | —CH$_3$ | —Cl |
| G59 a, b, c, d, e or f | —Cl | —CH$_3$ | —Br |
| G60 a, b, c, d, e or f | —Cl | —CH$_3$ | —F |
| G61 a, b, c, d, e or f | —Cl | —CH$_3$ | —CH$_3$ |
| G62 a, b, c, d, e or f | —Cl | —CH$_3$ | —OCH$_3$ |
| G63 a, b, c, d, e or f | —Cl | —CH$_3$ | —OCH$_2$CH$_3$ |
| G64 a, b, c, d, e or f | —Cl | —CH$_3$ | —CF$_3$ |
| G65 a, b, c, d, e or f | —Cl | —CH$_3$ | —OCF$_3$ |
| G66 a, b, c, d, e or f | —Cl | —CH$_3$ | iso-propyl |
| G67 a, b, c, d, e or f | —Cl | —CH$_3$ | tert-butyl |
| G68 a, b, c, d, e or f | —Cl | —CH$_3$ | —S(O)$_2$CF$_3$ |
| G69 a, b, c, d, e or f | —Cl | —CH$_3$ | —S(O)$_2$CH$_3$ |
| G70 a, b, c, d, e or f | —Cl | —CH$_3$ | —S(O)$_2$CH$_3$CH$_3$ |
| G71 a, b, c, d, e or f | —Cl | —OCH$_3$ | —H |
| G72 a, b, c, d, e or f | —Cl | —OCH$_3$ | —Cl |
| G73 a, b, c, d, e or f | —Cl | —OCH$_3$ | —Br |
| G74 a, b, c, d, e or f | —Cl | —OCH$_3$ | —F |
| G75 a, b, c, d, e or f | —Cl | —OCH$_3$ | —CH$_3$ |
| G76 a, b, c, d, e or f | —Cl | —OCH$_3$ | —OCH$_3$ |
| G77 a, b, c, d, e or f | —Cl | —OCH$_3$ | —OCH$_2$CH$_3$ |
| G78 a, b, c, d, e or f | —Cl | —OCH$_3$ | —CF$_3$ |
| G79 a, b, c, d, e or f | —Cl | —OCH$_3$ | —OCF$_3$ |
| G80 a, b, c, d, e or f | —Cl | —OCH$_3$ | iso-propyl |
| G81 a, b, c, d, e or f | —Cl | —OCH$_3$ | tert-butyl |
| G82 a, b, c, d, e or f | —Cl | —OCH$_3$ | —S(O)$_2$CF$_3$ |
| G83 a, b, c, d, e or f | —Cl | —OCH$_3$ | —S(O)$_2$CH$_3$ |
| G84 a, b, c, d, e or f | —Cl | —OCH$_3$ | —S(O)$_2$CH$_3$CH$_3$ |
| G85 a, b, c, d, e or f | —Cl | —OCH$_2$CH$_3$ | —H |
| G86 a, b, c, d, e or f | —Cl | —OCH$_2$CH$_3$ | —Cl |
| G87 a, b, c, d, e or f | —Cl | —OCH$_2$CH$_3$ | —Br |
| G88 a, b, c, d, e or f | —Cl | —OCH$_2$CH$_3$ | —F |
| G89 a, b, c, d, e or f | —Cl | —OCH$_2$CH$_3$ | —CH$_3$ |
| G90 a, b, c, d, e or f | —Cl | —OCH$_2$CH$_3$ | —OCH$_3$ |
| G91 a, b, c, d, e or f | —Cl | —OCH$_2$CH$_3$ | —OCH$_2$CH$_3$ |
| G92 a, b, c, d, e or f | —Cl | —OCH$_2$CH$_3$ | —CF$_3$ |
| G93 a, b, c, d, e or f | —Cl | —OCH$_2$CH$_3$ | —OCF$_3$ |

TABLE 7-continued

| | | | |
|---|---|---|---|
| G94 a, b, c, d, e or f | —Cl | —OCH₂CH₃ | iso-propyl |
| G95 a, b, c, d, e or f | —Cl | —OCH₂CH₃ | tert-butyl |
| G96 a, b, c, d, e or f | —Cl | —OCH₂CH₃ | —S(O)₂CF₃ |
| G97 a, b, c, d, e or f | —Cl | —OCH₂CH₃ | —S(O)₂CH₃ |
| G98 a, b, c, d, e or f | —Cl | —OCH₂CH₃ | —S(O)₂CH₃CH₃ |
| G99 a, b, c, d, e or f | —Cl | —CF₃ | —H |
| G100 a, b, c, d, e or f | —Cl | —CF₃ | —Cl |
| G101 a, b, c, d, e or f | —Cl | —CF₃ | —Br |
| G102 a, b, c, d, e or f | —Cl | —CF₃ | —F |
| G103 a, b, c, d, e or f | —Cl | —CF₃ | —CH₃ |
| G104 a, b, c, d, e or f | —Cl | —CF₃ | —OCH₃ |
| G105 a, b, c, d, e or f | —Cl | —CF₃ | —OCH₂CH₃ |
| G106 a, b, c, d, e or f | —Cl | —CF₃ | —CF₃ |
| G107 a, b, c, d, e or f | —Cl | —CF₃ | —OCF₃ |
| G108 a, b, c, d, e or f | —Cl | —CF₃ | iso-propyl |
| G109 a, b, c, d, e or f | —Cl | —CF₃ | tert-butyl |
| G110 a, b, c, d, e or f | —Cl | —CF₃ | —S(O)₂CF₃ |
| G111 a, b, c, d, e or f | —Cl | —CF₃ | —S(O)₂CH₃ |
| G112 a, b, c, d, e or f | —Cl | —CF₃ | —S(O)₂CH₃CH₃ |
| G113 a, b, c, d, e or f | —Cl | —OCF₃ | —H |
| G114 a, b, c, d, e or f | —Cl | —OCF₃ | —Cl |
| G115 a, b, c, d, e or f | —Cl | —OCF₃ | —Br |
| G116 a, b, c, d, e or f | —Cl | —OCF₃ | —F |
| G117 a, b, c, d, e or f | —Cl | —OCF₃ | —CH₃ |
| G118 a, b, c, d, e or f | —Cl | —OCF₃ | —OCH₃ |
| G119 a, b, c, d, e or f | —Cl | —OCF₃ | —OCH₂CH₃ |
| G120 a, b, c, d, e or f | —Cl | —OCF₃ | —CF₃ |
| G121 a, b, c, d, e or f | —Cl | —OCF₃ | —OCF₃ |
| G122 a, b, c, d, e or f | —Cl | —OCF₃ | iso-propyl |
| G123 a, b, c, d, e or f | —Cl | —OCF₃ | tert-butyl |
| G124 a, b, c, d, e or f | —Cl | —OCF₃ | —S(O)₂CF₃ |
| G125 a, b, c, d, e or f | —Cl | —OCF₃ | —S(O)₂CH₃ |
| G126 a, b, c, d, e or f | —Cl | —OCF₃ | —S(O)₂CH₃CH₃ |
| G127 a, b, c, d, e or f | —Cl | iso-propyl | —H |
| G128 a, b, c, d, e or f | —Cl | iso-propyl | —Cl |
| G129 a, b, c, d, e or f | —Cl | iso-propyl | —Br |
| G130 a, b, c, d, e or f | —Cl | iso-propyl | —F |
| G131 a, b, c, d, e or f | —Cl | iso-propyl | —CH₃ |
| G132 a, b, c, d, e or f | —Cl | iso-propyl | —OCH₃ |
| G133 a, b, c, d, e or f | —Cl | iso-propyl | —OCH₂CH₃ |
| G134 a, b, c, d, e or f | —Cl | iso-propyl | —CF₃ |
| G135 a, b, c, d, e or f | —Cl | iso-propyl | —OCF₃ |
| G136 a, b, c, d, e or f | —Cl | iso-propyl | iso-propyl |
| G137 a, b, c, d, e or f | —Cl | iso-propyl | tert-butyl |
| G138 a, b, c, d, e or f | —Cl | iso-propyl | —S(O)₂CF₃ |
| G139 a, b, c, d, e or f | —Cl | iso-propyl | —S(O)₂CH₃ |
| G140 a, b, c, d, e or f | —Cl | iso-propyl | —S(O)₂CH₃CH₃ |
| G141 a, b, c, d, e or f | —Cl | tert-butyl | —H |
| G142 a, b, c, d, e or f | —Cl | tert-butyl | —Cl |
| G143 a, b, c, d, e or f | —Cl | tert-butyl | —Br |
| G144 a, b, c, d, e or f | —Cl | tert-butyl | —F |
| G145 a, b, c, d, e or f | —Cl | tert-butyl | —CH₃ |
| G146 a, b, c, d, e or f | —Cl | tert-butyl | —OCH₃ |
| G147 a, b, c, d, e or f | —Cl | tert-butyl | —OCH₂CH₃ |
| G148 a, b, c, d, e or f | —Cl | tert-butyl | —CF₃ |
| G149 a, b, c, d, e or f | —Cl | tert-butyl | —OCF₃ |
| G150 a, b, c, d, e or f | —Cl | tert-butyl | iso-propyl |
| G151 a, b, c, d, e or f | —Cl | tert-butyl | tert-butyl |
| G152 a, b, c, d, e or f | —Cl | tert-butyl | —S(O)₂CF₃ |
| G153 a, b, c, d, e or f | —Cl | tert-butyl | —S(O)₂CH₃ |
| G154 a, b, c, d, e or f | —Cl | tert-butyl | —S(O)₂CH₃CH₃ |
| G155 a, b, c, d, e or f | —F | —H | —H |
| G156 a, b, c, d, e or f | —F | —H | —Cl |
| G157 a, b, c, d, e or f | —F | —H | —Br |
| G158 a, b, c, d, e or f | —F | —H | —F |
| G159 a, b, c, d, e or f | —F | —H | —CH₃ |
| G160 a, b, c, d, e or f | —F | —H | —OCH₃ |
| G161 a, b, c, d, e or f | —F | —H | —OCH₂CH₃ |
| G162 a, b, c, d, e or f | —F | —H | —CF₃ |
| G163 a, b, c, d, e or f | —F | —H | —OCF₃ |
| G164 a, b, c, d, e or f | —F | —H | iso-propyl |
| G165 a, b, c, d, e or f | —F | —H | tert-butyl |
| G166 a, b, c, d, e or f | —F | —H | —S(O)₂CF₃ |
| G167 a, b, c, d, e or f | —F | —H | —S(O)₂CH₃ |
| G168 a, b, c, d, e or f | —F | —H | —S(O)₂CH₃CH₃ |
| G169 a, b, c, d, e or f | —F | —Cl | —H |
| G170 a, b, c, d, e or f | —F | —Cl | —Cl |
| G171 a, b, c, d, e or f | —F | —Cl | —Br |
| G172 a, b, c, d, e or f | —F | —Cl | —F |
| G173 a, b, c, d, e or f | —F | —Cl | —CH₃ |
| G174 a, b, c, d, e or f | —F | —Cl | —OCH₃ |
| G175 a, b, c, d, e or f | —F | —Cl | —OCH₂CH₃ |
| G176 a, b, c, d, e or f | —F | —Cl | —CF₃ |
| G177 a, b, c, d, e or f | —F | —Cl | —OCF₃ |
| G178 a, b, c, d, e or f | —F | —Cl | iso-propyl |
| G179 a, b, c, d, e or f | —F | —Cl | tert-butyl |
| G180 a, b, c, d, e or f | —F | —Cl | —S(O)₂CF₃ |
| G181 a, b, c, d, e or f | —F | —Cl | —S(O)₂CH₃ |
| G182 a, b, c, d, e or f | —F | —Cl | —S(O)₂CH₃CH₃ |
| G183 a, b, c, d, e or f | —F | —Br | —H |
| G184 a, b, c, d, e or f | —F | —Br | —Cl |
| G185 a, b, c, d, e or f | —F | —Br | —Br |
| G186 a, b, c, d, e or f | —F | —Br | —F |
| G187 a, b, c, d, e or f | —F | —Br | —CH₃ |
| G188 a, b, c, d, e or f | —F | —Br | —OCH₃ |
| G189 a, b, c, d, e or f | —F | —Br | —OCH₂CH₃ |
| G190 a, b, c, d, e or f | —F | —Br | —CF₃ |
| G191 a, b, c, d, e or f | —F | —Br | —OCF₃ |
| G192 a, b, c, d, e or f | —F | —Br | iso-propyl |
| G193 a, b, c, d, e or f | —F | —Br | tert-butyl |
| G194 a, b, c, d, e or f | —F | —Br | —S(O)₂CF₃ |
| G195 a, b, c, d, e or f | —F | —Br | —S(O)₂CH₃ |
| G196 a, b, c, d, e or f | —F | —Br | —S(O)₂CH₃CH₃ |
| G197 a, b, c, d, e or f | —F | —F | —H |
| G198 a, b, c, d, e or f | —F | —F | —Cl |
| G199 a, b, c, d, e or f | —F | —F | —Br |
| G200 a, b, c, d, e or f | —F | —F | —F |
| G201 a, b, c, d, e or f | —F | —F | —CH₃ |
| G202 a, b, c, d, e or f | —F | —F | —OCH₃ |
| G203 a, b, c, d, e or f | —F | —F | —OCH₂CH₃ |
| G204 a, b, c, d, e or f | —F | —F | —CF₃ |
| G205 a, b, c, d, e or f | —F | —F | —OCF₃ |
| G206 a, b, c, d, e or f | —F | —F | iso-propyl |
| G207 a, b, c, d, e or f | —F | —F | tert-butyl |
| G208 a, b, c, d, e or f | —F | —F | —S(O)₂CF₃ |
| G209 a, b, c, d, e or f | —F | —F | —S(O)₂CH₃ |
| G210 a, b, c, d, e or f | —F | —F | —S(O)₂CH₃CH₃ |
| G211 a, b, c, d, e or f | —F | —CH₃ | —H |
| G212 a, b, c, d, e or f | —F | —CH₃ | —Cl |
| G213 a, b, c, d, e or f | —F | —CH₃ | —Br |
| G214 a, b, c, d, e or f | —F | —CH₃ | —F |
| G215 a, b, c, d, e or f | —F | —CH₃ | —CH₃ |
| G216 a, b, c, d, e or f | —F | —CH₃ | —OCH₃ |
| G217 a, b, c, d, e or f | —F | —CH₃ | —OCH₂CH₃ |
| G218 a, b, c, d, e or f | —F | —CH₃ | —CF₃ |
| G219 a, b, c, d, e or f | —F | —CH₃ | —OCF₃ |
| G220 a, b, c, d, e or f | —F | —CH₃ | iso-propyl |
| G221 a, b, c, d, e or f | —F | —CH₃ | tert-butyl |
| G222 a, b, c, d, e or f | —F | —CH₃ | —S(O)₂CF₃ |
| G223 a, b, c, d, e or f | —F | —CH₃ | —S(O)₂CH₃ |
| G224 a, b, c, d, e or f | —F | —CH₃ | —S(O)₂CH₃CH₃ |
| G225 a, b, c, d, e or f | —F | —OCH₃ | —H |
| G226 a, b, c, d, e or f | —F | —OCH₃ | —Cl |
| G227 a, b, c, d, e or f | —F | —OCH₃ | —Br |
| G228 a, b, c, d, e or f | —F | —OCH₃ | —F |
| G229 a, b, c, d, e or f | —F | —OCH₃ | —CH₃ |
| G230 a, b, c, d, e or f | —F | —OCH₃ | —OCH₃ |
| G231 a, b, c, d, e or f | —F | —OCH₃ | —OCH₂CH₃ |
| G232 a, b, c, d, e or f | —F | —OCH₃ | —CF₃ |
| G233 a, b, c, d, e or f | —F | —OCH₃ | —OCF₃ |
| G234 a, b, c, d, e or f | —F | —OCH₃ | iso-propyl |
| G235 a, b, c, d, e or f | —F | —OCH₃ | tert-butyl |
| G236 a, b, c, d, e or f | —F | —OCH₃ | —S(O)₂CF₃ |
| G237 a, b, c, d, e or f | —F | —OCH₃ | —S(O)₂CH₃ |
| G238 a, b, c, d, e or f | —F | —OCH₃ | —S(O)₂CH₃CH₃ |
| G239 a, b, c, d, e or f | —F | —OCH₂CH₃ | —H |
| G240 a, b, c, d, e or f | —F | —OCH₂CH₃ | —Cl |
| G241 a, b, c, d, e or f | —F | —OCH₂CH₃ | —Br |
| G242 a, b, c, d, e or f | —F | —OCH₂CH₃ | —F |
| G243 a, b, c, d, e or f | —F | —OCH₂CH₃ | —CH₃ |
| G244 a, b, c, d, e or f | —F | —OCH₂CH₃ | —OCH₃ |
| G245 a, b, c, d, e or f | —F | —OCH₂CH₃ | —OCH₂CH₃ |
| G246 a, b, c, d, e or f | —F | —OCH₂CH₃ | —CF₃ |
| G247 a, b, c, d, e or f | —F | —OCH₂CH₃ | —OCF₃ |
| G248 a, b, c, d, e or f | —F | —OCH₂CH₃ | iso-propyl |
| G249 a, b, c, d, e or f | —F | —OCH₂CH₃ | tert-butyl |
| G250 a, b, c, d, e or f | —F | —OCH₂CH₃ | —S(O)₂CF₃ |
| G251 a, b, c, d, e or f | —F | —OCH₂CH₃ | —S(O)₂CH₃ |
| G252 a, b, c, d, e or f | —F | —OCH₂CH₃ | —S(O)₂CH₃CH₃ |
| G253 a, b, c, d, e or f | —F | —CF₃ | —H |

TABLE 7-continued

| | | | |
|---|---|---|---|
| G254 a, b, c, d, e or f | —F | —CF₃ | —Cl |
| G255 a, b, c, d, e or f | —F | —CF₃ | —Br |
| G256 a, b, c, d, e or f | —F | —CF₃ | —F |
| G257 a, b, c, d, e or f | —F | —CF₃ | —CH₃ |
| G258 a, b, c, d, e or f | —F | —CF₃ | —OCH₃ |
| G259 a, b, c, d, e or f | —F | —CF₃ | —OCH₂CH₃ |
| G260 a, b, c, d, e or f | —F | —CF₃ | —CF₃ |
| G261 a, b, c, d, e or f | —F | —CF₃ | —OCF₃ |
| G262 a, b, c, d, e or f | —F | —CF₃ | iso-propyl |
| G263 a, b, c, d, e or f | —F | —CF₃ | tert-butyl |
| G264 a, b, c, d, e or f | —F | —CF₃ | —S(O)₂CF₃ |
| G265 a, b, c, d, e or f | —F | —CF₃ | —S(O)₂CH₃ |
| G266 a, b, c, d, e or f | —F | —CF₃ | —S(O)₂CH₃CH₃ |
| G267 a, b, c, d, e or f | —F | —OCF₃ | —H |
| G268 a, b, c, d, e or f | —F | —OCF₃ | —Cl |
| G269 a, b, c, d, e or f | —F | —OCF₃ | —Br |
| G270 a, b, c, d, e or f | —F | —OCF₃ | —F |
| G271 a, b, c, d, e or f | —F | —OCF₃ | —CH₃ |
| G272 a, b, c, d, e or f | —F | —OCF₃ | —OCH₃ |
| G273 a, b, c, d, e or f | —F | —OCF₃ | —OCH₂CH₃ |
| G274 a, b, c, d, e or f | —F | —OCF₃ | —CF₃ |
| G275 a, b, c, d, e or f | —F | —OCF₃ | —OCF₃ |
| G276 a, b, c, d, e or f | —F | —OCF₃ | iso-propyl |
| G277 a, b, c, d, e or f | —F | —OCF₃ | tert-butyl |
| G278 a, b, c, d, e or f | —F | —OCF₃ | —S(O)₂CF₃ |
| G279 a, b, c, d, e or f | —F | —OCF₃ | —S(O)₂CH₃ |
| G280 a, b, c, d, e or f | —F | —OCF₃ | —S(O)₂CH₃CH₃ |
| G281 a, b, c, d, e or f | —F | iso-propyl | —H |
| G282 a, b, c, d, e or f | —F | iso-propyl | —Cl |
| G283 a, b, c, d, e or f | —F | iso-propyl | —Br |
| G284 a, b, c, d, e or f | —F | iso-propyl | —F |
| G285 a, b, c, d, e or f | —F | iso-propyl | —CH₃ |
| G286 a, b, c, d, e or f | —F | iso-propyl | —OCH₃ |
| G287 a, b, c, d, e or f | —F | iso-propyl | —OCH₂CH₃ |
| G288 a, b, c, d, e or f | —F | iso-propyl | —CF₃ |
| G289 a, b, c, d, e or f | —F | iso-propyl | —OCF₃ |
| G290 a, b, c, d, e or f | —F | iso-propyl | iso-propyl |
| G291 a, b, c, d, e or f | —F | iso-propyl | tert-butyl |
| G292 a, b, c, d, e or f | —F | iso-propyl | —S(O)₂CF₃ |
| G293 a, b, c, d, e or f | —F | iso-propyl | —S(O)₂CH₃ |
| G294 a, b, c, d, e or f | —F | iso-propyl | —S(O)₂CH₃CH₃ |
| G295 a, b, c, d, e or f | —F | tert-butyl | —H |
| G296 a, b, c, d, e or f | —F | tert-butyl | —Cl |
| G297 a, b, c, d, e or f | —F | tert-butyl | —Br |
| G298 a, b, c, d, e or f | —F | tert-butyl | —F |
| G299 a, b, c, d, e or f | —F | tert-butyl | —CH₃ |
| G300 a, b, c, d, e or f | —F | tert-butyl | —OCH₃ |
| G301 a, b, c, d, e or f | —F | tert-butyl | —OCH₂CH₃ |
| G302 a, b, c, d, e or f | —F | tert-butyl | —CF₃ |
| G303 a, b, c, d, e or f | —F | tert-butyl | —OCF₃ |
| G304 a, b, c, d, e or f | —F | tert-butyl | iso-propyl |
| G305 a, b, c, d, e or f | —F | tert-butyl | tert-butyl |
| G306 a, b, c, d, e or f | —F | tert-butyl | —S(O)₂CF₃ |
| G307 a, b, c, d, e or f | —F | tert-butyl | —S(O)₂CH₃ |
| G308 a, b, c, d, e or f | —F | tert-butyl | —S(O)₂CH₃CH₃ |
| G309 a, b, c, d, e or f | —CF₃ | —H | —H |
| G310 a, b, c, d, e or f | —CF₃ | —H | —Cl |
| G311 a, b, c, d, e or f | —CF₃ | —H | —Br |
| G312 a, b, c, d, e or f | —CF₃ | —H | —F |
| G313 a, b, c, d, e or f | —CF₃ | —H | —CH₃ |
| G314 a, b, c, d, e or f | —CF₃ | —H | —OCH₃ |
| G315 a, b, c, d, e or f | —CF₃ | —H | —OCH₂CH₃ |
| G316 a, b, c, d, e or f | —CF₃ | —H | —CF₃ |
| G317 a, b, c, d, e or f | —CF₃ | —H | —OCF₃ |
| G318 a, b, c, d, e or f | —CF₃ | —H | iso-propyl |
| G319 a, b, c, d, e or f | —CF₃ | —H | tert-butyl |
| G320 a, b, c, d, e or f | —CF₃ | —H | —S(O)₂CF₃ |
| G321 a, b, c, d, e or f | —CF₃ | —H | —S(O)₂CH₃ |
| G322 a, b, c, d, e or f | —CF₃ | —H | —S(O)₂CH₃CH₃ |
| G323 a, b, c, d, e or f | —CF₃ | —Cl | —H |
| G324 a, b, c, d, e or f | —CF₃ | —Cl | —Cl |
| G325 a, b, c, d, e or f | —CF₃ | —Cl | —Br |
| G326 a, b, c, d, e or f | —CF₃ | —Cl | —F |
| G327 a, b, c, d, e or f | —CF₃ | —Cl | —CH₃ |
| G328 a, b, c, d, e or f | —CF₃ | —Cl | —OCH₃ |
| G329 a, b, c, d, e or f | —CF₃ | —Cl | —OCH₂CH₃ |
| G330 a, b, c, d, e or f | —CF₃ | —Cl | —CF₃ |
| G331 a, b, c, d, e or f | —CF₃ | —Cl | —OCF₃ |
| G332 a, b, c, d, e or f | —CF₃ | —Cl | iso-propyl |
| G333 a, b, c, d, e or f | —CF₃ | —Cl | tert-butyl |
| G334 a, b, c, d, e or f | —CF₃ | —Cl | —S(O)₂CF₃ |
| G335 a, b, c, d, e or f | —CF₃ | —Cl | —S(O)₂CH₃ |
| G336 a, b, c, d, e or f | —CF₃ | —Cl | —S(O)₂CH₃CH₃ |
| G337 a, b, c, d, e or f | —CF₃ | —Br | —H |
| G338 a, b, c, d, e or f | —CF₃ | —Br | —Cl |
| G339 a, b, c, d, e or f | —CF₃ | —Br | —Br |
| G340 a, b, c, d, e or f | —CF₃ | —Br | —F |
| G341 a, b, c, d, e or f | —CF₃ | —Br | —CH₃ |
| G342 a, b, c, d, e or f | —CF₃ | —Br | —OCH₃ |
| G343 a, b, c, d, e or f | —CF₃ | —Br | —OCH₂CH₃ |
| G344 a, b, c, d, e or f | —CF₃ | —Br | —CF₃ |
| G345 a, b, c, d, e or f | —CF₃ | —Br | —OCF₃ |
| G346 a, b, c, d, e or f | —CF₃ | —Br | iso-propyl |
| G347 a, b, c, d, e or f | —CF₃ | —Br | tert-butyl |
| G348 a, b, c, d, e or f | —CF₃ | —Br | —S(O)₂CF₃ |
| G349 a, b, c, d; e or f | —CF₃ | —Br | —S(O)₂CH₃ |
| G350 a, b, c, d, e or f | —CF₃ | —Br | —S(O)₂CH₃CH₃ |
| G351 a, b, c, d, e or f | —CF₃ | —F | —H |
| G352 a, b, c, d, e or f | —CF₃ | —F | —Cl |
| G353 a, b, c, d, e or f | —CF₃ | —F | —Br |
| G354 a, b, c, d, e or f | —CF₃ | —F | —F |
| G355 a, b, c, d, e or f | —CF₃ | —F | —CH₃ |
| G356 a, b, c, d, e or f | —CF₃ | —F | —OCH₃ |
| G357 a, b, c, d, e or f | —CF₃ | —F | —OCH₂CH₃ |
| G358 a, b, c, d, e or f | —CF₃ | —F | —CF₃ |
| G359 a, b, c, d, e or f | —CF₃ | —F | —OCF₃ |
| G360 a, b, c, d, e or f | —CF₃ | —F | iso-propyl |
| G361 a, b, c, d, e or f | —CF₃ | —F | tert-butyl |
| G362 a, b, c, d, e or f | —CF₃ | —F | —S(O)₂CF₃ |
| G363 a, b, c, d, e or f | —CF₃ | —F | —S(O)₂CH₃ |
| G364 a, b, c, d, e or f | —CF₃ | —F | —S(O)₂CH₃CH₃ |
| G365 a, b, c, d, e or f | —CF₃ | —CH₃ | —H |
| G366 a, b, c, d, e or f | —CF₃ | —CH₃ | —Cl |
| G367 a, b, c, d, e or f | —CF₃ | —CH₃ | —Br |
| G368 a, b, c, d, e or f | —CF₃ | —CH₃ | —F |
| G369 a, b, c, d, e or f | —CF₃ | —CH₃ | —CH₃ |
| G370 a, b, c, d, e or f | —CF₃ | —CH₃ | —OCH₃ |
| G371 a, b, c, d, e or f | —CF₃ | —CH₃ | —OCH₂CH₃ |
| G372 a, b, c, d, e or f | —CF₃ | —CH₃ | —CF₃ |
| G373 a, b, c, d, e or f | —CF₃ | —CH₃ | —OCF₃ |
| G374 a, b, c, d, e or f | —CF₃ | —CH₃ | iso-propyl |
| G375 a, b, c, d, e or f | —CF₃ | —CH₃ | tert-butyl |
| G376 a, b, c, d, e or f | —CF₃ | —CH₃ | —S(O)₂CF₃ |
| G377 a, b, c, d, e or f | —CF₃ | —CH₃ | —S(O)₂CH₃ |
| G378 a, b, c, d, e or f | —CF₃ | —CH₃ | —S(O)₂CH₃CH₃ |
| G379 a, b, c, d, e or f | —CF₃ | —OCH₃ | —H |
| G380 a, b, c, d, e or f | —CF₃ | —OCH₃ | —Cl |
| G381 a, b, c, d, e or f | —CF₃ | —OCH₃ | —Br |
| G382 a, b, c, d, e or f | —CF₃ | —OCH₃ | —F |
| G383 a, b, c, d, e or f | —CF₃ | —OCH₃ | —CH₃ |
| G384 a, b, c, d, e or f | —CF₃ | —OCH₃ | —OCH₃ |
| G385 a, b, c, d, e or f | —CF₃ | —OCH₃ | —OCH₂CH₃ |
| G386 a, b, c, d, e or f | —CF₃ | —OCH₃ | —CF₃ |
| G387 a, b, c, d, e or f | —CF₃ | —OCH₃ | —OCF₃ |
| G388 a, b, c, d, e or f | —CF₃ | —OCH₃ | iso-propyl |
| G389 a, b, c, d, e or f | —CF₃ | —OCH₃ | tert-butyl |
| G390 a, b, c, d, e or f | —CF₃ | —OCH₃ | —S(O)₂CF₃ |
| G391 a, b, c, d, e or f | —CF₃ | —OCH₃ | —S(O)₂CH₃ |
| G392 a, b, c, d, e or f | —CF₃ | —OCH₃ | —S(O)₂CH₃CH₃ |
| G393 a, b, c, d, e or f | —CF₃ | —OCH₂CH₃ | —H |
| G394 a, b, c, d, e or f | —CF₃ | —OCH₂CH₃ | —Cl |
| G395 a, b, c, d, e or f | —CF₃ | —OCH₂CH₃ | —Br |
| G396 a, b, c, d, e or f | —CF₃ | —OCH₂CH₃ | —F |
| G397 a, b, c, d, e or f | —CF₃ | —OCH₂CH₃ | —CH₃ |
| G398 a, b, c, d, e or f | —CF₃ | —OCH₂CH₃ | —OCH₃ |
| G399 a, b, c, d, e or f | —CF₃ | —OCH₂CH₃ | —OCH₂CH₃ |
| G400 a, b, c, d, e or f | —CF₃ | —OCH₂CH₃ | —CF₃ |
| G401 a, b, c, d, e or f | —CF₃ | —OCH₂CH₃ | —OCF₃ |
| G402 a, b, c, d, e or f | —CF₃ | —OCH₂CH₃ | iso-propyl |
| G403 a, b, c, d, e or f | —CF₃ | —OCH₂CH₃ | tert-butyl |
| G404 a, b, c, d, e or f | —CF₃ | —OCH₂CH₃ | —S(O)₂CF₃ |
| G405 a, b, c, d, e or f | —CF₃ | —OCH₂CH₃ | —S(O)₂CH₃ |
| G406 a, b, c, d, e or f | —CF₃ | —OCH₂CH₃ | —S(O)₂CH₃CH₃ |
| G407 a, b, c, d, e or f | —CF₃ | —CF₃ | —H |
| G408 a, b, c, d, e or f | —CF₃ | —CF₃ | —Cl |
| G409 a, b, c, d, e or f | —CF₃ | —CF₃ | —Br |
| G410 a, b, c, d, e or f | —CF₃ | —CF₃ | —F |
| G411 a, b, c, d, e or f | —CF₃ | —CF₃ | —CH₃ |
| G412 a, b, c, d, e or f | —CF₃ | —CF₃ | —OCH₃ |
| G413 a, b, c, d, e or f | —CF₃ | —CF₃ | —OCH₂CH₃ |

TABLE 7-continued

| | | | |
|---|---|---|---|
| G414 a, b, c, d, e or f | —CF₃ | —CF₃ | —CF₃ |
| G415 a, b, c, d, e or f | —CF₃ | —CF₃ | —OCF₃ |
| G416 a, b, c, d, e or f | —CF₃ | —CF₃ | iso-propyl |
| G417 a, b, c, d, e or f | —CF₃ | —CF₃ | tert-butyl |
| G418 a, b, c, d, e or f | —CF₃ | —CF₃ | —S(O)₂CF₃ |
| G419 a, b, c, d, e or f | —CF₃ | —CF₃ | —S(O)₂CH₃ |
| G420 a, b, c, d, e or f | —CF₃ | —CF₃ | —S(O)₂CH₃CH₃ |
| G421 a, b, c, d, e or f | —CF₃ | —OCF₃ | —H |
| G422 a, b, c, d, e or f | —CF₃ | —OCF₃ | —Cl |
| G423 a, b, c, d, e or f | —CF₃ | —OCF₃ | —Br |
| G424 a, b, c, d, e or f | —CF₃ | —OCF₃ | —F |
| G425 a, b, c, d, e or f | —CF₃ | —OCF₃ | —CH₃ |
| G426 a, b, c, d, e or f | —CF₃ | —OCF₃ | —OCH₃ |
| G427 a, b, c, d, e or f | —CF₃ | —OCF₃ | —OCH₂CH₃ |
| G428 a, b, c, d, e or f | —CF₃ | —OCF₃ | —CF₃ |
| G429 a, b, c, d, e or f | —CF₃ | —OCF₃ | —OCF₃ |
| G430 a, b, c, d, e or f | —CF₃ | —OCF₃ | iso-propyl |
| G431 a, b, c, d, e or f | —CF₃ | —OCF₃ | tert-butyl |
| G432 a, b, c, d, e or f | —CF₃ | —OCF₃ | —S(O)₂CF₃ |
| G433 a, b, c, d, e or f | —CF₃ | —OCF₃ | —S(O)₂CH₃ |
| G434 a, b, c, d, e or f | —CF₃ | —OCF₃ | —S(O)₂CH₃CH₃ |
| G435 a, b, c, d, e or f | —CF₃ | iso-propyl | —H |
| G436 a, b, c, d, e or f | —CF₃ | iso-propyl | —Cl |
| G437 a, b, c, d, e or f | —CF₃ | iso-propyl | —Br |
| G438 a, b, c, d, e or f | —CF₃ | iso-propyl | —F |
| G439 a, b, c, d, e or f | —CF₃ | iso-propyl | —CH₃ |
| G440 a, b, c, d, e or f | —CF₃ | iso-propyl | —OCH₃ |
| G441 a, b, c, d, e or f | —CF₃ | iso-propyl | —OCH₂CH₃ |
| G442 a, b, c, d, e or f | —CF₃ | iso-propyl | —CF₃ |
| G443 a, b, c, d, e or f | —CF₃ | iso-propyl | —OCF₃ |
| G444 a, b, c, d, e or f | —CF₃ | iso-propyl | iso-propyl |
| G445 a, b, c, d, e or f | —CF₃ | iso-propyl | tert-butyl |
| G446 a, b, c, d, e or f | —CF₃ | iso-propyl | —S(O)₂CF₃ |
| G447 a, b, c, d, e or f | —CF₃ | iso-propyl | —S(O)₂CH₃ |
| G448 a, b, c, d, e or f | —CF₃ | iso-propyl | —S(O)₂CH₃CH₃ |
| G449 a, b, c, d, e or f | —CF₃ | tert-butyl | —H |
| G450 a, b, c, d, e or f | —CF₃ | tert-butyl | —Cl |
| G451 a, b, c, d, e or f | —CF₃ | tert-butyl | —Br |
| G452 a, b, c, d, e or f | —CF₃ | tert-butyl | —F |
| G453 a, b, c, d, e or f | —CF₃ | tert-butyl | —CH₃ |
| G454 a, b, c, d, e or f | —CF₃ | tert-butyl | —OCH₃ |
| G455 a, b, c, d, e or f | —CF₃ | tert-butyl | —OCH₂CH₃ |
| G456 a, b, c, d, e or f | —CF₃ | tert-butyl | —CF₃ |
| G457 a, b, c, d, e or f | —CF₃ | tert-butyl | —OCF₃ |
| G458 a, b, c, d, e or f | —CF₃ | tert-butyl | iso-propyl |
| G459 a, b, c, d, e or f | —CF₃ | tert-butyl | tert-butyl |
| G460 a, b, c, d, e or f | —CF₃ | tert-butyl | —S(O)₂CF₃ |
| G461 a, b, c, d, e or f | —CF₃ | tert-butyl | —S(O)₂CH₃ |
| G462 a, b, c, d, e or f | —CF₃ | tert-butyl | —S(O)₂CH₃CH₃ |
| G463 a, b, c, d, e or f | —CH₃ | —H | —H |
| G464 a, b, c, d, e or f | —CH₃ | —H | —Cl |
| G465 a, b, c, d, e or f | —CH₃ | —H | —Br |
| G466 a, b, c, d, e or f | —CH₃ | —H | —F |
| G467 a, b, c, d, e or f | —CH₃ | —H | —CH₃ |
| G468 a, b, c, d, e or f | —CH₃ | —H | —OCH₃ |
| G469 a, b, c, d, e or f | —CH₃ | —H | —OCH₂CH₃ |
| G470 a, b, c, d, e or f | —CH₃ | —H | —CF₃ |
| G471 a, b, c, d, e or f | —CH₃ | —H | —OCF₃ |
| G472 a, b, c, d, e or f | —CH₃ | —H | iso-propyl |
| G473 a, b, c, d, e or f | —CH₃ | —H | tert-butyl |
| G474 a, b, c, d, e or f | —CH₃ | —H | —S(O)₂CF₃ |
| G475 a, b, c, d, e or f | —CH₃ | —H | —S(O)₂CH₃ |
| G476 a, b, c, d, e or f | —CH₃ | —H | —S(O)₂CH₃CH₃ |
| G477 a, b, c, d, e or f | —CH₃ | —Cl | —H |
| G478 a, b, c, d, e or f | —CH₃ | —Cl | —Cl |
| G479 a, b, c, d, e or f | —CH₃ | —Cl | —Br |
| G480 a, b, c, d, e or f | —CH₃ | —Cl | —F |
| G481 a, b, c, d, e or f | —CH₃ | —Cl | —CH₃ |
| G482 a, b, c, d, e or f | —CH₃ | —Cl | —OCH₃ |
| G483 a, b, c, d, e or f | —CH₃ | —Cl | —OCH₂CH₃ |
| G484 a, b, c, d, e or f | —CH₃ | —Cl | —CF₃ |
| G485 a, b, c, d, e or f | —CH₃ | —Cl | —OCF₃ |
| G486 a, b, c, d, e or f | —CH₃ | —Cl | iso-propyl |
| G487 a, b, c, d, e or f | —CH₃ | —Cl | tert-butyl |
| G488 a, b, c, d, e or f | —CH₃ | —Cl | —S(O)₂CF₃ |
| G489 a, b, c, d, e or f | —CH₃ | —Cl | —S(O)₂CH₃ |
| G490 a, b, c, d, e or f | —CH₃ | —Cl | —S(O)₂CH₃CH₃ |
| G491 a, b, c, d, e or f | —CH₃ | —Br | —H |
| G492 a, b, c, d, e or f | —CH₃ | —Br | —Cl |
| G493 a, b, c, d, e or f | —CH₃ | —Br | —Br |
| G494 a, b, c, d, e or f | —CH₃ | —Br | —F |
| G495 a, b, c, d, e or f | —CH₃ | —Br | —CH₃ |
| G496 a, b, c, d, e or f | —CH₃ | —Br | —OCH₃ |
| G497 a, b, c, d, e or f | —CH₃ | —Br | —OCH₂CH₃ |
| G498 a, b, c, d, e or f | —CH₃ | —Br | —CF₃ |
| G499 a, b, c, d, e or f | —CH₃ | —Br | —OCF₃ |
| G500 a, b, c, d, e or f | —CH₃ | —Br | iso-propyl |
| G501 a, b, c, d, e or f | —CH₃ | —Br | tert-butyl |
| G502 a, b, c, d, e or f | —CH₃ | —Br | —S(O)₂CF₃ |
| G503 a, b, c, d, e or f | —CH₃ | —Br | —S(O)₂CH₃ |
| G504 a, b, c, d, e or f | —CH₃ | —Br | —S(O)₂CH₃CH₃ |
| G505 a, b, c, d, e or f | —CH₃ | —F | —H |
| G506 a, b, c, d, e or f | —CH₃ | —F | —Cl |
| G507 a, b, c, d, e or f | —CH₃ | —F | —Br |
| G508 a, b, c, d, e or f | —CH₃ | —F | —F |
| G509 a, b, c, d, e or f | —CH₃ | —F | —CH₃ |
| G510 a, b, c, d, e or f | —CH₃ | —F | —OCH₃ |
| G511 a, b, c, d, e or f | —CH₃ | —F | —OCH₂CH₃ |
| G512 a, b, c, d, e or f | —CH₃ | —F | —CF₃ |
| G513 a, b, c, d, e or f | —CH₃ | —F | —OCF₃ |
| G514 a, b, c, d, e or f | —CH₃ | —F | iso-propyl |
| G515 a, b, c, d, e or f | —CH₃ | —F | tert-butyl |
| G516 a, b, c, d, e or f | —CH₃ | —F | —S(O)₂CF₃ |
| G517 a, b, c, d, e or f | —CH₃ | —F | —S(O)₂CH₃ |
| G518 a, b, c, d, e or f | —CH₃ | —F | —S(O)₂CH₃CH₃ |
| G519 a, b, c, d, e or f | —CH₃ | —CH₃ | —H |
| G520 a, b, c, d, e or f | —CH₃ | —CH₃ | —Cl |
| G521 a, b, c, d, e or f | —CH₃ | —CH₃ | —Br |
| G522 a, b, c, d, e or f | —CH₃ | —CH₃ | —F |
| G523 a, b, c, d, e or f | —CH₃ | —CH₃ | —CH₃ |
| G524 a, b, c, d, e or f | —CH₃ | —CH₃ | —OCH₃ |
| G525 a, b, c, d, e or f | —CH₃ | —CH₃ | —OCH₂CH₃ |
| G526 a, b, c, d, e or f | —CH₃ | —CH₃ | —CF₃ |
| G527 a, b, c, d, e or f | —CH₃ | —CH₃ | —OCF₃ |
| G528 a, b, c, d, e or f | —CH₃ | —CH₃ | iso-propyl |
| G529 a, b, c, d, e or f | —CH₃ | —CH₃ | tert-butyl |
| G530 a, b, c, d, e or f | —CH₃ | —CH₃ | —S(O)₂CF₃ |
| G531 a, b, c, d, e or f | —CH₃ | —CH₃ | —S(O)₂CH₃ |
| G532 a, b, c, d, e or f | —CH₃ | —CH₃ | —S(O)₂CH₃CH₃ |
| G533 a, b, c, d, e or f | —CH₃ | —OCH₃ | —H |
| G534 a, b, c, d, e or f | —CH₃ | —OCH₃ | —Cl |
| G535 a, b, c, d, e or f | —CH₃ | —OCH₃ | —Br |
| G536 a, b, c, d, e or f | —CH₃ | —OCH₃ | —F |
| G537 a, b, c, d, e or f | —CH₃ | —OCH₃ | —CH₃ |
| G538 a, b, c, d, e or f | —CH₃ | —OCH₃ | —OCH₃ |
| G539 a, b, c, d, e or f | —CH₃ | —OCH₃ | —OCH₂CH₃ |
| G540 a, b, c, d, e or f | —CH₃ | —OCH₃ | —CF₃ |
| G541 a, b, c, d, e or f | —CH₃ | —OCH₃ | —OCF₃ |
| G542 a, b, c, d, e or f | —CH₃ | —OCH₃ | iso-propyl |
| G543 a, b, c, d, e or f | —CH₃ | —OCH₃ | tert-butyl |
| G544 a, b, c, d, e or f | —CH₃ | —OCH₃ | —S(O)₂CF₃ |
| G545 a, b, c, d, e or f | —CH₃ | —OCH₃ | —S(O)₂CH₃ |
| G546 a, b, c, d, e or f | —CH₃ | —OCH₃ | —S(O)₂CH₃CH₃ |
| G547 a, b, c, d, e or f | —CH₃ | —OCH₂CH₃ | —H |
| G548 a, b, c, d, e or f | —CH₃ | —OCH₂CH₃ | —Cl |
| G549 a, b, c, d, e or f | —CH₃ | —OCH₂CH₃ | —Br |
| G550 a, b, c, d, e or f | —CH₃ | —OCH₂CH₃ | —F |
| G551 a, b, c, d, e or f | —CH₃ | —OCH₂CH₃ | —CH₃ |
| G552 a, b, c, d, e or f | —CH₃ | —OCH₂CH₃ | —OCH₃ |
| G553 a, b, c, d, e or f | —CH₃ | —OCH₂CH₃ | —OCH₂CH₃ |
| G554 a, b, c, d, e or f | —CH₃ | —OCH₂CH₃ | —CF₃ |
| G555 a, b, c, d, e or f | —CH₃ | —OCH₂CH₃ | —OCF₃ |
| G556 a, b, c, d, e or f | —CH₃ | —OCH₂CH₃ | iso-propyl |
| G557 a, b, c, d, e or f | —CH₃ | —OCH₂CH₃ | tert-butyl |
| G558 a, b, c, d, e or f | —CH₃ | —OCH₂CH₃ | —S(O)₂CF₃ |
| G559 a, b, c, d, e or f | —CH₃ | —OCH₂CH₃ | —S(O)₂CH₃ |
| G560 a, b, c, d, e or f | —CH₃ | —OCH₂CH₃ | —S(O)₂CH₃CH₃ |
| G561 a, b, c, d, e or f | —CH₃ | —CF₃ | —H |
| G562 a, b, c, d, e or f | —CH₃ | —CF₃ | —Cl |
| G563 a, b, c, d, e or f | —CH₃ | —CF₃ | —Br |
| G564 a, b, c, d, e or f | —CH₃ | —CF₃ | —F |
| G565 a, b, c, d, e or f | —CH₃ | —CF₃ | —CH₃ |
| G566 a, b, c, d, e or f | —CH₃ | —CF₃ | —OCH₃ |
| G567 a, b, c, d, e or f | —CH₃ | —CF₃ | —OCH₂CH₃ |
| G568 a, b, c, d, e or f | —CH₃ | —CF₃ | —CF₃ |
| G569 a, b, c, d, e or f | —CH₃ | —CF₃ | —OCF₃ |
| G570 a, b, c, d, e or f | —CH₃ | —CF₃ | iso-propyl |
| G571 a, b, c, d, e or f | —CH₃ | —CF₃ | tert-butyl |
| G572 a, b, c, d, e or f | —CH₃ | —CF₃ | —S(O)₂CF₃ |
| G573 a, b, c, d, e or f | —CH₃ | —CF₃ | —S(O)₂CH₃ |

TABLE 7-continued

| | | | |
|---|---|---|---|
| G574 a, b, c, d, e or f | —CH₃ | —CF₃ | —S(O)₂CH₃CH₃ |
| G575 a, b, c, d, e or f | —CH₃ | —OCF₃ | —H |
| G576 a, b, c, d, e or f | —CH₃ | —OCF₃ | —Cl |
| G577 a, b, c, d, e or f | —CH₃ | —OCF₃ | —Br |
| G578 a, b, c, d, e or f | —CH₃ | —OCF₃ | —F |
| G579 a, b, c, d, e or f | —CH₃ | —OCF₃ | —CH₃ |
| G580 a, b, c, d, e or f | —CH₃ | —OCF₃ | —OCH₃ |
| G581 a, b, c, d, e or f | —CH₃ | —OCF₃ | —OCH₂CH₃ |
| G582 a, b, c, d, e or f | —CH₃ | —OCF₃ | —CF₃ |
| G583 a, b, c, d, e or f | —CH₃ | —OCF₃ | —OCF₃ |
| G584 a, b, c, d, e or f | —CH₃ | —OCF₃ | iso-propyl |
| G585 a, b, c, d, e or f | —CH₃ | —OCF₃ | tert-butyl |
| G586 a, b, c, d, e or f | —CH₃ | —OCF₃ | —S(O)₂CF₃ |
| G587 a, b, c, d, e or f | —CH₃ | —OCF₃ | —S(O)₂CH₃ |
| G588 a, b, c, d, e or f | —CH₃ | —OCF₃ | —S(O)₂CH₃CH₃ |
| G589 a, b, c, d, e or f | —CH₃ | iso-propyl | —H |
| G590 a, b, c, d, e or f | —CH₃ | iso-propyl | —Cl |
| G591 a, b, c, d, e or f | —CH₃ | iso-propyl | —Br |
| G592 a, b, c, d, e or f | —CH₃ | iso-propyl | —F |
| G593 a, b, c, d, e or f | —CH₃ | iso-propyl | —CH₃ |
| G594 a, b, c, d, e or f | —CH₃ | iso-propyl | —OCH₃ |
| G595 a, b, c, d, e or f | —CH₃ | iso-propyl | —OCH₂CH₃ |
| G596 a, b, c, d, e or f | —CH₃ | iso-propyl | —CF₃ |
| G597 a, b, c, d, e or f | —CH₃ | iso-propyl | —OCF₃ |
| G598 a, b, c, d, e or f | —CH₃ | iso-propyl | iso-propyl |
| G599 a, b, c, d, e or f | —CH₃ | iso-propyl | tert-butyl |
| G600 a, b, c, d, e or f | —CH₃ | iso-propyl | —S(O)₂CF₃ |
| G601 a, b, c, d, e or f | —CH₃ | iso-propyl | —S(O)₂CH₃ |
| G602 a, b, c, d, e or f | —CH₃ | iso-propyl | —S(O)₂CH₃CH₃ |
| G603 a, b, c, d, e or f | —CH₃ | tert-butyl | —H |
| G604 a, b, c, d, e or f | —CH₃ | tert-butyl | —Cl |
| G605 a, b, c, d, e or f | —CH₃ | tert-butyl | —Br |
| G606 a, b, c, d, e or f | —CH₃ | tert-butyl | —F |
| G607 a, b, c, d, e or f | —CH₃ | tert-butyl | —CH₃ |
| G608 a, b, c, d, e or f | —CH₃ | tert-butyl | —OCH₃ |
| G609 a, b, c, d, e or f | —CH₃ | tert-butyl | —OCH₂CH₃ |
| G610 a, b, c, d, e or f | —CH₃ | tert-butyl | —CF₃ |
| G611 a, b, c, d, e or f | —CH₃ | tert-butyl | —OCF₃ |
| G612 a, b, c, d, e or f | —CH₃ | tert-butyl | iso-propyl |
| G613 a, b, c, d, e or f | —CH₃ | tert-butyl | tert-butyl |
| G614 a, b, c, d, e or f | —CH₃ | tert-butyl | —S(O)₂CF₃ |
| G615 a, b, c, d, e or f | —CH₃ | tert-butyl | —S(O)₂CH₃ |
| G616 a, b, c, d, e or f | —CH₃ | tert-butyl | —S(O)₂CH₃CH₃ |

TABLE 8

(IIIg)

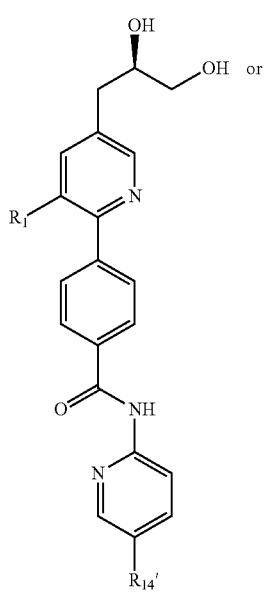

(IIIh)

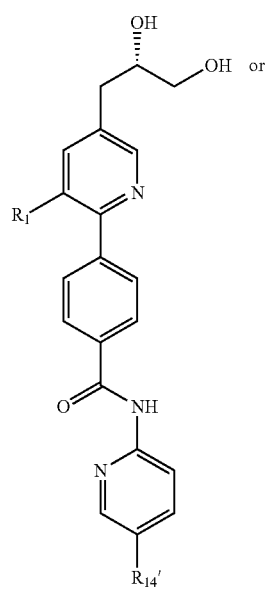

(IIIi)

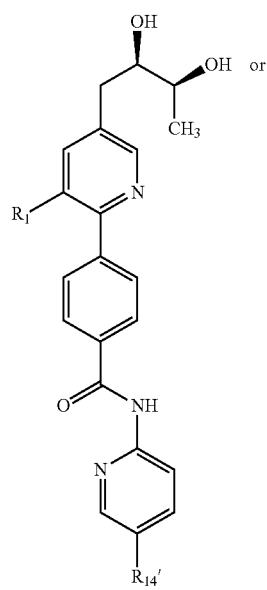

TABLE 8-continued

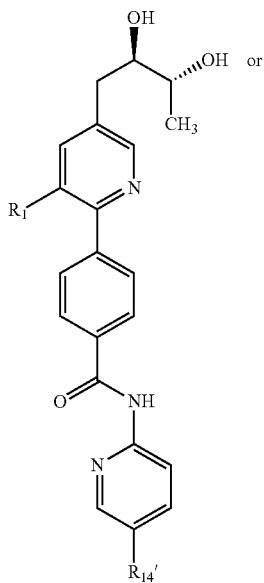

(IIIj)

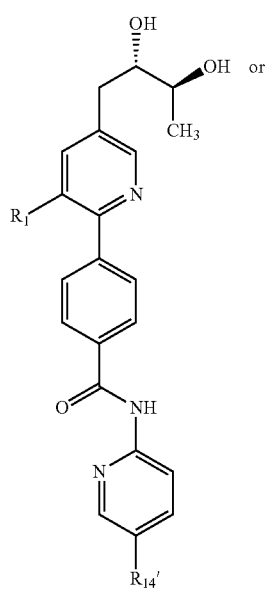

(IIIk)

TABLE 8-continued

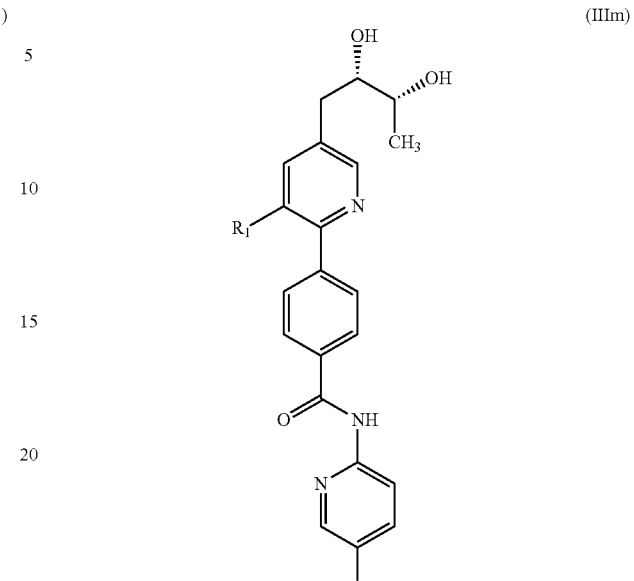

(IIIm)

and pharmaceutically acceptable derivatives thereof, where:

| Compound | | $R_1$ | $R_{14}'$ |
|---|---|---|---|
| H H1 | g, h, i, j, k or m | —Cl | —H |
| H2 | g, h, i, j, k or m | —Cl | —Cl |
| H3 | g, h, i, j, k or m | —Cl | —F |
| H4 | g, h, i, j, k or m | —Cl | —Br |
| H5 | g, h, i, j, k or m | —Cl | —CF$_3$ |
| H6 | g, h, i, j, k or m | —Cl | —OCF$_3$ |
| H7 | g, h, i, j, k or m | —Cl | —CH$_3$ |
| H8 | g, h, i, j, k or m | —Cl | —CH$_2$CH$_3$ |
| H9 | g, h, i, j, k or m | —Cl | -iso-propyl |
| H10 | g, h, i, j, k or m | —Cl | -tert-butyl |
| H11 | g, h, i, j, k or m | —Cl | —S(O)$_2$CF$_3$ |
| H12 | g, h, i, j, k or m | —Cl | —S(O)$_2$CH$_3$ |
| H13 | g, h, i, j, k or m | —Cl | —S(O)$_2$CH$_3$CH$_3$ |
| H14 | g, h, i, j, k or m | —Cl | —OCH$_3$ |
| H15 | g, h, i, j, k or m | —Cl | —OCH$_2$CH$_3$ |
| H16 | g, h, i, j, k or m | —Cl | —OCH(CH$_3$)$_2$ |
| H17 | g, h, i, j, k or m | —F | —H |
| H18 | g, h, i, j, k or m | —F | —Cl |
| H19 | g, h, i, j, k or m | —F | —F |
| H20 | g, h, i, j, k or m | —F | —Br |
| H21 | g, h, i, j, k or m | —F | —CF$_3$ |
| H22 | g, h, i, j, k or m | —F | —OCF$_3$ |
| H23 | g, h, i, j, k or m | —F | —CH$_3$ |
| H24 | g, h, i, j, k or m | —F | —CH$_2$CH$_3$ |
| H25 | g, h, i, j, k or m | —F | -iso-propyl |
| H26 | g, h, i, j, k or m | —F | -tert-butyl |
| H27 | g, h, i, j, k or m | —F | —S(O)$_2$CF$_3$ |
| H28 | g, h, i, j, k or m | —F | —S(O)$_2$CH$_3$ |
| H29 | g, h, i, j, k or m | —F | —S(O)$_2$CH$_3$CH$_3$ |
| H30 | g, h, i, j, k or m | —F | —OCH$_3$ |
| H31 | g, h, i, j, k or m | —F | —OCH$_2$CH$_3$ |
| H32 | g, h, i, j, k or m | —F | —OCH(CH$_3$)$_2$ |
| H33 | g, h, i, j, k or m | —CF$_3$ | —H |
| H34 | g, h, i, j, k or m | —CF$_3$ | —Cl |
| H35 | g, h, i, j, k or m | —CF$_3$ | —F |
| H36 | g, h, i, j, k or m | —CF$_3$ | —Br |
| H37 | g, h, i, j, k or m | —CF$_3$ | —CF$_3$ |
| H38 | g, h, i, j, k or m | —CF$_3$ | —OCF$_3$ |
| H39 | g, h, i, j, k or m | —CF$_3$ | —CH$_3$ |
| H40 | g, h, i, j, k or m | —CF$_3$ | —CH$_2$CH$_3$ |
| H41 | g, h, i, j, k or m | —CF$_3$ | -iso-propyl |
| H42 | g, h, i, j, k or m | —CF$_3$ | -tert-butyl |
| H43 | g, h, i, j, k or m | —CF$_3$ | —S(O)$_2$CF$_3$ |
| H44 | g, h, i, j, k or m | —CF$_3$ | —S(O)$_2$CH$_3$ |
| H45 | g, h, i, j, k or m | —CF$_3$ | —S(O)$_2$CH$_3$CH$_3$ |
| H46 | g, h, i, j, k or m | —CF$_3$ | —OCH$_3$ |

TABLE 8-continued

| | | |
|---|---|---|
| H47 g, h, i, j, k or m | —CF$_3$ | —OCH$_2$CH$_3$ |
| H48 g, h, i, j, k or m | —CF$_3$ | —OCH(CH$_3$)$_2$ |
| H49 g, h, i, j, k or m | —CH$_3$ | —H |
| H50 g, h, i, j, k or m | —CH$_3$ | —Cl |
| H51 g, h, i, j, k or m | —CH$_3$ | —F |
| H52 g, h, i, j, k or m | —CH$_3$ | —Br |
| H53 g, h, i, j, k or m | —CH$_3$ | —CF$_3$ |
| H54 g, h, i, j, k or m | —CH$_3$ | —OCF$_3$ |
| H55 g, h, i, j, k or m | —CH$_3$ | —CH$_3$ |
| H56 g, h, i, j, k or m | —CH$_3$ | —CH$_2$CH$_3$ |
| H57 g, h, i, j, k or m | —CH$_3$ | -iso-propyl |
| H58 g, h, i, j, k or m | —CH$_3$ | -tert-butyl |
| H59 g, h, i, j, k or m | —CH$_3$ | —S(O)$_2$CF$_3$ |
| H60 g, h, i, j, k or m | —CH$_3$ | —S(O)$_2$CH$_3$ |
| H61 g, h, i, j, k or m | —CH$_3$ | —S(O)$_2$CH$_3$CH$_3$ |
| H62 g, h, i, j, k or m | —CH$_3$ | —OCH$_3$ |
| H63 g, h, i, j, k or m | —CH$_3$ | —OCH$_2$CH$_3$ |
| H64 g, h, i, j, k or m | —CH$_3$ | —OCH(CH$_3$)$_2$ |

TABLE 9

(IIIn)

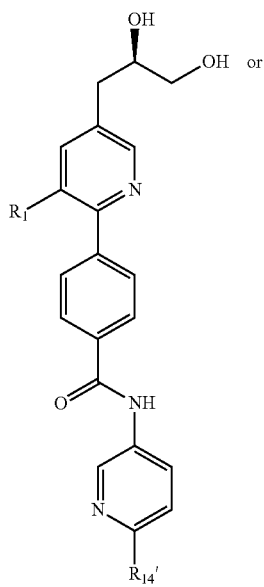

(IIIo)

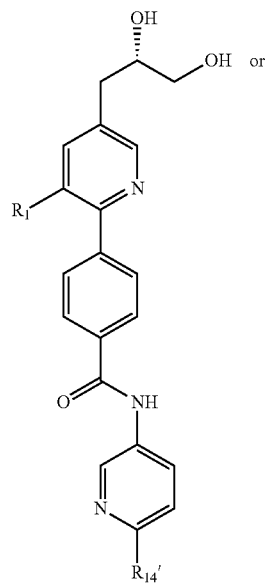

(IIIp)

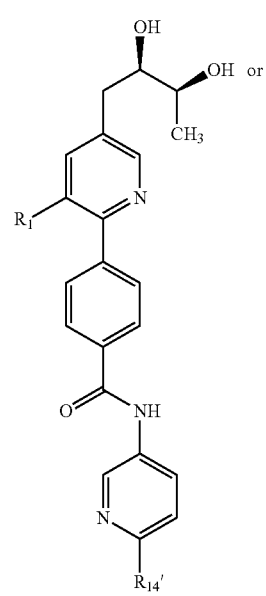

TABLE 9-continued

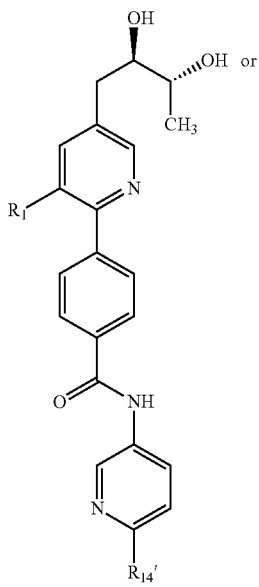

(IIIq)

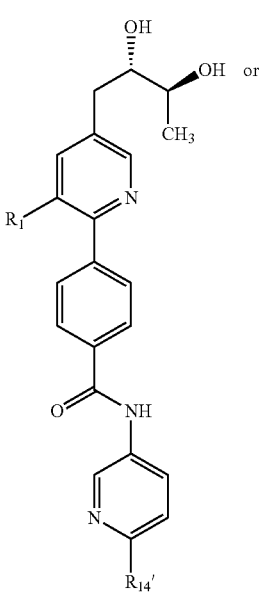

(IIIr)

TABLE 9-continued

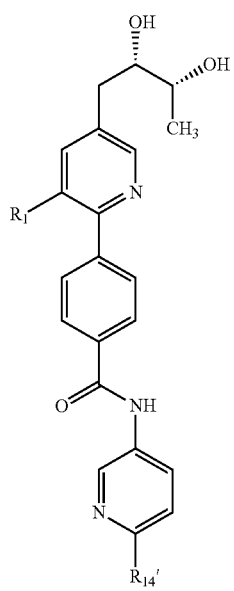

(IIIs)

and pharmaceutically acceptable derivatives thereof, where:

| Compound | $R_1$ | $R_{14}'$ |
|---|---|---|
| I 11 n,o,p,q,r or s | —Cl | —H |
| I2 n, o, p, q, r or s | —Cl | —Cl |
| I3 n, o, p, q, r or s | —Cl | —F |
| I4 n, o, p, q, r or s | —Cl | —Br |
| I5 n, o, p, q, r or s | —Cl | —CF$_3$ |
| I6 n, o, p, q, r or s | —Cl | —OCF$_3$ |
| I7 n, o, p, q, r or s | —Cl | —CH$_3$ |
| I8 n, o, p, q, r or s | —Cl | —CH$_2$CH$_3$ |
| I9 n, o, p, q, r or s | —Cl | -iso-propyl |
| I10 n, o, p, q, r or s | —Cl | -tert-butyl |
| I11 n, o, p, q, r or s | —Cl | —S(O)$_2$CF$_3$ |
| I12 n, o, p, q, r or s | —Cl | —S(O)$_2$CH$_3$ |
| I13 n, o, p, q, r or s | —Cl | —S(O)$_2$CH$_3$CH$_3$ |
| I14 n, o, p, q, r or s | —Cl | —OCH$_3$ |
| I15 n, o, p, q, r or s | —Cl | —OCH$_2$CH$_3$ |
| I16 n, o, p, q, r or s | —Cl | —OCH(CH$_3$)$_2$ |
| I17 n, o, p, q, r or s | —F | —H |
| I18 n, o, p, q, r or s | —F | —Cl |
| I19 n, o, p, q, r or s | —F | —F |
| I20 n, o, p, q, r or s | —F | —Br |
| I21 n, o, p, q, r or s | —F | —CF$_3$ |
| I22 n, o, p, q, r or s | —F | —OCF$_3$ |
| I23 n, o, p, q, r or s | —F | —CH$_3$ |
| I24 n, o, p, q, r or s | —F | —CH$_2$CH$_3$ |
| I25 n, o, p, q, r or s | —F | -iso-propyl |
| I26 n, o, p, q, r or s | —F | -tert-butyl |
| I27 n, o, p, q, r or s | —F | —S(O)$_2$CF$_3$ |
| I28 n, o, p, q, r or s | —F | —S(O)$_2$CH$_3$ |
| I29 n, o, p, q, r or s | —F | —S(O)$_2$CH$_3$CH$_3$ |
| I30 n, o, p, q, r or s | —F | —OCH$_3$ |
| I31 n, o, p, q, r or s | —F | —OCH$_2$CH$_3$ |
| I32 n, o, p, q, r or s | —F | —OCH(CH$_3$)$_2$ |
| I33 n, o, p, q, r or s | —CF$_3$ | —H |
| I34 n, o, p, q, r or s | —CF$_3$ | —Cl |
| I35 n, o, p, q, r or s | —CF$_3$ | —F |
| I36 n, o, p, q, r or s | —CF$_3$ | —Br |
| I37 n, o, p, q, r or s | —CF$_3$ | —CF$_3$ |
| I38 n, o, p, q, r or s | —CF$_3$ | —OCF$_3$ |
| I39 n, o, p, q, r or s | —CF$_3$ | —CH$_3$ |
| I40 n, o, p, q, r or s | —CF$_3$ | —CH$_2$CH$_3$ |
| I41 n, o, p, q, r or s | —CF$_3$ | -iso-propyl |
| I42 n, o, p, q, r or s | —CF$_3$ | -tert-butyl |
| I43 n, o, p, q, r or s | —CF$_3$ | —S(O)$_2$CF$_3$ |
| I44 n, o, p, q, r or s | —CF$_3$ | —S(O)$_2$CH$_3$ |
| I45 n, o, p, q, r or s | —CF$_3$ | —S(O)$_2$CH$_3$CH$_3$ |

TABLE 9-continued

| | | |
|---|---|---|
| I46 n, o, p, q, r or s | —CF$_3$ | —OCH$_3$ |
| I47 n, o, p, q, r or s | —CF$_3$ | —OCH$_2$CH$_3$ |
| I48 n, o, p, q, r or s | —CF$_3$ | —OCH(CH$_3$)$_2$ |
| I49 n, o, p, q, r or s | —CH$_3$ | —H |
| I50 n, o, p, q, r or s | —CH$_3$ | —Cl |
| I51 n, o, p, q, r or s | —CH$_3$ | —F |
| I52 n, o, p, q, r or s | —CH$_3$ | —Br |
| I53 n, o, p, q, r or s | —CH$_3$ | —CF$_3$ |
| I54 n, o, p, q, r or s | —CH$_3$ | —OCF$_3$ |
| I55 n, o, p, q, r or s | —CH$_3$ | —CH$_3$ |
| I56 n, o, p, q, r or s | —CH$_3$ | —CH$_2$CH$_3$ |
| I57 n, o, p, q, r or s | —CH$_3$ | -iso-propyl |
| I58 n, o, p, q, r or s | —CH$_3$ | -tert-butyl |
| I59 n, o, p, q, r or s | —CH$_3$ | —S(O)$_2$CF$_3$ |
| I60 n, o, p, q, r or s | —CH$_3$ | —S(O)$_2$CH$_3$ |
| I61 n, o, p, q, r or s | —CH$_3$ | —S(O)$_2$CH$_3$CH$_3$ |
| I62 n, o, p, q, r or s | —CH$_3$ | —OCH$_3$ |
| I63 n, o, p, q, r or s | —CH$_3$ | —OCH$_2$CH$_3$ |
| I64 n, o, p, q, r or s | —CH$_3$ | —OCH(CH$_3$)$_2$ |

4.4 Definitions

As used herein, the terms used above having following meaning:

"—(C$_1$-C$_{10}$)alkyl" means a straight chain or branched non-cyclic hydrocarbon having 1, 2, 3, 4, 5, 6, 7, 8, 9, or 10 carbon atoms. Representative straight chain —(C$_1$-C$_{10}$)alkyls include -methyl, -ethyl, -n-propyl, -n-butyl, -n-pentyl, -n-hexyl, -n-heptyl, -n-octyl, -n-nonyl, and -n-decyl. Representative branched —(C$_1$-C$_{10}$)alkyls include -iso-propyl, -sec-butyl, -iso-butyl, -tert-butyl, -iso-pentyl, -neo-pentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl.

"—(C$_1$-C$_6$)alkyl" means a straight chain or branched non-cyclic hydrocarbon having 1, 2, 3, 4, 5, or 6 carbon atoms. Representative straight chain —(C$_1$-C$_6$)alkyls include -methyl, -ethyl, -n-propyl, -n-butyl, -n-pentyl, and -n-hexyl. Representative branched —(C$_1$-C$_6$)alkyls include -iso-propyl, -sec-butyl, -iso-butyl, -tert-butyl, -iso-pentyl, -neo-pentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, and 3,3-dimethylbutyl.

"—(C$_2$-C$_6$)alkyl" means a straight chain or branched non-cyclic hydrocarbon having 2, 3, 4, 5, or 6 carbon atoms. Representative straight chain —(C$_2$-C$_6$)alkyls include -ethyl, -n-propyl, -n-butyl, -n-pentyl, and -n-hexyl. Representative branched —(C$_2$-C$_6$)alkyls include -iso-propyl, -sec-butyl, -iso-butyl, -tert-butyl, -iso-pentyl, -neo-pentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, and 3,3-dimethylbutyl.

"—(C$_1$-C$_4$)alkyl" means a straight chain or branched non-cyclic hydrocarbon having 1, 2, 3, or 4 carbon atoms. Representative straight chain —(C$_1$-C$_4$)alkyls include -methyl, -ethyl, -n-propyl, and -n-butyl. Representative branched —(C$_1$-C$_4$)alkyls include -iso-propyl, -sec-butyl, -iso-butyl, and -tert-butyl.

"—(C$_1$-C$_3$)alkyl" means a straight chain or branched non-cyclic hydrocarbon having 1, 2, or 3 carbon atoms. Representative straight chain —(C$_1$-C$_3$)alkyls include -methyl, -ethyl, - and n-propyl. Representative branched —(C$_1$-C$_3$)alkyls include -iso-propyl.

"—(C$_1$-C$_6$)haloalkyl" means a straight chain or branched non-cyclic hydrocarbon having 1, 2, 3, 4, 5, or 6 carbon atoms as defined above for —(C$_1$-C$_6$)alkyl that is substituted with 1, 2, or 3 independently selected halo groups.

"—(C$_1$-C$_3$)haloalkyl" means a straight chain or branched non-cyclic hydrocarbon having 1, 2, or 3 carbon atoms as defined above for —(C$_1$-C$_3$)alkyl that is substituted with 1, 2, or 3 independently selected halo groups.

"—(C$_1$-C$_6$)hydroxyalkyl" means a straight chain or branched non-cyclic hydrocarbon having 1, 2, 3, 4, 5, or 6 carbon atoms as defined above for —(C$_1$-C$_6$)alkyl that is substituted with 1, 2, or 3 hydroxyl groups.

"—(C$_2$-C$_6$)alkenyl" means a straight chain or branched non-cyclic hydrocarbon having 2, 3, 4, 5, or 6 carbon atoms and including at least one carbon-carbon double bond. Representative straight chain and branched (C$_2$-C$_6$)alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, 2-hexenyl, 3-hexenyl and the like.

"—(C$_2$-C$_4$)alkenyl" means a straight chain or branched non-cyclic hydrocarbon having 2, 3, or 4 carbon atoms and including at least one carbon-carbon double bond. Representative straight chain and branched (C$_2$-C$_4$)alkenyls include -vinyl, -allyl, -1-butenyl, -2-butenyl, -iso-butylenyl and the like.

"—(C$_2$-C$_6$)alkynyl" means a straight chain or branched non-cyclic hydrocarbon having 2, 3, 4, 5, or 6 carbon atoms and including at least one carbon-carbon triple bond. Representative straight chain and branched (C$_2$-C$_6$)alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl and the like.

"—(C$_2$-C$_4$)alkynyl" means a straight chain or branched non-cyclic hydrocarbon having 2, 3, or 4 carbon atoms and including at least one carbon-carbon triple bond. Representative straight chain and branched (C$_2$-C$_4$)alkynyls include -acetylenyl, -propynyl, -1-butynyl, -2-butynyl and the like.

"—(C$_1$-C$_6$)alkoxy" means a straight chain or branched non-cyclic hydrocarbon having one or more ether groups and 1, 2, 3, 4, 5, or 6 carbon atoms. Representative straight chain and branched (C$_1$-C$_6$)alkoxys include -methoxy, -ethoxy, -methoxymethyl, -2-methoxyethyl, -5-methoxypentyl, -3-ethoxybutyl, (methoxymethoxy)methyl-, 1-(methoxy)-1-methoxyethyl-, trimethoxymethyl-, 2-((methoxy)methoxy)-2-methylpropyl-, 3-(1,1,1-trimethoxypropane), (methoxy)trimethoxymethyl-, (2,2,2-trimethoxymethoxy)-, and the like.

"—(C$_1$-C$_6$)alkoxy(C$_2$-C$_6$)alkyl" means a straight chain or branched non cyclic hydrocarbon having one or more ether groups and 1, 2, 3, 4, 5, or 6 carbon atoms as defined above for —($C_1$-$C_6$)alkoxy group that is substituted with a —($C_2$-$C_6$) alkyl group.

"—($C_1$-$C_6$)alkoxy($C_3$-$C_8$)cycloalkyl" means a straight chain or branched non cyclic hydrocarbon having one or more ether groups and 1, 2, 3, 4, 5, or 6 carbon atoms as defined above for —($C_1$-$C_6$)alkyl group that is substituted with a —($C_3$-$C_8$)cycloalkyl group "—($C_3$-$C_{10}$)cycloalkyl" means a saturated cyclic hydrocarbon having 3, 4, 5, 6, 7, 8, 9, or 10 carbon atoms. Representative ($C_3$-$C_{10}$)cycloalkyls are -cyclopropyl, -cyclobutyl, -cyclopentyl, -cyclohexyl, -cycloheptyl, -cyclooctyl, -cyclononyl, and -cyclodecyl.

"—($C_3$-$C_8$)cycloalkyl" means a saturated cyclic hydrocarbon having 3, 4, 5, 6, 7, or 8 carbon atoms. Representative —($C_3$-$C_8$)cycloalkyls include -cyclopropyl, -cyclobutyl, -cyclopentyl, -cyclohexyl, -cycloheptyl, and -cyclooctyl.

"—($C_3$-$C_7$)cycloalkyl" means a saturated cyclic hydrocarbon having 3, 4, 5, 6, or 7 carbon atoms. Representative —($C_3$-$C_7$)cycloalkyls include -cyclopropyl, -cyclobutyl, -cyclopentyl, -cyclohexyl, and -cycloheptyl.

"—($C_5$-$C_8$)cycloalkenyl" means a cyclic non-aromatic hydrocarbon having at least one carbon-carbon double bond in the cyclic system and 5, 6, 7, or 8 carbon atoms. Representative —($C_5$-$C_8$)cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl and the like.

"-(3- to 7-membered)heterocycle" or "-(3- to 7-membered) heterocyclo" means a 3- to 7-membered monocyclic heterocyclic ring which is either saturated, unsaturated non-aromatic, or aromatic. A 3-membered heterocycle contains 1 heteroatom, a 4-membered heterocycle can contain 1 or 2 heteroatoms, a 5-membered heterocycle can contain 1, 2, 3, or 4 heteroatoms, a 6-membered heterocycle can contain 1, 2, 3, or 4 heteroatoms, and a 7-membered heterocycle can contain 1, 2, 3, 4, or 5 heteroatoms. Each heteroatom is independently selected from nitrogen, which can be quaternized; oxygen; and sulfur, including sulfoxide and sulfone. The -(3- to 7-membered)heterocycle can be attached via a nitrogen or carbon atom. Representative -(3- to 7-membered)heterocycles include pyridyl, furyl, thiophenyl, pyrrolyl, oxazolyl, imidazolyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like.

"—$CH_2$(halo)" means a methyl group where one of the hydrogens of the methyl group has been replaced with a halogen. Representative —$CH_2$(halo) groups include —$CH_2F$, —$CH_2Cl$, —$CH_2Br$, and —$CH_2I$.

"—CH(halo)$_2$" means a methyl group where two of the hydrogens of the methyl group have been replaced with a halogen. Representative —CH(halo)$_2$ groups include —$CHF_2$, —$CHCl_2$, —$CHBr_2$, CHBrCl, CHClI, and —$CHI_2$.

"—C(halo)$_3$" means a methyl group where each of the hydrogens of the methyl group has been replaced with a halogen. Representative —C(halo)$_3$ groups include —$CF_3$, —$CCl_3$, —$CBr_3$, and —$CI_3$.

"—Halogen" or "-halo" means —F, —Cl, —Br, or —I.

In connection with the $Ar_2$ group

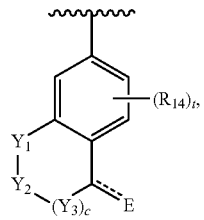

when E is —NH($C_1$-$C_6$)alkyl it is to be understood that the dashed line in the above $Ar_2$ group is absent, i.e., the $Ar_2$ group is

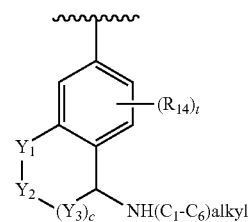

where $Y_1$, $Y_2$, $Y_3$, $R_{14}$, c and t are as defined above for Compounds of Formula (I). When E is =O, =S, =CH($C_1$-$C_6$)alkyl, =CH($C_2$-$C_6$)alkenyl, or =N—$OR_{20}$, it is to be understood that the dashed line in the above $Ar_2$ group is present, i.e., the $Ar_2$ group is

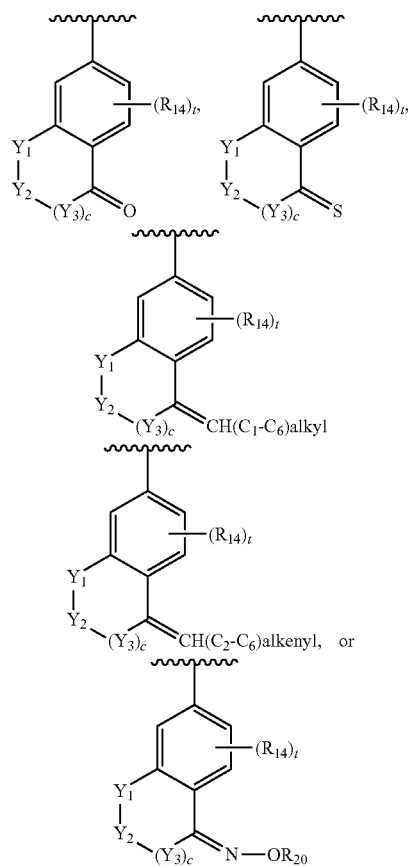

respectively, where $Y_1, Y_2, Y_3, R_{14}, R_{20}$, c and t are as defined above for Compounds of Formula (I).

The phrase "pyridyl group" means

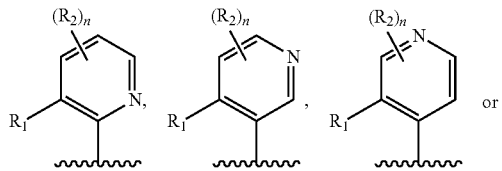

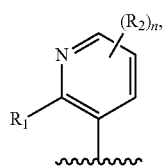

where $R_1$, $R_2$, and n are as defined above for Compounds of Formula (I), and where the numbers designate the position of each atom in the ring.

The phrase "pyrazinyl group" means

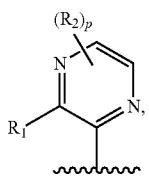

where $R_1$, $R_2$, and p are as defined above for Compounds of Formula (I).

The phrase "pyrimidinyl group" means

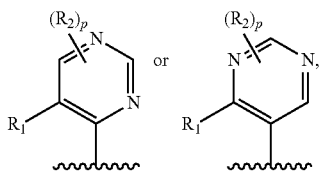

where $R_1$, $R_2$, and p are as defined above for Compounds of Formula (I).

The phrase "pyridazinyl group" means

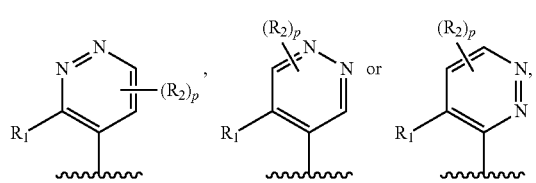

where $R_1$, $R_2$, and p are as defined above for Compounds of Formula (I).

The phrase "benzoimidiazolyl group" means

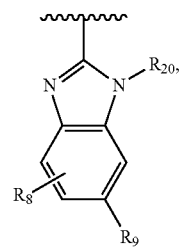

where $R_8$, $R_9$, and $R_{20}$ are as defined above for Compounds of Formula (I).

The phrase "benzothiazolyl group" means

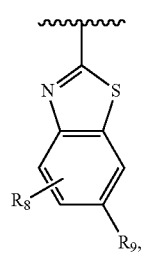

where $R_8$ and $R_9$ are as defined above for Compounds of Formula (I).

The phrase "benzooxazolyl group" means

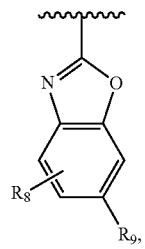

where $R_8$ and $R_9$ are as defined above for Compounds of Formula (I).

The phrase phenyl group means

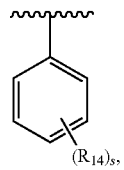

where $R_{14}$ and s are as defined for Compounds of Formula (I).

In connection with the substituent of the $Ar_1$ ring containing $Z_3$, the phrase "wherein $Z_3$ is —H and the carbon atom at the position of the a-b bond is in the (R) configuration" and the like means

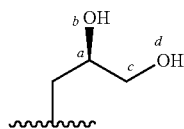

where the lower-case letters are used to designate a particular C—O bond in that substituent.

In connection with the substituent of the $Ar_1$ ring containing $Z_3$, the phrase "wherein $Z_3$ is —H and the carbon atom at the a position of the a-b bond is in the (S) configuration" and the like means

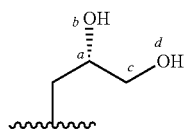

where the lower-case letters are used to designate a particular C—O bond in that substituent.

In connection with the substituent of the $Ar_1$ ring containing $Z_3$, the phrase "wherein $Z_3$ is —($C_1$-$C_3$)alkyl, e.g., —$CH_3$, and the carbon atoms at the a and c positions of the a-b bond and the c-d bond are each in the (R) configuration" and the like means

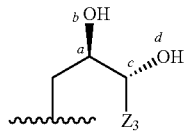

where the lower-case letters are used to designate a particular C—O bond in that substituent.

In connection with the substituent of the $Ar_1$ ring containing $Z_3$, the phrase "wherein $Z_3$ is —($C_1$-$C_3$)alkyl, e.g., —$CH_3$, and the carbon atoms at the a and c positions of the a-b bond and the c-d bond are each in the (S) configuration" and the like means

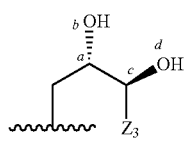

where the lower-case letters are used to designate a particular C—O bond in that substituent.

In connection with the substituent of the $Ar_1$ ring containing $Z_3$, the phrase "wherein $Z_3$ is —($C_1$-$C_3$)alkyl, e.g., —$CH_3$, the carbon atom at the a position of the a-b bond is in the (R) configuration, and the carbon atom at the c position of the c-d bond is in the (S) configuration" and the like means

where the lower-case letters are used to designate a particular C—O bond in that substituent.

In connection with the substituent of the $Ar_1$ ring containing $Z_3$, the phrase "wherein $Z_3$ is —($C_1$-$C_3$)alkyl, e.g., —$CH_3$, the carbon atom at the a position of the a-b bond is in the (S) configuration, and the carbon atom at the c position of the c-d bond is in the (R) configuration" and the like means

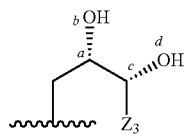

where the lower-case letters are used to designate a particular C—O bond in that substituent.

The term "animal," includes, but is not limited to, a cow, monkey, baboon, chimpanzee, horse, sheep, pig, chicken, turkey, quail, cat, dog, mouse, rat, rabbit, guinea pig, and human.

The phrase "pharmaceutically acceptable derivative", as used herein, includes any pharmaceutically acceptable salt, solvate, prodrug, radiolabeled form, stereoisomer, enantiomer, diastereomer, other stereoisomeric form, racemic mixture, geometric isomer, and/or tautomer, e.g., of a Compound of Formula (I) of the disclosure.

In one embodiment, the pharmaceutically acceptable derivative is a pharmaceutically acceptable salt, solvate, prodrug, radiolabeled form, stereoisomer, enantiomer, diastereomer, other stereoisomeric form, racemic mixture, geometric isomer, and/or tautomer, e.g., of a Compound of Formula (I) of the disclosure. In another embodiment, the pharmaceutically acceptable derivative is a pharmaceutically acceptable salt, solvate, radiolabeled form, stereoisomer, enantiomer, diastereomer, other stereoisomeric form, racemic mixture, geometric isomer, and/or tautomer, e.g., of a Compound of Formula (I) of the disclosure. In another embodiment, the pharmaceutically acceptable derivative is a pharmaceutically acceptable salt, radiolabeled form, stereoisomer, enantiomer, diastereomer, other stereoisomeric form, racemic mixture, geometric isomer, and/or tautomer, e.g., of a Compound of Formula (I) of the disclosure. In another embodiment, the pharmaceutically acceptable derivative is a pharmaceutically acceptable salt, radiolabeled form, stereoisomer, geometric isomer, and/or tautomer, e.g., of a Compound of Formula (I) of the disclosure. In another embodiment, the pharmaceutically acceptable derivative is a pharmaceutically acceptable salt, solvate, stereoisomer, enantiomer, diastereomer, other stereoisomeric form, racemic mixture, geometric isomer, and/or tautomer, e.g., of a Compound of Formula (I) of the disclosure. In another embodiment, the pharmaceutically acceptable derivative is a pharmaceutically acceptable salt, solvate, stereoisomer, geometric isomer, and/or tautomer, e.g., of a Compound of Formula (I) of the disclosure. In another embodiment, the pharmaceutically acceptable derivative is a pharmaceutically acceptable salt, stereoisomer, geometric isomer, and/or tautomer, e.g., of a Compound of Formula (I) of the disclosure. In another embodiment, the pharmaceutically acceptable derivative is a pharmaceutically acceptable salt, stereoisomer, and/or tautomer, e.g., of a Compound of Formula (I) of the disclosure. In another embodiment, the pharmaceutically acceptable derivative is a pharmaceutically acceptable salt, stereoisomer, and/or tautomer, e.g., of a Compound of Formula (I) of the disclosure.

In another embodiment, the pharmaceutically acceptable derivative is a pharmaceutically acceptable salt, e.g., of a Compound of Formula (I) of the disclosure. In another embodiment, the pharmaceutically acceptable derivative is a solvate, e.g., of a Compound of Formula (I) of the disclosure. In another embodiment, the pharmaceutically acceptable derivative is a prodrug, e.g., of a Compound of Formula (I) of the disclosure. In another embodiment, the pharmaceutically acceptable derivative is a radiolabeled form, e.g., of a Compound of Formula (I) of the disclosure. In another embodiment, the pharmaceutically acceptable derivative is a stereoisomer, e.g., of a Compound of Formula (I) of the disclosure. In another embodiment, the pharmaceutically acceptable derivative is an enantiomer, e.g., of a Compound of Formula (I) of the disclosure. In another embodiment, the pharmaceutically acceptable derivative is a diastereomer, e.g., of a Compound of Formula (I) of the disclosure. In another embodiment, the pharmaceutically acceptable derivative is a stereoisomeric form other than a stereoisomer, an enantiomer and a diastereomer, e.g., of a Compound of Formula (I) of the disclosure. In another embodiment, the pharmaceutically acceptable derivative is a racemic mixture, e.g., of a Compound of Formula (I) of the disclosure. In another embodiment, the pharmaceutically acceptable derivative is a geometric isomer, e.g., of a Compound of Formula (I) of the disclosure. In another embodiment, the pharmaceutically acceptable derivative is a tautomer, e.g., of a Compound of Formula (I) of the disclosure.

The phrase "pharmaceutically acceptable salt", as used herein, is any pharmaceutically acceptable salt that can be prepared from a Compound of Formula (I) including a salt formed from an acid and a basic functional group, such as a nitrogen group, of a Compound of Formula (I). Illustrative salts include, but are not limited, to sulfate, citrate, acetate, trifluoroacetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucoronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also includes a salt prepared from a Compound of Formula (I) having an acidic functional group, such as a carboxylic acid functional group, and a pharmaceutically acceptable inorganic or organic base. Suitable bases include, but are not limited to, hydroxides of alkali metals such as sodium, potassium, cesium, and lithium; hydroxides of alkaline earth metal such as calcium and magnesium; hydroxides of other metals, such as aluminum and zinc; ammonia and organic amines, such as unsubstituted or hydroxy-substituted mono-, di-, or trialkylamines; dicyclohexylamine; tributyl amine; pyridine; picoline; N-methyl-N-ethylamine; diethylamine; triethylamine; mono-, bis-, or tris-(2-hydroxy-($C_1$-$C_3$)alkyl amines), such as mono-, bis-, or tris-(2-hydroxyethyl)amine, 2-hydroxy-tert-butylamine, or tris-(hydroxymethyl)methylamine, N,N-di-[($C_1$-$C_3$)alkyl]-N-(hydroxy-($C_1$-$C_3$)alkyl)-amines, such as N,N-dimethyl-N-(2-hydroxyethyl)amine, or tri-(2-hydroxyethyl)amine; N-methyl-D-glucamine; and amino acids such as arginine, lysine, and the like. In one embodiment, the pharmaceutically acceptable salt is a hydrochloride-salt, a sulfate-salt, a sodium-salt, a potassium-salt, a benzene sulfonic acid-salt, a para-toluenesulfonic acid-salt, or a fumaric acid-salt. In another embodiment, the pharmaceutically acceptable salt is a hydrochloride-salt or a sulfate-salt. In another embodiment, the pharmaceutically acceptable salt is a hydrochloride-salt. In another embodiment, the pharmaceutically acceptable salt is a sulfate-salt. In another embodiment, the pharmaceutically acceptable salt is a sodium-salt. In another embodiment, the pharmaceutically acceptable salt is a potassium-salt. In another embodiment, the pharmaceutically acceptable salt is a para-toluenesulfonic acid-salt. In another embodiment, the pharmaceutically acceptable salt is a fumaric acid-salt. In another embodiment, the pharmaceutically acceptable fumaric acid-salt contains about one equivalent of a Compound of Formula (I) and about 0.5 equivalents of fumaric acid, e.g., from about 0.3 to about 0.7 equivalents of fumaric acid in one embodiment, from about 0.4 to about 0.6 equivalents of fumaric acid in another embodiment, from about 0.44 to about 0.56 equivalents of fumaric acid in another embodiment, or from about 0.47 to about 0.53 equivalents of fumaric acid in another embodiment. In another embodiment, the pharmaceutically acceptable fumaric acid-salt contains one equivalent of a Compound of Formula (I) and 0.5 equivalents of fumaric acid. One skilled in the art will recognize that, e.g., acid addition salts, of a Compound of Formula (I) can be prepared by reaction of the compounds with the appropriate acid by a variety of known methods.

The compounds of the disclosure provided herein also encompass all solvates of the Compounds of Formula (I). "Solvates" are known in the art and are considered to be a combination, physical association and/or solvation of a Compound of Formula (I) with a solvent molecule, e.g., a disolvate, monosolvate or hemisolvate when the solvent molecule: Compound of Formula (I) molecule molar ratio is 2:1, 1:1 or 1:2, respectively. This physical association involves varying degrees of ionic and covalent bonding, including hydrogen bonding. In certain instances, the solvate can be isolated, for example when one or more solvent molecules are incorporated into the crystal lattice of a crystalline solid. Thus, "solvate", as used herein, encompasses both solution-phase and isolatable solvates. A Compound of Formula (I) of the disclosure can be present as a solvated form with a pharmaceutically acceptable solvent, such as water, methanol, ethanol, and the like, and it is intended that the disclosure include both solvated and unsolvated Compound of Formula (I) forms. As "hydrate" relates to a particular subgroup of solvates, i.e., where the solvent molecule is water, hydrates are included within the solvates of the disclosure.

Preparation of solvates is known in the art. For example, Caira et al., "Preparation and Crystal Characterization of a Polymorph, a Monohydrate, and an Ethyl Acetate Solvate of the Antifungal Fluconazole," *J. Pharmaceut. Sci.*, 93(3):601-611 (2004), describes the preparation of solvates of fluconazole with ethyl acetate and with water. Similar preparations of solvates, hemisolvate, hydrates, and the like are described by Van Tonder et al., "Preparation and Physicochemical Characterization of 5 Niclosamide Solvates and 1 Hemisolvate," *AAPS Pharm. Sci. Tech.*, 5(1): Article 12 (2004), and Bingham et al., "Over one hundred solvates of sulfathiazole," *Chem. Comm.*, pp. 603-604 (2001). In one embodiment, a non-limiting, process involves dissolving the Compound of Formula (I) in a desired amount of the desired solvent (organic, water or mixtures thereof) at temperatures above about 20° C. to about 25° C., cooling the solution at a rate sufficient to form crystals, and isolating the crystals by known methods, e.g., filtration. Analytical techniques, for example, infrared spectroscopy, can be used to show the presence of the solvent in a crystal of the solvate.

The compounds disclosed herein also comprise all prodrugs of the Compounds of Formula (I). "Prodrugs" are known in the art and, while not necessarily possessing any pharmaceutical activity as such, are considered to be any covalently bonded carrier(s) that releases the active parent drug in vivo. In general, such prodrugs will be a functional derivative of a Compound of Formula (I) which is readily convertible in vivo, e.g., by being metabolized, into the required Compound of Formula (I). Conventional procedures for the selection and preparation of suitable prodrug derivatives are described in, for example, H. Bundgaard ed., *Design of Prodrugs*, Elsevier (1985); "Drug and Enzyme Targeting, Part A," Widder et al., eds., Vol. 112 in *Methods in Enzymology*, Academic Press (1985); Bundgaard, "Design and Application of Prodrugs," Chapter 5, pp. 113-191 in *A Textbook of Drug Design and Development*, Krogsgaard-Larsen and Bundgaard Eds., Harwood Academic Publishers (1991); Bundgaard et al., "(C) Means to Enhance Penetration (1) Prodrugs as a means to improve the delivery of peptide drugs," *Adv. Drug Delivery Revs.* 8:1-38 (1992); Bundgaard et al., "Glycolamide Esters as Biolabile Prodrugs of Carboxylic Acid Agents: Synthesis, Stability, Bioconversion, and Physicochemical Properties," *J. Pharmaceut. Sci.* 77(4):285-298 (1988); and Kakeya et al., "Studies on Prodrugs of Cephalosporins. I. Synthesis and Biological Properties of Glycyloxygenzoyloxymethyl and Glycylaminobenzoyloxymethyl Esters of 7β-[2-(2-Aminothiazol-4-yl)-(Z)-2-methoxyiminoacetamido]3-methyl-3-cephem-4-carboxylic Acid," *Chem. Pharm. Bull.* 32:692-698 (1984).

In addition, one or more hydrogen, carbon or other atoms of a Compound of Formula (I) can be replaced by a radioactive isotope of the hydrogen, carbon or other atoms. Such a "radiolabeled", "radiolabeled form", and the like of a Compound of Formula (I), each of which is encompassed by the disclosure, is useful as a research and/or diagnostic tool in metabolism pharmacokinetic studies and in binding assays. "Radioactive", as used herein with respect to an atom, means an atom that comprises a radioactive atom and therefore the specific radioactivity thereof is above the background level of radioactivity. Examples of radioactive isotopes that can be incorporated into a Compound of Formula (I) of the disclosure include isotopes of hydrogen, carbon, nitrogen, oxygen, phosphorous, sulfur, fluorine, chlorine, bromine, and iodine, such as $^{2}$H, $^{3}$H, $^{11}$C, $^{13}$C, $^{14}$C, $^{15}$N, $^{17}$O, $^{18}$O, $^{31}$P, $^{32}$P, $^{35}$S, $^{18}$F, $^{19}$F, $^{36}$Cl, $^{37}$Cl, $^{76}$Br, $^{77}$Br, $^{81}$Br, $^{123}$I, $^{124}$I, $^{125}$I, and $^{131}$I, respectively. In one embodiment, a radiolabeled Compound of Formula (I) contains 1, 2, 3, 4, or more radioactive isotopes, each of which is independently selected from hydrogen, carbon, nitrogen, oxygen, phosphorous, sulfur, fluorine, chlorine, bromine, and iodine. In another embodiment, a radiolabeled Compound of Formula (I) contains 1 or 2 radioactive isotopes, each of which is independently selected from hydrogen, carbon, nitrogen, oxygen, phosphorous, sulfur, fluorine, chlorine, bromine, and iodine. In another embodiment, a radiolabeled Compound of Formula (I) contains 1 radioactive isotope which is selected from hydrogen, carbon, nitrogen, oxygen, phosphorous, sulfur, fluorine, chlorine, bromine, and iodine. In another embodiment, a radiolabeled Compound of Formula (I) contains 1, 2, 3, 4, or more radioactive isotopes, each of which is independently selected from $^{2}$H, $^{3}$H, $^{11}$C, $^{13}$C, $^{14}$C, $^{15}$N, $^{17}$O, $^{18}$O, $^{31}$P, $^{32}$P, $^{35}$S, $^{18}$F, $^{19}$F, $^{36}$Cl, $^{37}$Cl, $^{76}$Br, $^{77}$Br, $^{81}$Br, $^{123}$I, $^{124}$I, $^{125}$I, and $^{131}$I. In another embodiment, a radiolabeled Compound of Formula (I) contains 1 or 2 radioactive isotopes, each of which is independently selected from $^{2}$H, $^{3}$H, $^{11}$C, $^{13}$C, $^{14}$C, $^{15}$N, $^{17}$O, $^{18}$O, $^{31}$P, $^{32}$P, $^{35}$S, $^{18}$F, $^{19}$F, $^{36}$Cl, $^{37}$Cl, $^{76}$Br, $^{77}$Br, $^{81}$Br, $^{123}$I, $^{124}$I, $^{125}$I, and $^{131}$I. In another embodiment, a radiolabeled Compound of Formula (I) contains 1 radioactive isotope which is selected from $^{2}$H, $^{3}$H, $^{11}$C, $^{13}$C, $^{14}$C, $^{15}$N, $^{17}$O, $^{18}$O, $^{31}$P, $^{32}$P, $^{35}$S, $^{18}$F, $^{19}$F, $^{36}$Cl, $^{37}$Cl, $^{76}$Br, $^{77}$Br, $^{81}$Br, $^{123}$I, $^{124}$I, $^{125}$I, and $^{131}$I. In another embodiment, a radiolabeled Compound of Formula (I) contains 1, 2, 3, 4, or more radioactive isotopes, each of which is independently selected from $^{2}$H, $^{3}$H, $^{13}$C, $^{14}$C, $^{15}$N, $^{18}$O, $^{32}$P, and $^{125}$I. In another embodiment, a radiolabeled Compound of Formula (I) contains 1 or 2 radioactive isotopes, each of which is independently selected from $^{3}$H, $^{14}$C, $^{15}$N, $^{18}$O, $^{32}$P, and $^{125}$I. In another embodiment, a radiolabeled Compound of Formula (I) contains 1 radioactive isotope which is selected from $^{3}$H, $^{14}$C, $^{15}$N, $^{18}$O, $^{32}$P, and $^{125}$I.

Radiolabeled compounds of the disclosure can be prepared by methods known in the art. For example, tritiated Compounds of Formula (I) can be prepared by introducing tritium into the particular Compound of Formula (I), for example, by catalytic dehalogenation with tritium. This method can include reacting a suitably halogen-substituted precursor of a Compound of Formula (I) with tritium gas in the presence of a suitable catalyst, for example, Pd/C, in the presence or absence of a base.

Other suitable methods for preparing tritiated compounds can be found in Filer, "The Preparation and Characterization of Tritiated Neurochemicals," Chapter 6, pp. 155-192 in *Isotopes in the Physical and Biomedical Sciences, Vol. 1, Labeled Compounds (Part A)* (1987). $^{14}$C-labeled compounds can be prepared by employing starting materials having a $^{14}$C carbon. Compounds containing piperazine isotopically enriched with $^{13}$C and/or $^{15}$N can be prepared as described in, e.g., FIG. 5A and the associated description, of U.S. Pat. No. 7,355,045 B2. Radiolabeled compounds containing $^{18}$F at the 6-position of an aniline ring can be prepared as described in column 27 of U.S. Pat. No. 6,562,319 B2.

A Compound of Formula (I) can contain one or more asymmetric centers and can thus give rise to enantiomers, diastereomers, and other stereoisomeric forms. Unless specifically otherwise indicated, the disclosure encompasses compounds with all such possible forms as well as their racemic and resolved forms or any mixture thereof. The art recognizes that a geometric isomer is encompassed by a stereoisomer (See, e.g., the definitions of "stereoisomers" and "cis-trans isomers" appearing in the IUPAC Compendium of Chemical Terminology, 2$^{nd}$ Ed. (the "Gold Book"), McNaught et al., eds., Blackwell Scientific Publications, Oxford (1997)). When a Compound of Formula (I) contains an olefinic double bond or other center of geometric asymmetry, and unless specifically otherwise indicated, it is intended to include all "geometric isomers", e.g., both E and Z geometric isomers. Unless specifically otherwise indicated, all "tautomers", e.g., ketone-enol, amide-imidic acid, lactam-lactim, enamine-imine, amine-imine, and enamine-enimine tautomers, are intended to be encompassed by the disclosure as well.

As used herein, the terms "stereoisomer", "stereoisomeric form", and the like are general terms for all isomers of individual molecules that differ only in the orientation of their atoms in space. It includes enantiomers and isomers of compounds with more than one chiral center that are not mirror images of one another ("diastereomers").

The term "chiral center" refers to a carbon atom to which four different groups are attached.

The term "enantiomer" or "enantiomeric" refers to a molecule that is nonsuperimposeable on its mirror image and hence optically active where the enantiomer rotates the plane of polarized light in one direction and its mirror image rotates the plane of polarized light in the opposite direction.

The term "racemic" refers to a mixture of equal parts of enantiomers which is optically inactive.

The term "resolution" refers to the separation or concentration or depletion of one of the two enantiomeric forms of a molecule. Optical isomers of a Compound of Formula (I) can be obtained by known techniques such as chiral chromatography or formation of diastereomeric salts from an optically active acid or base.

Optical purity can be stated in terms of enantiomeric excess (% ee), which is determined by the formula:

$$\% \ ee = \left[ \frac{\text{major enatiomer(mol)} - \text{minor enatiomer(mol)}}{\text{major enatiomer(mol)} + \text{major enatiomer(mol)}} \right] \times 100\%.$$

When a first group is "substituted with one or more" second groups, one or more hydrogen atoms of the first group is replaced with a corresponding number of second groups. When the number of second groups is two or greater, each second group can be the same or different. In one embodiment, a first group is substituted with up to three second groups. In another embodiment, a first group is substituted with one or two second groups. In another embodiment, a first group is substituted with two second groups. In another embodiment, a first group is substituted with two second groups and each second group is identical. In another embodiment, a first group is substituted with only one second group.

The term "MeOH" means methanol, i.e., methyl alcohol.

The term "EtOH" means ethanol, i.e., ethyl alcohol.

The term "t-BME" means tert-butyl methyl ether, i.e., 2-methoxy-2-methylpropane.

The term "t-BuOH" means tert-butyl alcohol, i.e., 2-methylpropan-2-ol.

The term "THF" means tetrahydrofuran.

The term "CME" means cyclopentyl methyl ether, i.e., methoxycyclopentane.

The term "DMF" means N,N-dimethylformamide.

The term "DCM" means methylene chloride, i.e., dichloromethane.

The term "DCE" means dichloroethane.

The term "DEE" means diethyl ether, i.e., ethoxyethane.

The term "DME" means 1,2-dimethoxyethane, i.e., ethylene glycol dimethyl ether.

The term "EtOAc" means ethyl acetate.

The term "NH$_4$OH" means ammonium hydroxide.

The term "TEA" means triethylamine.

The term "MeCN" means acetonitrile.

The term "NaH" means sodium hydride.

The term "AcOH" means acetic acid.

The term "DMSO" means dimethylsulfoxide, i.e., methylsulfinylmethane.

The term "BuLi" means butyl lithium.

The term "BOC" means tert-butyloxycarbonyl:

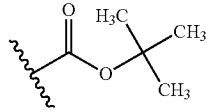 [SMILES: *C(=O)OC(C)(C)C]

The term "HOBT" means 1-hydroxybenzotriazole hydrate.

The term "EDCI" means 1-ethyl-3-[3-(dimethylamino)propyl]carbodiimide.

The term "IBD" means inflammatory-bowel disease.

The term "IBS" means irritable-bowel syndrome.

The term "ALS" means amyotrophic lateral sclerosis.

The phrase "effective amount," when used in connection with a Compound of Formula (I) means an amount effective for: (a) treating or preventing a Condition or symptom thereof; (b) detectably inhibiting TRPV1 receptor function in a cell, or (c) detectably activating TRPV1 receptor function in a cell.

The phrase "effective amount," when used in connection with an other therapeutic agent or a second therapeutic agent means an amount for providing the therapeutic effect of the second therapeutic agent.

The phrase "therapeutic index," describes the gap between the dose that is effective, and the dose that induces adverse effects.

The terms "modulate", "modulating", and the like as used herein with respect to the TRPV1 receptor mean the mediation of a pharmacodynamic response (e.g., analgesia) in an animal from (i) inhibiting or activating the receptor, or (ii) directly or indirectly affecting the normal regulation of the receptor activity. Compounds that modulate the receptor activity include agonists, partial agonists, antagonists, mixed agonists/antagonists, mixed partial agonists/antagonists and compounds which directly or indirectly affect regulation of the receptor activity.

As used herein, a compound that binds to a receptor and mimics the regulatory effect(s) of an endogenous ligand is defined as an "agonist". As used herein, a compound that binds to a receptor and is only partly effective as an agonist is defined as a "partial agonist". As used herein, a compound that binds to a receptor but produces no regulatory effect, but rather blocks binding of another agent to the receptor is defined as an "antagonist". (See Ross and Kenakin, *Pharmacodynamics: Mechanisms of Drug Action and the Relationship Between Drug Concentration and Effect*, Chapter 2 in *Goodman & Gilman's The Pharmacological Basis of Therapeutics* 31-32 (Hardman et al., eds., 10$^{th}$ ed 2001).

The phrases "treatment of," "treating" and the like include the amelioration or cessation of a Condition or a symptom thereof. In one embodiment, treating includes inhibiting, for example, decreasing the overall frequency of episodes of a Condition or a symptom thereof.

The phrases "prevention of," "preventing" and the like include the avoidance of the onset of a Condition or a symptom thereof.

A "disorder" includes, but is not limited to, the Conditions defined above.

In the event of doubt as to the agreement of a depicted chemical structure and a chemical name, the depicted chemical structure governs.

It is appreciated that various features of the disclosure which are, for clarity, described in the context of separate embodiments, can also be provided in combination in a single embodiment unless otherwise specifically herein excluded. Conversely, various features of the disclosure which are, for brevity, described in the context of a single embodiment, can also be provided separately and/or in any suitable subcombination unless otherwise specifically herein excluded.

4.5 Methods for Making Compounds of Formula (I)

The Compounds of Formula (I) can be made using conventional organic synthesis or by the illustrative methods shown in the schemes below.

4.5.1 Methods for Making Compounds of Formula (I) Using the Negishi Coupling Approach The Compounds of Formula (I) where X is O, R$_{22}$ is H, and either one of L$_1$ and L$_2$ is N or L$_1$ and L$_2$ are each C(H) can be obtained by the illustrative method shown below in Schemes 1 and 2a-2d, below.

4.5.1.1 Amide Formation

The production of an amide compound of formula 2 from a carboxylic acid compound of formula 1 is shown in Scheme 1, where $L_1$, $L_2$, $Ar_2$, $R_3$, and m are defined above and Y is a halogen, such as Cl or Br. Compounds of Formula (1) and the amines of formula $Ar_2$—$NH_2$ are commercially available or can be prepared by methods known to those skilled in the art.

Scheme 1

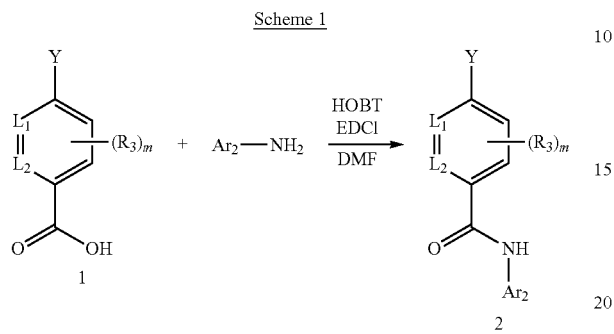

To a solution of 1 equivalent of the compound of formula 1 in DMF (0.22 M) is added 1 equivalent of amine $Ar_2$—$NH_2$, and the resulting solution is allowed to stir for about 5 min at a temperature of about 25° C. To the solution is then added 1 to 2 equivalents of HOBT and 1 equivalent of EDCI, and the resulting mixture is allowed to stir for from about 2 h to about 6 h at a temperature of about 25° C. Typically, a solid forms during stirring and the reaction mixture is filtered to remove the resultant solid compound of formula 2. If a solid does not form the reaction mixture is diluted with 2N aqueous sodium hydroxide and extracted between 2 and 3 times with ethyl acetate, the organic layers are combined, dried (with $Na_2SO_4$), and the solvent removed under reduced pressure to provide a residue. The residue is then washed with methanol and dried under reduced pressure to provide a compound of formula 2.

4.5.1.2 Negishi Coupling

Production of Compounds of Formula (I) can be carried out through Negishi coupling of a compound of formula 2 with an alkylzinc halide in the presence of a palladium catalyst. Four examples of such Negishi couplings are shown in Schemes 2a-2d, which result in the formation of compounds 4a-4d, all falling within the scope of Compounds of Formula (I). In Schemes 2a-2d, $L_1$, $L_2$, $Ar_2$, $R_1$, $R_2$, $R_3$, m, n, and Y are as defined above.

Scheme 2a

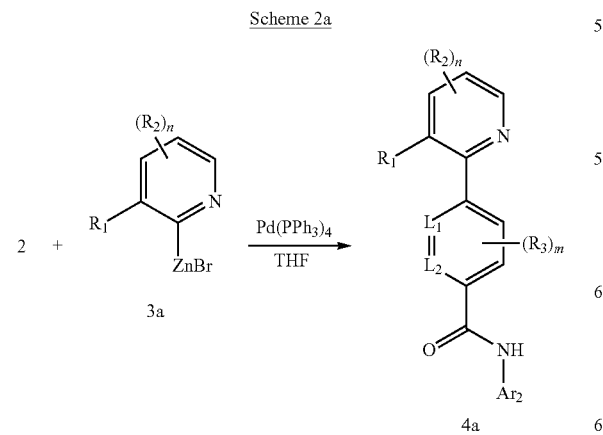

Scheme 2b

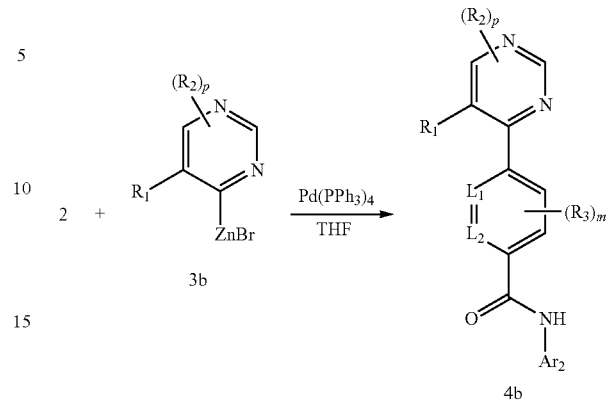

Scheme 2c

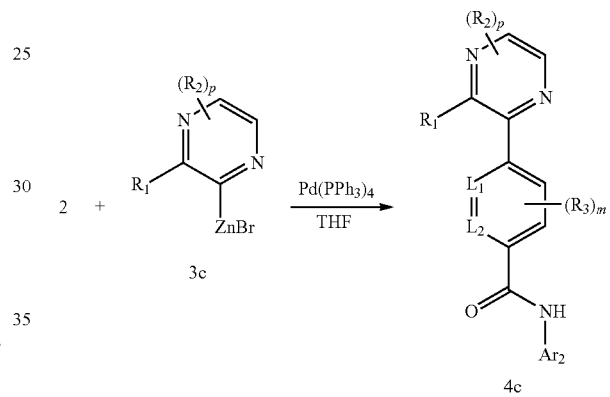

Scheme 2d

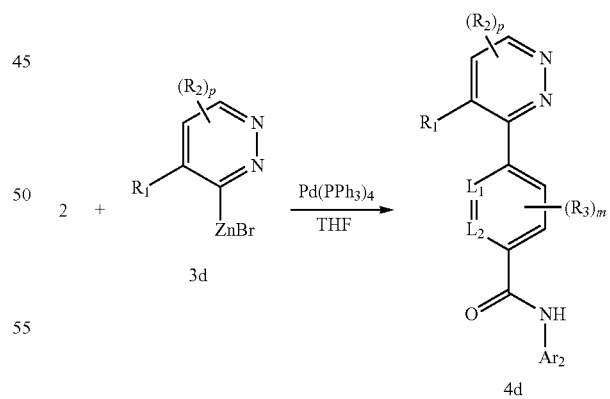

The compound of formula 2 is suspended in THF (0.04 moles/liter) under an argon atmosphere and about 3 equivalent of zinc bromide 3a-3d and about 0.05 to about 0.1 equivalents of $Pd(PPh_3)_4$ are added to the suspension. The suspension is allowed to stir for about 2 hours at a temperature of from about 70° C. to about 100° C. The solvent is then removed under reduced pressure to provide a solid, that, if desired, is purified using a silica gel column eluted with an ethyl acetate/hexane gradient, to provide the compounds of formulas 4a-4d. In the exemplary but non-limiting reactions shown in Schemes 2a-2d, the enantiomeric excess (ee) of the Compound of Formula (I) is at least about 60%. In another embodiment, the reaction produces a Compound of Formula (I) having a % ee of at least about 70%. In another embodiment, the reaction produces a Compound of Formula (I) having a % ee of at least about 80%. In another embodiment, the reaction produces a Compound of Formula (I) having a % ee of at least about 90%. In another embodiment, the reaction produces a Compound of Formula (I) having a % ee of at least about 93%. In another embodiment, the reaction produces a Compound of Formula (I) having a % ee of at least about 94%. In another embodiment, the reaction produces Compound of Formula (I) having a % ee of at least about 95%. In another embodiment, the reaction produces a Compound of Formula (I) having a % ee of greater than 95% (e.g., 95.1% to 99.9%).

If the compound of formula 2 is substituted with a hydroxyl or amino group, the hydroxyl or amino group is protected using a suitable protecting group before being reacted with bromide 3a-3d (shown in Schemes 2a-2d) or the counterpart chloride (not illustrated). Similarly, if $R_2$ contains a hydroxyl or amino group, the hydroxyl or amino group is protected before forming the zinc bromide reagent. Suitable protecting groups for such a hydroxyl group(s) include, but are not limited to, methyl ether, methoxymethyl ether, methoxythiomethyl ether, 2-methoxyethoxymethyl ether, bis(2-chloroethoxy)ethyl ether, tetrahydropyranyl ether, tetrahydrothiopyranyl ether, 4-methoxytetrahydropyranyl ether, methoxytetrahydrothiopyranyl ether, tetrahydrofuranyl ether, tetrahydrothiofuranyl ether, 1-ethoxyethyl ether, 1-methyl-1-methoxyethyl ether, 2-(phenylselenyl ether), tert-butyl ether, allyl ether, benzyl ether, o-nitrobenzyl ether, triphenylmethyl ether, o-napthyldiphenylmethyl ether, p-methoxydiphenylmethyl ether, 9-(9-phenyl-10-oxo)anthryl ether (tritylone), trimethylsilyl ether, iso-propyldimethylsilyl ether, tert-butyldimethylsilyl ether, tert-butyldiphenylsilyl ether, tribenzylsilyl ether, tri-iso-propylsilyl ether, formate ester, acetate ester, trichloroacetate ester, phenoxyacetate ester, isobutyrate ester, pivaloate ester, adamantoate ester, benzoate ester, 2,4,6-trimethyl(mesitoate) ester, methyl carbonate, 2,2,2-trichlorocarbonate, allyl carbonate, p-nitrophenyl carbonate, benzyl carbonate, p-nitrobenzyl carbonate, S-benzylthiocarbonate, N-phenylcarbamate, nitrate ester, and 2,4-dinitrophenylsulfenate ester (See, e.g., Greene, *Protective Groups in Organic Synthesis*, pp. 10-86, Wiley-Interscience, New York (1981)). Suitable protecting groups for such an amino group(s) include, but are not limited to, 1,1-dimethyl-2,2,2-trichloroethyl carbamate, 1-methyl-1-(4-biphenylyl) ethyl carbamate, 2-trimethylsilylethyl carbamate, and tert-butyl carbamate (Greene et al., *Protective Groups in Organic Synthesis*, 3$^{rd}$ Ed., pp. 494-653, Wiley-Interscience, New York (1999)).

Compounds of Formula 3a-3d can be prepared by methods known to those skilled in the art (See, Smith et al., *March's Advanced Organic Chemistry: Reaction Mechanisms and Structure*, 5$^{th}$ Ed., pp. 804-807, Wiley-Interscience, New York (2001); Fillon et al., "Electrosynthesis of functionalized organodizinc compounds from aromatic dihalides via a cobalt catalysis in acetonitrile/pyridine as solvent," *Tet. Lett.* 42:3843-3846 (2001); Amadji et al., "Chirons in the 1,3-dioxane series: Stereospecific cross-coupling reactions and chirality transfer," *Tetrahedron: Assymetry* 9:1657-1660 (1998); and Billotte, "Synthesis of C-Substituted Cyclic Amines Using Azacycloalkyl Organozinc Reagents," *Synlett.* pp. 379-380 (April 1998)).

4.5.2 Methods for Making Compounds of Formula (I) Using the Suzuki Coupling Approach The Compounds of Formula (I) where X is O, one $R_2$ group is Q, Q comprises a diol, and each of $L_1$ and $L_2$ is C(H) can be obtained by the illustrative methods shown below in Schemes 3-9. While Schemes 3-9 illustrate the conversion when W is in the 2-position of the pyridyl ring of compounds of formula 7a-7c and Q is in the 5-position, these transformations can be carried out with W and/or Q in other ring positions as well. Moreover, the same technique can be used when $Ar_1$ is, e.g., a pyrimidinyl, pyrazinyl, or pyridazinyl ring.

4.5.2.1 Methods for Installing Allyl Groups on $Ar_1$

The conversion of a compound of formula 5 to include a vinyl group via a Grignard reaction is shown in Scheme 3, where $Z_2$, $Z_3$, $R_1$, $R_2$, and n are as defined above, Y is a halogen such as Br or I, and W is a leaving group, such as a halogen.

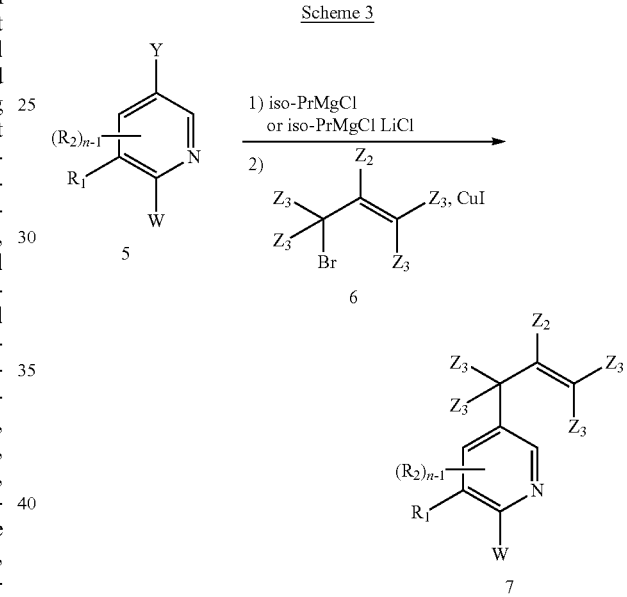

Scheme 3

To a solution of a compound of formula 5 in THF, DEE, t-BME, or CME is added 1 to 3 equivalents of iso-propylmagnesium chloride or 1 to 3 equivalent of iso-propylmagnesium chloride lithium chloride complex at a temperature of from −20° C. to 25° C. The resulting reaction mixture is then stirred at a temperature of from −20° C. to 25° C. for from 10 min to 24 hours, preferably from about 30 minutes to about 120 minutes. Next, 0.1 to 1 equivalents of copper iodide and 1 to 3 equivalents of allyl bromide compound 6 (shown in Scheme 3) or the counterpart allyl chloride compound (not illustrated) are added to the mixture at a temperature of from −20° C. to 25° C. The resulting reaction mixture is then stirred at a temperature of from −20° C. to 25° C. for about 10 minutes to about 24 hours, preferably from about 30 min to about 120 minutes. Then, the reaction mixture is quenched with an aqueous acidic solution and extracted with ethyl acetate or diethyl ether. The resulting organic layer is washed with brine, dried over, e.g., anhydrous sodium sulfate or magnesium sulfate, and concentrated under reduced pressure. The resulting product can be chromatographed with a silica gel column to provide a compound of formula 7.

4.5.2.2 Methods for Preparing Diols

Compounds such as compound 7 can undergo asymmetric hydroxylation to yield enantioenriched diols. Exemplified in Schemes 4a and 4b is the allyl group of compound 7', an exemplary compound of formula 7 in which $Z_2$ and one terminal $Z_3$ group are each hydrogen, undergoing an asymmetric dihydroxylation where W is a leaving group, such as halogen, and $Z_3$, $R_1$, $R_2$, and n are as defined above for Compounds of Formula (I).

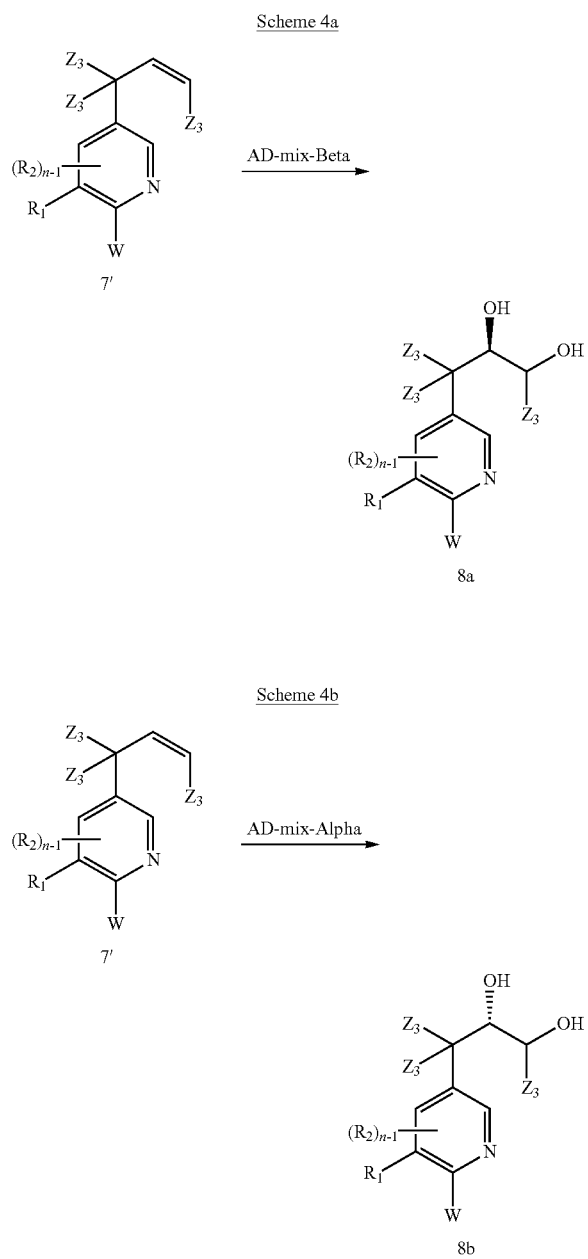

As demonstrated in Schemes 4a and 4b, the stereochemistry (R or S) of the resulting diol is dependent upon the chirality of the ligand used in the AD mix as described in Sharpless et al., *J. Org. Chem.* 57:2768-2771 (1992) and Schemes 1.14 and 1.15 of U.S. Patent Application Publication No. 2009/0170868 A1. AD-mix is composed of the following components: potassium osmate ($K_2OsO_2(OH)_4$), potassium ferricyanide ($K_3Fe(CN)_6$), potassium carbonate ($K_2CO_3$), and the chiral ligands $(DHQ)_2PHAL$ or $(DHQD)_2PHAL$, as shown in Scheme 5. In one embodiment, the reaction produces a chiral diol having an enantiomeric excess (ee) of at least about 60%. In another embodiment, the reaction produces a chiral diol having a % ee of at least about 70%. In another embodiment, the reaction produces a chiral diol having a % ee of at least about 80%. In another embodiment, the reaction produces a chiral diol having a % ee of at least about 90%. In another embodiment, the reaction produces a chiral diol having a % ee of at least about 93%. In another embodiment, the reaction produces a chiral diol having a % ee of at least about 94%. In another embodiment, the reaction produces a chiral diol having a % ee of at least about 95%. In another embodiment, the reaction produces a chiral diol having a % ee of greater than 95% (e.g., 95.1% to 99.9%).

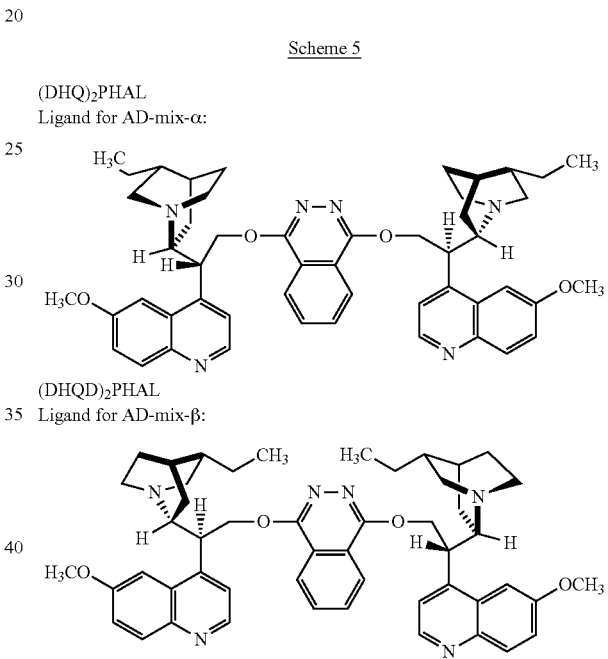

To carry out the asymmetric hydroxylation reaction, to a solution of a compound of formula 7' in a mixed solvent of water and t-butanol or isopropanol is added AD-mix β (about 0.6 g to 2 g per 1 mmol of 7') at a temperature of from 0° C. to 25° C. The resulting reaction mixture is stirred at a temperature from 0° C. to 25° C. for about 1 hour to about 48 hours. The mixture is diluted with ethyl acetate and saturated $Na_2S_2O_5$. The organic layer is washed with water and brine, dried, e.g., over anhydrous sodium sulfate or magnesium sulfate, and concentrated under reduced pressure. The resulting product can be chromatographed with a silica gel column or recrystallized to provide a compound of formula 8a (Scheme 4a). The other enantiomer, compound of formula 8b, can be synthesized by the reaction of a compound of formula 7' with AD-mix α (Scheme 4b).

The racemic diol, 8c, can be synthesized by methods known in the art, such as using osmium tetroxide ($OsO_4$) and N-methyl morpholine N-oxide (NMO) in an aqueous acetone solution, as shown in Scheme 6.

Scheme 6

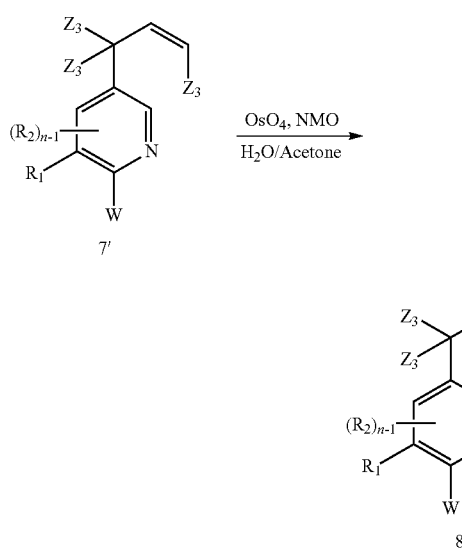

4.5.2.3 Protection of Hydroxyl Groups of Diols

The hydroxyl groups on compounds of formulae 8a, 8b, or 8c can be protected by adding 2,2-dimethoxy propane in the presence of para-toluene sulfonic acid. Addition of a hydroxyl protecting group to a compound of formula 8a to provide a compound of formula 9 is shown in Scheme 7, where $R_1$, $R_2$, $Z_3$, W, and n are as defined above.

Scheme 7

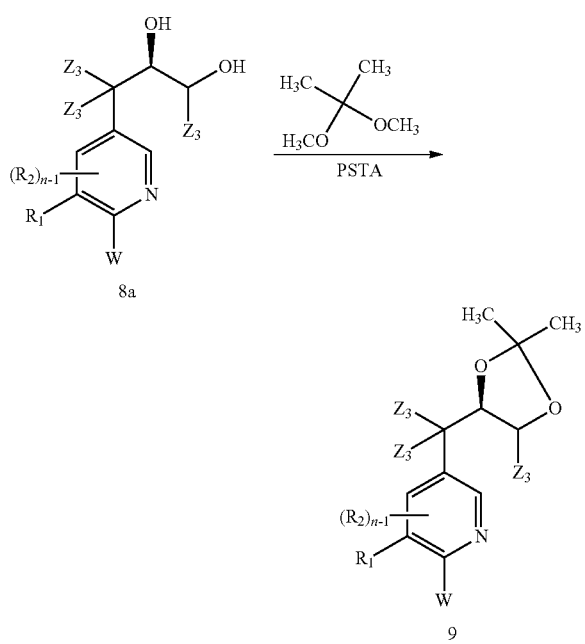

To a suspension of 1 equivalent of the compound of formula 8a in 2,2-dimethoxy propane at 0° C. is added about 0.1 equivalent of PSTA. The mixture is stirred at a temperature of about 25° C. for approximately 16 hours to provide a compound of formula 9.

4.5.2.4 Suzuki Coupling

Coupling of two aromatic moieties can be accomplished through a Suzuki Coupling reaction, as shown in Scheme 8, where $R_1$, $R_2$, $R_3$, $Z_3$, W, and n are as defined above.

Scheme 8

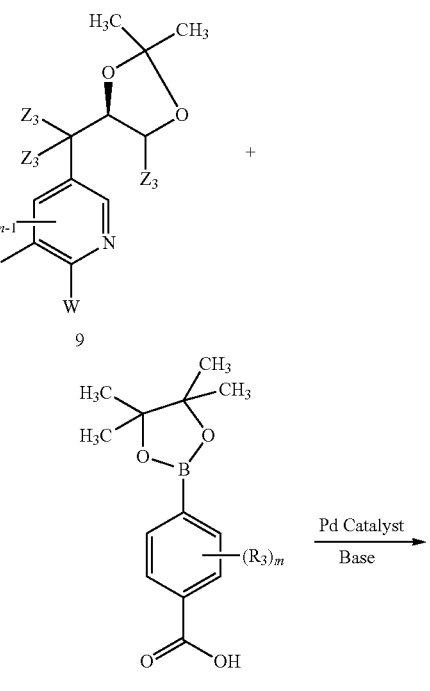

To a solution of 1 equivalent of a compound of formula 9 and 1 to 1.5 equivalents of a compound of formula 10 in an organic solvent such as ethanol, DME, 1,4-dioxane, toluene and THF is added 2-5 equivalents of base such as sodium carbonate or potassium carbonate and approximately 0.05-0.15 equivalents of palladium catalyst such as palladium acetate, bis(diphenylphosphino)ferrocene palladium chloride, tris(dibenzylideneacetone)dipalladium(0), or bis(triphenylphophine)palladium dichloride. The reaction mixture is heated, preferably from about 60° C. to the reflux temperature of the organic solvent, for approximately 1 to 8 hours, cooled to a temperature of about 25° C., diluted with water, and cooled further to 00° C. Then the reaction mixture is quenched with an aqueous acidic solution and extracted with ethyl acetate or diethyl ether. The resulting organic layer is washed with brine, dried, e.g., over anhydrous sodium sulfate or magnesium sulfate, and concentrated under reduced pressure. The resulting product can be chromatographed with a silica gel column or recrystallized to provide a compound of formula 11.

4.5.2.5 Amide Formation and Deprotection

A Compound of Formula (I) can be produced via amide formation followed by removal of the protecting group as shown in Scheme 9, where $Ar_2$, $R_1$, $R_2$, $R_3$, $R_{22}$, $Z_3$, W, and n are as defined above.

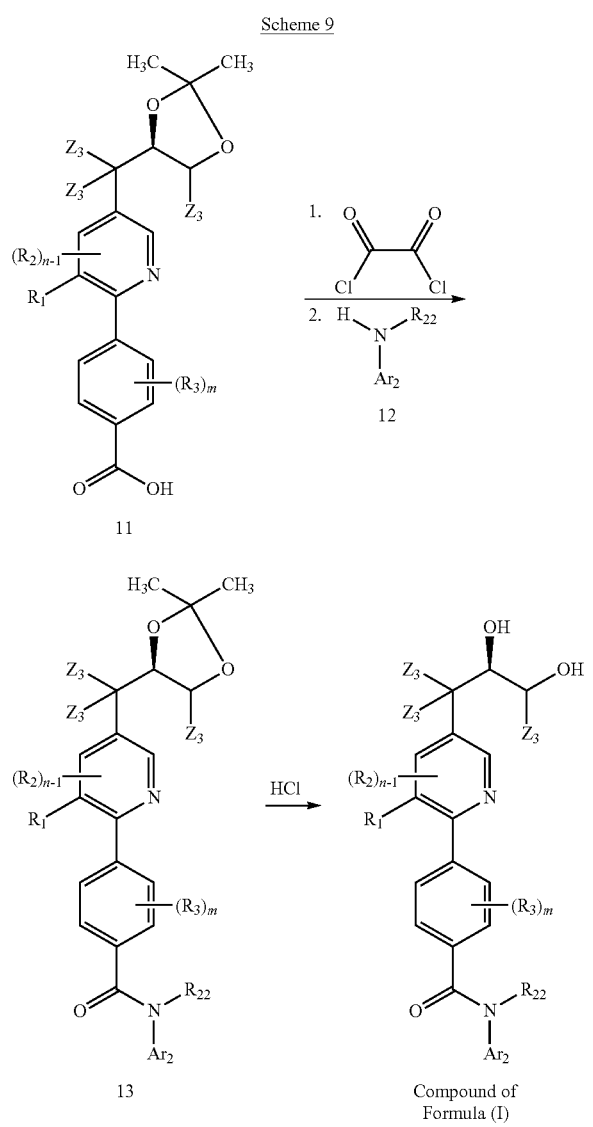

To a suspension of 1 equivalent of the compound of formula 11 in an organic solvent or a mixture of organic solvents is added 1-3 equivalents of oxalyl chloride dropwise. After stirring for approximately 1 to 2 hours, 1 to 2 equivalents of amine 12 and 2-5 equivalents of a base such as pyridine or triethylamine are added to the organic solvent and the reaction mixture is stirred for between 10 and 24 hours at a temperature of about 25° C. Following basic workup and chromatographic separation, a compound of formula 13 is produced. The compound of formula 13 is than reacted with excess HCl in dioxane to provide a Compound of Formula (I).

In the exemplary but non-limiting reaction shown in Scheme 9, the enantiomeric excess (ee) of the Compound of Formula (I) is at least about 60%. In another embodiment, the reaction produces a Compound of Formula (I) having a % ee of at least about 70%. In another embodiment, the reaction produces a Compound of Formula (I) having a % ee of at least about 80%. In another embodiment, the reaction produces a Compound of Formula (I) having a % ee of at least about 90%. In another embodiment, the reaction produces a Compound of Formula (I) having a % ee of at least about 93%. In another embodiment, the reaction produces a Compound of Formula (I) having a % ee of at least about 94%. In another embodiment, the reaction produces Compound of Formula (I) having a % ee of at least about 95%. In another embodiment, the reaction produces a Compound of Formula (I) having a % ee of greater than 95% (e.g., 95.1% to 99.9%).

4.5.3 Methods for Preparing Amino Alcohols

Compounds of Formula (I) where X is O, one $R_2$ group is Q, Q comprises a amino alcohol (e.g., J is $NH_2$ and $Z_1$ is OH) and each of $L_1$ and $L_2$ is C(H) can be obtained by methods described below. While Schemes 10a and 10b illustrate the conversion when W is in the 2-position of the pyridyl ring of compounds of formula 7' and Q is in the 5-position, these transformations can be carried out with W and/or Q in other ring positions as well. Moreover, the same technique can be used when $Ar_1$ is, e.g., a pyrimidinyl, pyrazinyl, or pyridazinyl ring.

Exemplified in Schemes 10a and 10b is the allyl group of compound 7', an exemplary compound of formula 7 in which $Z_2$ and one terminal $Z_3$ group are each hydrogen, undergoing conversion to an aminoalcohol, where W is a leaving group, such as halogen, and $Z_3$, $R_1$, $R_2$, and n are as defined above for Compounds of Formula (I).

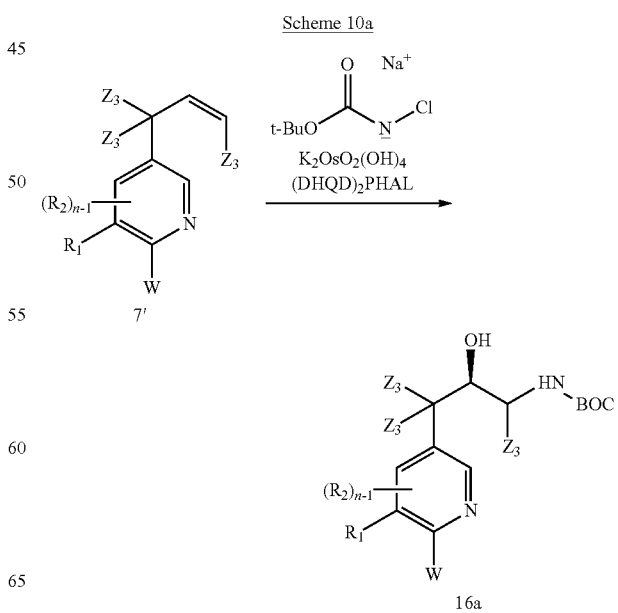

Scheme 10b

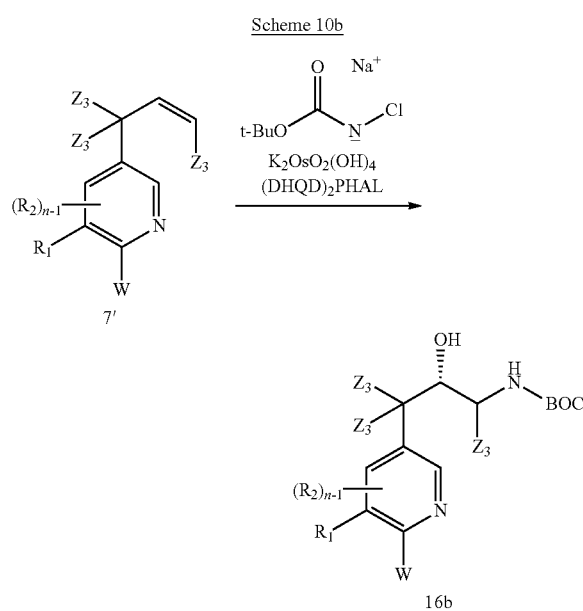

In connection with Scheme 10a, to a solution of a compound of formula 7' in a solvent, such as n-propanol, isopropanol, or the like, is added 0.01 to 0.1 equivalents of potassium osmate dihydrate and a prepared solution of 1 to 5 equivalents of sodium N-chloro tert-butyl carbamate in a mixed solvent of n-propanol, isopropanol, or the like and water. Sodium N-chloro tert-butyl carbamate can be prepared from tert-butyl carbamate, sodium hydroxide, and tert-butyl hypochlorite by combining the same at a temperature of from −20° C. to 25° C. and stirring at a temperature of from −20° C. to 25° C. for from 5 min to 1 hour. Then at a temperature of from −20° C. to 25° C., 0.01 to 0.1 equivalents of (DHQD)$_2$PHAL is added to form a reaction mixture that is stirred at a temperature of from −20° C. to 25° C. for 1 hour to 24 hours, preferably from about 1 hour to 6 hours. Thereafter, the reaction mixture is quenched with an aqueous NaHSO$_3$ solution and extracted with ethyl acetate or diethyl ether. The resulting organic layer is separated, washed with brine, dried over anhydrous sodium sulfate or magnesium sulfate, and concentrated under reduced pressure. The resulting product can be chromatographed with a silica gel column to provide a compound of formula 16a. As shown in Scheme 10b, the other enantiomer can be synthesized by the reaction of a compound of formula 7' with (DHQ)$_2$PHAL to provide a compound of formula 16b. As demonstrated in Schemes 10a and 10b, the stereochemistry (R or S) of the resulting aminoalcohol is dependent upon the chirality of the ligand used in the (DHQ)$_2$PHAL and (DHQD)$_2$PHAL as described in Sharpless et al., *J. Am. Chem. Soc.* 120:1207-1217 (1998).

Compound of Formula (I) where Z$_1$ is OH and J is NH$_2$ can be obtained from compound of formula 16a or the compound of formula 16b by the procedures described above in Schemes 7-9.

Compounds of Formula (I) where Z$_1$ is NH$_2$ and J is OH can be obtained in a similar manner.

Compounds of Formula (I) obtained by the above procedures, e.g., where Z$_1$ is OH and J is NH$_2$, can be converted to Compounds of Formula (I) where Z$_1$ is OR$_{20}$, where R$_{20}$ is not H, and J is NH$_2$; Z$_1$ is OH and J is NH(R$_{20}$), where R$_{20}$ is not H; Z$_1$ is OH and J is N(R$_{20}$)$_2$, where each R$_{20}$ is not H; Z$_1$ is OR$_{20}$ and J is NH(R$_{20}$), where each R$_{20}$ is not H; or Z$_1$ is OR$_{20}$ and J is N(R$_{20}$)$_2$, where each R$_{20}$ is not H, using ordinary methods known to one skilled in the art. Compounds of Formula (I) obtained by the above procedures, e.g., where Z$_1$ is NH$_2$ and J is OH, can be converted to Compounds of Formula (I) where Z$_1$ is NH$_2$ and J is OR$_{20}$, where R$_{20}$ is not H; Z$_1$ is NH(R$_{20}$), where R$_{20}$ is not H, and J is OH; Z$_1$ is N(R$_{20}$)$_2$, where each R$_{20}$ is not H, and J is OH; Z$_1$ is NH(R$_{20}$) and J is OR$_{20}$, where each R$_{20}$ is not H; or Z$_1$ is N(R$_{20}$)$_2$ and J is OR$_{20}$, where each R$_{20}$ is not H, using ordinary methods known to one skilled in the art.

4.5.4 Methods for Making Compounds of Formula (I) where X is S

The Compounds of Formula (I) where X is S can be obtained by reacting a Compound of Formula (I) where X is O, prepared as described above, with Lawesson's reagent at a temperature of about 100° C. (See, e.g., March, *Advanced Organic Chemistry: Reactions, Mechanisms, and Structure*, 4$^{th}$ Ed., pp. 891-892, Wiley-Interscience, New York (1992)).

Compounds of Formula (I) where X is S can be obtained by a method analogous to that described above in Scheme 9 to provide Compounds of Formula (I), where X is O, except that a compound of formula 17, shown below

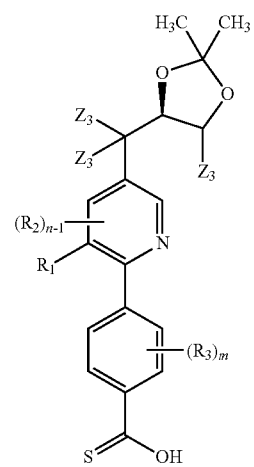

where R$_1$, R$_2$, R$_3$, Z$_3$, m, and n are as defined above, is used in place of a compound of formula 11. The compounds of formula 17 can be obtained by a method analogous to that described above in Scheme 8 except that a thioic O-acid compound is used in place of the carboxylic acid compound of formula 10.

While these schemes illustrate the conversion when Q is in the 5-position of the pyridyl ring of, e.g., the compound of formula 17, these transformations can be carried out with Q in other ring positions as well. Moreover, the same technique can be used when Ar$_1$ is, e.g., a pyrimidinyl, pyrazinyl, or pyridazinyl ring.

4.5.5 Methods for Making Compounds of Formula (I) where X is N—OH

Compounds of Formula (I) where X is N—OH can be obtained as shown below in Scheme 11:

Scheme 11

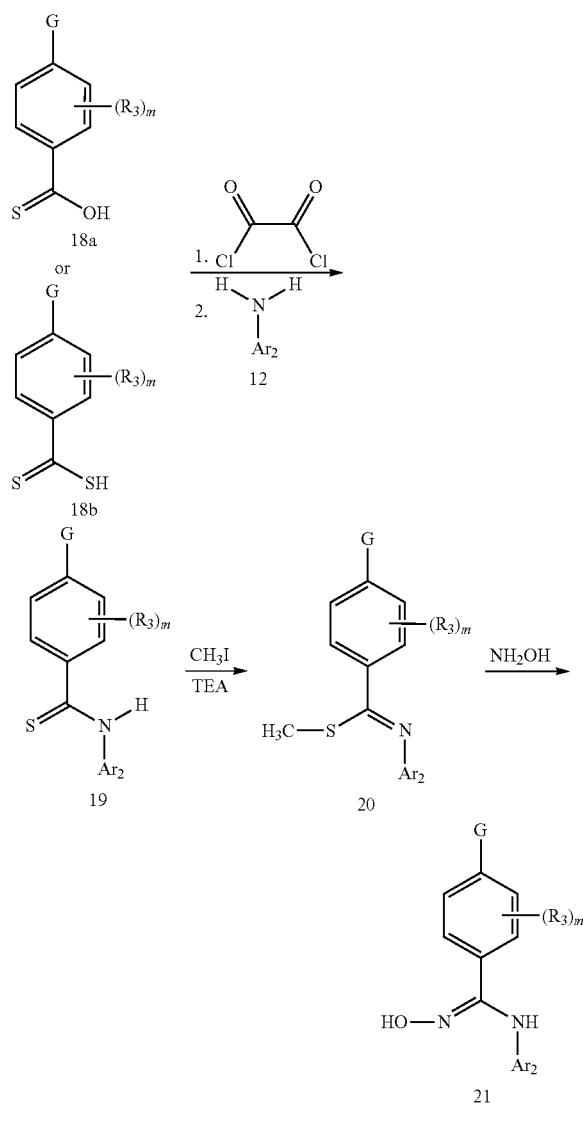

where $Ar_2$, $R_3$, and m are as defined above and G is either Y, as described in Scheme 1 above, or the group

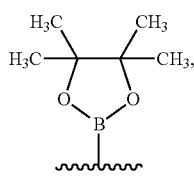

as described in Scheme 8 above.

A solution of a compound of formula 19 (about 0.6 mmol), obtained from the compound of formula 18a or 18b via the first step of Scheme 9 as described above, in DCM is reacted with iodomethane (about 0.9 mmol) in about 3 mL of THF with stirring at about 25° C. for about 12 h. Excess iodomethane is removed from the reaction mixture under reduced pressure. A solution of triethylamine (about 1.74 mmol) in about 2.5 mL of ethyl acetate is then added to the mixture and the mixture is allowed to stir for about 2 h. The mixture is then concentrated under reduced pressure to provide the compound of formula 20 that can then be further treated if desired. In one embodiment, the compound of formula 20 is further treated using column chromatography or recrystallization.

The compound of formula 20 (about 0.3 mmol) is reacted with hydroxylamine (50 weight percent in water, about 5.8 mmol) in about 1.5 mL of ethanol with stirring at a temperature of about 80° C. for about 2 h. The mixture is then concentrated under reduced pressure to provide a compound of formula 21. In one embodiment, the compound of formula 21 is further treated using column chromatography or recrystallized. Thereafter, Compounds of Formula (I) can be obtained from the compound of formula 21 by either the Negishi Coupling approach (see Schemes 2a-2d) or the Suzuki Coupling approach (see Scheme 8), depending upon which G group is present.

Compounds of formula 18a and 18b are commercially available or can be prepared by procedures known in the art, e.g., by using a reagent comprising a thioic O-acid or dithioic acid, respectively.

4.5.6 Methods for Making Compounds of Formula (I) where X is N—OR$_{10}$

The Compounds of Formula (I) where X is N—OR$_{10}$ can be obtained as shown below in Scheme 12:

Scheme 12

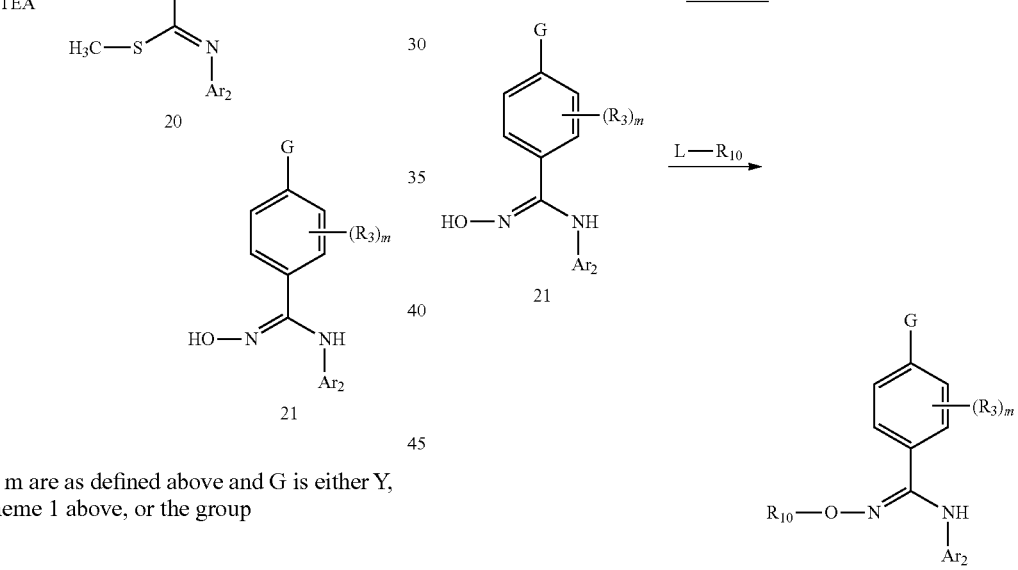

where $Ar_2$, $R_3$, $R_{10}$, m, and G are as defined above and L is -halo, e.g., —I, —Br, or —Cl The compound of formula 22 can be prepared by reacting the compound of formula 21 with L-R$_{10}$ in the presence of sodium hydride in DMF at about 25° C. In one embodiment, L is —I or —Br. Thereafter, Compounds of Formula (I) can be obtained from the compound of formula 22 by either the Negishi Coupling approach (see Schemes 2a-2d) or the Suzuki Coupling approach (see Scheme 8), depending upon which G group is present.

4.5.7 Methods for Preparing Benzothiazol-2-Amines

An Ar$_2$—NH(R$_{22}$) compound of formula 24 can be prepared by the addition of potassium thiocyanate, bromine, and acetic acid to a compound of formula 23 as shown in Scheme 13, where R$_8$, R$_9$, and R$_{22}$ are as defined above. The compound of formula 24 is precipitated from solution following the addition of ammonium hydroxide. Compounds of formula 23 are commercially available or can be prepared by procedures known in the art.

Scheme 13

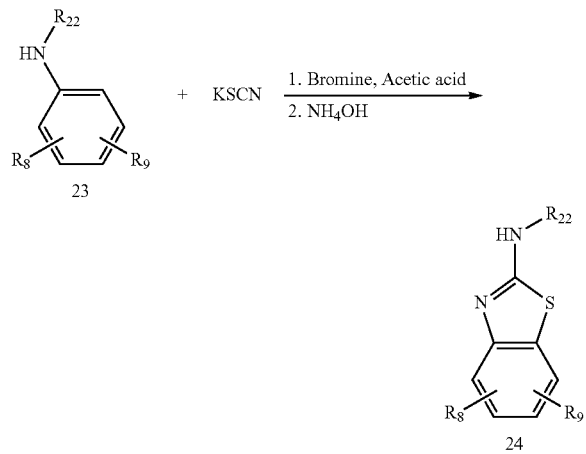

Suitable aprotic organic solvents for use in the illustrative methods include, but are not limited to, DCM, DMSO, chloroform, toluene, benzene, acetonitrile, carbon tetrachloride, pentane, hexane, ligroin, and diethyl ether. In one embodiment, the aprotic organic solvent is DCM.

Certain Compounds of Formula (I) can have one or more asymmetric centers and therefore exist in different enantiomeric and diastereomeric forms. A Compound of Formula (I) can be in the form of an optical isomer or a diastereomer. Accordingly, the disclosure encompasses compounds of formula (I) and their uses as described herein in the form of their optical isomers, diastereomers, and mixtures thereof, including a racemic mixture.

In addition, one or more hydrogen, carbon or other atoms of a Compound of Formula (I) can be replaced by an isotope of the hydrogen, carbon or other atoms. Such compounds, which are encompassed by the disclosure, are useful, e.g., as research and diagnostic tools in metabolism pharmacokinetic studies and in binding assays.

4.6 Therapeutic Uses of Compounds of Formula (I)

In accordance with the disclosure, the Compounds of Formula (I) are administered to an animal in need of treatment or prevention of a Condition.

In one embodiment, an effective amount of a Compound of Formula (I) can be used to treat or prevent any condition treatable or preventable by inhibiting TRPV1. Examples of Conditions that are treatable or preventable by inhibiting TRPV1 include, but are not limited to, pain, UI, an ulcer, IBD, and IBS.

The Compounds of Formula (I), or a pharmaceutically acceptable derivative thereof, can be used to treat or prevent acute or chronic pain. Examples of pain that can be treated or prevented using a Compound of Formula (I) include, but are not limited to, cancer pain, neuropathic pain, labor pain, myocardial infarction pain, pancreatic pain, colic pain, post-operative pain, headache pain, muscle pain, arthritic pain, and pain associated with a periodontal disease, including gingivitis and periodontitis.

The Compounds of Formula (I), or a pharmaceutically acceptable derivative thereof, can also be used for treating or preventing pain associated with inflammation or with an inflammatory disease in an animal. Such pain can arise where there is an inflammation of the body tissue which can be a local inflammatory response and/or a systemic inflammation. For example, the Compounds of Formula (I) can be used to treat or prevent pain associated with inflammatory diseases including, but not limited to: organ transplant rejection; reoxygenation injury resulting from organ transplantation (see Grupp et al., "Protection against Hypoxia-reoxygenation in the Absence of Poly (ADP-ribose) Synthetase in Isolated Working Hearts," *J. Mol. Cell Cardiol.* 31:297-303 (1999)) including, but not limited to, transplantation of the heart, lung, liver, or kidney; chronic inflammatory diseases of the joints, including arthritis, rheumatoid arthritis, osteoarthritis and bone diseases associated with increased bone resorption; inflammatory bowel diseases, such as ileitis, ulcerative colitis, Barrett's syndrome, and Crohn's disease; inflammatory lung diseases, such as asthma, adult respiratory distress syndrome, and chronic obstructive airway disease; inflammatory diseases of the eye, including corneal dystrophy, trachoma, onchocerciasis, uveitis, sympathetic ophthalmitis and endophthalmitis; chronic inflammatory diseases of the gum, including gingivitis and periodontitis; tuberculosis; leprosy; inflammatory diseases of the kidney, including uremic complications, glomerulonephritis and nephrosis; inflammatory diseases of the skin, including sclerodermatitis, psoriasis and eczema; inflammatory diseases of the central nervous system, including chronic demyelinating diseases of the nervous system, multiple sclerosis, AIDS-related neurodegeneration and Alzheimer s disease, infectious meningitis, encephalomyelitis, Parkinson's disease, Huntington's disease, amyotrophic lateral sclerosis and viral or autoimmune encephalitis; autoimmune diseases, including Type I and Type II diabetes mellitus; diabetic complications, including, but not limited to, diabetic cataract, glaucoma, retinopathy, nephropathy (such as microalbuminuria and progressive diabetic nephropathy), polyneuropathy, mononeuropathies, autonomic neuropathy, gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection or necrobiosis lipoidica diabeticorum); immune-complex vasculitis, and systemic lupus erythematosus (SLE); inflammatory diseases of the heart, such as cardiomyopathy, ischemic heart disease hypercholesterolemia, and atherosclerosis; as well as various other diseases that can have significant inflammatory components, including preeclampsia, chronic liver failure, brain and spinal cord trauma, and cancer. The Compounds of Formula (I) can also be used for inhibiting, treating, or preventing pain associated with inflammatory disease that can, for example, be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is adminstered as a treatment for cancer.

The Compounds of Formula (I), or a pharmaceutically acceptable derivative thereof, can also be used to treat or prevent pain associated with nerve injury (i.e., neuropathic pain). Chronic neuropathic pain is a heterogenous disease state with an unclear etiology. In chronic neuropathic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. The chronic pain is different from acute pain in that chronic neuropathic pain patients suffer the abnormal pain sensations that can be described as spontaneous pain, continuous superficial burning and/or deep aching pain. The pain can be evoked by heat-, cold-, and mechano-hyperalgesia, or by heat-, cold-, or mechano-allodynia.

Chronic neuropathic pain can be caused by injury or infection of peripheral sensory nerves. It includes, but is not limited to, pain from peripheral nerve trauma, herpes virus infection, diabetes mellitus, causalgia, plexus avulsion, neuroma, limb amputation, and vasculitis. Neuropathic pain can also be caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can cause nerve injury. Neuropathic pain includes but is not limited to pain caused by nerve injury such as, for example, the pain from which diabetics suffer.

The Compounds of Formula (I), or a pharmaceutically acceptable derivative thereof, can be used to treat or prevent a migraine including, but not limited to, migraine without aura ("common migraine"), migraine with aura ("classic migraine"), migraine without headache, basilar migraine, familial hemiplegic migraine, migrainous infarction, and migraine with prolonged aura.

The Compounds of Formula (I), or a pharmaceutically acceptable derivative thereof, can be used to treat or prevent UI. Examples of UI treatable or preventable using the Compounds of Formula (I) include, but are not limited to, urge incontinence, stress incontinence, overflow incontinence, neurogenic incontinence, and total incontinence.

The Compounds of Formula (I), or a pharmaceutically acceptable derivative thereof, can be used to treat or prevent an ulcer. Examples of ulcers treatable or preventable using the Compounds of Formula (I) include, but are not limited to, a duodenal ulcer, a gastric ulcer, a marginal ulcer, an esophageal ulcer, or a stress ulcer.

The Compounds of Formula (I), or a pharmaceutically acceptable derivative thereof, can be used to treat or prevent IBD, including Crohn's disease and ulcerative colitis.

The Compounds of Formula (I), or a pharmaceutically acceptable derivative thereof, can be used to treat or prevent IBS. Examples of IBS treatable or preventable using the Compounds of Formula (I) include, but are not limited to, spastic-colon-type IBS and constipation-predominant IBS.

Applicants believe that the Compounds of Formula (I), or a pharmaceutically acceptable derivative thereof, are antagonists for TRPV1. The disclosure also relates to methods for inhibiting TRPV1 function in a cell comprising contacting a cell capable of expressing TRPV1 with an effective amount of a Compound of Formula (I), or a pharmaceutically acceptable derivative thereof. This method can be used in vitro, for example, as an assay to select cells that express TRPV1 and, accordingly, are useful as part of an assay to select compounds useful for treating or preventing pain, UI, an ulcer, IBD, or IBS. The method is also useful for inhibiting TRPV1 function in a cell in vivo, in an animal, a human in one embodiment, by contacting a cell, in an animal, with an effective amount of a Compound of Formula (I), or a pharmaceutically acceptable derivative thereof. In one embodiment, the method is useful for treating or preventing pain in an animal. In another embodiment, the method is useful for treating or preventing UI in an animal. In another embodiment, the method is useful for treating or preventing an ulcer in an animal. In another embodiment, the method is useful for treating or preventing IBD in an animal. In another embodiment, the method is useful for treating or preventing IBS in an animal.

Examples of tissue comprising cells capable of expressing TRPV1 include, but are not limited to, neuronal, brain, kidney, urothelium, and bladder tissue. Methods for assaying cells that express TRPV1 are known in the art.

4.7 Therapeutic/Prophylactic Administration and Compositions of the Disclosure Due to their activity, Compounds of Formula (I), or a pharmaceutically acceptable derivative thereof, are advantageously useful in veterinary and human medicine. As described above, Compounds of Formula (I), or a pharmaceutically acceptable derivative thereof, are useful for treating or preventing a Condition.

When administered to an animal, Compounds of Formula (I), or a pharmaceutically acceptable derivative thereof, are, in one embodiment, administered as a component of a composition that comprises a pharmaceutically acceptable carrier or excipient. The compositions, which comprise a Compound of Formula (I), or a pharmaceutically acceptable derivative thereof, can be administered orally. Compounds of Formula (I), or a pharmaceutically acceptable derivative thereof, can also be administered by any other convenient route, for example, by infusion or bolus injection, by absorption through epithelial or mucocutaneous linings (e.g., oral, rectal, and intestinal mucosa, etc.) and can be administered together with another therapeutically active agent. Administration can be systemic or local. Various delivery systems are known, e.g., encapsulation in liposomes, microparticles, microcapsules, capsules, etc., and can be used to administer the Compound of Formula (I), or a pharmaceutically acceptable derivative thereof.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. The mode of administration is left to the discretion of the practitioner. In most instances, administration will result in the release of Compounds of Formula (I), or a pharmaceutically acceptable derivative thereof, into the bloodstream.

In specific embodiments, it can be desirable to administer the Compounds of Formula (I), or a pharmaceutically acceptable derivative thereof, locally. This can be achieved, for example, and not by way of limitation, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, it can be desirable to introduce the Compounds of Formula (I), or a pharmaceutically acceptable derivative thereof, into the central nervous system or gastrointestinal tract by any suitable route, including intraventricular, intrathecal, and epidural injection, and enema. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the Compounds of Formula (I) can be formulated as a suppository, with traditional binders and excipients such as triglycerides.

In another embodiment, the Compounds of Formula (I), or a pharmaceutically acceptable derivative thereof, can be delivered in a vesicle, in particular a liposome (see Langer, "New Methods of Drug Delivery," *Science* 249:1527-1533 (1990); Lopez-Berestein, "Treatment of Systemic Fungal Infections with Liposomal-Amphotericin B," *Liposomes in the Therapy of Infectious Disease and Cancer*, pp. 317-327 (1989); and Treat et al., "Liposome encapsulated doxorubicin—preliminary results of phase I and phase II trials" *Liposomes in the Theory of Infectious Disease and Cancer*, pp. 353-365 (1989).

In yet another embodiment, the Compounds of Formula (I), or a pharmaceutically acceptable derivative thereof, can be delivered in a controlled-release system or sustained-release system (see, e.g., Goodson, "Dental Applications," pp. 115-138 in *Medical Applications of Controlled Release, Vol. 2, Applications and Evaluation*, Langer and Wise, eds., CRC Press (1984), hereafter "Goodson"). Other controlled- or sustained-release systems discussed in the review by Langer, *Science* 249:1527-1533 (1990) can be used. In one embodiment, a pump can be used (Langer, *Science* 249:1527-1533 (1990); Sefton, "Implantable Pumps," in *CRC Crit. Rev. Biomed. Eng.* 14(3):201-240 (1987); Buchwald et al., "Long-term, Continuous Intravenous Heparin Administration by an Implantable Infusion Pump in Ambulatory Patients with Recurrent Venous Thrombosis," *Surgery* 88:507-516 (1980); and Saudek et al., "A Preliminary Trial of the Programmable Implantable Medication System for Insulin Delivery," *New Engl. J. Med.* 321:574-579 (1989)). In another embodiment, polymeric materials can be used (see Goodson; Smolen et al., "Drug Product Design and Performance," *Controlled Drug Bioavailability Vol.* 1, John Wiley & Sons, New York (1984); Langer et al., "Chemical and Physical Structure of Polymers as Carriers for Controlled Release of Bioactive Agents: A Review," *J. Macromol. Sci. Rev. Macromol. Chem.* C23(1): 61-126 (1983); Levy et al., "Inhibition of Calcification of Bioprosthetic Heart Valves by Local Controlled-Release Diphosphonate," *Science* 228:190-192 (1985); During et al., "Controlled Release of Dopamine from a Polymeric Brain Implant: In Vivo Characterization," *Ann. Neurol.* 25:351-356 (1989); and Howard et al., "Intracerebral drug delivery in rats with lesion-induced memory deficits," *J. Neurosurg.* 71:105 (1989)). In yet another embodiment, a controlled- or sustained-release system can be placed in proximity of a target of the Compounds of Formula (I), e.g., the spinal column, brain, or gastrointestinal tract, thus requiring only a fraction of the systemic dose.

The compositions can optionally comprise a suitable amount of a pharmaceutically acceptable excipient so as to provide the form for proper administration to the animal. Such a pharmaceutical excipient can be a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to an animal. Water is a particularly useful excipient when a Compound of Formula (I) is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The compositions, if desired, can also contain minor amounts of wetting or emulsifying agents, or pH buffering agents. Specific examples of pharmaceutically acceptable carriers and excipients that can be used to formulate oral dosage forms are described in the *Handbook of Pharmaceutical Excipients*, (Amer. Pharmaceutical Ass'n, Washington, D.C., 1985), incorporated herein by reference.

The compositions can take the form of solutions, suspensions, emulsion, tablets, pills, pellets, multiparticulates, capsules, capsules containing liquids, powders, multiparticulates, sustained-release formulations, suppositories, emulsions, aerosols, sprays, suspensions, or any other form suitable for use. In one embodiment, the composition is in the form of a capsule (see, e.g., U.S. Pat. No. 5,698,155). Other examples of suitable pharmaceutical excipients are described by Radebough et al., "Preformulation," pp. 1447-1676 in *Remington's Pharmaceutical Sciences Vol.* 2 (Gennaro, ed., $19^{th}$ ed., Mack Publishing, Easton, Pa., 1995), incorporated herein by reference.

In one embodiment, the Compounds of Formula (I) are formulated in accordance with routine procedures as a composition adapted for oral administration to human beings. A Compound of Formula (I) to be orally delivered can be in the form of tablets, capsules, gelcaps, caplets, lozenges, aqueous or oily solutions, suspensions, granules, powders, emulsions, syrups, or elixirs, for example. When a Compound of Formula (I) is incorporated into oral tablets, such tablets can be compressed, tablet triturates, enteric-coated, sugar-coated, film-coated, multiply compressed or multiply layered. Techniques and compositions for making solid oral dosage forms are described in *Pharmaceutical Dosage Forms: Tablets* (Lieberman et al., eds., $2^{nd}$ ed., Marcel Dekker, Inc., 1989 & 1990). Techniques and compositions for making tablets (compressed and molded), capsules (hard and soft gelatin) and pills are also described by King, "Tablets, Capsules, and Pills," pp. 1553-1593 in *Remington's Pharmaceutical Sciences* (Osol, ed., $16^{th}$ ed., Mack Publishing, Easton, Pa., 1980).

Liquid oral dosage forms include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and composition for making liquid oral dosage forms are described in *Pharmaceutical Dosage Forms: Disperse Systems* (Lieberman et al., eds., $2^{nd}$ ed., Marcel Dekker, Inc., 1996 & 1998).

When a Compound of Formula (I) is to be injected parenterally, it can be, e.g., in the form of an isotonic sterile solution. Alternatively, when a Compound of Formula (I) is to be inhaled, it can be formulated into a dry aerosol or can be formulated into an aqueous or partially aqueous solution.

An orally administered Compound of Formula (I) can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

In another embodiment, the Compounds of Formula (I) can be formulated for intravenous administration. In one embodiment, compositions for intravenous administration comprise sterile isotonic aqueous buffer. Where necessary, the compositions can also include a solubilizing agent. A Compound of Formula (I) for intravenous administration can optionally include a local anesthetic such as benzocaine or prilocaine to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where a Compound of Formula (I) is to be administered by infusion, it can be dispensed, for example, with an infusion bottle containing sterile pharmaceutical grade water or saline. Where a Compound of Formula (I) is administered by injection, an ampule of sterile water for injection or saline can be provided so that the ingredients can be mixed prior to administration.

The Compounds of Formula (I), or a pharmaceutically acceptable derivative thereof, can be administered by controlled-release or sustained-release means or by delivery devices that are known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or more active ingredients using, for example, hydropropylmethyl cellulose, ethylcellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those of ordinary skill in the art, including those described herein, can be readily selected for use with the active ingredients of the disclosure. The disclosure thus encompasses single unit dosage forms suitable for oral administration such as, but not limited to, tablets, capsules, gelcaps, and caplets that are adapted for controlled- or sustained-release.

Controlled- or sustained-release pharmaceutical compositions can have a common goal of improving drug therapy over that achieved by their non-controlled or non-sustained release counterparts. In one embodiment, a controlled- or sustained-release composition comprises a minimal amount of a Compound of Formula (I) to cure or control the condition in a minimum amount of time. Advantages of controlled- or sustained-release compositions include extended activity of the drug, reduced dosage frequency, and increased patient compliance. In addition, controlled- or sustained-release compositions can favorably affect the time of onset of action or other characteristics, such as blood levels of the Compound of Formula (I), and can thus reduce the occurrence of adverse side effects.

Controlled- or sustained-release compositions can be designed to immediately release an amount of a Compound of Formula (I), or a pharmaceutically acceptable derivative thereof, that promptly produces the desired therapeutic or prophylactic effect, and gradually and continually release other amounts of the Compound of Formula (I) to maintain this level of therapeutic or prophylactic effect over an extended period of time. To maintain a constant level of the Compound of Formula (I) in the body, the Compound of Formula (I) can be released from the dosage form at a rate that will replace the amount of Compound of Formula (I) being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

The amount of the Compound of Formula (I), or a pharmaceutically acceptable derivative thereof, that is effective in the treatment or prevention of a Condition can be determined by standard clinical techniques. In addition, in vitro or in vivo assays can optionally be employed to help identify optimal dosage ranges. The precise dose to be employed will also depend on the route of administration, and the seriousness of the Condition and can be decided according to the judgment of a practitioner and/or each animal's circumstances. Suitable effective dosage amounts, however, will, in one embodiment, range from about 0.01 mg/kg of body weight to about 2500 mg/kg of body weight, although they are, in another embodiment, about 100 mg/kg of body weight or less. In one embodiment, the effective dosage amount ranges from about 0.01 mg/kg of body weight to about 100 mg/kg of body weight of a Compound of Formula (I); in another embodiment, about 0.02 mg/kg of body weight to about 50 mg/kg of body weight; and in another embodiment, about 0.025 mg/kg of body weight to about 20 mg/kg of body weight.

In one embodiment, an effective dosage amount is administered about every 24 h until the Condition is abated. In another embodiment, an effective dosage amount is administered about every 12 h until the Condition is abated. In another embodiment, an effective dosage amount is administered about every 8 h until the Condition is abated. In another embodiment, an effective dosage amount is administered about every 6 h until the Condition is abated. In another embodiment, an effective dosage amount is administered about every 4 h until the Condition is abated.

The effective dosage amounts described herein refer to total amounts administered; that is, if more than one Compound of Formula (I), or a pharmaceutically acceptable derivative thereof, is administered, the effective dosage amounts correspond to the total amount administered.

Where a cell capable of expressing TRPV1 is contacted with a Compound of Formula (I) in vitro, the amount effective for inhibiting the TRPV1 receptor function in a cell will range from about 0.01 µg/L to about 5 mg/L; in one embodiment, from about 0.01 µg/L to about 2.5 mg/L; in another embodiment, from about 0.01 µg/L to about 0.5 mg/L; and in another embodiment, from about 0.01 µg/L to about 0.25 mg/L, of a solution or suspension of a pharmaceutically acceptable carrier or excipient. In one embodiment, the volume of solution or suspension comprising the Compound of Formula (I), or a pharmaceutically acceptable derivative thereof, is from about 0.01 µL to about 1 mL. In another embodiment, the volume of solution or suspension is about 200 µL.

The Compounds of Formula (I), or a pharmaceutically acceptable derivative thereof, can be assayed in vitro or in vivo for the desired therapeutic or prophylactic activity prior to use in humans. Animal model systems can be used to demonstrate safety and efficacy.

The methods for treating or preventing a Condition in an animal in need thereof can further comprise administering to the animal being administered a Compound of Formula (I), or a pharmaceutically acceptable derivative thereof (i.e., a first therapeutic agent) a second therapeutic agent. In one embodiment, the second therapeutic agent is administered in an effective amount. In one embodiment, the second therapeutic agent is administered in an effective amount.

The methods for inhibiting TRPV1 function in a cell capable of expressing TRPV1 can further comprise contacting the cell with an effective amount of a second therapeutic agent.

An effective amount of the second therapeutic agent(s) will be known to those skilled the art depending on the agent. However, it is well within the skilled artisan's purview to determine the second therapeutic agent's optimal effective-amount range. A Compound of Formula (I) and the second therapeutic agent combined can act either additively or synergistically to treat the same Condition, or they can act independently of each other such that the Compound of Formula (I) treats or prevents a first Condition and the second therapeutic agent treats or prevents a second disorder, which can be the same as the first Condition or another disorder. In one embodiment of the disclosure, where a second therapeutic agent is administered to an animal for treatment of a Condition (e.g., pain), the minimal effective amount of the Compound of Formula (I) will be less than its minimal effective amount would be where the second therapeutic agent is not administered. In this embodiment, the Compound of Formula (I) and the second therapeutic agent can act synergistically to treat or prevent a Condition. In one embodiment, a Compound of Formula (I) is administered concurrently with a second therapeutic agent as a single composition comprising an effective amount of a Compound of Formula (I) and an effective amount of the second therapeutic agent. Alternatively, a composition comprising an effective amount of a Compound of Formula (I) and a second composition comprising an effective amount of the second therapeutic agent are concurrently administered. In another embodiment, an effective amount of a Compound of Formula (I) is administered prior or subsequent to administration of an effective amount of the second therapeutic agent. In this embodiment, the Compound of Formula (I) is administered while the second therapeutic agent exerts its therapeutic effect, or the second therapeutic agent is administered while the Compound of Formula (I) exerts its therapeutic effect for treating or preventing a Condition.

The second therapeutic agent can be, but is not limited to, an opioid agonist, a non-opioid analgesic, a non-steroid anti-inflammatory agent, an antimigraine agent, a Cox-II inhibitor, an antiemetic, a β-adrenergic blocker, an anticonvulsant, an antidepressant, a $Ca^{2+}$-channel blocker, an anticancer agent, an agent for treating or preventing UI, an agent for treating or preventing an ulcer, an agent for treating or preventing IBD, an agent for treating or preventing IBS, an agent for treating addictive disorder, an agent for treating Parkinson's disease and parkinsonism, an agent for treating anxiety, an agent for treating epilepsy, an agent for treating a stroke, an agent for treating a seizure, an agent for treating a pruritic condition, an agent for treating psychosis, an agent for treating Huntington's chorea, an agent for treating ALS, an agent for treating a cognitive disorder, an agent for treating a migraine, an agent for treating vomiting, an agent for treating dyskinesia, an agent for treating depression, a pharmaceutically acceptable derivative thereof, or any mixture thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable derivatives thereof, or any mixture thereof.

In certain embodiments, the opioid agonist is codeine, hydromorphone, hydrocodone, oxycodone, dihydrocodeine, dihydromorphine, morphine, tramadol, oxymorphone, pharmaceutically acceptable derivatives thereof, or any mixture thereof.

Examples of useful non-opioid analgesics include, but are not limited to, non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, a pharmaceutically acceptable derivative thereof, or any mixture thereof. Other suitable non-opioid analgesics include the following, non-limiting, chemical classes of analgesic, antipyretic, non-steroidal anti-inflammatory drugs: salicylic acid derivatives, including aspirin, sodium salicylate, choline magnesium trisalicylate, salsalate, diflunisal, salicylsalicylic acid, sulfasalazine, and olsalazin; para-aminophenol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); alkanones, including nabumetone; a pharmaceutically acceptable derivative thereof; or any mixture thereof. For a more detailed description of the NSAIDs, see Insel, "Analgesic-Antipyretic and Anti-inflammatory Agents and Drugs Employed in the Treatment of Gout," pp. 617-657 in *Goodman & Gilman's The Pharmacological Basis of Therapeutics* (Goodman et al., Eds., 9th Ed., McGraw-Hill, New York 1996), and Hanson, "Analgesic, Antipyretic and Anti-Inflammatory Drugs," pp. 1196-1221 in *Remington: The Science and Practice of Phar-* macy Vol 2 (Gennaro, ed., 19th ed., Mack Publishing, Easton, Pa., 1995), which are hereby incorporated by reference in their entireties.

Examples of useful antimigraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, a pharmaceutically acceptable derivative thereof, or any mixture thereof.

Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, celecoxib, DUP-697, flosulide, meloxicam, 6-MNA, L-745337, rofecoxib, nabumetone, nimesulide, NS-398, SC-5766, T-614, L-768277, GR-253035, JTE-522, RS-57067-000, SC-58125, SC-078, PD-138387, NS-398, flosulide, D-1367, SC-5766, PD-164387, etoricoxib, valdecoxib, parecoxib, a pharmaceutically acceptable derivative thereof, or any mixture thereof.

The second therapeutic agent can also be an agent useful for reducing any potential side effects of a Compound of Formula (I). For example, the second therapeutic agent can be an antiemetic agent. Examples of useful antiemetic agents include, but are not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, a pharmaceutically acceptable derivative thereof, or any mixture thereof.

Examples of useful β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, xibenolol, a pharmaceutically acceptable derivative thereof, or any mixture thereof.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenytoin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenytoin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, zonisamide, a pharmaceutically acceptable derivative thereof, or any mixture thereof.

Examples of useful antidepressants include, but are not limited to, binedaline, caroxazone, citalopram, (S)-citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, zimeldine, a pharmaceutically acceptable derivative thereof, or any mixture thereof.

Examples of useful $Ca^{2+}$-channel blockers include, but are not limited to, bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, perhexiline, a pharmaceutically acceptable derivative thereof, or any mixture thereof.

Examples of useful anticancer agents include, but are not limited to, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, flurocitabine, fosquidone, fostriecin sodium, gemcitabine, gemcitabine hydrochloride, hydroxyurea, idarubicin hydrochloride, ifosfamide, ilmofosine, interleukin II (including recombinant interleukin II or rIL2), interferon alpha-2a, interferon alpha-2b, interferon alpha-n1, interferon alpha-n3, interferon beta-I a, interferon gamma-I b, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozocin, sulofenur, talisomycin, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride, a pharmaceutically acceptable derivative thereof, or any mixture thereof.

Examples of other anticancer drugs include, but are not limited to, 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dihydrotaxol; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; 4-ipomeanol; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur, tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, a pharmaceutically acceptable derivative thereof, or any mixture thereof.

Examples of useful therapeutic agents for treating or preventing UI include, but are not limited to, propantheline, imipramine, hyoscyamine, oxybutynin, dicyclomine, a pharmaceutically acceptable derivative thereof, or any mixture thereof.

Examples of useful therapeutic agents for treating or preventing an ulcer include, antacids such as aluminum hydroxide, magnesium hydroxide, sodium bicarbonate, and calcium bicarbonate; sucraflate; bismuth compounds such as bismuth subsalicylate and bismuth subcitrate; $H_2$ antagonists such as cimetidine, ranitidine, famotidine, and nizatidine; $H^+$, $K^+$-ATPase inhibitors such as omeprazole, iansoprazole, and lansoprazole; carbenoxolone; misprostol; antibiotics such as tetracycline, metronidazole, timidazole, clarithromycin, and amoxicillin; a pharmaceutically acceptable derivative thereof; or any mixture thereof.

Examples of useful therapeutic agents for treating or preventing IBD include, but are not limited to, anticholinergic drugs; diphenoxylate; loperamide; deodorized opium tincture; codeine; broad-spectrum antibiotics such as metronidazole; sulfasalazine; olsalazie; mesalamine; prednisone; azathioprine; mercaptopurine; methotrexate; a pharmaceutically acceptable derivative thereof, or any mixture thereof.

Examples of useful therapeutic agents for treating or preventing IBS include, but are not limited to, propantheline; muscarine receptor antagonists such as pirenzapine, methoctramine, ipratropium, tiotropium, scopolamine, methscopolamine, homatropine, homatropine methylbromide, and methantheline; antidiarrheal drugs such as diphenoxylate and loperamide; a pharmaceutically acceptable derivative thereof, or any mixture thereof.

Examples of useful therapeutic agents for treating or preventing an addictive disorder include, but are not limited to, methadone, desipramine, amantadine, fluoxetine, buprenorphine, an opiate agonist, 3-phenoxypyridine, levomethadyl acetate hydrochloride, serotonin antagonists, a pharmaceutically acceptable derivative thereof, or any mixture thereof.

Examples of useful therapeutic agents for treating or preventing Parkinson's disease and parkinsonism include, but are not limited to, carbidopa/levodopa, pergolide, bromocriptine, ropinirole, pramipexole, entacapone, tolcapone, selegiline, amantadine, trihexyphenidyl hydrochloride, a pharmaceutically acceptable derivative thereof, or any mixture thereof.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, tenazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; propanediol carbamates, such as meprobamate and tybamate; a pharmaceutically acceptable derivative thereof; or any mixture thereof.

Examples of useful therapeutic agents for treating or preventing epilepsy include, but are not limited to, carbamazepine, ethosuximide, gabapentin, lamotrigine, phenobarbital, phenytoin, primidone, valproic acid, trimethadione, benzodiazepines, γ vinyl GABA, acetazolamide, felbamate, a pharmaceutically acceptable derivative thereof, or any mixture thereof.

Examples of useful therapeutic agents for treating or preventing stroke include, but are not limited to, anticoagulants such as heparin, agents that break up clots such as streptokinase or tissue plasminogen activator, agents that reduce swelling such as mannitol or corticosteroids, acetylsalicylic acid, a pharmaceutically acceptable derivative thereof, or any mixture thereof.

Examples of useful therapeutic agents for treating or preventing a seizure include, but are not limited to, carbamazepine, ethosuximide, gabapentin, lamotrignine, phenobarbital, phenytoin, primidone, valproic acid, trimethadione, bemzodiaepines, gabapentin, lamotrigine, γ-vinyl GABA, acetazolamide, felbamate, a pharmaceutically acceptable derivative thereof, or any mixture thereof.

Examples of useful therapeutic agents for treating or preventing a pruritic condition include, but are not limited to, naltrexone; nalmefene; danazol; tricyclics such as amitriptyline, imipramine, and doxepin; antidepressants such as those given below, menthol; camphor; phenol; pramoxine; capsaicin; tar; steroids; antihistamines; a pharmaceutically acceptable derivative thereof, or any mixture thereof.

Examples of useful therapeutic agents for treating or preventing psychosis include, but are not limited to, phenothiazines such as chlorpromazine hydrochloride, mesoridazine besylate, and thoridazine hydrochloride; thioxanthenes such as chloroprothixene and thiothixene hydrochloride; clozapine; risperidone; olanzapine; quetiapine; quetiapine fumarate; haloperidol; haloperidol decanoate; loxapine succinate; molindone hydrochloride; pimozide; ziprasidone; a pharmaceutically acceptable derivative thereof; or any mixture thereof.

Examples of useful therapeutic agents for treating or preventing Huntington's chorea include, but are not limited to, haloperidol, pimozide, a pharmaceutically acceptable derivative thereof, or any mixture thereof.

Examples of useful therapeutic agents for treating or preventing ALS include, but are not limited to, baclofen, neurotrophic factors, riluzole, tizanidine, benzodiazepines such as clonazepan, dantrolene, a pharmaceutically acceptable derivative thereof, or any mixture thereof.

Examples of useful therapeutic agents for treating or preventing cognitive disorders include, but are not limited to, agents for treating or preventing dementia such as tacrine; donepezil; ibuprofen; antipsychotic drugs such as thioridazine and haloperidol; antidepressant drugs such as those given above; a pharmaceutically acceptable derivative thereof; or any mixture thereof.

Examples of useful therapeutic agents for treating or preventing a migraine include, but are not limited to, alpipropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, a pharmaceutically acceptable derivative thereof, or any mixture thereof.

Examples of useful therapeutic agents for treating or preventing vomiting include, but are not limited to, 5-$HT_3$ receptor antagonists such as ondansetron, dolasetron, granisetron, and tropisetron; dopamine receptor antagonists such as prochlorperazine, thiethylperazine, chlorpromazin, metoclopramide, and domperidone; glucocorticoids such as dexamethasone; benzodiazepines such as lorazepam and alprazolam; a pharmaceutically acceptable derivative thereof; or any mixture thereof.

Examples of useful therapeutic agents for treating or preventing dyskinesia include, but are not limited to, reserpine, tetrabenazine, a pharmaceutically acceptable derivative thereof, or any mixture thereof.

Examples of useful therapeutic agents for treating or preventing depression include, but are not limited to, tricyclic antidepressants such as amitryptyline, amoxapine, bupropion, clomipramine, desipramine, doxepin, imipramine, maprotilinr, nefazadone, nortriptyline, protriptyline, trazodone, trimipramine, and venlaflaxine; selective serotonin reuptake inhibitors such as citalopram, (S)-citalopram, fluoxetine, fluvoxamine, paroxetine, and setraline; monoamine oxidase inhibitors such as isocarboxazid, pargyline, phenelzine, and tranylcypromine; psychostimulants such as dextroamphetamine and methylphenidate; a pharmaceutically acceptable derivative thereof; or any mixture thereof.

A Compound of Formula (I), or a pharmaceutically acceptable derivative thereof, and the second therapeutic agent can act additively or, in one embodiment, synergistically. In one embodiment, a Compound of Formula (I) is administered concurrently with a second therapeutic agent; for example, a composition comprising an effective amount of a Compound of Formula (I) and an effective amount of a second therapeutic agent can be administered. Alternatively, a composition comprising an effective amount of a Compound of Formula (I) and a different composition comprising an effective amount of a second therapeutic agent can be concurrently administered. In another embodiment, an effective amount of a Compound of Formula (I) is administered prior or subsequent to administration of an effective amount of a second therapeutic agent. In this embodiment, the Compound of Formula (I) is administered while the second therapeutic agent exerts its therapeutic effect, or the second therapeutic agent is administered while the Compound of Formula (I) exerts its therapeutic effect for treating or preventing a Condition.

A composition of the disclosure is prepared by a method comprising admixing a Compound of Formula (I) or a pharmaceutically acceptable derivative thereof with a pharmaceutically acceptable carrier or excipient. Admixing can be accomplished using methods known for admixing a compound (or derivative) and a pharmaceutically acceptable carrier or excipient. In one embodiment, the Compound of Formula (I) is present in the composition in an effective amount.

4.8 Kits

The disclosure further provides kits that can simplify the handling and administration of a Compound of Formula (I) to an animal.

In one embodiment, a kit of the disclosure comprises a unit dosage form of a Compound of Formula (I). In one embodiment, the unit dosage form comprises a first container, which can be sterile, containing an effective amount of a Compound of Formula (I) and a pharmaceutically acceptable carrier or excipient. The kit can further comprise a label or printed instructions instructing the use of the Compound of Formula (I) to treat or prevent a Condition. The kit can further comprise a unit dosage form of a second therapeutic agent, for example, a second container containing an effective amount of the second therapeutic agent and a pharmaceutically acceptable carrier or excipient. In another embodiment, the kit comprises a container containing an effective amount of a Compound of Formula (I), an effective amount of a second therapeutic agent and a pharmaceutically acceptable carrier or excipient. Examples of second therapeutic agents include, but are not limited to, those listed above.

Kits of the disclosure can further comprise a device that is useful for administering the unit dosage forms. Examples of such a device include, but are not limited to, a syringe, a drip bag, a patch, an inhaler, and an enema bag.

The following examples are set forth to assist in understanding the invention and should not be construed as specifically limiting the invention described and claimed herein. Such variations of the invention, including the substitution of all equivalents now known or later developed, that would be within the purview of those skilled in the art, and changes in formulation or changes in experimental design, are to be considered to fall within the scope of the invention incorporated herein.

5. EXAMPLES

Examples 1-8 relate to the synthesis of illustrative Compounds of Formulae (I), (II), and/or (III).

5.1 Reference Example 1

Preparation of Compound 46

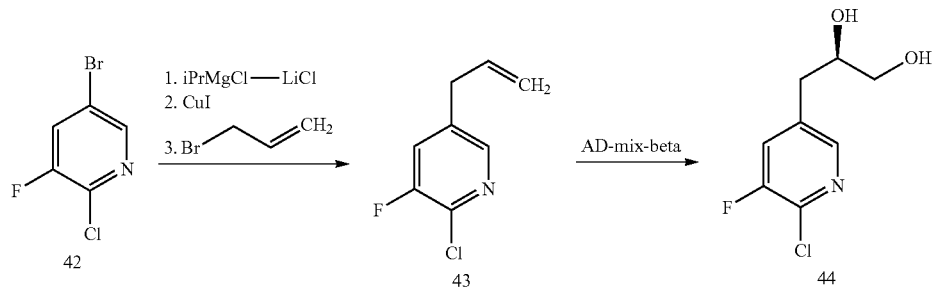

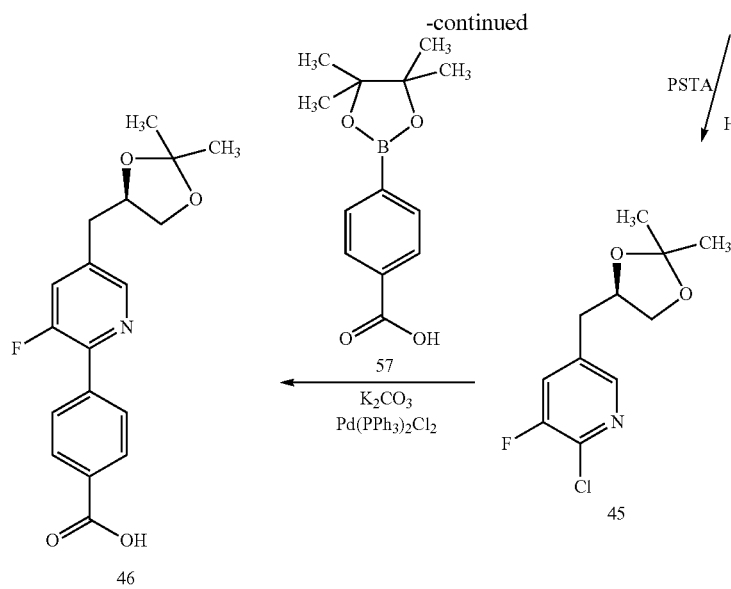
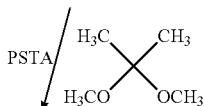

Under an argon atmosphere and at 0° C., in a dry 3-necked flask containing a solution of 5-bromo-2-chloro-3-fluoropyridine (42, 4.0 g, 19.05 mmol, Oakwood Products, Inc., West Columbia, S.C.) in THF (20 mL) was added isopropyl magnesium chloride-lithium chloride complex (1.3M THF solution, 24.8 mmol, 19.1 mL, Sigma-Aldrich) over 10 min. After an additional 10 min of stirring at 0° C., CuI (0.73 g, 3.81 mmol, Sigma-Aldrich) was added, and the mixture was stirred for 10 min at 0° C. Then a solution of allyl bromide (38.1 mmol, 3.3 mL, Sigma-Aldrich) in THF (4.0 mL) was added over 10 min at 0° C. After further stirring for 1 h at 0° C., the reaction was quenched with 10% citric acid and extracted twice with EtOAc (100 mL for each extraction). The organic portions were combined, washed with brine, dried ($Na_2SO_4$), concentrated under reduced pressure, and chromatographed on a silica gel column eluted sequentially with hexane then 10:90 EtOAc:hexane to provide 2.5 g of Compound 43, 5-allyl-2-chloro-3-fluoropyridine, as a colorless oil (yield 77%).

The identity of Compound 43 was confirmed using $^1$H NMR and LC/MS.

Compound 43: $^1$H NMR: $\delta_H$ (ppm, $CDCl_3$): 3.40 (2H, d, J=6.60 Hz), 5.16 (2H, m), 5.91 (1H, m), 7.32 (1H, dd, J=2.20, 9.00 Hz), 8.06 (1H, d, J=1.76 Hz); LC/MS: m/z=172 [M+1].

To a solution of Compound 43 (2.7 g, 16.2 mmol) in t-butanol (80 mL) and $H_2O$ (80 mL), AD-mix-beta (27.8 g, Sigma-Aldrich) was added portion-wise at 0° C. The resulting reaction mixture was slowly heated to a temperature of about 25° C. and further stirred for 16 h at this temperature. The mixture was cooled to 5° C., quenched by adding sodium sulfite (30 g), and stirred for 20 min. The resulting mixture was diluted with water (100 mL) and extracted twice with EtOAc (100 mL for each extraction). The organic portions were combined, washed with brine, dried ($Na_2SO_4$), concentrated under reduced pressure, and chromatographed on a silica gel column eluted with a gradient of from 20:80 EtOAc:hexane to 100:0 EtOAc:hexane to provide 3.2 g of Compound 44, (R)-3-(6-chloro-5-fluoropyridin-3-yl)propane-1,2-diol, as a colorless oil which slowly solidified (yield 98%).

The identity of Compound 44 was confirmed using $^1$H NMR and LC/MS.

Compound 44: $^1$H NMR: $\delta_H$ (ppm, $CDCl_3$): 2.36 (1H, t, J=4.96 Hz), 2.79 (3H, m), 3.51 (1H, m), 3.72 (1H, m), 3.92 (1H, m), 7.46 (1H, dd, J=1.96, 8.76 Hz), 8.07 (1H, d, J=1.76 Hz); LC/MS: m/z=206 [M+1].

A suspension of Compound 44 (2.50 g, 12.2 mmol) in 2,2-dimethoxypropane (25 mL, Sigma-Aldrich) was cooled with an ice bath. Para-toluene sulfonic acid monohydrate (PSTA, 0.23 g, 1.22 mmol, Sigma-Aldrich) was added. After the ice bath was removed, the resulting reaction mixture was stirred for 16 h at a temperature of about 25° C. Thereafter, the mixture was cooled to 5° C., saturated aqueous $NaHCO_3$ was added, and the mixture was extracted with EtOAc. The organic layer was separated, washed with brine, dried ($Na_2SO_4$), and concentrated under reduced pressure to provide 2.90 g of Compound 45, (R)-2-chloro-5-[(2,2-dimethyl-1,3-dioxolan-4-yl)methyl]-3-fluoropyridine, as an oil (yield 97%).

The identity of Compound 45 was confirmed using $^1$H NMR and LC/MS.

Compound 45: $^1$H NMR: $\delta_H$ (ppm, $CDCl_3$): 1.34 (3H, s), 1.42 (3H, s), 2.87 (2H, d, J=6.0 Hz), 3.62 (1H, t, J=7.0 Hz), 4.08 (1H, t, J=6.0 Hz), 4.30 (1H, q, J=6.0 Hz), 7.46 (1H, d, J=9.0 Hz), 8.12 (1H, s); LC/MS: m/z=247 [M+1].

Under an argon atmosphere, to a solution of Compound 45 (4.50 g, 18.3 mmol) and 4-(4,4,5,5-tetramethyl-1,3,2-dioxaborolan-2-yl)benzoic acid (57, 4.54 g, 18.3 mmol, Sigma-Aldrich) in a mixture of EtOH (48.0 mL) and THF (48.0 mL) was added $K_2CO_3$ (7.57 g, 54.9 mmol) and bis(triphenylphosphine)dichloropalladium (II) catalyst (1.03 g, 1.46 mmol, Sigma-Aldrich). The resulting reaction mixture was heated for 5 h at 85° C. The mixture was cooled to a temperature of about 25° C., diluted with water, and cooled further to 0° C. After the pH of the mixture was adjusted to 6.5 with aqueous 2N HCl, the resulting suspension was extracted twice with EtOAc (200 mL for each extraction). The organic portions were combined, washed with brine, and concentrated under reduced pressure to provide a residue. Thereafter, diethyl ether (150 mL) was added to the residue and the mixture was stirred for about 16 h. The solid that formed was collected by filtration, washed several times with diethyl ether, and dried under reduced pressure to provide 4.29 g of Compound 46, (R)-4-{5-[(2,2-dimethyl-1,3-dioxolan-4-yl)methyl]-3-fluoropyridin-2-yl}benzoic acid (yield 71%).

The identity of Compound 46 was confirmed using ¹H NMR and LC/MS.

Compound 46: ¹H NMR: δ_H (ppm, DMSO-d_6): 1.26 (3H, s), 1.35 (3H, s), 2.92 (2H, m), 3.63 (1H, m), 4.02 (1H, m), 4.36 (1H, m), 7.72 (1H, dd, J=1.47, 12.53 Hz), 7.81 (2H, m), 7.97 (2H, m), 8.44 (1H, s); LC/MS: m/z=332 [M+1].

5.2 Example 2

Preparation of Compound G158a

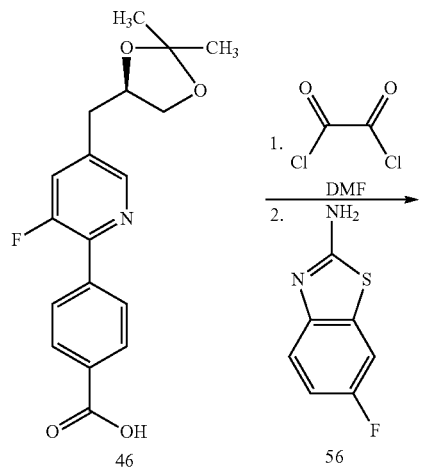

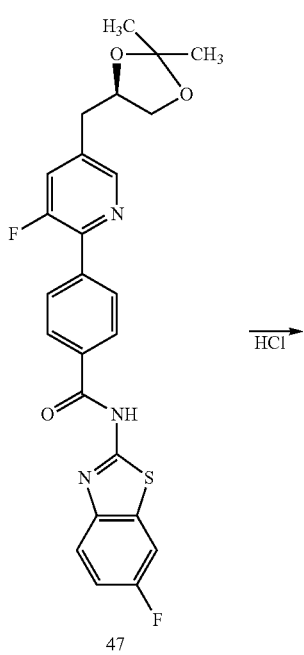

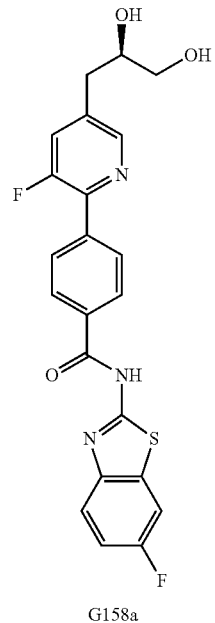

G158a

To a suspension of Compound 46 (0.60 g, 1.81 mmol) in anhydrous DCM (6.0 mL) at 0° C. was added DMF (6 drops). Oxalyl chloride (0.41 g, 3.20 mmol, Sigma-Aldrich) diluted with DCM (0.40 mL) was then added dropwise. The resulting clear solution was stirred for 1 h at a temperature of about 25° C. then 6-fluorobenzo[d]thiazol-2-amine (56, 0.46 g, 2.72 mmol, Sigma-Aldrich) was added, followed by the addition of pyridine (0.60 mL, 7.24 mmol). The resulting reaction mixture was stirred for 16 h at a temperature of about 25° C. 10% Aqueous Na_2CO_3 was added and then the mixture was extracted with 15:85 MeOH:DCM. The organic layer was separated, concentrated onto silica under reduced pressure, and chromatographed with a silica gel column eluted with 50:50 EtOAc:DCM to provide a residue. The residue was triturated with diethyl ether to provide 0.43 g of Compound 47, (R)-4-(5-((2,2-dimethyl-1,3-dioxolan-4-yl)methyl)-3-fluoropyridin-2-yl)-N-(6-fluorobenzo[d]thiazol-2-yl)benzamide (yield 49%).

To a solution of Compound 47 (0.348 g, 0.722 mmol), taken directly from the previous step, in DCM (3.30 mL) and MeOH (0.53 mL) in a sealed flask at a temperature of about 25° C. was added 4N HCl in dioxane (2.89 mmol, 0.72 mL). The resulting reaction mixture was stirred for 16 h at that temperature. When additional DCM was added thereafter, a precipitate formed. The mixture was stirred for an additional 30 min at a temperature of about 25° C. then filtered to obtain a solid. To the solid was added aqueous 0.5N NaOH (8 mL). The mixture was stirred for 30 min at a temperature of about 25° C., filtered, and the solid washed with H_2O. The solid was then dried under reduced pressure and triturated with 20:80 MeOH:DCM to provide 0.170 g of Compound G158a, (R)-4-[5-(2,3-dihydroxypropyl)-3-fluoropyridin-2-yl]-N-(6-fluorobenzo[d]thiazol-2-yl)benzamide, as a solid (yield 53%).

The identity of Compound G158a was confirmed using ¹H NMR and LC/MS.

Compound G158a: ¹H NMR: δ$_H$ (ppm, DMSO-d$_6$): 2.58 (1H, m), 2.86 (1H, dd, J=3.64, 13.78 Hz), 3.28 (2H, m), 3.66 (1H, m), 4.65 (1H, t, J=5.59 Hz), 4.72 (1H, d, J=5.39 Hz), 7.27 (1H, m), 7.68 (1H, dd, J=1.21, 12.57 Hz), 7.76 (1H, m), 7.90 (1H, dd, J=2.60, 8.67 Hz), 8.03 (2H, m), 8.20 (2H, m), 8.41 (1H, s), 12.96 (1H, s); LC/MS: m/z=442 [M+1].

5.3 Example 3

Preparation of Compound G156a

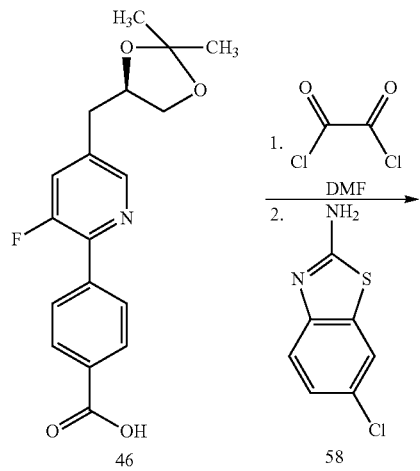

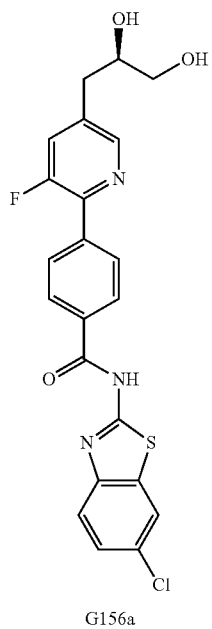

G156a

Compound G156a, (R)—N-(6-chlorobenzo[d]thiazol-2-yl)-4-[5-(2,3-dihydroxypropyl)-3-fluoropyridin-2-yl]benzamide, was obtained from Compound 46 in the same manner as described in Example 2 except that 6-chlorobenzo[d]thiazol-2-amine (58, Sigma-Aldrich) was used in place of Compound 56 (yield 24% from Compound 46).

The identity of Compound G156a was confirmed using ¹H NMR and LC/MS.

Compound G156a: ¹H NMR: δ$_H$ (ppm, DMSO-d$_6$): 2.65 (1H, m), 2.93 (1H, dd, J=3.56, 13.63 Hz), 3.36 (2H, m), 3.72 (1H, m), 4.71 (1H, t, J=5.65 Hz), 4.78 (1H, d, J=5.48 Hz), 7.49 (1H, dd, J=2.14, 8.61 Hz), 7.75 (2H, m), 8.09 (2H, m), 8.16 (1H, d, J=1.95 Hz), 8.26 (2H, m), 8.46 (1H, s), 13.09 (1H, s); LC/MS: m/z=458 [M+1].

5.4 Example 4

Preparation of Compound G159a

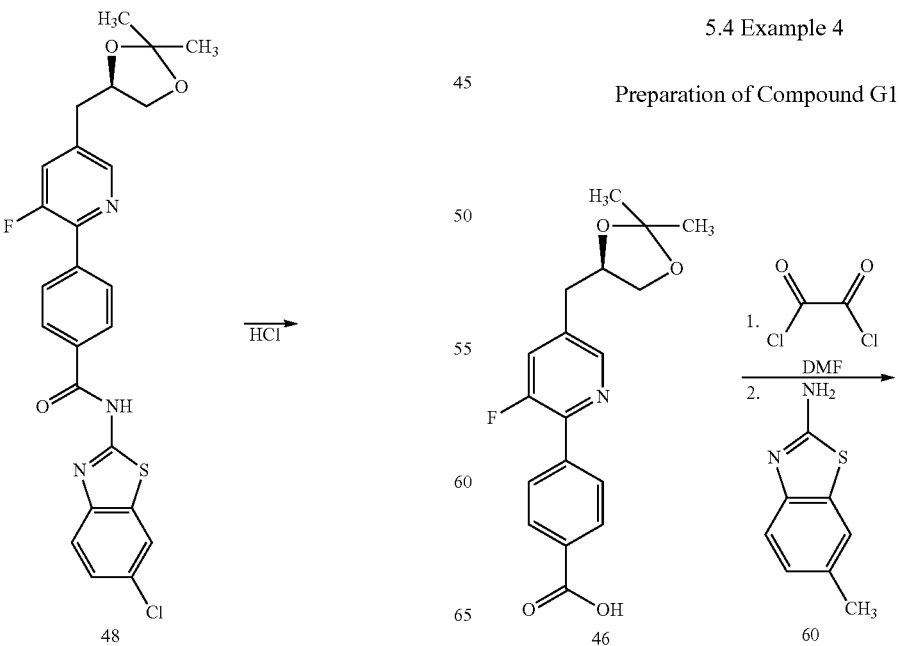

177
-continued

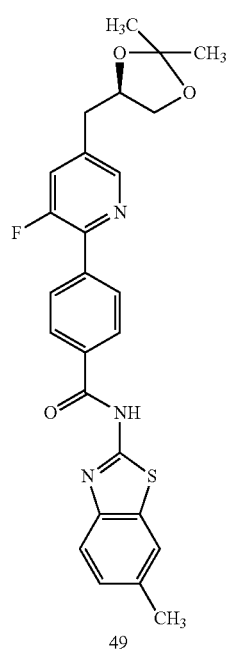
49

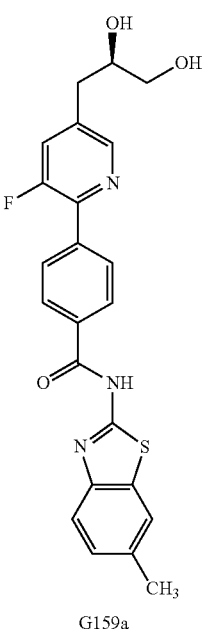
G159a

Compound G159a, (R)-4-[5-(2,3-dihydroxypropyl)-3-fluoropyridin-2-yl]-N-(6-methylbenzo[d]thiazol-2-yl)benzamide, was obtained from Compound 46 in the same manner as described in Example 2 except that 6-methylbenzo[d]thiazol-2-amine (60, Sigma-Aldrich) was used in place of Compound 56 (yield 26% from Compound 46).

The identity of Compound G159a was confirmed using ¹H NMR and LC/MS.

Compound G159a: ¹H NMR: $\delta_H$ (ppm, DMSO-$d_6$): 2.43 (3H, s), 2.65 (1H, m), 2.92 (1H, dd, J=3.74, 13.82 Hz), 3.38 (2H, m), 3.73 (1H, m), 4.71 (1H, m), 4.79 (1H, d, J=5.27 Hz),

178

7.23 (1H, d, J=8.29 Hz), 7.61 (1H, d, J=8.17 Hz), 7.75 (2H, m), 8.07 (2H, m), 8.26 (2H, m), 8.46 (1H, s), 12.94 (1H, s); LC/MS: m/z=438 [M+1].

5.5 Example 5

Preparation of Compound G215a

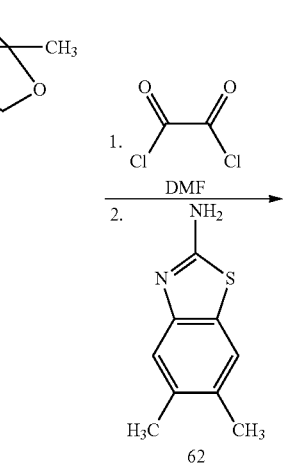
46          62

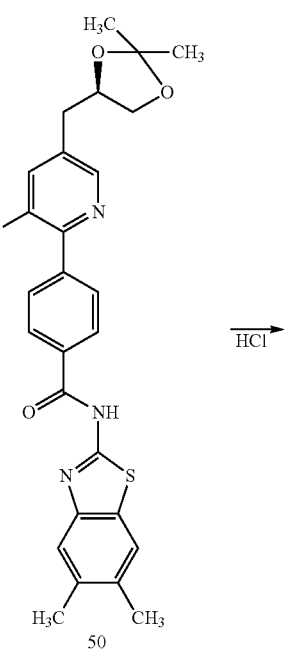
50

-continued

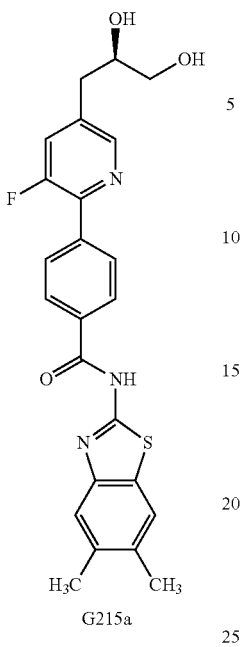

G215a

Compound G215a, (R)-4-[5-(2,3-dihydroxypropyl)-3-fluoropyridin-2-yl]-N-(5,6-dimethylbenzo[d]thiazol-2-yl)benzamide, was obtained from Compound 46 in the same manner as described in Example 2 except that 5,6-dimethyl-benzo[d]thiazol-2-amine (62, Sigma-Aldrich) was used in place of Compound 56 (yield 26% from Compound 46).

The identity of Compound G215a was confirmed using $^1$H NMR and LC/MS.

Compound G215a: $^1$H NMR: $\delta_H$ (ppm, DMSO-d$_6$): 2.35 (6H, s), 2.66 (1H, m), 2.92 (1H, m), 3.37 (2H, m), 3.71 (1H, m), 4.79 (2H, m), 7.58 (1H, s), 7.76 (2H, m), 8.07 (2H, m), 8.25 (2H, m), 8.46 (1H, s), 12.90 (1H, s); LC/MS: m/z=452 [M+1].

5.6 Example 6

Preparation of Compound G155a

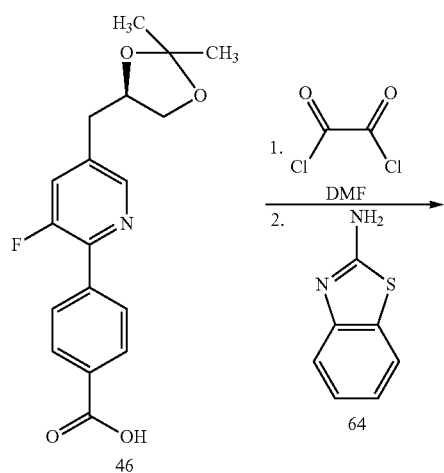

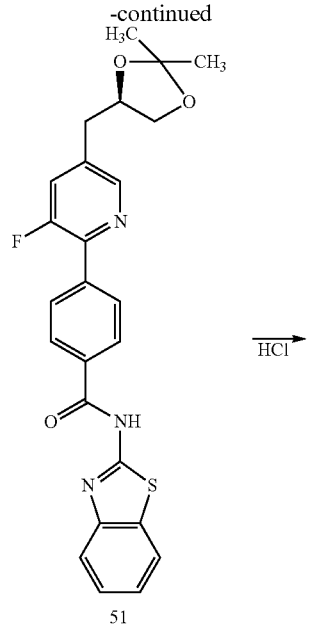

51

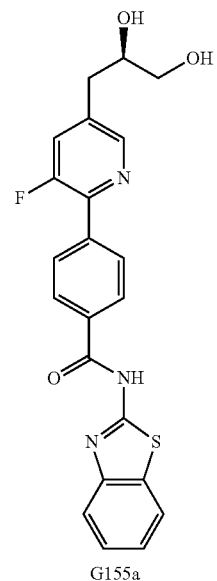

G155a

Compound G155a, (R)—N-(benzo[d]thiazol-2-yl)-4-[5-(2,3-dihydroxypropyl)-3-fluoropyridin-2-yl]benzamide, was obtained from Compound 46 in the same manner as described in Example 2 except that benzo[d]thiazol-2-amine (64, Sigma-Aldrich) was used in place of Compound 56 (yield 17% from Compound 46).

The identity of Compound G155a was confirmed using $^1$H NMR and LC/MS.

Compound G155a: $^1$H NMR: $\delta_H$ (ppm, DMSO-d$_6$): 2.64 (1H, m), 2.92 (1H, dd, J=3.76, 13.86 Hz), 3.36 (2H, m), 3.72 (1H, m), 4.71 (1H, t, J=5.58 Hz), 4.78 (1H, d, J=5.37 Hz), 7.19 (1H, t, J=7.89 Hz), 7.36 (1H, t, J=8.41 Hz), 7.63 (1H, d, J=7.79 Hz), 7.70 (1H, d, J=12.69 Hz), 7.85 (1H, d, J=6.98 Hz), 8.02 (2H, m), 8.27 (2H, m), 8.45 (1H, s), 13.00 (1H, s); LC/MS: m/z=424 [M+1].

5.7 Reference Example 7

Preparation of Compound 54

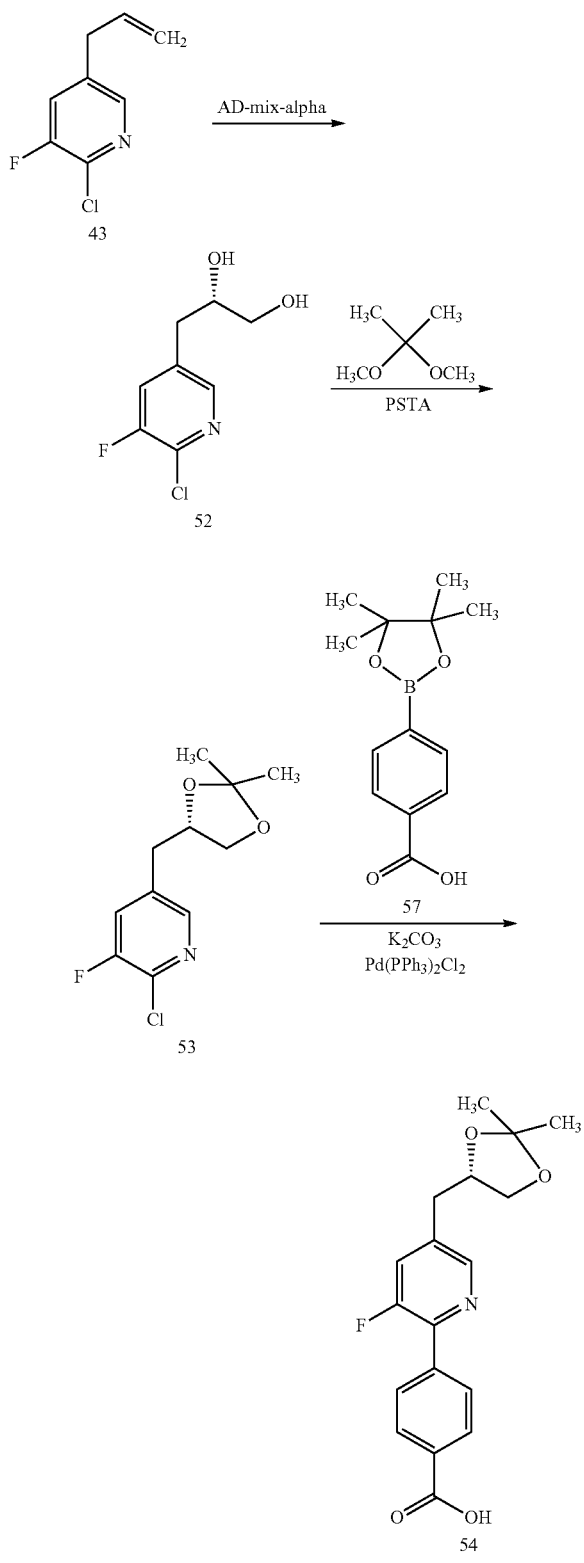

To a solution of Compound 43 (2.7 g, 16.2 mmol) in t-butanol (80 mL) and H$_2$O (80 mL), AD-mix-alpha (27.8 g, Sigma-Aldrich) was added portion-wise at 0° C. The resulting reaction mixture was slowly heated to a temperature of about 25° C. and further stirred for 16 h at this temperature. The mixture was cooled to 5° C., quenched by adding sodium sulfite (30 g), and stirred for 20 min. The resulting mixture was diluted with water (100 mL) and extracted twice with EtOAc (100 mL for each extraction). The organic portions were combined, washed with brine, dried (Na$_2$SO$_4$), concentrated under reduced pressure, and chromatographed on a silica gel column eluted with a gradient of from 20:80 EtOAc:hexane to 100:0 EtOAc:hexane to provide 3.2 g of Compound 52, (S)-3-(6-chloro-5-fluoropyridin-3-yl)propane-1,2-diol, as a colorless oil which slowly solidified (yield 98%).

The identity of Compound 52 was confirmed using $^1$H NMR and LC/MS.

Compound 52: $^1$H NMR: $\delta_H$ (ppm, CDCl$_3$): 2.36 (1H, t, J=4.96 Hz), 2.79 (3H, m), 3.51 (1H, m), 3.72 (1H, m), 3.92 (1H, m), 7.46 (1H, dd, J=1.96, 8.76 Hz), 8.07 (1H, d, J=1.76 Hz); LC/MS: m/z=206 [M+1].

A suspension of Compound 52 (2.50 g, 12.2 mmol) in 2,2-dimethoxypropane (25 mL) was cooled with an ice bath. PSTA (0.23 g, 1.22 mmol) was added. After the ice bath was removed, the resulting reaction mixture was stirred for 16 h at a temperature of about 25° C. Thereafter, the mixture was cooled to 5° C., saturated aqueous NaHCO$_3$ was added, and the mixture was extracted with EtOAc. The organic layer was separated, washed with brine, dried (Na$_2$SO$_4$), and concentrated under reduced pressure to provide 2.90 g of Compound 53, (S)-2-chloro-5-[(2,2-dimethyl-1,3-dioxolan-4-yl)methyl]-3-fluoropyridine, as an oil (yield 97%).

The identity of Compound 53 was confirmed using $^1$H NMR and LC/MS.

Compound 53: $^1$H NMR: $\delta_H$ (ppm, CDCl$_3$): 1.34 (3H, s), 1.42 (3H, s), 2.87 (2H, d, J=6.0 Hz), 3.62 (1H, t, J=7.0 Hz), 4.08 (1H, t, J=6.0 Hz), 4.30 (1H, q, J=6.0 Hz), 7.46 (1H, d, J=9.0 Hz), 8.12 (1H, s); LC/MS: m/z=247 [M+1].

Under an argon atmosphere, to a solution of Compound 53 (2.00 g, 8.13 mmol) and Compound 57 (2.02 g, 8.13 mmol) in a mixture of EtOH (22.1 mL) and THF (22.1 mL) was added K$_2$CO$_3$ (3.37 g, 24.4 mmol) and bis(triphenylphosphine)dichloropalladium (II) catalyst (0.46 g, 0.65 mmol). The resulting reaction mixture was heated for 16 h at 75° C. Thereafter, volatiles were removed under reduced pressure to provide a residue. The residue was dissolved in H$_2$O and extracted twice with diethyl ether; the diethyl ether portions were discarded. The aqueous portion was cooled with an ice bath and the pH adjusted to 6.0 with aqueous 2.4N HCl. The resulting suspension was extracted with EtOAc, washed with brine, and concentrated under reduced pressure to provide 2.35 g of Compound 54, (S)-4-{5-[(2,2-dimethyl-1,3-dioxolan-4-yl)methyl]-3-fluoropyridin-2-yl}benzoic acid, as a solid (yield 87%).

The identity of Compound 54 was confirmed using $^1$H NMR and LC/MS.

Compound 54: $^1$H NMR: $\delta_H$ (ppm, DMSO-d$_6$): 1.26 (3H, s), 1.35 (3H, s), 2.92 (1H, m), 3.63 (1H, m), 4.02 (1H, m), 4.36 (1H, m), 7.72 (1H, dd, J=1.47, 12.53 Hz), 7.81 (2H, m), 7.97 (2H, m), 8.44 (1H, s); LC/MS: m/z=332 [M+1].

5.8 Example 8

Preparation of Compound G155b

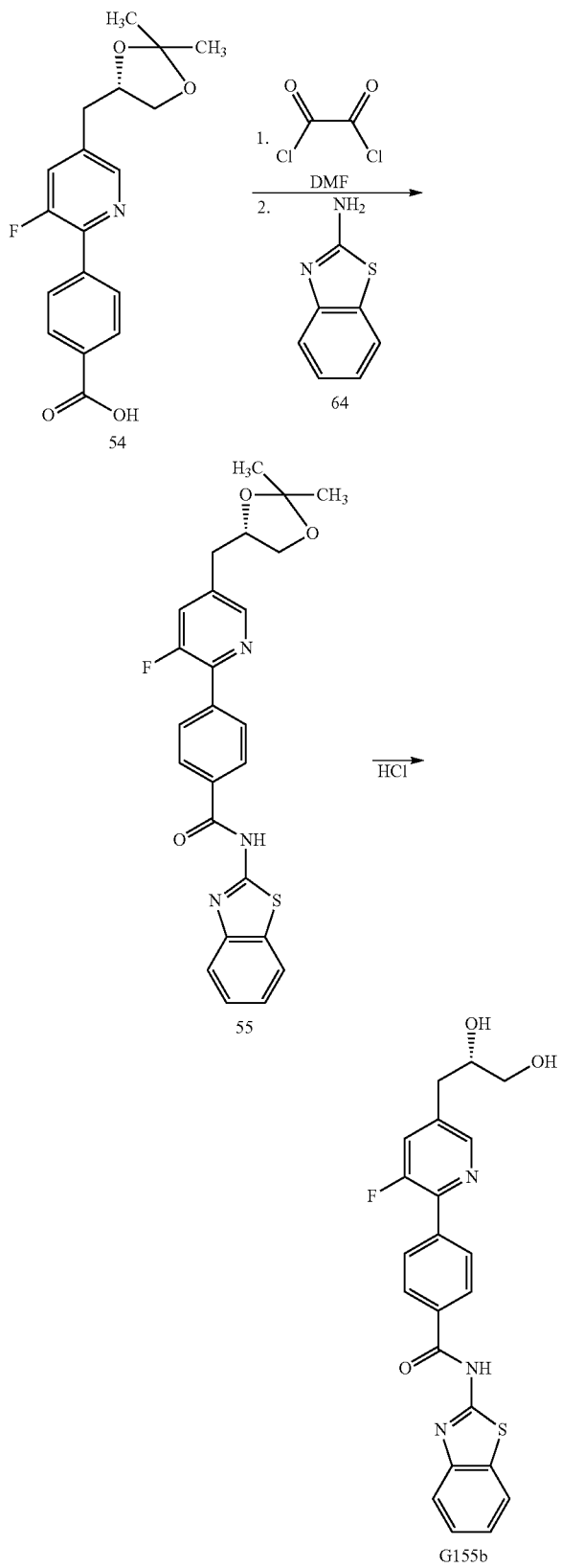

To a suspension of Compound 54 (0.50 g, 1.51 mmol) in anhydrous DCM (5.0 mL) at 0° C. was added DMF (5 drops). Oxalyl chloride (0.34 g, 2.72 mmol) diluted with DCM (0.40 mL) was then added dropwise. The resulting clear solution was stirred for 30 min at a temperature of 0° C. then Compound 64 (0.51 g, 3.40 mmol) was added, followed by the addition of pyridine (0.49 mL, 6.04 mmol). The resulting reaction mixture was stirred for 16 h at 0° C. then heated to 35° C. and stirred for 2.5 h more at that temperature. Saturated aqueous NaHCO$_3$ was then added and the mixture was extracted with DCM. The organic layer was separated and concentrated under reduced pressure to provide a residue. The residue was chromatographed with a silica gel column eluted sequentially with 33:67 EtOAc:DCM then 50:50 EtOAc:DCM to provide a residue. The residue was triturated with 2:1 hexane:diethyl ether to provide 0.24 g of Compound 55, (S)—N-(benzo[d]thiazol-2-yl)-4-(5-((2,2-dimethyl-1,3-dioxolan-4-yl)methyl)-3-fluoropyridin-2-yl)benzamide (yield 34%).

To a solution of Compound 55 (0.24 g, 0.517 mmol), taken directly from the previous step, in DCM (2.5 mL) and MeOH (0.40 mL) in a sealed flask at a temperature of about 25° C. was added 4N HCl in dioxane (3.10 mmol, 0.78 mL). The resulting reaction mixture was stirred for 16 h at that temperature. When diethyl ether was added thereafter, a precipitate formed. The mixture was stirred for an additional 30 min at a temperature of about 25° C. then filtered to obtain a solid. The solid was washed with diethyl ether then washed with DCM. Thereafter, 10% aqueous Na$_2$CO$_3$ was added, the mixture was stirred for 2 h at a temperature of about 25° C., filtered, washed with H$_2$O, and dried under reduced pressure to provide 0.191 g of Compound G155b, (S)—N-(benzo[d]thiazol-2-yl)-4-[5-(2,3-dihydroxypropyl)-3-fluoropyridin-2-yl]benzamide, as a solid (yield 87.2%).

The identity of Compound G155b was confirmed using $^1$H NMR and LC/MS.

Compound G155b: $^1$H NMR: $\delta_H$ (ppm, DMSO-d$_6$): 2.66 (1H, m), 2.95 (1H, dd, J=3.73, 13.83 Hz), 3.33 (2H, m), 3.71 (1H, m), 4.73 (1H, m), 4.81 (1H, d, J=5.39 Hz), 7.36 (1H, m), 7.49 (1H, m), 7.76 (1H, dd, J=1.48, 12.59 Hz), 7.81 (1H, d, J=7.56 Hz), 8.04 (1H, d, J=7.86 Hz), 8.11 (2H, m), 8.28 (2H, m), 8.47 (1H, m), 13.01 (1H, s); LC/MS: m/z=424 [M+1].

5.9 Example 9

Binding of Compounds of Formula (I) to TRPV1

Methods for assaying compounds capable of inhibiting TRPV1 are known in the art, for example, those methods disclosed in U.S. Pat. No. 6,239,267 to Duckworth et al.; U.S. Pat. No. 6,406,908 to McIntyre et al.; or U.S. Pat. No. 6,335,180 to Julius et al. The results of these assays will demonstrate that Compounds of Formula (I) bind to and modulate the activity of TRPV1.

Protocol 1

Human TRPV1 Cloning:

Human spinal cord RNA (commercially available from Clontech, Palo Alto, Calif.) is used. Reverse transcription is conducted on 1.0 µg total RNA using Thermoscript Reverse Transcriptase (commercially available from Invitrogen, Carlsbad, Calif.) and oligo dT primers as detailed in its product description. Reverse transcription reactions are incubated at 55° C. for 1 h, heat-inactivated at 85° C. for 5 min, and RNase H-treated at 37° C. for 20 min.

Human TRPV1 cDNA sequence is obtained by comparison of the human genomic sequence, prior to annotation, to the published rat sequence. Intron sequences are removed and flanking exonic sequences are joined to generate the hypothetical human cDNA. Primers flanking the coding region of human TRPV1 are designed as follows: forward primer GAAGATCTTCGCTGGTTGCACACTGGGCCACA (SEQ ID NO: 1), and reverse primer GAAGATCTTCGGGGA-CAGTGACGGTTGGATGT (SEQ ID NO: 2).

Using these primers, PCR of TRPV1 is performed on one tenth of the Reverse transcription reaction mixture using Expand Long Template Polymerase and Expand Buffer 2 in a final volume of 50 µL according to the manufacturer's instructions (Roche Applied Sciences, Indianapolis, Ind.). After denaturation at 94° C. for 2 min PCR amplification is performed for 25 cycles at 94° C. for 15 sec, 58° C. for 30 sec, and 68° C. for 3 min followed by a final incubation at 72° C. for 7 min to complete the amplification. The PCR product of about 2.8 kb is gel-isolated using a 1.0% agarose, Tris-Acetate gel containing 1.6 g/mL of crystal violet and purified with a S.N.A.P. UV-Free Gel Purification Kit (commercially available from Invitrogen). The TRPV1 PCR product is cloned into the pIND/V5-His-TOPO vector (commercially available from Invitrogen) according to the manufacturer's instructions to result in the TRPV1-pIND construct. DNA preparations, restriction enzyme digestions, and preliminary DNA sequencing are performed according to standard protocols. Full-length sequencing confirms the identity of the human TRPV1.

Generation of Inducible Cell Lines:

Unless noted otherwise, cell culture reagents are purchased from Life Technologies of Rockville, Md. HEK293-EcR cells expressing the ecdysone receptor (commercially available from Invitrogen) are cultured in Growth Medium (Dulbecco's Modified Eagles Medium containing 10% fetal bovine serum (commercially available from Hyclone, Logan, Utah)), Lx penicillin/streptomycin, 1x glutamine, 1 mM sodium pyruvate and 400 µg/mL Zeocin (commercially available from Invitrogen)). The TRPV1-pIND constructs are transfected into the HEK293-EcR cell line using Fugene transfection reagent (commercially available from Roche Applied Sciences, Basel, Switzerland). After 48 h, cells are transferred to Selection Medium (Growth Medium containing 300 µg/mL G418 (commercially available from Invitrogen)). Approximately 3 weeks later individual Zeocin/G418 resistant colonies are isolated and expanded. To identify functional clones, multiple colonies are plated into 96-well plates and expression is induced for 48 h using Selection Medium supplemented with 5 µM ponasterone A ("PonA") (commercially available from Invitrogen). On the day of assay, cells are loaded with Fluo-4 (a calcium-sensitive dye that is commercially available from Molecular Probes, Eugene, Oreg.) and CAP-mediated calcium influx is measured using a Fluorescence Imaging Plate Reader ("FLIPR") as described below. Functional clones are re-assayed, expanded, and cryopreserved.

pH-Based Assay:

Two days prior to performing this assay, cells are seeded on poly-D-lysine-coated 96-well clear-bottom black plates (commercially available from Becton-Dickinson) at 75,000 cells/well in growth media containing 5 µM PonA (commercially available from Invitrogen) to induce expression of TRPV1. On the day of the assay, the plates are washed with 0.2 mL 1x Hank's Balanced Salt Solution (commercially available from Life Technologies) containing 1.6 mM $CaCl_2$ and 20 mM HEPES, pH 7.4 ("wash buffer"), and loaded using 0.1 mL of wash buffer containing Fluo-4 (3 µM final concentration, commercially available from Molecular Probes). After 1 h, the cells are washed twice with 0.2 mL wash buffer and resuspended in 0.05 mL 1x Hank's Balanced Salt Solution (commercially available from Life Technologies) containing 3.5 mM $CaCl_2$ and 10 mM Citrate, pH 7.4 ("assay buffer"). Plates are then transferred to a FLIPR for assay. The test compound is diluted in assay buffer, and 50 µL of the resultant solution is added to the cell plates and the solution is monitored for two minutes. The final concentration of the test compound is adjusted to range from about 50 picoM to about 3 µM. Agonist buffer (wash buffer titrated with 1N HCl to provide a solution having a pH of 5.5 when mixed 1:1 with assay buffer) (0.1 mL) is then added to each well, and the plates are incubated for 1 additional minute. Data are collected over the entire time course and analyzed using Excel and Graph Pad Prism to determine the $IC_{50}$.

Capsaicin-Based Assay:

Two days prior to performing this assay, cells are seeded in poly-D-lysine-coated 96-well clear-bottom black plates (50,000 cells/well) in growth media containing 5 µM PonA (commercially available from Invitrogen) to induce expression of TRPV1. On the day of the assay, the plates are washed with 0.2 mL 1x Hank's Balanced Salt Solution (commercially available from Life Technologies) containing 1 mM $CaCl_2$ and 20 mM HEPES, pH 7.4, and cells are loaded using 0.1 mL of wash buffer containing Fluo-4 (3 µM final). After one hour, the cells are washed twice with 0.2 mL of wash buffer and resuspended in 0.1 mL of wash buffer. The plates are transferred to a FLIPR for assay. 50 µL of test compound diluted with assay buffer (1x Hank's Balanced Salt Solution containing 1 mM $CaCl_2$ and 20 mM HEPES, pH 7.4) are added to the cell plates and incubated for 2 min. The final concentration of the compound is adjusted to range from about 50 picoM to about 3 µM. Human TRPV1 is activated by the addition of 50 µL of capsaicin (400 nM), and the plates are incubated for an additional 3 min. Data are collected over the entire time course and analyzed using Excel and GraphPad Prism to determine the $IC_{50}$.

Protocol 2

For Protocol 2, a Chinese Hamster Ovary cell line (CHO) that has been engineered to constitutively express human recombinant TRPV1 was used (TRPV1/CHO cells). The TRPV1/CHO cell line was generated as described below.

Human TRPV1 Cloning:

A cDNA for the human TRPV1 receptor (hTRPV1) was amplified by PCR (KOD-Plus DNA polymerase, ToYoBo, Japan) from a human brain cDNA library (BioChain) using primers designed surrounding the complete hTRPV1 open reading frame (forward 5'-GGATCCAGCAAGGATGAA-GAAATGG (SEQ ID NO: 3) and reverse 5'-TGTCTGCGT-GACGTCCTCACTTCT (SEQ ID NO: 4)). The resulting PCR products were purified from agarose gels using Gel Band Purification Kit (GE Healthcare Bioscience) and were subcloned into pCR-Blunt vector (Invitrogen). The cloned cDNA was fully sequenced using a fluorescent dye-terminator reagent (BigDye Terminator ver3.1 Cycle Sequencing Kit, Applied Biosystems) and ABI Prism 3100 genetic analyzer (Applied Biosystems). The pCR-Blunt vector containing the hTRPV1 cDNA was subjected to restriction digestion with EcoR1. The restriction fragment was subcloned into expression vector pcDNA3.1(−) (Invitrogen) and named pcDNA3.1 (−)-hVR1 plasmid. The sequence of the cDNA encoding TRPV1 is available at GenBank accession number AJ277028.

Generation of the TRPV1/CHO Cell Line:

CHO-K1 cells were maintained in growth medium consisting of α-MEM, 10% FBS (Hyclone), and 100 IU/mL of penicillin—100 µg/mL of streptomycin mixed solution (Nacalai Tesque, Japan) at 37° C. in an environment of humidified 95% air and 5% $CO_2$. The cells were transfected with the pcDNA3.1(−)-hVR1 plasmid using FuGENE6 (Roche) according to the manufacturer's protocol. 24 hr after transfection, neomycin-resistant cells were selected using 1 mg/mL G418 (Nacalai Tesque). After 2 weeks, individual colonies were picked, expanded, and screened for the expression of hTRPV1 in the capsaicin-induced $Ca^{2+}$ influx assay (see below) with a FLIPR (Molecular Devices). A clone with the largest $Ca^{2+}$ response to capsaicin was selected and re-cloned by the same procedure. The cells expressing hTRPV1 were cultured in the growth medium supplemented with 1 mg/mL G418. Approximately 1 month later, stable expression of functional TRPV1 receptors in the selected cell line was confirmed by validating $Ca^{2+}$ responses with or without capsazepine (Sigma, at 1 nM-10 µM) in capsaicin assay.

Capsaicin-Induced $Ca^{2+}$ Influx Assay for Cell Selection:

The following assay was performed to identify cells with hTRPV1 expression. CHO-K1 cells transfected with pcDNA3.1(−)-hVR1 plasmid were seeded in 384-well black-wall clear-bottom plates (Corning) and cultivated in growth medium (see above) for 1 day. On the day of the experiment, culture medium was exchanged to assay buffer (20 mM HEPES, 137 mM NaCl, 2.7 mM KCl, 0.9 mM $MgCl_2$, 5.0 mM $CaCl_2$, 5.6 mM D-glucose, 2.5 mM probenecid, pH 7.4) containing 4 µM Fluo-3-AM (Dojin, Japan). After the incubation at 37° C. for 1 hr, each well was washed 3 times with assay buffer using an EMBLA 384 plate washer (Molecular Devices) and refilled with assay buffer. The plates were incubated at a temperature of about 25° C. for 10 min. Subsequently, the plates were inserted into a FLIPR, and 1.5 µM capsaicin (Sigma) solution prepared in assay buffer was added to each well (final concentration was 500 nM). Cellular responses were monitored for 5 min.

Cell Culture:

1. Cell Culture Media

1. Alpha-MEM (Gibco, CAT: 12561-056, LOT: 1285752): 450 mL.
2. Fetal Bovine Serum (FBS), heat inactivated (Gibco, CAT: 16140-071, LOT: 1276457): 50 mL.
3. HEPES Buffer Solution, 1M stock (Gibco, CAT: 15630-080): 10 mL (final 20 mM).
4. Geneticin, 50 mg/mL stock (Gibco, CAT: 10135-035): 10 mL (final 1 mg/mL).
5. Antimicotic Antibiotic Mixed Solution, 100× stock (Nacalai Tesque, CAT: 02892-54): 5 mL.

Components 1-5 above were combined at the indicated amounts and stored at 4° C. The cell culture media were brought to about 37° C. before use. Optionally, component 5 can be replaced by penicillin-streptomycin solution (for example, Gibco 15140-122 or Sigma P-0781).

2. Thawing the Cells

TRPV1/CHO cells were frozen in CELLBANKER™ (Juji-Field, Inc., Japan, CAT: BLC-1) and stored at −80° C. Optimized cryopreservation solution containing dimethyl sulfoxide and FBS was used.

Vials containing the TRPV1/CHO cells were stored at −80° C. After removal from −80° C., the vial was immediately transferred to a 37° C. water bath to thaw for ca. 1-2 minutes. Once completely thawed, the contents of the vial (1 mL/vial) was transferred to a sterile 15 mL test tube and 9 mL warm culture media were slowly added. The test tube was subsequently centrifuged at 1000 rpm for 4 min at a temperature of about 25° C. The supernatant was removed and the pellet resuspended in 10 mL of culture media. The cell suspension was transferred to a sterile 75 $cm^2$ plastic flask and incubated at humidified 5% $CO_2$/95% air at 37° C. To monitor viability, the cells were visually inspected and/or counted, beginning at approximately 1 hr after incubation.

3. Passaging the Cells

The cells in a flask were close to confluence at the time of passaging. Cell culture media were removed from the culture flask and 10 mL of sterile PBS(−) added and the flask gently shaken. The PBS was removed from the flask and 2 mL of trypsin/EDTA solution (0.05% trypsin with EDTA-4Na; Gibco, CAT: 25300-054) was added and the flask gently shaken. The flask was incubated at 37° C. for about 2 min. 8 mL cell culture media were subsequently added to the flask and the flask shaken to ensure that all cells were in solution. The cell suspension was then transferred to a sterile 15 mL or 50 mL plastic tube, centrifuged at 1,000 rpm for 4 min at a temperature of about 25° C. The supernatant was removed and the pellet resuspended in ca. 5 mL of culture media. The cell count was measured using the Burker-Turk hemocytometer.

The cells were seeded into a sterile 75 $cm^2$ plastic flask in ca. $0.8 \times 10^5$ cells/mL for 72 hr and incubated in humidified 5% $CO_{2/95}$% air at 37° C.

4. Freezing the Cells

The procedure up to the measurement of the cell count was the same as in the Section entitled "Passaging the Cells" above. Subsequently, the cell suspension was centrifuged at 1,000 rpm for 4 min at a temperature of about 25° C. The supernatant was removed and the pellet resuspended in CELLBANKER™ solution to get a final concentration of from $5 \times 10^5$ to $5 \times 10^6$ cells/mL. The cell suspension was transferred into appropriately labeled 1 mL cryovials and then placed into the −80° C. freezer.

pH-Based Assay:

The following assay was conducted to determine the concentration of sulfuric acid that would give rise to a pH that induces a $Ca^{2+}$ response optimal to test compounds for their effect on TRPV1.

1. Cells

TRPV1/CHO cells were seeded in the 96-well clear-bottom black-wall plate (Nunc) at densities of $1-2 \times 10^4$ cells/well and grown in 100 µL of culture medium (alpha-MEM supplemented with 10% FBS, 20 mM HEPES, 1 mg/mL geneticin and 1% antibiotic-antimycotic mixed stock solution) for 1-2 days before the experiment.

2. Determination of pH Sensitivity and Agonist Dose 2.1. Agonist Solution

Seven different agonist solutions with sulfuric acid concentrations of 15.0, 15.5, 16.0, 16.5, 17.0, 17.5, and 18.0 mM were prepared by diluting 1M sulfuric acid with measuring buffer (see, e.g., FIG. 1 of U.S. Patent Application Publication No. US 2009/0170868 A1). The different sulfuric acid concentrations in the agonist solutions were selected such that a 1:4 dilution would result in a final sulfuric acid concentration of 3.0, 3.1, 3.2, 3.3, 3.4, 3.5, and 3.6 mM, denoted "B" through "H" respectively. Buffer without sulfuric acid, denoted "A", was also used.

2.2. Assay pH dependent $Ca^{2+}$ responses in TRPV1/CHO cells cultured in a 96-well plate were determined (see, e.g., FIG. 2 of U.S. Patent Application Publication No. US 2009/0170868 A1). In particular, $Ca^{2+}$ influx into TRPV1/CHO cells in response to low pH as measured by Fura-2 AM fluorescence was determined. The cells were stimulated using 3.0 mM (well numbers B1-B6), 3.1 mM (C1-C6), 3.2 mM (D1-D6), 3.3 mM (E1-E6), 3.4 mM (F1-F6), 3.5 mM (G1-G6), or 3.6 mM (H1-H6) $H_2SO_4$ or pH 7.2 measuring buffer without $H_2SO_4$ (A1-A6).

(1) Culture medium was removed using an 8-channel-pipette (Rainin, USA) from the 96-well plate and the wells were refilled with 100 µL of loading buffer (20 mM HEPES, 115 mM NaCl, 5.4 mM KCl, 0.8 mM $MgCl_2$, 1.8 mM $CaCl_2$, 13.8 mM D-glucose, 2.5 mM probenecid, pH 7.4) containing 5 µM Fura-2 AM (Dojin, Japan).

(2) The 96-well plate was incubated at 37° C. for 45 min.

(3) The loading buffer was removed from each well. The cells were subsequently washed twice with 150 µL of measuring buffer (20 mM HEPES, 115 mM NaCl, 5.4 mM KCl, 0.8 mM $MgCl_2$, 5.0 mM $CaCl_2$, 13.8 mM D-glucose, 0.1% BSA, pH 7.4) (no probenecid). The wells were then refilled with 80 µL of measuring buffer.

(4) After an incubation at 4° C. for 15 min, the 96-well plate was transferred to a model FDSS-3000 plate reader apparatus (Hamamatsu Photonics K.K., Japan).

(5) The Fura-2 fluorescent intensity was monitored at a wavelength of 340 nm and at 380 nm, respectively, at a rate of 0.5 Hz for a total of 240 seconds. After 16 time points (32 sec) of baseline detection, 20 µL of agonist solution was added to each well. The final volume was 100 µL/well.

(6) Fluorescence intensity ratio refers to the fluorescence intensity at 340 nm over the fluorescence intensity at 380 nm at a particular time point. The baseline was set as the average of the fluorescent intensity ratios for the first 16 time points before the addition of agonist solution. The maximum response was the highest fluorescent intensity ratio during the 60 time points following addition of agonist solution.

(7) Maximal signal ratios from each well were calculated as output data using the FDSS-3000 analysis program. Data were analyzed using Excel (Microsoft) and XLfit (idbs) software.

2.3. pH Determination

After the observation of $Ca^{2+}$ responses, the buffer of each lane of the 96-well plate (50 µL/well, 8-20 wells/plate) was collected well by well and the pH values were measured using a portable pH meter (Shindengen, Japan).

The $Ca^{2+}$ responses in lanes D and E were intermediate and therefore optimal for testing the effects of compounds on the TRPV1 calcium channel (see, e.g., FIG. 2 of U.S. Patent Application Publication No. US 2009/0170868 A1). The final sulfuric acid concentrations in the wells of these lanes were 3.2 mM and 3.3 mM, respectively. These final sulfuric acid concentrations were obtained using agonist solutions with 16.0 mM and 16.5 mM sulfuric acid concentrations, respectively (lanes D and E). The pH obtained using these sulfuric acid concentrations was from about 5.0 to about 5.1.

Thus, agonist solutions with 16.0 mM and 16.5 mM sulfuric acid concentrations, respectively (lanes D and E), were selected for the experiments described below in Section 3.

3. pH Assay 3.1. Agonist

In an "agonist plate," two different agonist solutions with different $H_2SO_4$ concentrations were used for the pH assay (see, e.g., FIG. 3A of U.S. Patent Application Publication No. US 2009/0170868 A1). For the first half of a 96-well plate one agonist solution was used; for the second half the other agonist solution was used. The agonist solutions were obtained by diluting sulfuric acid (1M $H_2SO_4$) with measuring buffer. The concentrations for the two agonist solutions were determined as described above in Section 2 of Protocol 2.

The sulfuric acid concentrations between the two agonist solutions differed by 0.5 mM. In the experiment described in Section 2 of Protocol 2, the sulfuric acid concentrations in the agonist solutions were determined to be 16 mM and 16.5 mM, respectively. After 1:4 dilution of the agonist solutions, the final sulfuric acid concentration was 3.2 mM and 3.3 mM, respectively. The resulting pH value for the pH assay was 5.0 to 5.1.

3.2. Test Compounds

Test compounds were dissolved in DMSO to yield 1 mM stock solutions. The stock solutions were further diluted using DMSO in 1:3 serial dilution steps with 6 points (1000, 250, 62.5, 15.625, 3.9062, and 0.977 µM). The thereby-obtained solutions were further diluted in measuring buffer (1:100) as 10× stock serial dilutions with a DMSO concentration of 1%. 10 µL of a 10× stock was added into each well of an "antagonist plate" (see step 3.3.(4) below). Thus, the final concentrations of antagonists was as follows: 0.977, 3.906, 15.63, 62.5, 250, and 1000 nM containing 0.1% DMSO (see, e.g., FIG. 3B of U.S. Patent Application Publication No. US 2009/0170868 A1).

3.3. Assay

Steps (1) and (2) of this Assay were the same as steps 2.2.(1) and 2.2.(2), respectively, of Protocol 2.

(3) The cells were washed twice with 150 µL of measuring buffer (mentioned in step 2.2.(3) of Protocol 2, no probenecid). The wells were subsequently refilled with 70 µL of measuring buffer.

(4) Either 10 µL of measuring buffer or 10 µL of 10× stock serial dilution of test compound (described in step 3.2. above) were applied to each well. Usually, only one test compound was tested per 96-well plate. The number of replicates per 96-well plate for a particular antagonist at a particular concentration was 2×7 since, as described for the "agonist plate," two different sulfuric acid concentrations were used per 96-well plate and seven lanes (A-C, E-H) per 96-well plate were used (N=2×7).

Step (5) was the same as step 2.2.(4) above.

(6) Fura-2 fluorescent intensity was monitored as described in step 2.2.(5) above. After 16 time points of baseline detection, 20 µL of agonist solution (measuring buffer titrated with $H_2SO_4$ to yield a pH in the range of from about 5.0 to about 5.1 when mixed 1:4 with the measuring buffer containing test compound) was added to each well (final volume 100 µL/well).

Steps (7) and (8) were as described in steps 2.2.(6) and 2.2.(7) above, respectively.

3.4. pH Check (1) The pH values of the buffer in the wells of A1 through H1 and A7 through H7 were measured one by one using a portable pH meter.

(2) When a well was confirmed as having a pH of from about 5.0 to about 5.1, the next five wells to its right (e.g., for well B1, wells B2 through B6) were checked one after another.

(3) For $IC_{50}$ calculation, only the data from wells with pH values of 5.0-5.1 were used.

The number of wells tested for their pH varied among plates (from about 16 to 60 wells/plate). The number depended on the results of step 3.4.(1) above and the $Ca^{2+}$ responses.

Capsaicin-Based Assay:

One day prior to assay, TRPV1/CHO cells were seeded in 96-well clear-bottom black plates (20,000 cells/well) in growth media. On the day of the experiment, the cells were washed with 0.2 mL 1× Hank's Balanced Salt Solution (Life Technologies) containing 1.6 mM $CaCl_2$ and 20 mM HEPES, pH 7.4 ("wash buffer"). Subsequently, the cells were loaded by incubation in 0.1 mL of wash buffer containing Fluo-4 at 3 µM final concentration. After 1 hour, the cells were washed twice with 0.2 mL wash buffer and resuspended in 0.1 mL wash buffer. The plates were then transferred to a Fluorescence Imaging Plate Reader (Molecular Devices). Fluorescence intensity was monitored for 15 seconds to establish a baseline. Subsequently, test compounds diluted in assay buffer (1× Hank's Balanced Salt Solution containing 1 mM CaCl$_2$ and 20 mM HEPES, pH 7.4) containing 1% DMSO were added to the cell plate and fluorescence was monitored for 2 minutes. The final concentration of the compound was adjusted to range from 100 μM to 1.5625 μM. If the test compound was an especially potent antagonist, the final concentration of the compound was adjusted to range from 10 μM to 1.5625 nM. Human TRPV1 was then activated by the addition of 50 μL capsaicin (100 nM final concentration) and plates incubated for an additional 3 min. Data were collected over the entire time course and analyzed using Excel and the curve-fitting formula GraphPad Prism.

The results of the assays of Protocol 2 are shown in Table 10.

Human TRPV1 Heat-Based Assay:

CHO cells stably expressing human TRPV1 (hTRPV1) were used. Functional assessment of heat-induced activation of hTRPV1 was carried out in a cell-based Ca$^{2+}$ flux assay using ABI7500 Fast Real-Time PCR System as described in Reubish et al., "Functional assessment of temperature-gated ion-channel activity using a real-time PCR machine," www.BioTechniques.com 47(3):iii-ix (2009), which is hereby incorporated by reference. Briefly, hTRPV1/CHO cells were cultured in growth media in a tissue culture dish at 37° C. in a CO$_2$ incubator. On the day of the assay, culture media were removed and the cells were then detached using 0.05% trypsin at 37° C. with 5% CO$_2$, for 90 s. The detached cells were centrifuged (1000 rpm, 4 min) to remove trypsin-containing supernatant and resuspended in assay buffer (115 mM NaCl, 5.4 mM KCl, 0.8 mM MgCl$_2$.6H$_2$O, 1.8 mM CaCl$_2$.2H$_2$O, 13.8 mM D-glucose, and 20 mM HEPES). Then, the cells were loaded with 5 μM Fluo-4, a Ca$^{2+}$ reporter dye, in the presence of 2.5 mM probenecid at 37° C. with 5% CO$_2$, for 45 min. Thereafter, the cells were washed twice with measuring buffer (assay buffer supplemented with 0.1% BSA and 3.2 mM CaCl$_2$) then transferred to a Fast 96-well Reaction Plate (0.1 mL) (Part no. 4346907, MICROAMP, Applied Biosystems, Foster City, Calif.). The cell density was 100,000 cells/24 μL/well. A solution of the compound under test (6 μL/well) was added into each well of the 96-well plate. Thus, the reaction volume per well was 30 μL.

The plates were then placed inside an ABI7500 Fast Real-Time PCR instrument (Applied Biosystems) to read fluorescence at different temperatures using 7500 software, version 2.0.2 (Applied Biosystems). The initial temperature was set at 25° C. for 1 min. followed by a temperature ramp to 45° C. in 100 s to deliver heat to cells. [Ca$^{2+}$]$_i$ response of hTRPV1/CHO cells to heat was determined as:

[fluorescence read at 45° C.–fluorescence read at 25° C.].

Compound concentration response curves and IC$_{50}$ values were analyzed using GraphPad Prism 4 software (GraphPad Software, La Jolla, Calif.).

The IC$_{50}$ data provided in Table 10 are shown as mean±standard error of the mean; the number of trials conducted for each assay is shown in parentheses except for only a single trial where no number of trials is shown in parentheses. The results in Table 10 demonstrate that many Compounds of Formula (I) have superior potency.

TABLE 10

| | TRPV1 IC$_{50}$ Potency | | | |
|---|---|---|---|---|
| Compound | Human Capsaicin CHO (hCAP-CHO) (nM) | Human pH CHO (hpH-CHO) (nM) | Human Heat CHO (hHeat-CHO) (nM) | Structure |
| G155a | 31.9 ± 7.6 (3) | 44.3 ± 6.2 (2) | 307 ± 10 (3) | 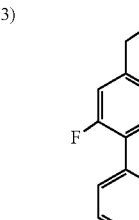 |
| G155b | 116.5 ± 9.6 (3) | 45.0 ± 03.3 (4) | 580 (1) | 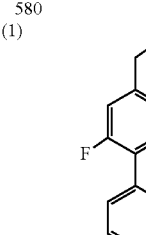 |
| G156a | 28.7 ± 6.8 (3) | 18.8 ± 1.8 (3) | >10,000 (2) | 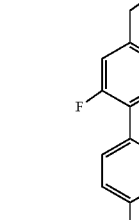 |

TABLE 10-continued

TRPV1 IC$_{50}$ Potency

| Compound | Human Capsaicin CHO (hCAP-CHO) (nM) | Human pH CHO (hpH-CHO) (nM) | Human Heat CHO (hHeat-CHO) (nM) | Structure |
|---|---|---|---|---|
| G158a | 77 ± 29 (3) | 23.1 ± 3.1 (2) | 598 ± 296 (2) | 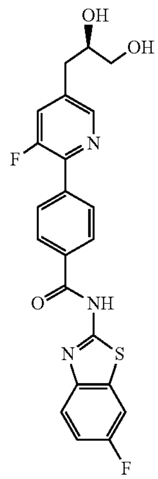 [SMILES: O=C(Nc1nc2ccc(F)cc2s1)c1ccc(-c2ncc(C[C@@H](O)CO)cc2F)cc1] |
| G159a | 29.6 ± 7.9 (3) | 13.7 ± 0.2 (2) | 879 ± 13 (2) | 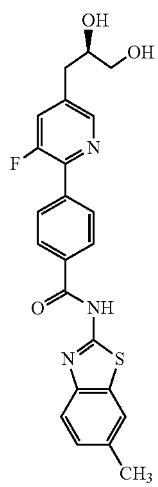 |
| G215a | 219 ± 58 (3) | 105 ± 14 (3) | — | 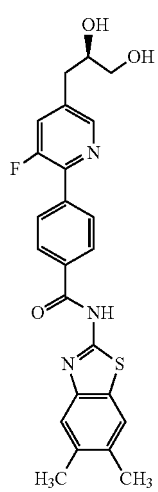 |
| Compound A* | >25,000 (2)* | >25,000 (2)* | — | 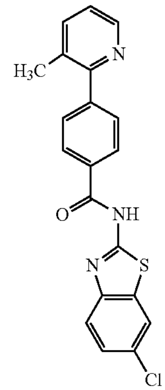 [SMILES: Cc1cccnc1-c1ccc(C(=O)Nc2nc3ccc(Cl)cc3s2)cc1] |
| Compound B* | 1144 ± 270 (4)* | >25,000 (4)* | — | 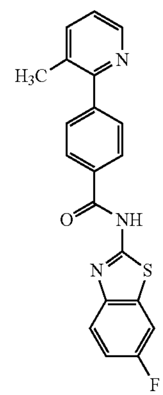 [SMILES: Cc1cccnc1-c1ccc(C(=O)Nc2nc3ccc(F)cc3s2)cc1] |

*Compounds A and B correspond to compounds J35 and J37, respectively, described at page 93 of WO2005/030766 and were prepared and evaluated according to the methods described therein.

5.10 Example 10

In Vivo Assays for Prevention or Treatment of Pain

Test Animals:

Each experiment uses rats weighing between 200-260 g at the start of the experiment. The rats are group-housed and have free access to food and water at all times, except prior to oral administration of a Compound of Formula (I) when food is removed for 16 hours before dosing. A control group acts as a comparison to rats treated with a Compound of Formula (I). The control group is administered the carrier for the Compound of Formula (I). The volume of carrier administered to the control group is the same as the volume of carrier and Compound of Formula (I) administered to the test group.

Acute Pain:

To assess the actions of a Compound of Formula (I) for the treatment or prevention of acute pain, the rat tail flick test can be used. Rats are gently restrained by hand and the tail exposed to a focused beam of radiant heat at a point 5 cm from the tip using a tail flick unit (Model 7360, commercially available from Ugo Basile of Italy). Tail flick latencies are defined as the interval between the onset of the thermal stimulus and the flick of the tail. Animals not responding within 20 seconds are removed from the tail flick unit and assigned a withdrawal latency of 20 seconds. Tail flick latencies are measured immediately before (pre-treatment) and 1, 3, and 5 hours following administration of a Compound of Formula (I). Data are expressed as tail flick latency(s) and the percentage of the maximal possible effect (% MPE), i.e., 20 seconds, is calculated as follows:

$$\% \, MPE = \frac{[(\text{post administration latency}) - (\text{pre-administration})]}{(20 \, s \, \text{pre-administration latency})}$$

The rat tail flick test is described in D'Amour et al., "A Method for Determining Loss of Pain Sensation," *J. Pharmacol. Exp. Ther.* 72:74-79 (1941).

Inflammatory Pain:

To assess the actions of a Compound of Formula (I) for the treatment or prevention of inflammatory pain, the Freund's complete adjuvant ("FCA") model of inflammatory pain can be used. FCA-induced inflammation of the rat hind paw is associated with the development of persistent inflammatory mechanical hyperalgesia and provides reliable prediction of the antihyperalgesic action of clinically useful analgesic drugs (Bartho et al., "Involvement of capsaicin-sensitive neurons in hyperalgesia and enhanced opioid antinociception in inflammation," *Naunyn-Schmiedeberg's Archives of Pharmacol.* 342:666-670 (1990)). The left hind paw of each animal is administered a 50 µL intraplantar injection of 50% FCA. 24 hour post injection, the animal is assessed for response to noxious mechanical stimuli by determining the PWT, as described below. Rats are then administered a single injection of 1, 3, 10, or 30 mg/kg of either a Compound of Formula (I); 30 mg/kg of a control selected from Celebrex, indomethacin, and naproxen; or carrier. Responses to noxious mechanical stimuli are then determined 1, 3, 5, and 24 hours post administration. Percentage reversal of hyperalgesia for each animal is defined as:

$$\% \, \text{Reversal} = \frac{[(\text{post administration} \, PWT) - (\text{pre-administration} \, PWT)]}{[(\text{baseline} \, PWT) - (\text{pre-administration} \, PWT)]} \times 100$$

Neuropathic Pain:

To assess the actions of a Compound of Formula (I) for the treatment or prevention of neuropathic pain, either the Seltzer model or the Chung model can be used.

In the Seltzer model, the partial sciatic nerve ligation model of neuropathic pain is used to produce neuropathic hyperalgesia in rats (Seltzer et al., "A Novel Behavioral Model of Neuropathic Pain Disorders Produced in Rats by Partial Sciatic Nerve Injury," *Pain* 43:205-218 (1990)). Partial ligation of the left sciatic nerve is performed under isoflurane/$O_2$ inhalation anaesthesia. Following induction of anesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a ⅜ curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anesthesia. Animals are then returned to their home cages until behavioral testing begins. The animal is assessed for response to noxious mechanical stimuli by determining PWT, as described below, prior to surgery (baseline), then immediately prior to and 1, 3, and 5 hours after drug administration for rear paw of the animal. Percentage reversal of neuropathic hyperalgesia is defined as:

$$\% \, \text{Reversal} = \frac{[(\text{post administration} \, PWT) - (\text{pre-administration} \, PWT)]}{[(\text{baseline} \, PWT) - (\text{pre-administration} \, PWT)]} \times 100$$

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anaesthesia. Following induction of anaesthesia, a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after being administered a Compound of Formula (I) for the left rear paw of the animal. The animal can also be assessed for response to noxious thermal stimuli or for tactile allodynia, as described below. The Chung model for neuropathic pain is described in Kim, "An Experimental Model for Peripheral Neuropathy Produced by Segmental Spinal Nerve Ligation in the Rat," *Pain* 50(3):355-363 (1992).

Response to Mechanical Stimuli as an Assessment of Mechanical Hyperalgesia:

The paw pressure assay can be used to assess mechanical hyperalgesia. For this assay, hind paw withdrawal thresholds (PWT) to a noxious mechanical stimulus are determined using an analgesymeter (Model 7200, commercially available from Ugo Basile of Italy) as described in Stein, "Unilateral Inflammation of the Hindpaw in Rats as a Model of Prolonged Noxious Stimulation: Alterations in Behavior and Nociceptive Thresholds," *Pharmacol. Biochem. and Behavior* 31:451-455 (1988). The maximum weight that can be applied to the hind paw is set at 250 g and the end point is taken as complete withdrawal of the paw. PWT is determined once for each rat at each time point and either only the affected (ipsilateral) paw is tested, or both the ipsilateral and contralateral (non-injured) paw are tested.

Response to Thermal Stimuli as an Assessment of Thermal Hyperalgesia:

The plantar test can be used to assess thermal hyperalgesia. For this test, hind paw withdrawal latencies to a noxious thermal stimulus are determined using a plantar test apparatus (commercially available from Ugo Basile of Italy) following the technique described by Hargreaves et al., "A New and Sensitive Method for Measuring Thermal Nociception in Cutaneous Hyperalgesia," Pain 32(1):77-88 (1988). The maximum exposure time is set at 32 seconds to avoid tissue damage and any directed paw withdrawal from the heat source is taken as the end point. Three latencies are determined at each time point and averaged. Either only the affected (ipsilateral) paw is tested, or both the ipsilateral and contralateral (non-injured) paw are tested.

Assessment of Tactile Allodynia:

To assess tactile allodynia, rats are placed in clear, plexiglass compartments with a wire mesh floor and allowed to habituate for a period of at least 15 minutes. After habituation, a series of von Frey monofilaments are presented to the plantar surface of the left (operated) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal or licking of the paw are considered nociceptive behavioral responses.

Capsaicin-Induced Eye Wipe Test:

To assess the effect of Compounds of Formula (I) on TRPV1 receptor-mediated pain, the capsaicin-induced eye wipe test is used (Gavva et al., "AMG 9810 [(E)-3-(4-t-Butylphenyl)-N-(2,3-dihydrobenzo[b][1,4]dioxin-6-yl)acrylamide], a Novel Vanilloid Receptor 1 (TRPV1) Antagonist with Antihyperalgesic Properties", J. Pharmacol. Exp. Ther. 313:474-484 (2005)). The eye wipe test is a reliable high-throughput test of the effect of TRPV1 antagonists. Rats are given a single injection of 1, 3, 10, or 30 mg/kg of either a Compound of Formula (I); 30 mg/kg of a control selected from Celebrex, indomethacin, or naproxen; or a carrier. At 1, 3, or 5 hours after drug administration, 3 μL of a 100 μM capsaicin solution (in 10% EtOH/PBS) is instilled in one eye of each animal with a pipette. The number of forelimb movements (touching or wiping of the capsaicin-treated eye) is counted during a 2 minute period following instillation of capsaicin into the eye.

5.11 Example 11

In Vivo Assay of Body Temperature Increase

Test Animals:

Selection of rats (Crl/SD rats, 7 weeks, male) was based on rectal body temperature measured during the morning of the day of dosing as described below. In addition, to minimize spontaneous, stress-induced increases in body temperature, rats were acclimated in advance to both the rectal measurement procedure and to being handled and dosed. All lodging and testing took place in animal care laboratories with constant room temperature and humidity. The rats were free to move and ingest food and water throughout. Each rat was coded with a colored line on the tail, housed in a separate cage, and permitted the normal range of movement. Immediately before each body temperature measurement, a rat was transferred to a measurement cage. To reduce stress which could influence its body temperature, each rat was covered with towels during the measurement. A thermistor probe was then carefully inserted into the rectum of each rat and left in place until the temperature reading on the digital display had stabilized; this value was recorded.

Assay:

On the day before dosing, rectal body temperature was measured at 9:00, 10:00, 11:00, 12:30, 13:30, 14:30, and 15:30 o'clock to familiarize the rats with the measurement procedure prior to administration of the test or control treatments. The rats were also dosed by oral gavage without vehicle at 12:30 o'clock to acclimate and familiarize them with the handling and dosing procedure.

On the day of dosing, only rats with rectal body temperatures within the range of from 37.0° C. to 37.7° C. were selected for study. Rectal body temperatures were measured at 9:00, 10:00, and 11:00 o'clock. Rats were excluded from the study if either their rectal body temperature was over 37.9° C. at 10:00 o'clock or was outside the range of from 37.0° C. to 37.7° C. at 11:00 o'clock. The selected rats were divided into several groups based on their rectal body temperatures at 11:00 o'clock. Rectal body temperatures of the selected rats were measured again at 12:30 o'clock and any rat with a rectal body temperature of 38.0° C. or greater was also excluded from the study.

Following assignment to either a test or control group, a test compound or a control was administered to the rats. Each test compound was dissolved in a vehicle of 0.5% aqueous methylcellulose solution and the final concentration of the test compound was adjusted to 1 mg/mL. Each test compound was orally administered once at a dose of 10 mL/kg. The same volume of the control (vehicle only) was administered once to the control group. Rectal body temperatures were measured at the following time points: 0.5, 1, and 2 hrs after administration.

The body temperature increase (ΔTb) for each test compound was calculated by subtracting, at each time point, the average temperature of the control group from the average temperature of the group administered that test compound. The greatest ΔTb obtained for each test compound at any of the time points is shown in Table 11 below, along with the ΔTb of the control.

TABLE 11

Body Temperature Increase

| Compound | ΔTb (° C.) | Structure |
|---|---|---|
| Control | 0.0 | — |
| G155a | 0.31 | |
| G156a | 0.30 | |
| G158a | 0.23 | |
| G159a | 0.31 | |
| G215a | −0.09 | |

TABLE 11-continued

Body Temperature Increase

| Compound | ΔTb (° C.) | Structure |
|---|---|---|
| BA | 0.9 | 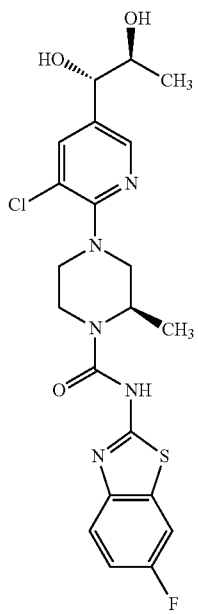 [SMILES: C[C@H](O)[C@@H](O)c1cnc(N2CCN(C(=O)Nc3nc4ccc(F)cc4s3)[C@H](C)C2)c(Cl)c1] |
| BB | 0.5 | 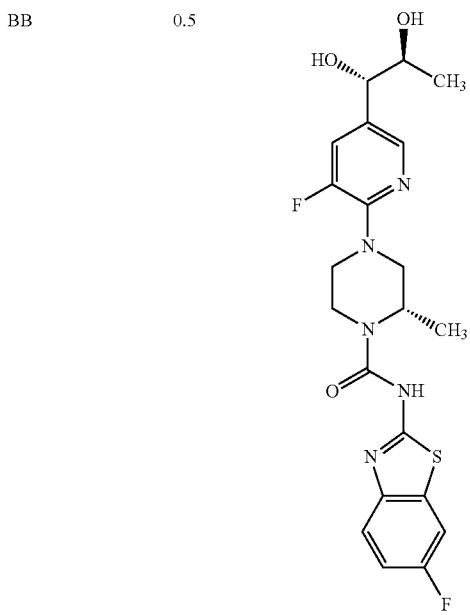 |
| BC | 0.7 | 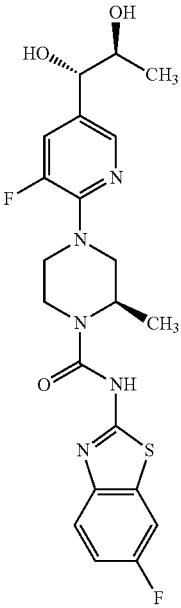 [SMILES: C[C@H](O)[C@@H](O)c1cnc(N2CCN(C(=O)Nc3nc4ccc(F)cc4s3)[C@H](C)C2)c(F)c1] |

As demonstrated by the data above, Compounds of Formula (I) are capable of ameliorating the undesirable side effect of an increase in body temperature that can occur upon in vivo administration of a compound which modulates the TRPV1 receptor. For example, the body temperature increase after administration of Compounds of Formula (I) is less than 0.7° C. in one embodiment, 0.6° C. or less in another embodiment, less than 0.6° C. in another embodiment, 0.5° C. or less in another embodiment, less than 0.5° C. in another embodiment, 0.4° C. or less in another embodiment, less than 0.4° C. in another embodiment, 0.33° C. or less in another embodiment, less than 0.33° C. in another embodiment, 0.31° C. or less in another embodiment, 0.3° C. or less in another embodiment, less than 0.3° C. in another embodiment, 0.25° C. or less in another embodiment, less than 0.25° C. in another embodiment, 0.23° C. or less in another embodiment, 0.2° C. or less in another embodiment, less than 0.2° C. in another embodiment, 0.1° C. or less in another embodiment, or less than 0.1° C. in another embodiment.

In particular, the body temperature increase after administration of Compounds of Formulae (I), (II), and/or (III) was determined to be less than 0.5° C., in some cases much less than 0.5° C., e.g., no increase at all for Compound G215a; less than 0.25° C. for Compound G158a; and 0.31° C. or less for Compounds G155a, G156a, and G159a. In contrast, the body temperature increase after administration of other compounds was determined to be 0.5° C. or greater, in some cases much greater than 0.5° C., e.g., 0.7° C. for Compound BC and 0.9° C. for Compound BA.

The invention is not to be limited in scope by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims. A number of references have been cited, the entire disclosures of which are incorporated herein by reference for all purposes.

What is claimed:

1. A compound of formula (I):

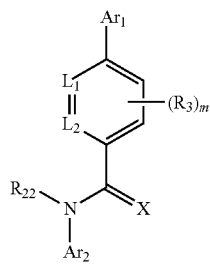

or a pharmaceutically acceptable salt thereof, wherein:

X is O, S, or N—OR$_{10}$;

L$_1$ and L$_2$ are each C(R$_3$);

Ar$_1$ is:

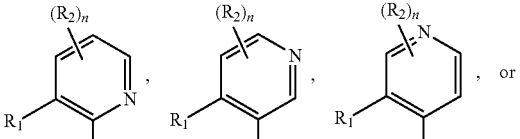

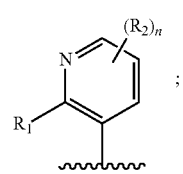

Ar$_2$ is:

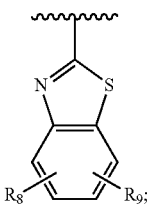

R$_1$ is -halo, —(C$_1$-C$_4$)alkyl, —NO$_2$, —CN, —S(O)$_2$N(R$_{20}$)$_2$, —OH, —OCH$_3$, —NH$_2$, —C(halo)$_3$, —CH(halo)$_2$, —CH$_2$(halo), —OC(halo)$_3$, —OCH(halo)$_2$, or —OCH$_2$(halo);

each R$_2$ is independently:
  (a) -halo, —OH, —O(C$_1$-C$_4$)alkyl, —CN, —NO$_2$, —NH$_2$, —(C$_1$-C$_{10}$)alkyl, —(C$_2$-C$_6$)alkenyl, —(C$_2$-C$_6$)alkynyl, —S(O)$_2$(C$_1$-C$_6$)alkyl, —N(R$_{20}$)S(O)$_2$(C$_1$-C$_6$)alkyl, or -phenyl; or
  (b) a group of formula Q, wherein Q is:

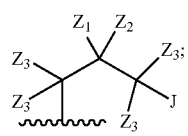

Z$_1$ is independently —H, —OR$_{20}$, —N(R$_{20}$)$_2$, —CH$_2$OR$_{20}$, or —CH$_2$N(R$_{20}$)$_2$;
Z$_2$ is independently —H, —(C$_1$-C$_6$)alkyl, or —CH$_2$OR$_{20}$;
each Z$_3$ is independently —H, —(C$_1$-C$_6$)alkyl, or —(C$_3$-C$_8$)cycloalkyl;
J is —OR$_{20}$ or —N(R$_{20}$)$_2$;
provided that at least one R$_2$ group is a group of formula Q;
each R$_3$ is independently —H, —OCF$_3$, -halo, —(C$_1$-C$_6$)alkyl, —(C$_1$-C$_6$)haloalkyl, —(C$_1$-C$_6$)alkoxy, —N(R$_{20}$)S(O)$_2$(C$_1$-C$_6$)alkyl, -(3- to 7-membered)heterocycle, —OR$_{23}$, —SR$_{23}$, —N(R$_{20}$)(R$_{23}$), —C(O)OR$_{23}$, —C(O)R$_{23}$, —OC(O)R$_{23}$, —OC(O)NHR$_{20}$, —NHC(O)R$_{13}$, —C(O)N(R$_{13}$)$_2$, —S(O)$_2$R$_{20}$, —N(R$_{20}$)S(O)$_2$R$_{13}$, or —CH$_2$OR$_7$;
each R$_7$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, —(C$_1$-C$_6$)haloalkyl, —(C$_1$-C$_6$)hydroxyalkyl, —(C$_1$-C$_6$)alkoxy(C$_2$-C$_6$)alkyl, —(C$_1$-C$_6$)alkyl-N(R$_{20}$)$_2$, or —C(O)N(R$_{20}$)$_2$;
each R$_8$ and R$_9$ is independently:
  (a) —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, or -phenyl, each of which is optionally substituted with 1 or 2 —OH groups; or
  (b) —H, —CH$_2$C(halo)$_3$, —C(halo)$_3$, —CH(halo)$_2$, —CH$_2$(halo), —OC(halo)$_3$, —OCH(halo)$_2$, —OCH$_2$(halo), —SC(halo)$_3$, —SCH(halo)$_2$, —SCH$_2$(halo), —CN, —O—CN, —OH, -halo, —N$_3$, —NO$_2$, —CH=NR$_7$, —N(R$_7$)$_2$, —NR$_7$OH, —OR$_7$, —C(O)R$_7$, —C(O)OR$_7$, —OC(O)R$_7$, —OC(O)OR$_7$, —SR$_7$, —S(O)R$_7$, or —S(O)$_2$R$_7$;
R$_{10}$ is —H, —(C$_1$-C$_4$)alkyl, or —(C$_3$-C$_7$)cycloalkyl;
each R$_{13}$ is independently —H, —(C$_1$-C$_4$)alkyl, —(C$_2$-C$_4$)alkenyl, —(C$_2$-C$_4$)alkynyl, -(3- to 7-membered)heterocycle, or -phenyl;
each R$_{20}$ is independently —H, —(C$_1$-C$_6$)alkyl, or —(C$_3$-C$_8$)cycloalkyl;

R$_{22}$ is —H, —(C$_1$-C$_6$)alkyl, or —(C$_3$-C$_8$)cycloalkyl;
each R$_{23}$ is independently —(C$_1$-C$_6$)alkyl or —(C$_3$-C$_8$)cycloalkyl;
each -halo is independently —F, —Cl, —Br, or —I;
m is the integer 0, 1, or 2; and
n is the integer 1, 2, or 3.

2. The compound of claim 1 or a pharmaceutically acceptable salt thereof, wherein X is O.

3. The compound of claim 2 or a pharmaceutically acceptable salt thereof, wherein R$_{22}$ is —H.

4. The compound of claim 3 or a pharmaceutically acceptable salt thereof, wherein R$_1$ is -halo, —(C$_1$-C$_4$)alkyl, or —C(halo)$_3$.

5. The compound of claim 3 or a pharmaceutically acceptable salt thereof, wherein R$_1$ is —Cl, —F, —CF$_3$, or —CH$_3$.

6. The compound of claim 4 or a pharmaceutically acceptable salt thereof, wherein m is 1.

7. The compound of claim 6 or a pharmaceutically acceptable salt thereof, wherein each R$_3$ is independently —H, —(C$_1$-C$_3$)alkyl, —C(halo)$_3$, —CH(halo)$_2$, or —CH$_2$(halo).

8. The compound of claim 4 or a pharmaceutically acceptable salt thereof, wherein Ar$_1$ is:

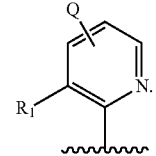

9. The compound of claim 4 or a pharmaceutically acceptable salt thereof, wherein Ar$_1$ is:

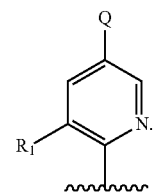

10. The compound of claim 8 or a pharmaceutically acceptable salt thereof, wherein the R$_3$ of each L$_1$ and L$_2$C(R$_3$) group is H.

11. The compound of claim 4 or a pharmaceutically acceptable salt thereof, wherein:
Q is:

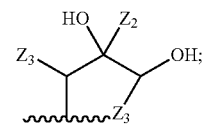

Z$_2$ is —H or —(C$_1$-C$_3$)alkyl; and
each Z$_3$ is independently —H or —(C$_1$-C$_3$)alkyl.

12. The compound of claim 11 or a pharmaceutically acceptable salt thereof, wherein:

Ar₂ is:

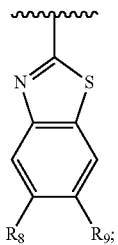

and each R₈ and R₉ is independently —H, —Cl, —Br, —F, —CH₃, —OCH₃, —OCH₂CH₃, —CF₃, —OCF₃, -isopropyl, -tert-butyl, —S(O)₂CF₃, —S(O)₂CH₃, or —S(O)₂CH₂CH₃.

13. The compound of claim 12 or a pharmaceutically acceptable salt thereof, wherein $R_{14}$ is —CF₃, —Cl, or —F.

14. The compound of claim 11 or a pharmaceutically acceptable salt thereof, wherein:

Ar₂ is:

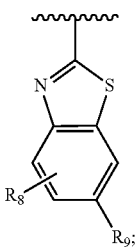

and each R₈ and R₉ is independently —H, —Cl, —Br, —F, —CH₃, —OCH₃, —OCH₂CH₃, —CF₃, —OCF₃, -isopropyl, -tert-butyl, —S(O)₂CF₃, —S(O)₂CH₃, or —S(O)₂CH₂CH₃.

15. The compound of claim 11 or a pharmaceutically acceptable salt thereof, wherein Ar₂ is:

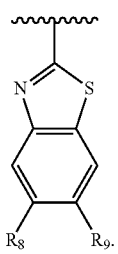

16. The compound of claim 15 or a pharmaceutically acceptable salt thereof, wherein each R₈ and R₉ is independently —H, —F, —CH₃, —OCH₃, —OCH₂CH₃, or —CF₃.

17. A compound of formula (III):

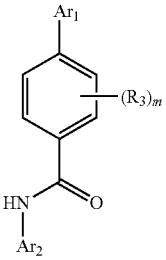

(III)

or a pharmaceutically acceptable salt thereof, wherein:

Ar₁ is:

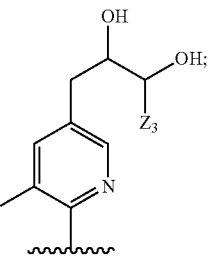

Ar₂ is:

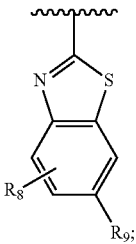

$Z_3$ is —H or —(C₁-C₃)alkyl;
$R_1$ is -halo, —(C₁-C₄)alkyl, —OCH₃, —C(halo)₃, —CH(halo)₂, —CH₂(halo), —OC(halo)₃, —OCH(halo)₂, or —OCH₂(halo);
each $R_3$ is independently —H, —OCF₃, -halo, —(C₁-C₃)alkyl, —(C₁-C₃)haloalkyl, —(C₁-C₆)alkoxy, —N(R₂₀)S(O)₂(C₁-C₃)alkyl, —OR₂₃, —N(R₂₀)(R₂₃), —NHC(O)R₁₃, —C(O)N(R₁₃)₂, —S(O)₂R₂₀, —N(R₂₀)S(O)₂R₁₃, or —CH₂OR₇;
each $R_7$ is independently —H, —(C₁-C₃)alkyl, —(C₂-C₄)alkenyl, —(C₂-C₄)alkynyl, —(C₃-C₈)cycloalkyl, —(C₅-C₈)cycloalkenyl, -phenyl, —(C₁-C₃)haloalkyl, —(C₁-C₆)hydroxyalkyl, —(C₁-C₆)alkoxy(C₂-C₆)alkyl, —(C₁-C₃)alkyl-N(R₂₀)₂, or —C(O)N(R₂₀)₂;
each $R_8$ and $R_9$ is independently —H, —Cl, —Br, —F, —CH₃, —OCH₃, —OCH₂CH₃, —CF₃, —OCF₃, -isopropyl, -tert-butyl, —S(O)₂CF₃, —S(O)₂CH₃, or —S(O)₂CH₂CH₃;
each $R_{13}$ is independently —H, —(C₁-C₄)alkyl, —(C₂-C₄)alkenyl, —(C₂-C₄)alkynyl, -(3- to 7-membered)heterocycle, or -phenyl;
each $R_{20}$ is independently —H, —(C₁-C₆)alkyl, or —(C₃-C₈)cycloalkyl;
each $R_{23}$ is independently —(C₁-C₆)alkyl or —(C₃-C₈)cycloalkyl;
each -halo is independently —F, —Cl, —Br, or —I; and
m is the integer 0, 1, or 2.

18. The compound of claim 17 or a pharmaceutically acceptable salt thereof, wherein m is 1 and $R_3$ is —H, —OCF₃, -halo, —(C₁-C₃)alkyl, or —(C₁-C₃)haloalkyl.

19. The compound of claim 18 or a pharmaceutically acceptable salt thereof, wherein $R_3$ is —H, —CH$_3$, or —CF$_3$.

20. The compound of claim 17 or a pharmaceutically acceptable salt thereof, wherein Ar$_2$ is:

21. The compound of claim 17 or a pharmaceutically acceptable salt thereof, wherein $Z_3$ is —H.

22. The compound of claim 17 or a pharmaceutically acceptable salt thereof, wherein $Z_3$ is —CH$_3$.

23. The compound of claim 17 or a pharmaceutically acceptable salt thereof, wherein the pharmaceutically acceptable salt is a hydrochloride-salt, a sodium-salt, a potassium-salt, or a para-toluenesulfonic acid-salt.

24. The compound of claim 17 or a pharmaceutically acceptable salt thereof, which comprises the Q group

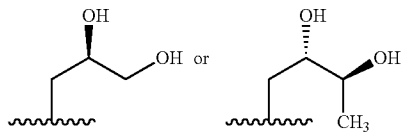

and has an enantiomeric excess of at least about 60%.

25. A composition comprising a compound of claim 17 or a pharmaceutically acceptable salt thereof and a pharmaceutically acceptable carrier or excipient.

26. A method for preparing a composition comprising admixing a compound of claim 17 or a pharmaceutically acceptable salt thereof with a pharmaceutically acceptable carrier or excipient.

27. A method for treating pain in an animal, comprising administering to an animal in need thereof, an effective amount of the compound of claim 1 or a pharmaceutically acceptable salt thereof.

28. A method of inhibiting TRPV1 function in a cell comprising contacting a cell capable of expressing TRPV1 with an effective amount of a compound of claim 1 or a pharmaceutically acceptable salt thereof.

29. A method for treating pain in an animal, comprising administering to an animal in need thereof, an effective amount of the compound of claim 17 or a pharmaceutically acceptable salt thereof.

30. A method of inhibiting TRPV1 function in a cell comprising contacting a cell capable of expressing TRPV1 with an effective amount of a compound of claim 17 or a pharmaceutically acceptable salt thereof.

31. A composition comprising a compound of claim 1 or a pharmaceutically acceptable salt thereof and a pharmaceutically acceptable carrier or excipient.

32. A method for preparing a composition comprising admixing a compound of claim 1 or a pharmaceutically acceptable salt thereof with a pharmaceutically acceptable carrier or excipient.

* * * * *

SEQUENCE LISTING

```
<160> NUMBER OF SEQ ID NOS: 4

<210> SEQ ID NO 1
<211> LENGTH: 32
<212> TYPE: DNA
<213> ORGANISM: Artificial Sequence
<220> FEATURE:
<223> OTHER INFORMATION: forward primer for human TRPV1

<400> SEQUENCE: 1
gaagatcttc gctggttgca cactgggcca ca                                        32

<210> SEQ ID NO 2
<211> LENGTH: 32
<212> TYPE: DNA
<213> ORGANISM: Artificial Sequence
<220> FEATURE:
<223> OTHER INFORMATION: reverse primer for human TRPV1

<400> SEQUENCE: 2
gaagatcttc ggggacagtg acggttggat gt                                        32

<210> SEQ ID NO 3
<211> LENGTH: 25
<212> TYPE: DNA
<213> ORGANISM: Artificial Sequence
<220> FEATURE:
<223> OTHER INFORMATION: forward primer for complete hTRPV1 ORF

<400> SEQUENCE: 3
ggatccagca aggatgaaga aatgg                                                25

<210> SEQ ID NO 4
<211> LENGTH: 24
<212> TYPE: DNA
<213> ORGANISM: Artificial Sequence
<220> FEATURE:
<223> OTHER INFORMATION: reverse primer for complete hTRPV1 ORF

<400> SEQUENCE: 4
tgtctgcgtg acgtcctcac ttct                                                 24
```